US010053465B2

(12) United States Patent
Li et al.

(10) Patent No.: US 10,053,465 B2
(45) Date of Patent: Aug. 21, 2018

(54) PYRROLOPYRIMIDINE DERIVATIVES AS TAM INHIBITORS

(71) Applicant: Incyte Corporation, Wilmington, DE (US)

(72) Inventors: Yun-Long Li, Chadds Ford, PA (US); David M. Burns, Glen Mills, PA (US); Hao Feng, Glen Mills, PA (US); Joseph Glenn, Mount Royal, NJ (US); Chunhong He, Chadds Ford, PA (US); Taisheng Huang, Wilmington, DE (US); Song Mei, Wilmington, DE (US); Jun Pan, Media, PA (US); Xiaozhao Wang, Mt. Laurel, NJ (US); Yingda Ye, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 15/247,499

(22) Filed: Aug. 25, 2016

(65) Prior Publication Data
US 2017/0057965 A1    Mar. 2, 2017

Related U.S. Application Data

(60) Provisional application No. 62/210,284, filed on Aug. 26, 2015.

(51) Int. Cl.
*C07D 487/04* (2006.01)
*C07D 519/00* (2006.01)
*C07D 471/04* (2006.01)

(52) U.S. Cl.
CPC ......... *C07D 487/04* (2013.01); *C07D 471/04* (2013.01); *C07D 519/00* (2013.01)

(58) Field of Classification Search
None
See application file for complete search history.

(56) References Cited

U.S. PATENT DOCUMENTS

| 9,708,333 | B2 | 7/2017 | Li et al. |
| 2010/0298334 | A1 | 11/2010 | Rodgers et al. |
| 2011/0015212 | A1 | 1/2011 | Li et al. |
| 2011/0059951 | A1 | 3/2011 | Rodgers et al. |
| 2011/0183985 | A1 | 7/2011 | Li et al. |
| 2011/0224190 | A1 | 9/2011 | Huang et al. |
| 2012/0015937 | A1 | 1/2012 | Ding et al. |
| 2012/0088768 | A1 | 4/2012 | Singh et al. |
| 2012/0149681 | A1 | 6/2012 | Rodgers et al. |
| 2012/0149682 | A1 | 6/2012 | Rodgers et al. |
| 2012/0157430 | A1 | 6/2012 | Li et al. |
| 2012/0184535 | A1 | 7/2012 | Brzozka et al. |
| 2012/0219522 | A1 | 8/2012 | Xi |
| 2012/0230993 | A1 | 9/2012 | Graham et al. |
| 2012/0264740 | A1 | 10/2012 | Goff et al. |
| 2012/0283261 | A1 | 11/2012 | Bearss et al. |
| 2013/0018034 | A1 | 1/2013 | Yao et al. |
| 2013/0018051 | A1 | 1/2013 | Singh et al. |
| 2013/0045963 | A1 | 2/2013 | Rodgers et al. |
| 2013/0059835 | A1 | 3/2013 | Li et al. |
| 2013/0090330 | A1 | 4/2013 | Ding et al. |
| 2013/0197070 | A1 | 8/2013 | De Franciscis et al. |
| 2013/0281468 | A1 | 10/2013 | Goff et al. |
| 2014/0005166 | A1 | 1/2014 | Rodgers et al. |
| 2014/0018365 | A1 | 1/2014 | Schultz-Fademrecht et al. |
| 2014/0121198 | A1 | 5/2014 | Li et al. |
| 2014/0128390 | A1* | 5/2014 | Lin ...................... A61K 31/517 514/234.2 |
| 2014/0128400 | A1 | 5/2014 | Singh et al. |
| 2014/0275023 | A1 | 9/2014 | Namdev et al. |
| 2016/0333008 | A1 | 11/2016 | Sun et al. |

(Continued)

FOREIGN PATENT DOCUMENTS

| CN | 102408411 | 4/2012 |
| EP | 2465505 | 6/2012 |
| EP | 2484679 | 8/2012 |

(Continued)

OTHER PUBLICATIONS

"Urbonas et al., ""A Novel Highly Site-Selective Synthesis of 2,4,7-Triarylpyrrolo[2,3-d]pyrimidines by a Combination of Palladium(0)-, Nickel(0)-, and Copper(I)-Catalyzed Cross-Coupling Reactions,"" Synlett, 2013, 24(11):1383-1386".

Affouard et al., "Multi-Kilo Delivery of AMG 925 Featuring a Buchwald-Hartwig Amination and Processing with Insoluble Synthetic Intermediates," Organic Process Research & Development, 2015, 19: 476-485.

Angelillo-Scherrer et al., "Role of Gas6 in erythropoiesis and anemia in mice," J. Clin. Invest., 2008, 118: 583-596.

Borovik et al., "Pyrimidines. XLIX. Synthesis of 9-phenylpyrimido[4,5-b] indoles," Izvestiya Sibirskogo Otdeleniya Akademii Nauk SSSR, Seriya Khimicheskikh Nauk, 1975, 137-41 (English abstract only).

(Continued)

*Primary Examiner* — Anna Pagonakis
(74) *Attorney, Agent, or Firm* — Fish & Richardson P.C.

(57) ABSTRACT

This application relates to compounds of Formula I:

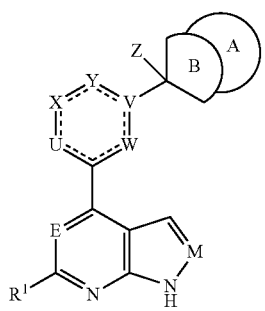

or pharmaceutically acceptable salts thereof, which are inhibitors of TAM kinases which are useful for the treatment of disorders such as cancer.

37 Claims, No Drawings

(56) References Cited

U.S. PATENT DOCUMENTS

| | | |
|---|---|---|
| 2017/0044164 A1 | 2/2017 | Li et al. |
| 2017/0275290 A1 | 9/2017 | Li et al. |

FOREIGN PATENT DOCUMENTS

| | | |
|---|---|---|
| WO | WO 2004/035580 | 4/2004 |
| WO | WO 2005/025515 | 3/2005 |
| WO | WO 2006/046023 | 5/2006 |
| WO | WO 2007/061737 | 5/2007 |
| WO | WO 2007/070514 | 6/2007 |
| WO | WO 2007/120752 | 10/2007 |
| WO | WO 2007/125315 | 11/2007 |
| WO | WO 2008/076392 | 6/2008 |
| WO | WO 2009/023269 | 2/2009 |
| WO | WO 2009/047514 | 4/2009 |
| WO | WO 2009/053737 | 4/2009 |
| WO | WO 2009/054864 | 4/2009 |
| WO | WO 2009/085185 | 7/2009 |
| WO | WO 2009/087225 | 7/2009 |
| WO | WO 2009/127417 | 10/2009 |
| WO | WO 2010/005876 | 1/2010 |
| WO | WO 2010/005879 | 1/2010 |
| WO | WO 2010/008454 | 1/2010 |
| WO | WO 2010/014755 | 2/2010 |
| WO | WO 2010/025073 | 3/2010 |
| WO | WO 2010/071885 | 6/2010 |
| WO | WO 2010/090764 | 8/2010 |
| WO | WO 2011/038185 | 3/2011 |
| WO | WO 2011/045084 | 4/2011 |
| WO | WO 2011/139273 | 11/2011 |
| WO | WO 2012/028332 | 3/2012 |
| WO | WO 2012/048129 | 4/2012 |
| WO | WO 2012/129344 | 9/2012 |
| WO | WO 2012/135800 | 10/2012 |
| WO | WO 2013/052417 | 4/2013 |
| WO | WO 2013/074633 | 5/2013 |
| WO | WO 2013/085802 | 6/2013 |
| WO | WO 2013/115280 | 8/2013 |
| WO | WO 2013/162061 | 10/2013 |
| WO | WO 2014/062774 | 4/2014 |
| WO | WO 2014/079545 | 5/2014 |
| WO | WO 2014/109858 | 7/2014 |
| WO | WO 2014/164729 | 10/2014 |
| WO | WO 2015/012298 | 1/2015 |
| WO | WO 2015/068767 | 5/2015 |
| WO | WO 2016/097918 | 6/2016 |
| WO | WO 2017/027717 | 2/2017 |
| WO | WO 2017/062797 | 4/2017 |
| WO | WO 2017/083788 | 5/2017 |
| WO | WO 2017/083789 | 5/2017 |

OTHER PUBLICATIONS

Borovik et al., "Synthesis of 2-substituted pyrimido[4,5-b]indoles and N-phenyl-2,2-diethoxy-3-arylideneindolines," v sb., Khimiya i Farmakol. Indol'n. Soedinenii, 1975, 50 (English abstract only).

Cecil Textbook of Medicine, edited by Bennet, J.C., and Plum F., 20th edition, vol. 1, 1004-1010, 1996.

Chung et al., "Synthesis of certain [6:5:6] linear tricyclic nucleosides as potential antitumor agents," Journal of Medicinal Chemistry, Nov. 1980, 23(11): 1158-66.

Cohen., "The development and therapeutic potential of protein kinase inhibitors," Current Opinion in Chemical Biology, 1999, 3: 459-465, 1999.

Cosemans et al., "Potentiating role of Gas6 and Tryo3, Axl and Mer (TAM) receptors in human and murine platelet activation and thrombus stabilization," J. of Thrombosis and Haemostasis, 2010, 8: 1797-1808.

Dermer et al., "Another Anniversary for the War on Cancer," Bio/Technology, Mar. 1994, 12: 320.

Dodonova et al., "Synthesis of 4-aryl-, 2, 4-diaryl-and 2, 4, 7-triarylpyrrolo [2, 3-d] pyrimidines by a combination of the Suzuki cross-coupling and N-arylation reactions," Tetrahedron, 2012, 68(1):329-339.

Freshney et al., "Culture of Animal Cells," A Manual of Basic Technique, Alan R. Liss, Inc., 1983, New York, p. 4.

Ghosh, "Synthesis of 4-oxazolinephenylboronic acid and heterobiaryl oxazolines via a Suzuki reaction," Journal of Chemical Research, Apr. 2009, 4:205-207.

Golub et al., "Molecular Classification of Cancer: Class Discovery and Class Prediction by Gene Expression Monitoring," Science, 1999, 286: 531-537.

International Search Report and Written Opinion in International Application No. PCT/US2016/046574, dated Oct. 21, 2016, 14 pages.

International Search Report and Written Opinion in International Application No. PCT/US2016/048716, dated Nov. 2, 2016, 12 pages.

Keegan et al., "Preclinical Evaluation of AMG 925, a FLT3/CDK4 Kinase Inhibitor for Treating Acute Myeloid Leukemia," Molecular Cancer Therapeutics, Apr. 2014, 13(4): 880-889.

Kerekes et al., "Aurora kinase inhibitors based on the imidazo[1,2-a]pyrazine core: fluorine and deuterium incorporation improve oral absorption and exposure," J. Med. Chem., 2011, 54: 201-210.

Klimke and Ludemann, "Further evidence for a S-syn correlation in the purine (β) ribosides: the solution conformation of two tricyclic analogs of adenosine and guanosine," Journal of Biosciences, 1979, 34C(9-10): 653-7.

Lemke, "Biology of the TAM Receptors," Cold Spring Harb Perspect Biol., 2013, 5: 1-17.

Li et al., "Discovery of AMG 925, a FLT3 and CDK4 Dual Kinase Inhibitor with Preferential Affinity for the Activated State of FLT3," Journal of Medicinal Chemistry, 2014, 57(8): 3430-3449.

Liu et al., "UNC1062, a new and potent Mer inhibitor," European Journal of Medicinal Chemistry, 2013, 65: 83-93.

Okamoto et al., "Oligonucleotides containing 7-vinyl-7-deazaguanine as a facile strategy for expanding the functional diversity of DNA," Bioorganic & Medicinal Chemistry Letters, 2002, 12(15): 1895-1896.

Singer et al., "Photochromism of Diarylethene-Functionalized 7-Deazaguanosines," European Journal of Organic Chemistry, 2013, 14: 2766-2769.

Shibata et al., "Axl receptor blockade ameliorates pulmonary pathology resulting from primary viral infection and viral exacerbation of asthma," The Journal of Immunology, 2014, 192: 3569-3581.

Skardziute, "Optical study of the formation of pyrrolo[2,3-d]pyrimidine-based fluorescent nanoaggregates," Tetrahedron, 2013, 69(46):9566-9572.

Strassmaier and Karpen, "Novel N7-and N1-Substituted cGMP Derivatives Are Potent Activators of Cyclic Nucleotide-Gated Channels," Journal of Medicinal Chemistry, Aug. 2007, 50: 4186-4194.

Tumkevicius, "Pyrrolo [2, 3-d] pyrimidine-Core-Extended π-Systems: Synthesisof 2, 4, 7-Triarylpyrrolo [2, 3-d] pyrimidines," Synlett, 2011, 12:1705-1708.

Tumkevicius, "Synthesis and photophysical properties of oligoarylenes with a pyrrolo [2, 3-d] pyrimidine core," Tetrahedron Letters (2010), 51(30), 3902-3906.

Xu et al., "Design, synthesis and biological evaluation of deuterated nintedanib for improving pharmacokinetic properties," J. Label Compd. Radiopharm., 2015, 58: 308-312.

Yamazoe et al., "Mechanism of formation and structural characterization of DNA adducts derived from peroxidative activation of benzidine," Carcinogenesis, Sep. 1988, 9(9): 1635-41.

Zhao, et al., "Discovery of novel Bruton's tyrosine kinase (BTK) inhibitors bearing a pyrrolo [2, 3-d] pyrimidine scaffold," Bioorganic & Medicinal Chemistry, Feb. 2015, 23(4):891-901.

Zhou et al., "Synthesis and evaluation of Janus type nucleosides as potential HCV NS5B polymerase inhibitors," Bioorganic & Medicinal Chemistry Letters, Jun. 2013, 23: 3385-3388.

Burbridge et al., "S49076 Is a Novel Kinase Inhibitor of MET, AXL, and FGFR with Strong Preclinical Activity Alone and in Association with Bevacizumab," AACR Journals, 2013, 1749-1762.

(56) References Cited

OTHER PUBLICATIONS

Berge, "Pharmaceutical Salts," Journal of Pharmaceutical Science, 66, 2 (1977).
Blom et al., "Optimizing Preparative LC/MS Configurations and Methods for Parallel Synthesis Purification," J. Comb. Chem., 2003, 5: 670-683.
Blom et al., "Preparative LC-MS Purification: Improved Compound-Specific Method Optimization," J. Comb. Chem., 2004, 6: 874-883.
Blom, "Two-Pump at-Column-Dilution Configuration for Preparative Liquid Chromatography-Mass Spectrometry," J. Comb. Chem., 2002, 4: 295-301.
Chambers et al., "Lymphoproliferation in CTLA-4-deficient mice is mediated by costimulation-dependent activation of CD4+ T cells," Immunity, Dec. 1997, 7(6): 885-95.
Cook et al., "MerTK inhibition in tumor leukocytes decreases tumor growth and metastasis," J. Clin. Invest., Aug. 2013, 123(8): 3231-42.
Demarest et al., "Evaluation of Tyro3 expression, Gas6-mediated Akt phosphorylation, and the impact of anti-Tyro3 antibodies in melanoma cell lines," Biochemistry, May 2013, 52(18): 3102-18.
Feneyrolles et al., "Axl kinase as a key target for oncology: focus on small molecule inhibitors," Mol Cancer Therapy, Sep. 2014, 13(9): 2141-8.
Graham et al., "Cloning and developmental expression analysis of the murine c-mer tyrosine kinase," Oncogene, Jun. 1995, 10(12): 2349-59.
Graham et al., "The TAM family: phosphatidylserine sensing receptor tyrosine kinases gone awry in cancer," Nat. Rev. Cancer, Dec. 2014, 14(12): 769-85.
Holland et al., "R428, a Selective Small Molecule Inhibitor of Axl Kinase, Blocks Tumor Spread and Prolongs Survival in Models of Metastatic Breast Cancer," Cancer Research, Feb. 2010, 70(4): 1544-1554.
Huang et al., "Structural insights into the inhibited states of the Mer receptor tyrosine kinase," Journal of Structural Biology, 2009, 165: 88-96.
International Search Report and Written Opinion in International Application No. PCT/US2016/031625, dated Jul. 7, 2016, 11 pages.
Koorstra et al., "The Axl receptor tyrosine kinase confers an adverse prognostic influence in pancreatic cancer and represents a new threapeutic target," Cancer Biol. Ther., Apr. 2009, 8(7): 618-26.
Lai and Lemke, "An extended family of protein-tyrosine kinase genes differentially expressed in the vertebrate nervous system," Neuron, May 1991, 6(5): 691-704.
Lee-Sherick et al., "Aberrant Mer receptor tyrosine kinase expression contributes to leukemogenesis in acute myeloid leukemia," Oncogene, Nov. 2013, 32(46): 5359-68.
Lew et al., "Differential TAM receptor-ligand-phospholipid interactions delimit differential TAM bioactivities," Elife, Sep. 2014, e03385.
Li et al., "Axl as a potential therapeutic target in cancer: role of Axl in tumor growth, metastasis and angiogenesis," Oncogene, Oct. 2009, 28(39): 3442-55.
Linger et al., "Mer or Axl receptor tyrosine kinase inhibition promotes apoptosis, blocks growth and enhances chemosensitivity of human non-small cell lung cancer," Oncogene, Jul. 2013, 32(29): 3420-31.
Linger et al., "Taking aim at Mer and Axl receptor tyrosine kinases as novel therapeutic targets in solid tumors," Expert Opin. Ther. Targets, Oct. 2010, 14(10): 1073-1090.
Linger et al., "TAM Receptor Tyrosine Kinases: Biologic Functions, Signaling, and Potential Therapeutic Targeting in Human Cancer," Adv. Cancer Research, 2008, 100: 35-83.
Liu et al., "Discovery of Novel Small Molecule Mer Kinase Inhibitors for the Treatment of Pediatric Acute Lymphoblastic Leukemia," ACS Med. Chem. Lett., 2012, 3(2): 129-134.
Liu et al., "Discovery of Small Molecule Mer Kinase Inhibitors for the Treatment of Pediatric Acute Lymphoblastic Leukemia," ACS Medicinal Chemistry Letters, 2012, 3: 129-134.
Lu and Lemke, "Homeostatic regulation of the immune system by receptor tyrosine kinases of the Tyro 3 family," Science, Jul. 2001, 293(5528): 306-11.
Mollard et al., "Design, Synthesis, and Biological Evaluation of a Series of Novel AXL Kinase Inhibitors," ACS Medicinal Chemistry Letters, 2011, 2: 907-912.
Myers et al., "AXL inhibitors in cancer: A medicinal chemistry perspective," Journal of Medicinal Chemistry, 2015, 54 pages.
Nishimura et al., "Autoimmune dilated cardiomyopathy in PD-1 receptor-deficient mice," Science, 2001, 291(5502): 319-22.
O'Bryan et al., "axl, a transforming gene isolated from primary human myeloid leukemia cells, encodes a novel receptor tyrosine kinase," Mol. Cell Biol., Oct. 1991, 11(10): 5016-31.
Paolino et al., "The E3 ligase Cbl-b and TAM receptors regulate cancer metastasis via natural killer cells," Nature, 2014, 19 pages.
Pardoll, "The blockade of immune checkpoints in cancer immunotherapy," Nat. Rev. Cancer, Mar. 2012, 12(4): 252-64.
Powell et al., "Highly selective 2,4-diaminopyrimidine-5-carboxamide inhibitors of Sky kinase," Bioorganic & Medicinal Chemistry Letters, 2013, 23: 1046-1050.
Powell et al., "Novel and selective spiroindoline-based inhibitors of sky kinase," Bioorganic & Medicinal Chemistry Letters, 2012, 22: 190-193.
Remington's Pharmaceutical Sciences, 17th ed., Mack Publishing Company, Easton, Pa., 1985, p. 1418.
Rho et al., "MET and AXL Inhibitor NPS-1034 Exerts Efficacy against Lung Cancer Cells Resistant to EGFR Kinase Inhibitors Because of MET or AXL Activation," AARC Journals, 2013, 253-262.
Schlegel et al., "MERTK receptor tyrosine kinase is a therapeutic target in melanoma," The Journal of Clinical Investigation, May 2013, 123(5): 2257-2267.
Schroeder et al., "Discovery of N-(4-(2-Amino-3-chloropyridin-4-yloxy)-3-fluorophenyl)-4-ethoxy-1-(4-fluorophenyl)-2-oxo-1,2-dihydropyridine-3-carboxamide (BMS-777607), a Selective and Orally Efficacious Inhibitor of the Met Kinase Superfamily," J. Med. Chem., 2009, 52: 1251-1254.
Suarez et al., "Inhibitors of the TAM subfamily of tyrosine kinsases: Synthesis and biological evaluation," European Journal of Medicinal Chemistry, 2013, 61: 2-25.
Tai et al., "Axl promotes cell invasion by inducing MMP-9 activity through activation of NF-kappaB and Brg-1," Oncogene, Jul. 2008, 27(29): 4044-55.
Traore et al., "New aminopyrimidine derivatives as inhibitors of the TAM family," European Journal of Medicinal Chemistry, 2013, 70: 789-801.
Waizeneggar et al., "Role of Growth arrest-specific gene 6-Mer axis in multiple myeloma," Leukemia, 2015, 29: 696-704.
Wang et al., "Mer receptor tyrosine kinase promotes invasion and survival in glioblastoma multiforme," Oncogene, Feb. 2013, 32(7): 872-82.
Wu et al., "Multisubstituted quinoxalines and pyrido[2,3-d]pyrimidines: Synthesis and SAR study as tyrosine kinase c-Met inhibitors," Bioorganic & Medicinal Chemistry Letters, 2012, 22: 6368-6372.
Zhang et al., "Activation of the AXL kinase causes resistance to EGFR-targeted therapy in lung cancer," Nat. Genet, 2012, 44(8): 852-60.
Zhang et al., "Discovery of Mer Specific Tyrosine Kinase Inhibitors for the Treatment and Prevention of Thrombosis," Journal of Medicinal Chemistry, 2013, 56: 9693-9700.
Zhang et al., "Discovery of novel type II c-Met inhibitors based on BMS-777607," European Journal of Medicinal Chemistry, 2014, 80: 254-266.
Zhang et al., "Pseudo-Cyclization through Intramolecular Hydrogen Bond Enables Discovery of Pyridine Substituted Pyrimidines as New Mer Kinase Inhibitors," Journal of Medicinal Chemistry, 2013, 56: 6983-9692.
Zhang et al., "UNC20205, a Potent and Orally Bioavailable MER/FLT3 Dual Inhibitor," Journal of Medicinal Chemistry, 2014, 57: 7031-7041.

(56) References Cited

OTHER PUBLICATIONS

Baladi et al., "State-of-the-art of small molecule inhibitors of the TAM family: The point of view of the chemist," European Journal of Medicinal Chemistry, Oct. 2015, 105: 220-237.
Balupuri et al., "Molecular modeling study on Mer kinase inhibitors using 3D-QSAR and docking approaches," Medicinal Chemistry Research, Jul. 2015, 24(10): 3730-3742.
International Search Report and Written Opinion in International Application No. PCT/US2017/024270, dated Jun. 14, 2017, 18 pages.
Liu et al., "Discovery of Novel Small Molecule Mer Kinase Inhibitors for the Treatment of Pediatric Acute Lymphoblastic Leukemia," Supporting Information, 2012, 53 pages.

* cited by examiner

PYRROLOPYRIMIDINE DERIVATIVES AS TAM INHIBITORS

CROSS-REFERENCE TO RELATED APPLICATIONS

This application claims priority to U.S. Provisional Patent Application No. 62/210,284 entitled "Pyrrolopyrimidine Derivatives as TAM Inhibitors" filed on Aug. 26, 2015, which is incorporated herein by reference in its entirety.

TECHNICAL FIELD

This application relates to pyrrolo[2,3-d]pyrimidine inhibitors of TAM kinases, which are useful in the treatment of disorders such as cancer, as well as pharmaceutical compositions related thereto.

BACKGROUND OF INVENTION

Receptor tyrosine kinases (RTKs) are cell surface proteins that transmit signals from the extracellular environment to the cell cytoplasm and nucleus to regulate cellular events such as survival, growth, proliferation, differentiation, adhesion and migration.

The TAM subfamily consists of three RTKs including Tyro3, AXL and Mer (Graham et al., 2014, Nature Reviews Cancer 14, 769-785; Linger et al., 2008, Advances in Cancer Research 100, 35-83). TAM kinases are characterized by an extracellular ligand binding domain consisting of two immunoglobulin-like domains and two fibronectin type III domains. Two ligands, growth arrest specific 6 (GAS6) and protein S (PROS1), have been identified for TAM kinases. GAS6 can bind to and activate all three TAM kinases, while PROS1 is a ligand for Mer and Tyro3 (Graham et al., 2014, Nature Reviews Cancer 14, 769-785).

AXL (also known as UFO, ARK, JTK11 and TYRO7) was originally identified as a transforming gene from DNA of patients with chronic myelogenous leukemia (O'Bryan et al., 1991, Mol Cell Biol 11, 5016-5031; Graham et al., 2014, Nature Reviews Cancer 14, 769-785; Linger et al., 2008, Advances in Cancer Research 100, 35-83). GAS6 binds to AXL and induces subsequent auto-phosphorylation and activation of AXL tyrosine kinase. AXL activates several downstream signaling pathways including PI3K-Akt, Raf-MAPK, PLC-PKC (Feneyrolles et al., 2014, Molecular Cancer Therapeutics 13, 2141-2148; Linger et al., 2008, Advances in Cancer Research 100, 35-83).

MER (also known as MERTK, EYK, RYK, RP38, NYK and TYRO12) was originally identified as a phospho-protein from a lymphoblastoid expression library (Graham et al., 1995, Oncogene 10, 2349-2359; Graham et al., 2014, Nature Reviews Cancer 14, 769-785; Linger et al., 2008, Advances in Cancer Research 100, 35-83). Both GAS6 and PROS1 can bind to Mer and induce the phosphorylation and activation of Mer kinase (Lew et al., 2014). Like AXL, MER activation also conveys downstream signaling pathways including PI3K-Akt and Raf-MAPK (Linger et al., 2008, Advances in Cancer Research 100, 35-83).

TYRO3 (also known as DTK, SKY, RSE, BRT, TIF, ETK2) was originally identified through a PCR-based cloning study (Lai et al., Neuron 6, 691-70, 1991; Graham et al., 2014, Nature Reviews Cancer 14, 769-785; Linger et al., 2008, Advances in Cancer Research 100, 35-83). Both ligands, GAS6 and PROS1, can bind to and activate TYRO3. Although the signaling pathways downstream of TYRO3 activation are the least studied among TAM RTKs, it appears that both PI3K-Akt and Raf-MAPK pathways are involved (Linger et al., 2008, Advances in Cancer Research 100, 35-83). AXL, MER and TYRO3 are found to be over-expressed in cancer cells.

Accordingly, there is a need in the art for compounds and methods of use thereof for the modulation of TAM kinases in treatment of cancer.

SUMMARY OF INVENTION

In one aspect, the present disclosure relates to compounds having Formula I:

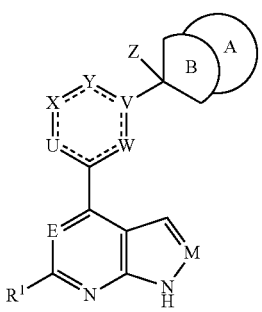

or a pharmaceutically acceptable salt thereof, wherein ring A, ring B, E, M, $R^1$, U, X, Y, W, V, and Z are defined infra.

The present application further provides compositions comprising a compound described herein, or a pharmaceutically acceptable salt thereof, and at least one pharmaceutically acceptable carrier.

The present application also provides methods of inhibiting TAM kinases, comprising contacting one or more TAM kinase with a compound described herein, or a pharmaceutically acceptable salt thereof.

The present invention also provides a compound described herein, or a pharmaceutically acceptable salt thereof, for use in any of the methods described herein.

The present invention further provides use of a compound described herein, or a pharmaceutically acceptable salt thereof, for the manufacture of a medicament for use in any of the methods described herein.

DETAILED DESCRIPTION

Compounds

In one aspect, the present disclosure provides a compound of Formula I:

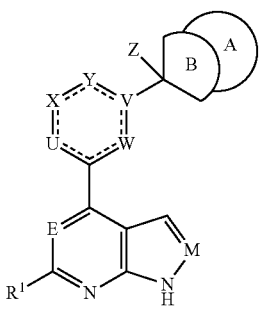

or a pharmaceutically acceptable salt thereof, wherein:

each ====== in the ring formed by U, X, Y, V, and W is independently a single or double bond;

E is —N= or =CR$^9$—;

M is —N= or =CR$^2$—;

U is —N= or =CR$^3$—;

X is —N= or =CR$^4$—;

Y is —N= or =CR$^5$—;

W is —N= or =CR$^6$—;

V is —CR$^{AB}$=, wherein R$^{AB}$ is the fused A-B moiety; alternatively, Y is C=O, X is —NR$^{4a}$—, and V is —CR$^{AB}$=; or Y is C=O, X is =CR$^4$— and V is —NR$^{AB}$—;

provided that no more than two of U, X, Y, and W are —N=;

R$^1$ is H, halo, CN, C$_{1-6}$ alkyl, C$_{2-6}$ alkenyl, C$_{2-6}$ alkynyl, C$_{1-4}$ haloalkyl, OR$^{a1}$, SR$^{a1}$, C(O)R$^{b1}$, C(O)NR$^{c1}$R$^{d1}$, C(O)OR$^{a1}$, OC(O)R$^{b1}$, OC(O)NR$^{c1}$R$^{d1}$, NR$^{c1}$R$^{d1}$, NR$^{c1}$OR$^{d1}$, NR$^{c1}$C(O)R$^{b1}$, NR$^{c1}$C(O)OR$^{b1}$, NR$^{c1}$C(O)NR$^{c1}$R$^{d1}$, NR$^{c1}$S(O)R$^{b1}$, NR$^{c1}$S(O)$_2$R$^{b1}$, NR$^{c1}$S(O)$_2$NR$^{c1}$R$^{d1}$, S(O)R$^{b1}$, S(O)NR$^{c1}$R$^{d1}$, S(O)$_2$R$^{b1}$, S(O)$_2$NR$^{c1}$R$^{d1}$, C$_{3-7}$ cycloalkyl, phenyl, 5-6 membered heteroaryl, 4-6 membered heterocycloalkyl, C$_{3-7}$ cycloalkyl-C$_{1-3}$ alkylene, phenyl-C$_{1-3}$ alkylene, 5-6 membered heteroaryl-C$_{1-3}$ alkylene, or 4-6 membered heterocycloalkyl-C$_{1-3}$ alkylene; wherein said C$_{1-6}$ alkyl, C$_{2-6}$ alkenyl, C$_{2-6}$ alkynyl, C$_{1-4}$ haloalkyl, C$_{3-7}$ cycloalkyl, phenyl, 5-6 membered heteroaryl, 4-6 membered heterocycloalkyl, C$_{3-7}$ cycloalkyl-C$_{1-3}$ alkylene, phenyl-C$_{1-3}$ alkylene, 5-6 membered heteroaryl-C$_{1-3}$ alkylene, and 4-6 membered heterocycloalkyl-C$_{1-3}$ alkylene are each optionally substituted with 1, 2, 3, or 4 independently selected R$^{11}$ groups;

R$^2$ is H, halo, OH, CN, C$_{1-4}$ alkyl, C$_{1-4}$ haloalkyl, C$_{1-6}$ alkoxy, C$_{1-4}$ haloalkoxy, amino, C$_{1-6}$ alkylamine, or di(C$_{1-6}$ alkyl)amino;

R$^3$, R$^4$, R$^5$, and R$^6$ are each independently selected from H, halo, OH, CN, C$_{1-3}$ alkyl, C$_{1-3}$ haloalkyl, C$_{1-3}$ alkoxy, C$_{1-3}$ haloalkoxy, amino, C$_{1-3}$ alkylamine, and di(C$_{1-3}$ alkyl)amino;

R$^{4a}$ is H, C$_{1-4}$ alkyl, or C$_{1-4}$ haloalkyl;

ring A is a monocyclic C$_{3-7}$ cycloalkyl ring, a monocyclic 4-7 membered heterocycloalkyl ring, a phenyl ring, or a monocyclic 5-6 membered heteroaryl ring, each of which is fused to Ring B;

ring B is a monocyclic 4-7 membered heterocycloalkyl ring or a monocyclic C$_{3-7}$ cycloalkyl ring, wherein the fused A-B moiety is optionally substituted by 1, 2, 3, or 4 independently selected R$^7$ groups;

Z is C$_{1-6}$ alkyl, C$_{1-6}$ haloalkyl, or —C$_{1-6}$ alkylene-Z$^1$;

Z$^1$ is CN, Cy$^3$, OR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{b3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, or S(O)$_2$NR$^{c3}$R$^{d3}$;

each R$^7$ is independently selected from halo, C$_{1-6}$ alkyl, C$_{2-6}$ alkenyl, C$_{2-6}$ alkynyl, C$_{1-4}$ haloalkyl, CN, NO$_2$, Cy, —C$_{1-4}$ alkylene-Cy, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^b$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^8$ groups;

each R$^8$ is independently selected from halo, CN, NO$_2$, C$_{1-6}$ alkyl, C$_{2-6}$ alkenyl, C$_{2-6}$ alkynyl, C$_{1-4}$ haloalkyl, Cy$^2$, —C$_{1-4}$ alkylene-Cy$^2$, OR$^{a2}$, SR$^{a2}$, C(O)R$^{b2}$, C(O)NR$^{c2}$R$^{d2}$, C(O)OR$^{a2}$, OC(O)R$^{b2}$, OC(O)NR$^{c2}$R$^{d2}$, NR$^{c2}$R$^{d2}$, NR$^{c2}$OR$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^e$)R$^{b2}$, C(=NR$^e$)NR$^{c2}$R$^{d2}$, NR$^{c2}$C(=NR$^e$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^g$ groups;

R$^9$ is H, halo, OH, CN, C$_{1-4}$ alkyl, C$_{1-4}$ haloalkyl, C$_{1-4}$ alkoxy, C$_{1-4}$ haloalkoxy, amino, C$_{1-6}$ alkylamine, di(C$_{1-6}$ alkyl)amino, cyano-C$_{1-4}$ alkyl, HO—C$_{1-4}$ alkyl, or C$_{1-3}$ alkoxy-C$_{1-4}$ alkyl;

each R$^{11}$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, di(C$_{1-6}$ alkyl)aminocarbonylamino, C$_{3-7}$ cycloalkyl, phenyl, 5-6 membered heteroaryl, 4-6 membered heterocycloalkyl, C$_{3-7}$ cycloalkyl-C$_{1-3}$ alkylene, phenyl-C$_{1-3}$ alkylene, 5-6 membered heteroaryl-C$_{1-3}$ alkylene, and 4-6 membered heterocycloalkyl-C$_{1-3}$ alkylene; wherein said C$_{1-6}$ alkyl, C$_{3-7}$ cycloalkyl, phenyl, 5-6 membered heteroaryl, 4-6 membered heterocycloalkyl, C$_{3-7}$ cycloalkyl-C$_{1-3}$ alkylene, phenyl-C$_{1-3}$ alkylene, 5-6 membered heteroaryl-C$_{1-3}$ alkylene, and 4-6 membered heterocycloalkyl-C$_{1-3}$ alkylene are each optionally substituted with 1, 2, 3, or 4 groups independently selected from OH, CN, halo, C$_{1-4}$ alkyl, C$_{1-3}$ haloalkyl, C$_{1-4}$ alkoxy, C$_{1-3}$ haloalkoxy, cyano-C$_{1-3}$ alkyl, HO—C$_{1-3}$ alkyl, amino, C$_{1-4}$ alkylamino, di(C$_{1-4}$ alkyl)amino, C$_{1-4}$ alkylsulfinyl, C$_{1-4}$ alkylsulfonyl, carbamyl, C$_{1-4}$ alkylcarbamyl, di(C$_{1-4}$ alkyl)carbamyl, carboxy, C$_{1-4}$ alkylcarbonyl, C$_{1-4}$ alkoxycarbonyl, C$_{1-4}$ alkylcarbonylamino, C$_{1-4}$ alkylsulfonylamino, aminosulfonyl, C$_{1-4}$ alkylaminosulfonyl, and di(C$_{1-4}$ alkyl)aminosulfonyl;

each Cy is independently selected from 3-12 membered cycloalkyl, 6-10 membered aryl, 5-10 membered heteroaryl, and 4-12 membered heterocycloalkyl, each of which is optionally substituted by 1, 2, 3, or 4 independently selected R$^8$ groups;

each Cy$^1$ is independently selected from 3-7 membered cycloalkyl, phenyl, 5-6 membered heteroaryl, and 4-6 membered heterocycloalkyl, each of which is optionally substituted by 1, 2, 3, or 4 independently selected R$^{11}$ groups;

each Cy$^2$ is independently selected from 3-7 membered cycloalkyl, phenyl, 5-6 membered heteroaryl, and 4-6 membered heterocycloalkyl, each of which is optionally substituted by 1, 2, 3, or 4 independently selected R$^g$ groups;

each Cy$^3$ is independently selected from 3-7 membered cycloalkyl, phenyl, 5-6 membered heteroaryl, and 4-6 membered heterocycloalkyl, each of which is optionally substituted by 1, 2, 3, or 4 groups independently selected from halo, OH, CN, C$_{1-3}$ alkyl, C$_{1-3}$ haloalkyl, C$_{1-3}$ alkoxy, C$_{1-3}$ haloalkoxy, amino, C$_{1-3}$ alkylamine, and di(C$_{1-3}$ alkyl)amino;

each R$^a$, R$^c$, and R$^d$ is independently selected from H, C$_{1-6}$ alkyl, C$_{2-6}$ alkenyl, C$_{2-6}$ alkynyl, C$_{1-4}$ haloalkyl, Cy, and —C$_{1-4}$ alkylene-Cy; wherein said C$_{1-6}$ alkyl, C$_{2-6}$ alkenyl, C$_{2-6}$ alkynyl, and C$_{1-4}$ haloalkyl are each optionally substituted with 1, 2, 3, or 4 independently selected R$^8$ groups;

each $R^b$ is independently selected from $C_{1-6}$ alkyl, $C_{2-6}$ alkenyl, $C_{2-6}$ alkynyl, $C_{1-4}$ haloalkyl, Cy, and —$C_{1-4}$ alkylene-Cy; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^8$ groups;

alternatively, any $R^c$ and $R^d$ attached to the same N atom, together with the N atom to which they are attached, form a 4-6 membered heterocycloalkyl group or a 5-6 membered heteroaryl group, each optionally substituted with 1, 2, or 3 independently selected $R^8$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

$R^{a1}$, $R^{c1}$, and $R^{d1}$ are each independently selected from H, $C_{1-6}$ alkyl, $C_{2-6}$ alkenyl, $C_{2-6}$ alkynyl, $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^{11}$ groups;

$R^{b1}$ is independently selected from $C_{1-6}$ alkyl, $C_{2-6}$ alkenyl, $C_{2-6}$ alkynyl, $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^{11}$ groups; or alternatively, any $R^{c1}$ and $R^{d1}$ attached to the same N atom, together with the N atom to which they are attached, form a 4-, 5-, 6- or 7-membered heterocycloalkyl group optionally substituted with 1, 2 or 3 independently selected $R^{11}$ groups;

each $R^{a2}$, $R^{c2}$, and $R^{d2}$ are independently selected from H, $C_{1-6}$ alkyl, $C_{2-6}$ alkenyl, $C_{2-6}$ alkynyl, $C_{1-4}$ haloalkyl, $Cy^2$, and —$C_{1-4}$ alkylene-$Cy^2$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^g$ groups;

each $R^{b2}$ is independently selected from $C_{1-6}$ alkyl, $C_{2-6}$ alkenyl, $C_{2-6}$ alkynyl, $C_{1-4}$ haloalkyl, $Cy^2$, and —$C_{1-4}$ alkylene-$Cy^2$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4 independently selected $R^g$ groups; or alternatively, any $R^{c2}$ and $R^{d2}$ attached to the same N atom, together with the N atom to which they are attached, form a 4-, 5-, 6- or 7-membered heterocycloalkyl group optionally substituted with 1, 2 or 3 independently selected $R^g$ groups;

$R^{a3}$, $R^{c3}$, and $R^{d3}$ are each independently selected from H, $C_{1-6}$ alkyl, $C_{2-6}$ alkenyl, $C_{2-6}$ alkynyl, $C_{1-4}$ haloalkyl, $Cy^3$, and —$C_{1-4}$ alkylene-$Cy^3$;

$R^{b3}$ is selected from $C_{1-6}$ alkyl, $C_{2-6}$ alkenyl, $C_{2-6}$ alkynyl, $C_{1-4}$ haloalkyl, $Cy^3$, and —$C_{1-4}$ alkylene-$Cy^3$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is H, halo, CN, $C_{1-6}$ alkyl, $C_{1-4}$ haloalkyl, $OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}S(O)_2R^{b1}$, $S(O)_2R^{b1}$, or $S(O)_2NR^{c1}R^{d1}$; wherein said $C_{1-6}$ alkyl and $C_{1-4}$ haloalkyl are each optionally substituted with 1, 2, 3, or 4 independently selected $R^{11}$ groups.

In some embodiments, $R^1$ is H, halo, CN, $C_{1-6}$ alkyl, $C_{1-4}$ haloalkyl, $OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}S(O)_2R^{b1}$, $S(O)_2R^{b1}$, or $S(O)_2NR^{c1}R^{d1}$; wherein said $C_{1-6}$ alkyl and $C_{1-4}$ haloalkyl are each optionally substituted with 1, 2, 3, or 4 independently selected $R^{11}$ groups.

In some embodiments, $R^1$ is H or $NR^{c1}R^{d1}$.

In some embodiments, $R^{a1}$, $R^{c1}$, and $R^{d1}$ are each independently selected from H, $C_{1-6}$ alkyl, $Cy^1$; and $R^{b1}$ is $C_{1-6}$ alkyl or $Cy^1$.

In some embodiments, each $Cy^1$ is independently selected from 3-7 membered cycloalkyl, phenyl, 5-6 membered heteroaryl, and 4-6 membered heterocycloalkyl, each of which is optionally substituted by 1 or 2 independently selected $R^{11}$ groups.

In some embodiments, each $R^{11}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene.

In some embodiments, $R^1$ is H, methylamino, ethylamino, isopropylamino, n-butylamino, cyclobutylamino, cyclopentylamino, cyclohexylamino, 1-ethyl-1H-imidazol-4-yl-amino, 1-methyl-1H-pyrazol-4-yl-amino, and 4-(morpholinylmethyl)phenylamino.

In some embodiments, $R^2$ is H, halo, CN, $C_{1-4}$ alkyl, or $C_{1-4}$ haloalkyl.

In some embodiments, $R^2$ is H or $C_{1-4}$ alkyl.

In some embodiments, $R^2$ is H or methyl.

In some embodiments, $R^3$, $R^4$, $R^5$, and $R^6$ are each independently selected from H, halo, CN, $C_{1-3}$ alkyl, and $C_{1-3}$ haloalkyl.

In some embodiments, one of $R^3$, $R^4$, $R^5$, and $R^6$ is independently selected from halo, CN, $C_{1-3}$ alkyl, and $C_{1-3}$ haloalkyl; and the remaining $R^3$, $R^4$, $R^5$, and $R^6$ are each H.

In some embodiments, $R^3$, $R^4$, $R^5$, and $R^6$ are each H.

In some embodiments, ring A is a phenyl ring or monocyclic 5-6 membered heteroaryl ring, which is fused to Ring B, wherein the fused A-B moiety is optionally substituted by 1, 2, 3, or 4 independently selected $R^7$ groups.

In some embodiments, ring A is a phenyl ring, which is fused to Ring B, wherein the fused A-B moiety is optionally substituted by 1, 2, 3, or 4 independently selected $R^7$ groups.

In some embodiments, ring A is a monocyclic 5-6 membered heteroaryl ring, which is fused to Ring B, wherein the fused A-B moiety is optionally substituted by 1, 2, 3, or 4 independently selected $R^7$ groups.

In some embodiments, ring A is a monocyclic 6-membered heteroaryl ring, which is fused to Ring B, wherein the fused A-B moiety is optionally substituted by 1, 2, 3, or 4 independently selected $R^7$ groups.

In some embodiments, ring A is a pyridine ring, which is fused to Ring B, wherein the fused A-B moiety is optionally substituted by 1, 2, 3, or 4 independently selected $R^7$ groups.

In some embodiments, ring B is a monocyclic $C_{3-7}$ cycloalkyl ring, wherein the fused A-B moiety is optionally substituted by 1, 2, 3, or 4 independently selected $R^7$ groups.

In some embodiments, ring B is a monocyclic $C_{5-6}$ cycloalkyl ring, wherein the fused A-B moiety is optionally substituted by 1, 2, 3, or 4 independently selected $R^7$ groups.

In some embodiments, ring B is a cyclohexyl ring, wherein the fused A-B moiety is optionally substituted by 1, 2, 3, or 4 independently selected $R^7$ groups.

In some embodiments, ring B is a cyclopentyl ring, wherein the fused A-B moiety is optionally substituted by 1, 2, 3, or 4 independently selected $R^7$ groups.

In some embodiments, ring B is a cyclobutyl ring, wherein the fused A-B moiety is optionally substituted by 1, 2, 3, or 4 independently selected $R^7$ groups.

In some embodiments, ring B is a cyclopentyl or cyclohexyl ring, wherein the fused A-B moiety is optionally substituted by 1, 2, 3, or 4 independently selected $R^7$ groups.

In some embodiments, ring B is tetrahydrofuran, wherein the fused A-B moiety is optionally substituted by 1, 2, 3, or 4 independently selected $R^7$ groups.

In some embodiments, ring B is a pyrrolidine ring, wherein the fused A-B moiety is optionally substituted by 1, 2, 3, or 4 independently selected $R^7$ groups.

In some embodiments, ring B is tetrahydrothiophene, wherein the fused A-B moiety is optionally substituted by 1, 2, 3, or 4 independently selected $R^7$ groups.

In some embodiments, ring B is a monocyclic 4-7 membered heterocycloalkyl ring, wherein the fused A-B moiety is optionally substituted by 1, 2, 3, or 4 independently selected $R^7$ groups.

In some embodiments, ring B is a monocyclic 5-6 membered heterocycloalkyl ring, wherein the fused A-B moiety is optionally substituted by 1, 2, 3, or 4 independently selected $R^7$ groups.

It is intended that the description include embodiments, wherein each of the preceding definitions of ring A and B are combined individually to form the A-B fused moiety.

In some embodiments, ring A is a phenyl or pyridine ring, which is fused to ring B; and ring B is a cyclopentyl ring; wherein the fused A-B moiety is optionally substituted by 1, 2, or 3 independently selected $R^7$ groups.

In some embodiments, the fused A-B moiety is an 2,3-dihydro-1H-indene ring, a 6,7-dihydro-5H-cyclopenta[b]pyridine ring, or a 6,7-dihydro-5H-cyclopenta[c]pyridine ring, each of which is optionally substituted by 1, 2, or 3 independently selected $R^7$ groups.

In some embodiments, each $R^7$ is independently selected from halo, $C_{1-6}$ alkyl, $C_{1-4}$ haloalkyl, CN, Cy, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl and $C_{1-4}$ haloalkyl are optionally substituted with 1, 2, 3, or 4 independently selected $R^8$ groups.

In some embodiments, each $R^7$ is independently selected from halo, $C_{1-6}$ alkyl, $C_{1-4}$ haloalkyl, CN, Cy, —$C_{1-4}$ alkylene-Cy, $OR^a$, $C(O)R^b$, $C(O)NR^cR^d$, $NR^cR^d$, $NR^cC(O)R^b$, $NR^cS(O)_2R^b$, $S(O)_2R^b$, and $S(O)_2NR^cR^d$; wherein said $C_{1-6}$ alkyl and $C_{1-4}$ haloalkyl are optionally substituted with 1, 2, 3, or 4 independently selected $R^8$ groups.

In some embodiments, each $R^7$ is independently selected from $C_{1-6}$ alkyl, CN, OH, $NR^cR^d$, Cy, and —$C_{1-4}$ alkylene-Cy; wherein said $C_{1-6}$ alkyl is optionally substituted with 1, 2, 3, or 4 independently selected $R^8$ groups.

In some embodiments, each $R^7$ is independently selected from $C_{1-6}$ alkyl, CN, OH, $NR^cR^d$, —$CH_2$—$R^8$, Cy, and —$CH_2$-Cy.

In some embodiments, each $R^a$, $R^c$ and $R^d$ is independently selected from H, $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups; and each $R^b$ is independently selected from $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups.

In some embodiments, each Cy is independently selected from azetidinyl, pyrrolidinyl, piperidinyl, morpholinyl, phenyl, imidazolyl, pyridinyl, imidazo[1,2-a]pyridinyl, and imidazo[4,5-b]pyridinyl; each of which is optionally substituted by 1, 2, 3, or 4 independently selected $R^8$ groups.

In some embodiments, each $R^8$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{b2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups.

In some embodiments, each $R^8$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $NR^{c2}R^{d2}$, $NR^{c2}C(O)R^{b2}$, $NR^{c2}S(O)_2R^{b2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups.

In some embodiments, each $R^8$ is independently selected from halo, CN, $C_{1-6}$ alkyl, $Cy^2$, $OR^{a2}$, $C(O)NR^{c2}R^{d2}$, and $NR^{c2}R^{d2}$; wherein said $C_{1-6}$ alkyl is optionally substituted with 1, 2, 3, or 4 independently selected $R^g$ groups.

In some embodiments, each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl is optionally substituted with 1 or 2 independently selected $R^g$ groups; and each $R^{b2}$ is independently selected from $C_{1-6}$ alkyl and $C_{1-4}$ haloalkyl; wherein said $C_{1-6}$ alkyl and $C_{1-4}$ haloalkyl is optionally substituted with 1 or 2 independently selected $R^g$ groups.

In some embodiments, each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

In some embodiments, Z is $C_{1-4}$ alkyl, —$CH_2F$, —$CHF_2$, —$CH_2$—$Z^1$, —$CH_2$—$CH_2$—$Z^1$, or —$CH_2$—$CH_2$—$CH_2$—$Z^1$.

In some embodiments, Z is —$CH_2F$, —$CHF_2$, —$CH_2$—$Z^1$, or —$CH_2$—$CH_2$—Z.

In some embodiments, $Z^1$ is CN, $OR^{a3}$, $NR^{c3}R^{d3}$, $NR^{c3}C(O)R^{b3}$, $NR^{c3}C(O)OR^{b3}$, or $NR^{c3}S(O)_2R^{b3}$.

In some embodiments, $Z^1$ is $NR^{c3}R^{d3}$.

In some embodiments, Z is —$CH_2$—$NH_2$.

In some embodiments, $R^{a3}$, $R^{c3}$ and $R^{d3}$ are each independently selected from H, $C_{1-6}$ alkyl, and $Cy^3$; and each $Cy^3$ is independently 3-7 membered cycloalkyl, phenyl, 5-6 membered heteroaryl, or 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino; $R^{b3}$ is selected from $C_{1-6}$ alkyl, and $Cy^3$; and each $Cy^3$ is independently selected from 3-7 membered cycloalkyl, phenyl, 5-6 membered heteroaryl, and 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino.

In some embodiments, $R^{a3}$, $R^{c3}$ and $R^{d3}$ are each independently selected from H, methyl, ethyl, isopropyl, and $Cy^3$; $R^{b3}$ is selected from methyl, ethyl, isopropyl, and $Cy^3$; and each $Cy^3$ is independently selected from cyclopropyl, cyclobutyl, cyclopentyl, morpholinyl, phenyl, pyrazolyl, furanyl, thienyl, isooxazolyl, and oxazolyl, each of which is optionally substituted by 1 or 2 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino.

In some embodiments, U is —$CR^3$=.
In some embodiments, U is —CH=.
In some embodiments, U is —N=.
In some embodiments, X is —$CR^4$=.
In some embodiments, X is —CH=.
In some embodiments, X is —N=.
In some embodiments, Y is —$CR^5$=.
In some embodiments, Y is —CH=.
In some embodiments, Y is —N=.
In some embodiments, W is —$CR^6$=.
In some embodiments, W is —CH=.
In some embodiments, W is —N=.
In some embodiments, V is —$CR^{AB}$=.
In some embodiments, E is —N=.
In some embodiments, E is —$CR^9$=.
In some embodiments, $R^9$ is H, $C_{1-3}$ alkyl, or $C_{1-3}$ alkoxy.
In some embodiments, $R^9$ is H, methyl, or methoxy.
In some embodiments, $R^9$ is H.
In some embodiments, $R^9$ is methyl.
In some embodiments, $R^9$ is methoxy.
In some embodiments, M is —N=.
In some embodiments, M is —$CR^2$=.
In some embodiments, $R^2$ is H.
In some embodiments, Y is C=O, X is =$CR^4$— and V is —$NR^{AB}$—.
In some embodiments, U is —$CR^3$=, W is —$CR^6$=, Y is C=O, X is =$CR^4$— and V is —$NR^{AB}$—.
In some embodiments, U is —CH=, W is —CH=, Y is C=O, X is =CH— and V is —$NR^{AB}$—.
In some embodiments, no more than one of U, X, Y, and W is —N=.

In some embodiments:
each ====== in the ring formed by U, X, Y, V, and W is independently a single or double bond;
E is —N= or —$CR^9$=;
M is —N= or —$CR^2$=;
U is —N= or —$CR^3$=;
X is —N= or —$CR^4$=;
Y is —N= or —$CR^5$=;
W is —N= or —$CR^6$=;
V is —$CR^{AB}$=;
alternatively, Y is C=O, X is =$CR^4$— and V is —$NR^{AB}$—;
provided that no more than one of U, X, Y, and W is —N=;
$R^1$ is H, halo, CN, $C_{1-6}$ alkyl, $C_{1-4}$ haloalkyl, $OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}S(O)_2R^{b1}$, $S(O)_2R^{b1}$, or $S(O)_2NR^{c1}R^{d1}$; wherein said $C_{1-6}$ alkyl and $C_{1-4}$ haloalkyl are each optionally substituted with 1, 2, 3, or 4 independently selected $R^{11}$ groups;
$R^2$ is H, halo, CN, $C_{1-4}$ alkyl, or $C_{1-4}$ haloalkyl;
$R^3$, $R^4$, $R^5$, and $R^6$ are each independently selected from H, halo, CN, $C_{1-3}$ alkyl, or $C_{1-3}$ haloalkyl;
$R^9$ is H, $C_{1-3}$ alkyl, or $C_{1-3}$ alkoxy;
ring A is a phenyl ring or a monocyclic 5-6 membered heteroaryl ring, each of which is fused to Ring B;
ring B is a monocyclic 4-7 membered heterocycloalkyl ring or a monocyclic $C_{3-7}$ cycloalkyl ring, wherein the fused A-B moiety is optionally substituted by 1, 2, 3, or 4 independently selected $R^7$ groups;
Z is $C_{1-4}$ alkyl, —$CH_2F$, —$CHF_2$, —$CH_2$—$Z^1$, —$CH_2$—$CH_2$—$Z^1$, or —$CH_2$—$CH_2$—$CH_2$—$Z^1$;
$Z^1$ is CN, $OR^{a3}$, $NR^{c3}R^{d3}$, $NR^{c3}C(O)R^{b3}$, $NR^{c3}C(O)OR^{b3}$, or $NR^3S(O)_2R^{b3}$;
each $R^7$ is independently selected from halo, $C_{1-6}$ alkyl, $C_{1-4}$ haloalkyl, CN, Cy, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^dNR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl and $C_{1-4}$ haloalkyl are optionally substituted with 1, 2, 3, or 4 independently selected $R^8$ groups;
each $R^8$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{b2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups;
each $R^{11}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$alkylene;
each Cy is independently 3-10 membered cycloalkyl, 6-10 membered aryl, 5-10 membered heteroaryl, or 4-10 membered heterocycloalkyl, each of which is optionally substituted by 1, 2, 3, or 4 independently selected $R^8$ groups;
each $Cy^1$ is independently selected from 3-7 membered cycloalkyl, phenyl, 5-6 membered heteroaryl, and 4-6 membered heterocycloalkyl, each of which is optionally substituted by 1 or 2 independently selected $R^{11}$ groups;
each $Cy^2$ is independently 3-7 membered cycloalkyl or 4-6 membered heterocycloalkyl;
each $Cy^3$ is independently selected from 3-7 membered cycloalkyl, phenyl, 5-6 membered heteroaryl, and 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino;
each $R^a$, $R^c$ and $R^d$ is independently selected from H, $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups;
each $R^b$ is independently selected from $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups;
$R^{a1}$, $R^{c1}$ and $R^{d1}$ are each independently selected from H, $C_{1-6}$ alkyl, and $Cy^1$; $R^{b1}$ is selected from $C_{1-6}$ alkyl and $Cy^1$;
each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl is optionally substituted with 1 or 2 independently selected $R^g$ groups;

each $R^{b2}$ is independently selected from $C_{1-6}$ alkyl and $C_{1-4}$ haloalkyl; wherein said $C_{1-6}$ alkyl and $C_{1-4}$ haloalkyl is optionally substituted with 1 or 2 independently selected $R^g$ groups;

$R^{a3}$, $R^{b3}$ and $R^{d3}$ are each independently selected from H, $C_{1-6}$ alkyl, and $Cy^3$;

$R^{b3}$ is selected from H, $C_{1-6}$ alkyl, and $Cy^3$; and each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

In some embodiments:

each ------ in the ring formed by U, X, Y, V, and W is independently a single or double bond;

E is —N= or —CR$^9$=;
M is —N= or —CR$^2$=;
U is —N= or —CH=;
X is —N= or —CH=;
Y is —N= or —CH=;
W is —N= or —CH=;
V is —CR$^{AB}$=;

alternatively, Y is C=O, X is =CR$^4$— and V is —NR$^{AB}$—;

provided that no more than one of U, X, and Y is —N=;
$R^1$ is H or NR$^{c1}$R$^{d1}$;
$R^2$ is H or $C_{1-4}$ alkyl;
$R^9$ is H, methyl, ethyl, methoxy, or ethoxy;

each $R^{11}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene;

ring A is a phenyl ring or a monocyclic 6-membered heteroaryl ring, each of which is fused to Ring B;

ring B is a monocyclic 5-6 membered heterocycloalkyl ring or a monocyclic $C_{5-6}$ cycloalkyl ring, wherein the fused A-B moiety is optionally substituted by 1, 2, 3, or 4 independently selected $R^7$ groups;

Z is —CH$_2$F, —CHF$_2$, —CH$_2$—Z$^1$, or —CH$_2$—CH$_2$—Z;
$Z^1$ is CN, OR$^{a3}$, NR$^{c3}$R$^{d3}$, NR$^{c3}$C(O)R$^{b3}$, NR$^{c3}$C(O)OR$^{b3}$, or NR$^{c3}$S(O)$_2$R$^{b3}$;

each $R^7$ is independently selected from halo, $C_{1-6}$ alkyl, $C_{1-4}$ haloalkyl, CN, Cy, —$C_{1-4}$ alkylene-Cy, OR$^a$, C(O)R$^b$, C(O)NR$^c$R$^d$, NR$^c$R$^d$, NR$^c$C(O)R$^b$, NR$^c$S(O)$_2$R$^b$, S(O)$_2$R$^b$, and S(O)$_2$NR$^c$R$^d$; wherein said $C_{1-6}$ alkyl and $C_{1-4}$ haloalkyl are optionally substituted with 1, 2, 3, or 4 independently selected $R^8$ groups;

each $R^8$ is independently selected from halo, CN, $C_{1-6}$ alkyl, $C_{1-4}$ haloalkyl, Cy$^2$, —$C_{1-4}$ alkylene-Cy$^2$, OR$^{a2}$, C(O)R$^{b2}$, C(O)NR$^{c2}$R$^{d2}$, NR$^{c2}$R$^{d2}$, NR$^{c2}$C(O)R$^{b2}$, NR$^{c2}$S(O)$_2$R$^{b2}$, S(O)$_2$R$^{b2}$, and S(O)$_2$NR$^{c2}$R$^{d2}$; wherein said $C_{1-6}$ alkyl and $C_{1-4}$ haloalkyl are each optionally substituted with 1, 2, 3, or 4 independently selected $R^g$ groups;

each Cy is independently 3-10 membered cycloalkyl, 6-10 membered aryl, 5-10 membered heteroaryl, or 4-10 membered heterocycloalkyl, each of which is optionally substituted by 1, 2, 3, or 4 independently selected $R^8$ groups;

each Cy$^1$ is independently selected from 3-7 membered cycloalkyl, phenyl, 5-6 membered heteroaryl, and 4-6 membered heterocycloalkyl, each of which is optionally substituted by 1 or 2 independently selected $R^{11}$ groups;

each Cy$^2$ is independently 3-7 membered cycloalkyl or 4-6 membered heterocycloalkyl;

each Cy$^3$ is independently 3-7 membered cycloalkyl, phenyl, 5-6 membered heteroaryl, or 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino;

each $R^a$, $R^c$ and $R^d$ is independently selected from H, $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups;

each $R^b$ is independently selected from $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups;

$R^{c1}$ and $R^{d1}$ are each independently selected from H, $C_{1-6}$ alkyl, and Cy$^1$;

each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl is optionally substituted with 1 or 2 independently selected $R^g$ groups;

each $R^{b2}$ is independently selected from $C_{1-6}$ alkyl and $C_{1-4}$ haloalkyl; wherein said $C_{1-6}$ alkyl and $C_{1-4}$ haloalkyl is optionally substituted with 1 or 2 independently selected $R^g$ groups;

$R^{a3}$, $R^{c3}$ and $R^{d3}$ are each independently selected from H, $C_{1-6}$ alkyl, and Cy$^3$;

$R^{b3}$ is selected from H, $C_{1-6}$ alkyl, and Cy$^3$; and each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

In some embodiments:

each ------ in the ring formed by U, X, Y, V, and W is independently a single or double bond;

E is —N= or —CR$^9$=;
M is —N= or —CR$^2$=;
U is —N= or —CH=;
X is —N= or —CH=;
Y is —N= or —CH=;
W is —N= or —CH=;
V is —CR$^{AB}$=;

alternatively, Y is C=O, X is =CR$^4$— and V is —NR$^B$—;

provided that no more than one of U, X, and Y is —N=;
$R^1$ is H or NR$^{c1}$R$^{d1}$;
$R^2$ is H or methyl;
$R^9$ is H, methyl, ethyl, methoxy, or ethoxy;

ring A is a phenyl ring or a pyridine ring, each of which is fused to Ring B;

ring B is a monocyclic 5-6 membered heterocycloalkyl ring or a monocyclic $C_{5-6}$ cycloalkyl ring, wherein the fused A-B moiety is optionally substituted by 1, 2, 3, or 4 independently selected $R^7$ groups;

Z is —CH$_2$F, —CHF$_2$, —CH$_2$—Z$^1$, or —CH$_2$—CH$_2$—Z;
$Z^1$ is CN, OR$^{a3}$, NR$^{c3}$R$^{d3}$, NR$^{c3}$C(O)R$^{b3}$, NR$^{c3}$C(O)OR$^{b3}$, or NR$^{c3}$S(O)$_2$R$^{b3}$;

each $R^7$ is independently selected from $C_{1-6}$ alkyl, CN, OH, NR$^c$R$^d$, Cy, and —$C_{1-4}$ alkylene-Cy; wherein said $C_{1-6}$ alkyl is optionally substituted with 1, 2, 3, or 4 independently selected $R^8$ groups;

each $R^8$ is independently selected from halo, CN, $C_{1-6}$ alkyl, Cy$^2$, OR$^{a2}$, C(O)NR$^{c2}$R$^{d2}$, and NR$^{c2}$R$^{d2}$; wherein said $C_{1-6}$ alkyl is optionally substituted with 1, 2, 3, or 4 independently selected $R^g$ groups;

each $R^{11}$ is independently selected from $C_{1-6}$ alkyl and 4-6 membered heterocycloalkyl-$C_{1-3}$ alkylene;

each Cy is independently 3-10 membered cycloalkyl, 6-10 membered aryl, 5-10 membered heteroaryl, or 4-10 membered heterocycloalkyl, each of which is optionally substituted by 1, 2, 3, or 4 independently selected $R^8$ groups;

each $Cy^1$ is independently selected from 3-7 membered cycloalkyl, phenyl, 5-6 membered heteroaryl, and 4-6 membered heterocycloalkyl, each of which is optionally substituted by 1 or 2 independently selected $R^{11}$ groups;

each $Cy^2$ is independently 3-7 membered cycloalkyl or 4-6 membered heterocycloalkyl;

each $Cy^3$ is independently selected from 3-7 membered cycloalkyl, phenyl, 5-6 membered heteroaryl, or 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino;

each $R^c$ and $R^d$ is independently selected from H, $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups;

$R^{c1}$ and $R^{d1}$ are each independently selected from H, $C_{1-6}$ alkyl, and $Cy^1$;

each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl is optionally substituted with 1 or 2 independently selected $R^g$ groups;

$R^{a3}$, $R^{c3}$ and $R^{d3}$ are each independently selected from H, $C_{1-6}$ alkyl, and $Cy^3$;

$R^{b3}$ is selected from H, $C_{1-6}$ alkyl, and $Cy^3$; and each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

In some embodiments:

each ====== in the ring formed by U, X, Y, V, and W is independently a single or double bond;

E is —N= or —$CR^9$=;

M is —N= or —$CR^2$=;

U is —N= or —CH=;

X is —N= or —CH=;

Y is —N= or —CH=;

W is —N= or —CH=;

V is —$CR^{AB}$=;

alternatively, Y is C=O, X is =$CR^4$— and V is —$NR^{AB}$—;

provided that no more than one of U, X, and Y is —N=;

$R^1$ is H or $NR^{c1}R^{d1}$;

$R^2$ is H or methyl;

ring A is a phenyl ring or a pyridine ring, each of which is fused to Ring B;

ring B is a monocyclic 5-6 membered heterocycloalkyl ring or a monocyclic $C_{5-6}$ cycloalkyl ring, wherein the fused A-B moiety is optionally substituted by 1, 2, 3, or 4 independently selected $R^7$ groups;

Z is —$CH_2F$, —$CHF_2$, —$CH_2$—$Z^1$, or —$CH_2$—$CH_2$—Z;

$Z^1$ is CN, $OR^{a3}$, $NR^{c3}R^{d3}$, $NR^{c3}C(O)R^{b3}$, $NR^{c3}C(O)OR^{b3}$, or $NR^{c3}S(O)_2R^{b3}$;

each $R^7$ is independently selected from $C_{1-6}$ alkyl, CN, OH, $NR^cR^d$, Cy, and —$C_{1-4}$ alkylene-Cy; wherein said $C_{1-6}$ alkyl is optionally substituted with 1, 2, 3, or 4 independently selected $R^8$ groups;

each $R^8$ is independently selected from halo, CN, $C_{1-6}$ alkyl, $Cy^2$, $OR^{a2}$, $C(O)NR^{c2}R^{d2}$, and $NR^{c2}R^{d2}$; wherein said $C_{1-6}$ alkyl is optionally substituted with 1, 2, 3, or 4 independently selected $R^g$ groups;

$R^9$ is H, methyl or methoxy;

each $R^{11}$ is independently selected from $C_{1-6}$ alkyl and 4-6 membered heterocycloalkyl-$C_{1-3}$ alkylene;

each Cy is independently 3-10 membered cycloalkyl, 6-10 membered aryl, 5-10 membered heteroaryl, or 4-10 membered heterocycloalkyl, each of which is optionally substituted by 1, 2, 3, or 4 independently selected $R^8$ groups;

each $Cy^1$ is independently selected from 3-7 membered cycloalkyl, phenyl, 5-6 membered heteroaryl, and 4-6 membered heterocycloalkyl, each of which is optionally substituted by 1 or 2 independently selected $R^{11}$ groups;

each $Cy^2$ is independently 3-7 membered cycloalkyl or 4-6 membered heterocycloalkyl;

each $Cy^3$ is independently 3-7 membered cycloalkyl, phenyl, 5-6 membered heteroaryl, or 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino;

$R^{c1}$ and $R^{d1}$ are each independently selected from H, $C_{1-6}$ alkyl, and $Cy^1$;

each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl is optionally substituted with 1 or 2 independently selected $R^g$ groups;

$R^{a3}$, $R^{c3}$ and $R^{d3}$ are each independently selected from H, $C_{1-6}$ alkyl, and $Cy^3$;

$R^{b3}$ is selected from H, $C_{1-6}$ alkyl, and $Cy^3$; and each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

In some embodiments:

each ====== in the ring formed by U, X, Y, V, and W is independently a single or double bond;

E is —N= or —$CR^9$=;

M is —N= or —$CR^2$=;

U is —N= or —CH=;

X is —N= or —CH=;

Y is —N= or —CH=;

W is —N= or —CH=;

V is —$CR^{AB}$=;

alternatively, Y is C=O, X is =$CR^4$— and V is —$NR^{AB}$—;

provided that no more than one of U, X, and Y is —N=;

$R^1$ is H, methylamino, ethylamino, isopropylamino, n-butylamino, cyclobutylamino, cyclopentylamino, cyclohexylamino, 1-ethyl-1H-imidazol-4-yl-amino, 1-methyl-1H-pyrazol-4-yl-amino, and 4-(morpholinylmethyl)phenylamino;

$R^2$ is H or methyl;

ring A is a phenyl ring or a pyridine ring, each of which is fused to Ring B;

the fused A-B moiety is an 2,3-dihydro-1H-indene ring, a 6,7-dihydro-5H-cyclopenta[b]pyridine ring, a 6,7-dihydro-5H-cyclopenta[c]pyridine ring, or a 1,2,3,4-tetrahydronaphthalene ring, each of which is optionally substituted by 1, 2, 3, or 4 independently selected $R^7$ group;

$R^9$ is H or methoxy;

Z is —$CH_2F$, —$CHF_2$, —$CH_2$—$Z^1$, or —$CH_2$—$CH_2$—Z;

$Z^1$ is CN, $OR^{a3}$, $NR^{c3}R^{d3}$, $NR^{c3}C(O)R^{b3}$, $NR^{c3}C(O)OR^{b3}$, or $NR^3S(O)_2R^{b3}$;

each $R^7$ is independently $C_{1-6}$ alkyl, CN, OH, $NR^cR^d$, —$CH_2$—$R^8$, Cy, or —$CH_2$—Cy;

each $R^8$ is independently selected from halo, CN, $C_{1-6}$ alkyl, $Cy^2$, $OR^{a2}$, $C(O)NR^{c2}R^{d2}$, and $NR^{c2}R^{d2}$; wherein said $C_{1-6}$ alkyl is optionally substituted with 1, 2, 3, or 4 independently selected $R^g$ groups.

each Cy is independently selected from azetidinyl, pyrrolidinyl, piperidinyl, morpholinyl, phenyl, imidazolyl, pyridinyl, imidazo[1,2-a]pyridinyl, and imidazo[4,5-b]pyridinyl; each of which is optionally substituted by 1, 2, 3, or 4 independently selected $R^8$ groups;

each $Cy^2$ is independently 3-7 membered cycloalkyl or 4-6 membered heterocycloalkyl;

each $Cy^3$ is independently selected from cyclopropyl, cyclobutyl, cyclopentyl, morpholinyl, phenyl, pyrazolyl, furanyl, thienyl, isooxazolyl, and oxazolyl, each of which is optionally substituted by 1 or 2 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino;

each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl is optionally substituted with 1 or 2 independently selected $R^g$ groups;

$R^{a3}$, $R^{c3}$ and $R^{d3}$ are each independently selected from H, methyl, ethyl, isopropyl, and $Cy^3$;

$R^{b3}$ is selected from H, methyl, ethyl, isopropyl, and $Cy^3$; and each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

In some embodiments, the compound is a compound of Formula IIa, IIb, IIc, IId, or IIe:

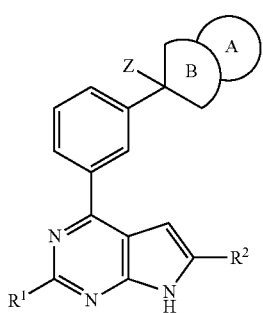

IIa

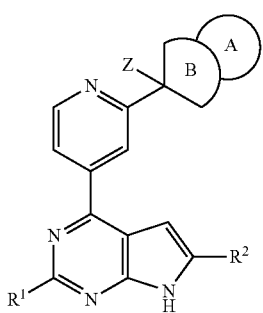

IIb

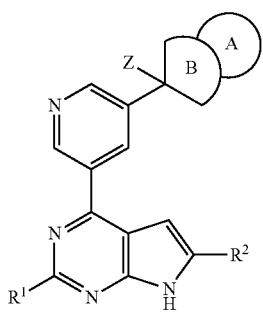

IIc

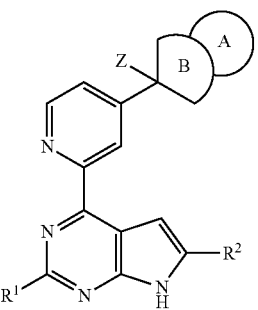

IId

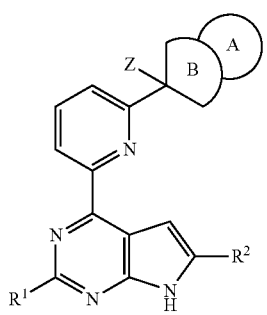

IIe or a pharmaceutically acceptable salt thereof.

In some embodiments, the compound is a compound of Formula IIf, IIg, IIh, IIi or IIj:

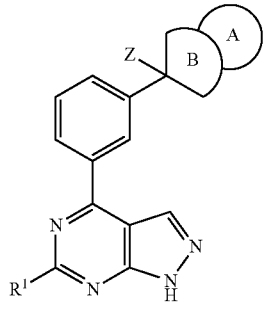

IIf

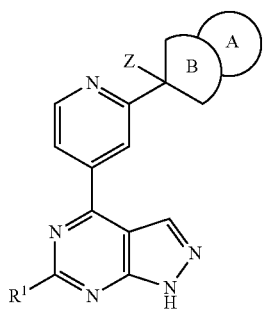

IIg

IIh
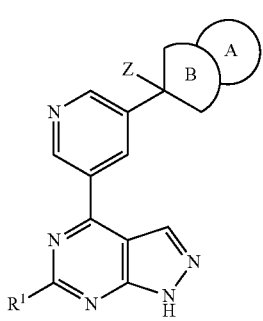
IIi
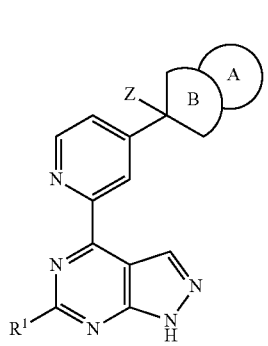
IIj
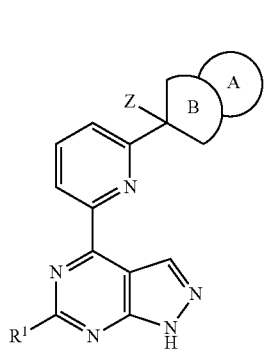
or a pharmaceutically acceptable salt thereof.
In some embodiments, the compound is a compound of Formula IIIa, IIIb, IIIc, IIId, or IIIe:
IIIa
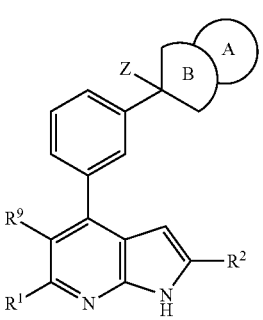
IIIb
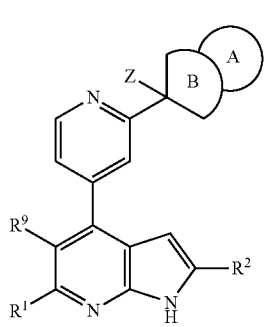
IIIc
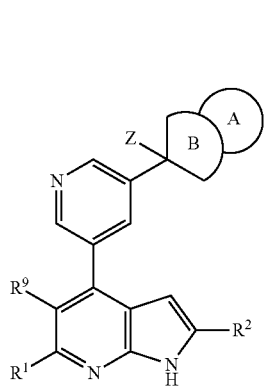
IIId
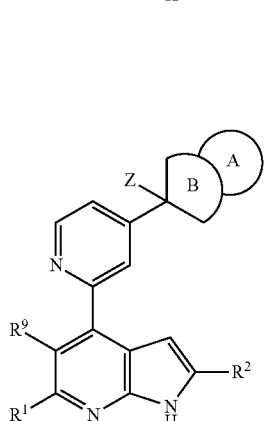
IIIe
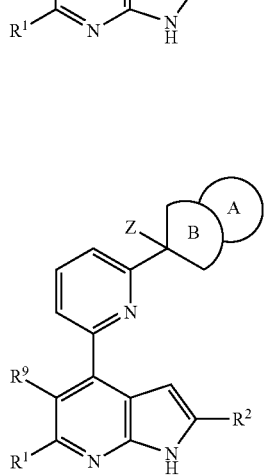
or a pharmaceutically acceptable salt thereof.
In some embodiments, the compound is a compound of Formula IIIf, IIIg, IIIh, IIIi, or IIIj:

or a pharmaceutically acceptable salt thereof.

In some embodiments, the compound is a compound of Formula IVa, IVb, IVc, IVd, or IVe:

or a pharmaceutically acceptable salt thereof.

In some embodiments, the compound is a compound of Formula IVf, IVg, IVh, IVi or IVj:

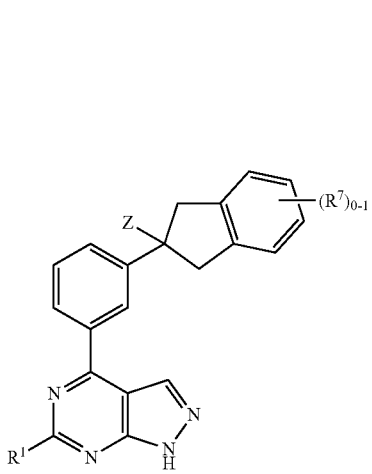

IVf

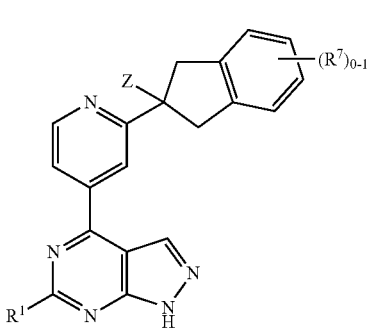

IVg

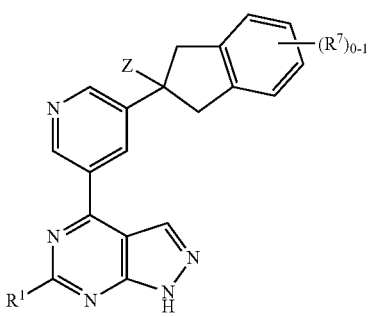

IVh

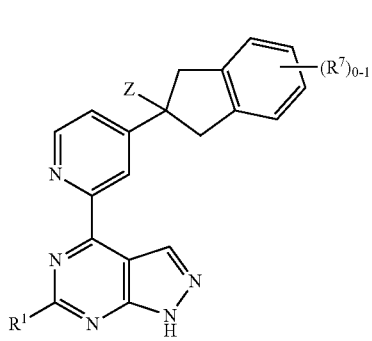

IVi

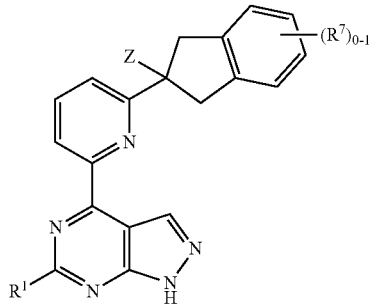

IVj or a pharmaceutically acceptable salt thereof.

In some embodiments, the compound is a compound of Formula IVa:

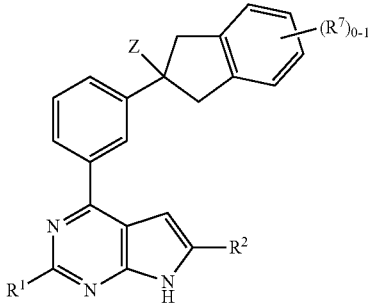

IVa or a pharmaceutically acceptable salt thereof.

In some embodiments, the compound is a compound of Formula IVb:

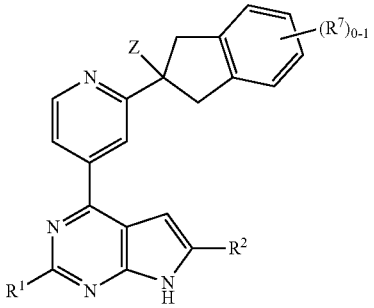

IVb or a pharmaceutically acceptable salt thereof.

In some embodiments, the compound is a compound of Formula IVc:

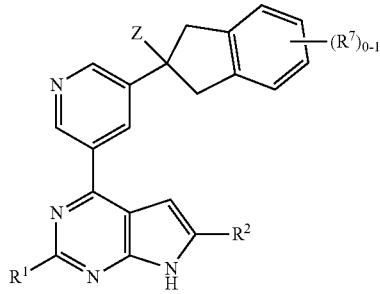
IVc or a pharmaceutically acceptable salt thereof.

In some embodiments, the compound is a compound of Formula IVd:

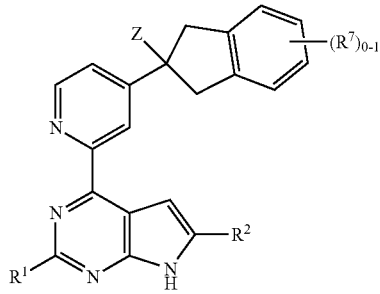
IVd or a pharmaceutically acceptable salt thereof.

In some embodiments, the compound is a compound of Formula IVe:

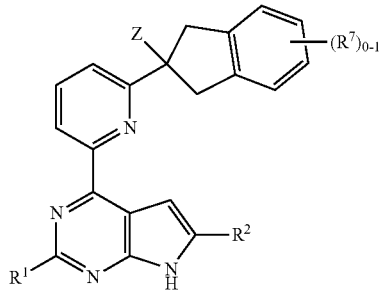
IVe or a pharmaceutically acceptable salt thereof.

In some embodiments, the compound is a compound of Formula Va, Vb, Vc, Vd, or Ve:

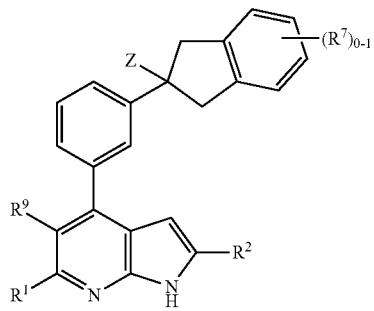
Va

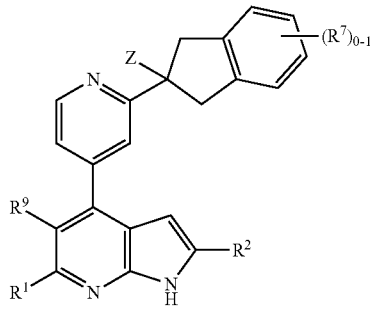
Vb

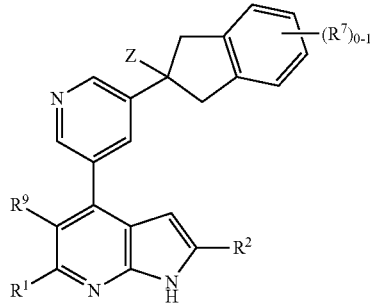
Vc

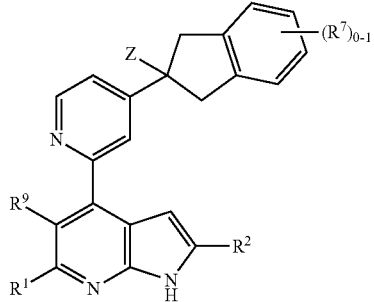
Vd

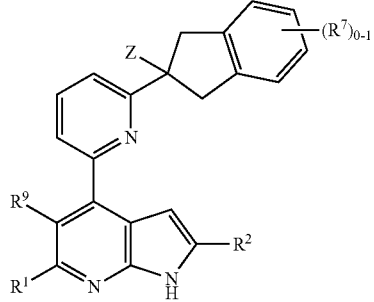
Ve or a pharmaceutically acceptable salt thereof.

In some embodiments, the compound is a compound of Formula Vf, Vg, Vh, Vi, or Vj:

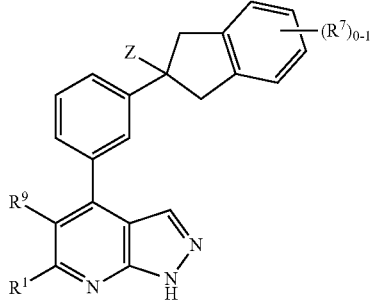
Vf

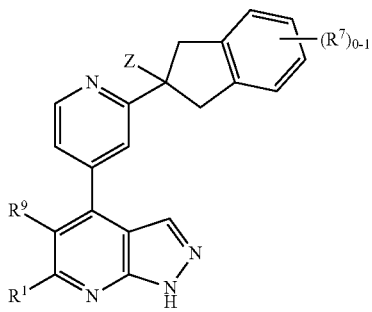
Vg

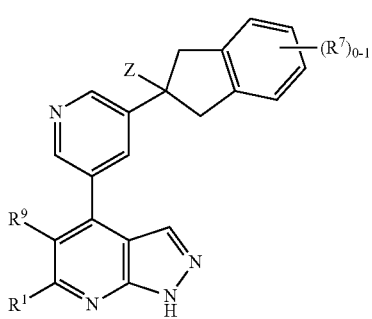
Vh

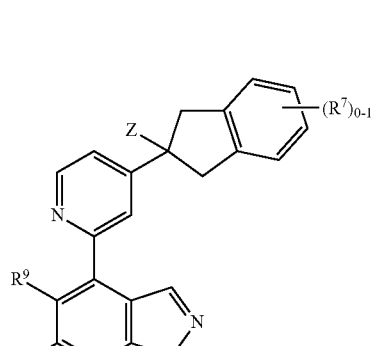
Vi

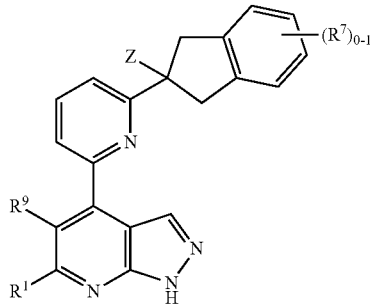
Vj or a pharmaceutically acceptable salt thereof.

In some embodiments, the compound is a compound of Formula Vb:

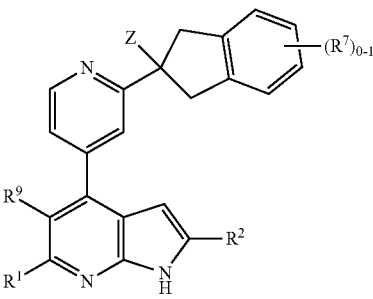
Vb or a pharmaceutically acceptable salt thereof.

In some embodiments, the compound is a compound of Formula Vg:

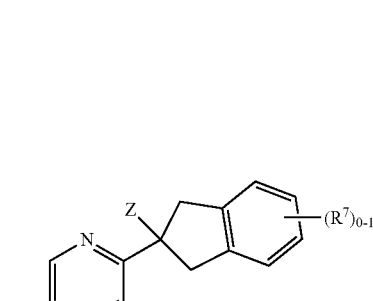
Vg or a pharmaceutically acceptable salt thereof.

In some embodiments, the compound is a compound of Formula VIa, VIb, VIc, or VId:

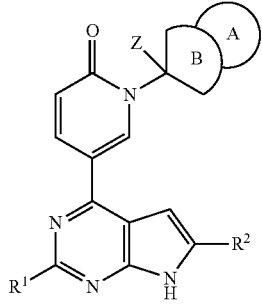
VIa
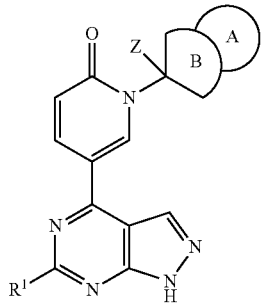
VIb
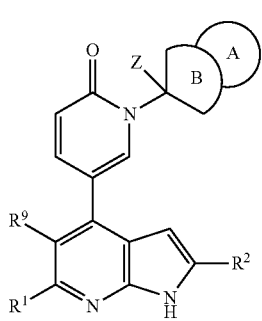
VIc
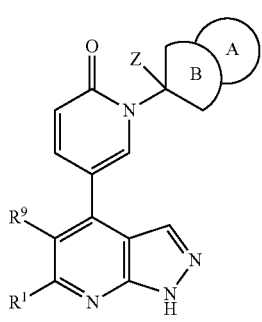
VId
or a pharmaceutically acceptable salt thereof.
In some embodiments, the compound is a compound of Formula VIe, VIf, VIg, or VIh:
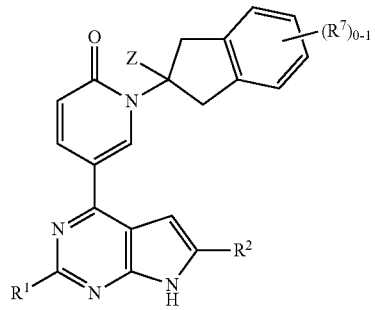
VIe
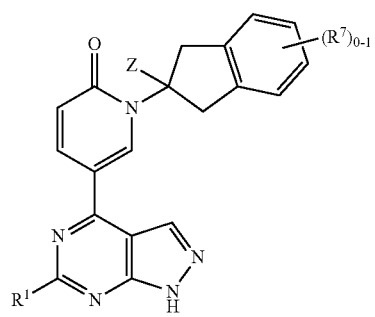
VIf
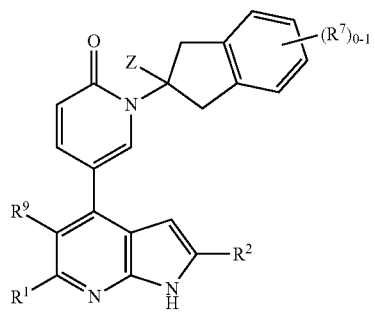
VIg
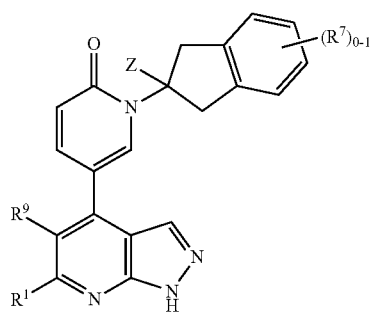
VIh
or a pharmaceutically acceptable salt thereof.
In some embodiments, the compound is a compound of Formula VIi, VIj, VIk, or VIm:

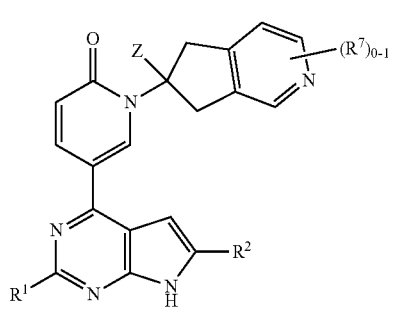
VIi
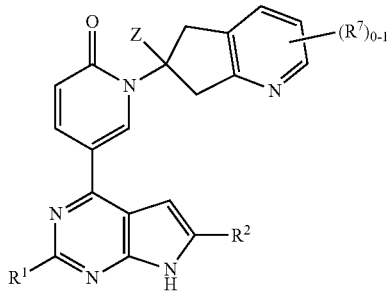
VIn
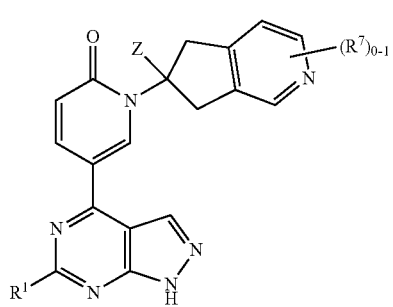
VIj
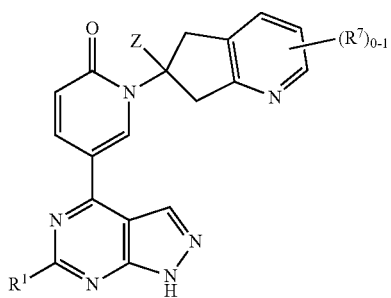
VIo
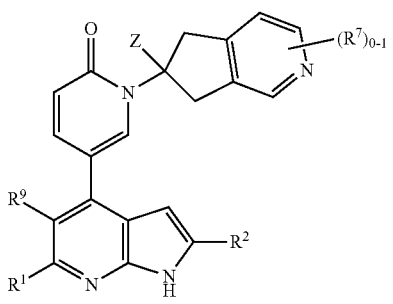
VIk
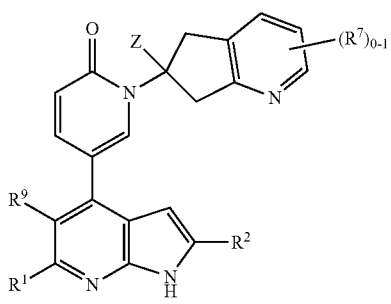
VIp
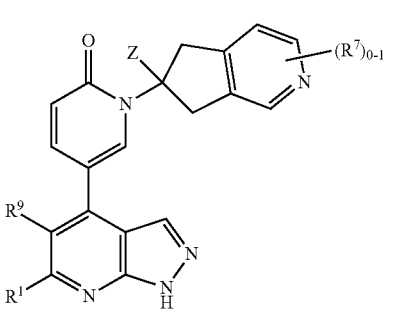
VIm
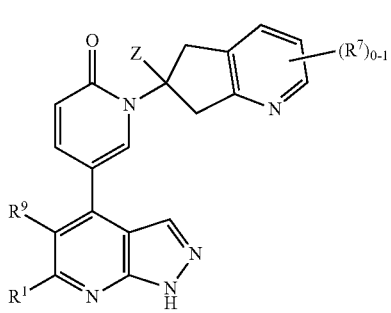
VIq
or a pharmaceutically acceptable salt thereof.
In some embodiments, the compound is a compound of Formula VIn, VIo, VIp, or VIq:
or a pharmaceutically acceptable salt thereof.
In some embodiments, the compound is a compound of Formula VIr, VIs, VIt, or VIu:

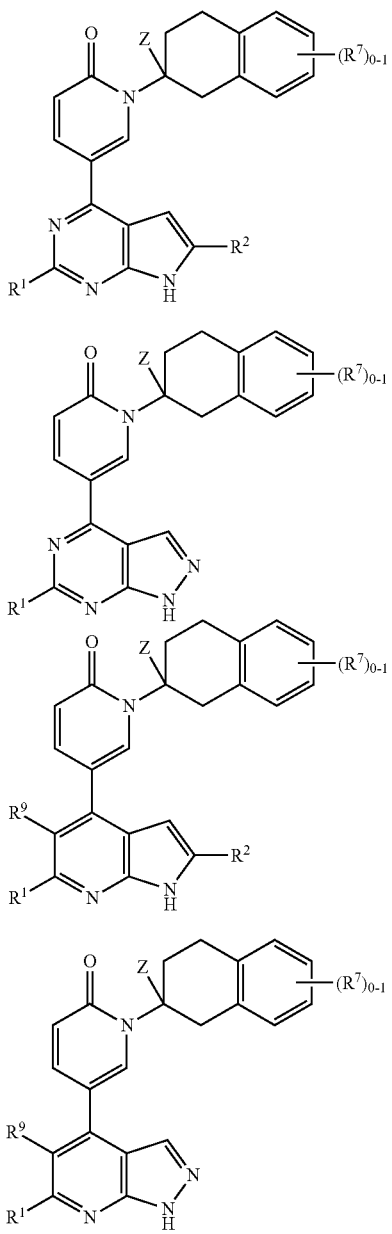
or a pharmaceutically acceptable salt thereof.
In some embodiments, the compound is a compound of Formula VIa:
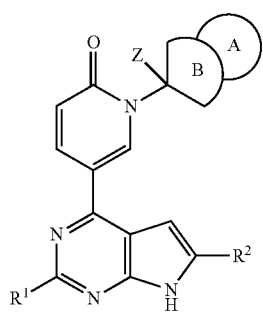
or a pharmaceutically acceptable salt thereof.
In some embodiments, the compound is a compound of Formula VIe:
or a pharmaceutically acceptable salt thereof.
In some embodiments, the compound is a compound of Formula VIIa, VIIb, VIIc, VIId, or VIIe:
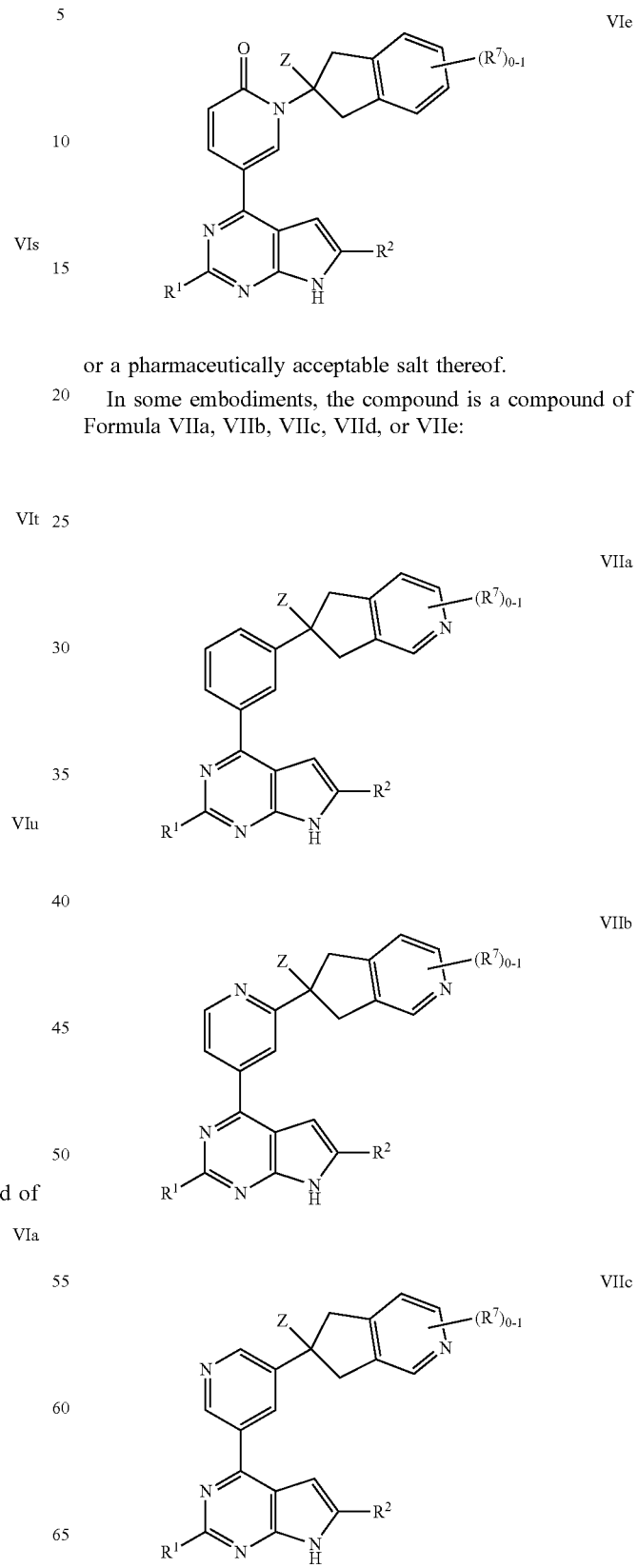

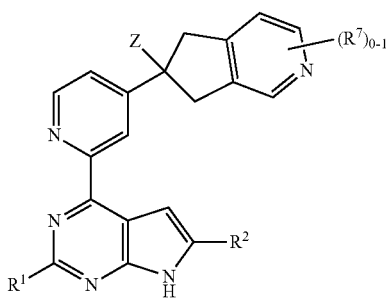
VIId
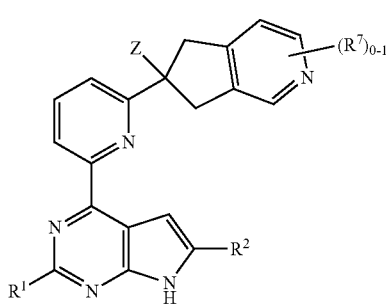
VIIe
or a pharmaceutically acceptable salt thereof.
In some embodiments, the compound is a compound of Formula VIIf, VIIg, VIIh, VIIi, or VIIj:
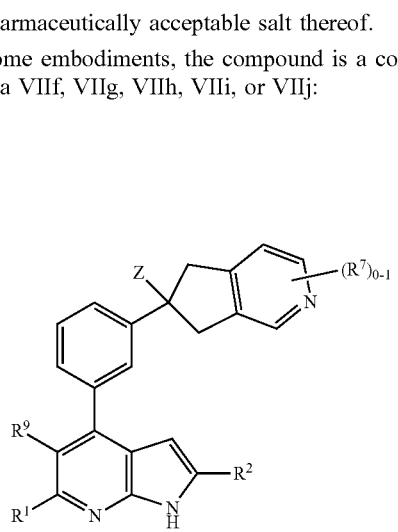
VIIf
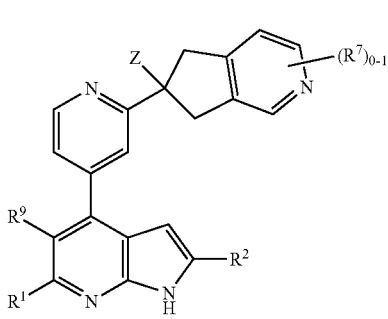
VIIg
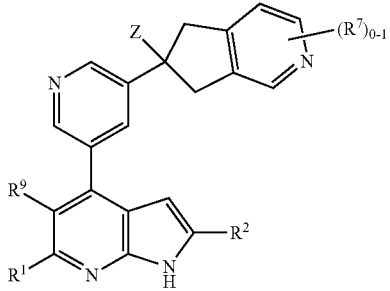
VIIh
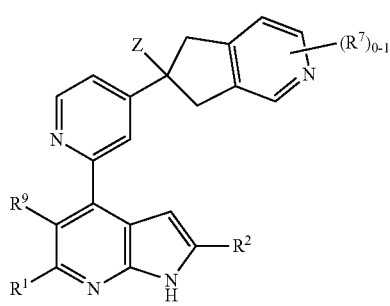
VIIi
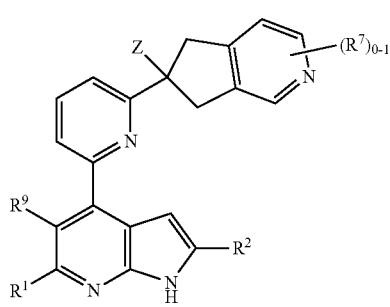
VIIj
or a pharmaceutically acceptable salt thereof.
In some embodiments, the compound is a compound of Formula VIIk, VIIm, VIIn, VIIo, or VIIp:
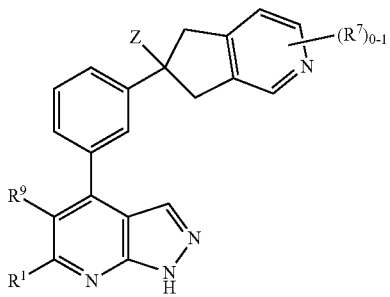
VIIk

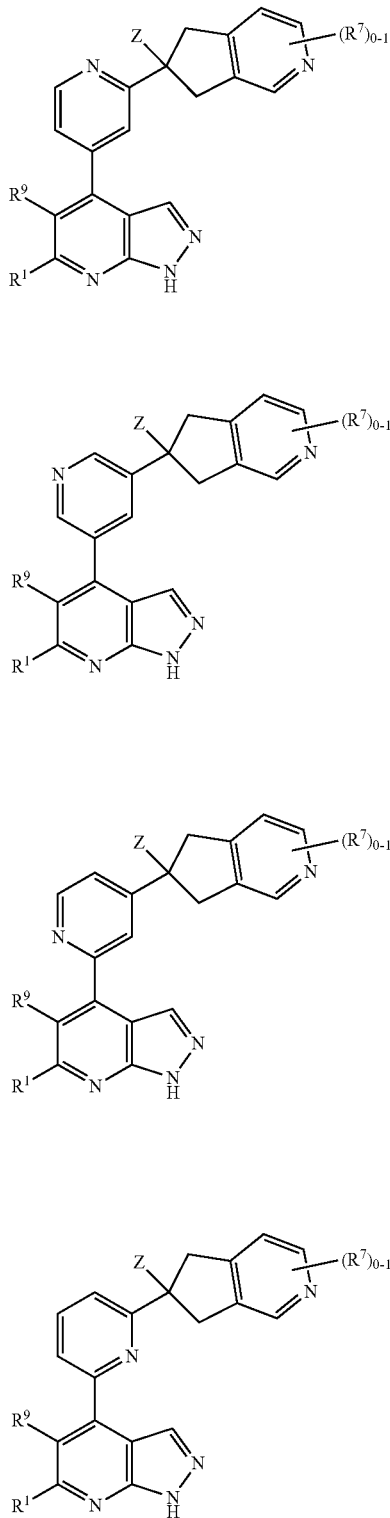
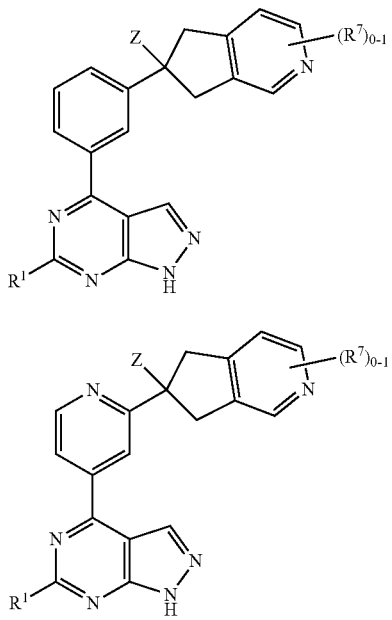
or a pharmaceutically acceptable salt thereof.
In some embodiments, the compound is a compound of Formula VIIq, VIIr, VIIs, VIIt, or VIIu:
or a pharmaceutically acceptable salt thereof.
In some embodiments, the compound is a compound of Formula VIIa:

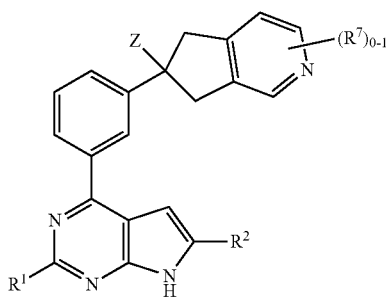
VIIa
or a pharmaceutically acceptable salt thereof.
In some embodiments, the compound is a compound of Formula VIIIa, VIIIb, VIIIc, VIIId, or VIIIe:
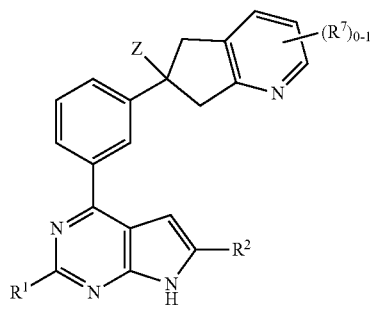
VIIIa
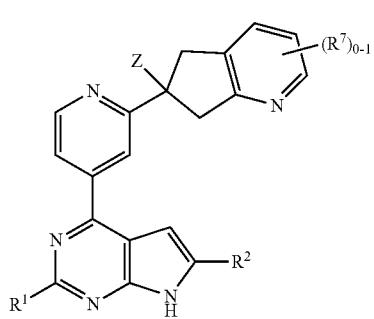
VIIIb
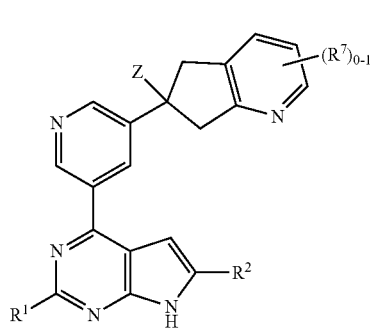
VIIIc
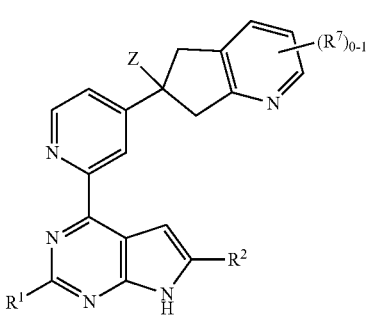
VIIId
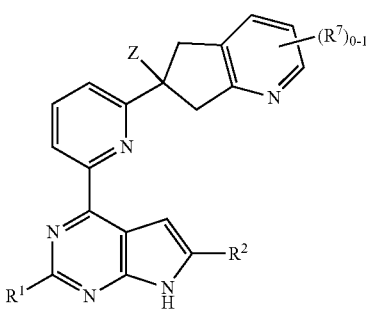
VIIIe
or a pharmaceutically acceptable salt thereof.
In some embodiments, the compound is a compound of Formula VIIIf, VIIIg, VIIIh, VIIIi, or VIIIj:
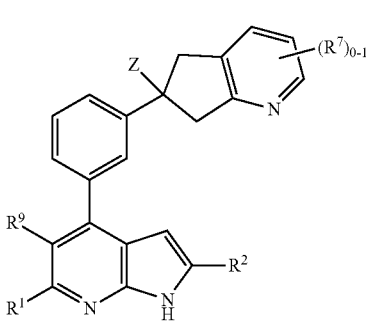
VIIIf
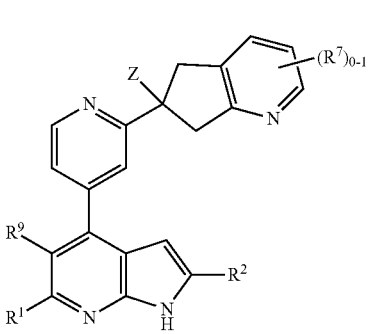
VIIIg

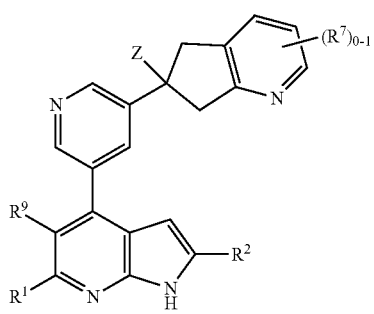
VIIIh
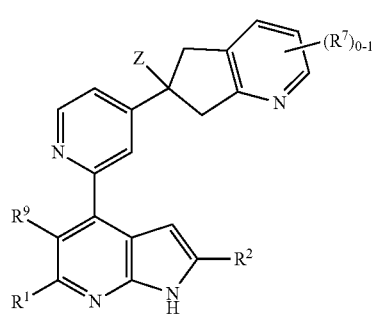
VIIIi
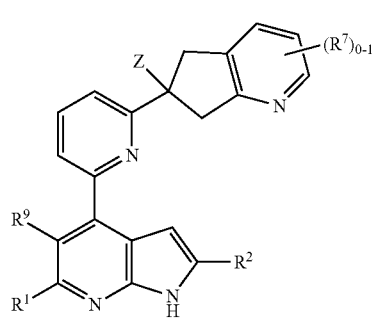
VIIIj
or a pharmaceutically acceptable salt thereof.
In some embodiments, the compound is a compound of Formula VIIIk, VIIIm, VIIIn, VIIIo, or VIIIp:
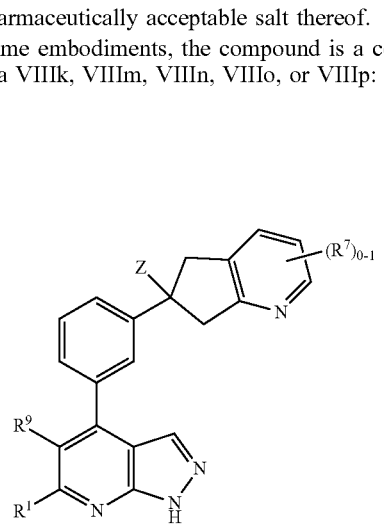
VIIIk
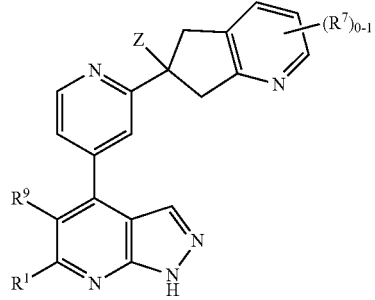
VIIIm
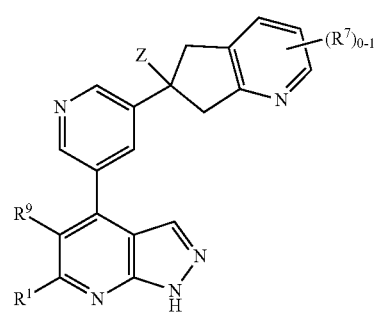
VIIIn
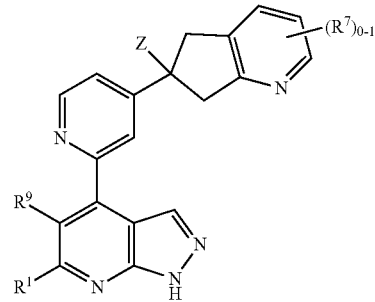
VIIIo
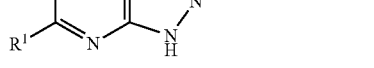
VIIIp
or a pharmaceutically acceptable salt thereof.
In some embodiments, the compound is a compound of Formula VIIIq, VIIIr, VIIIs, VIIIt, or VIIIu:

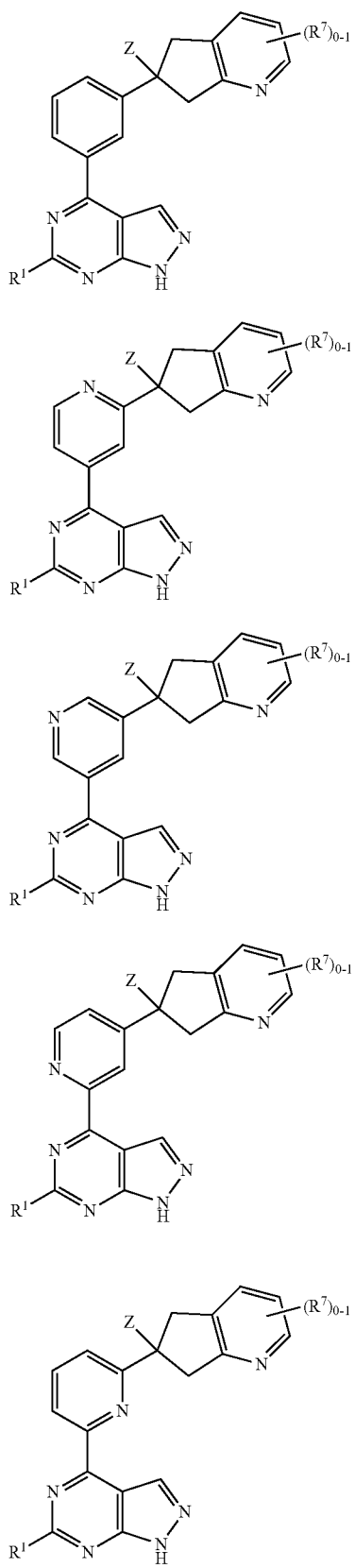
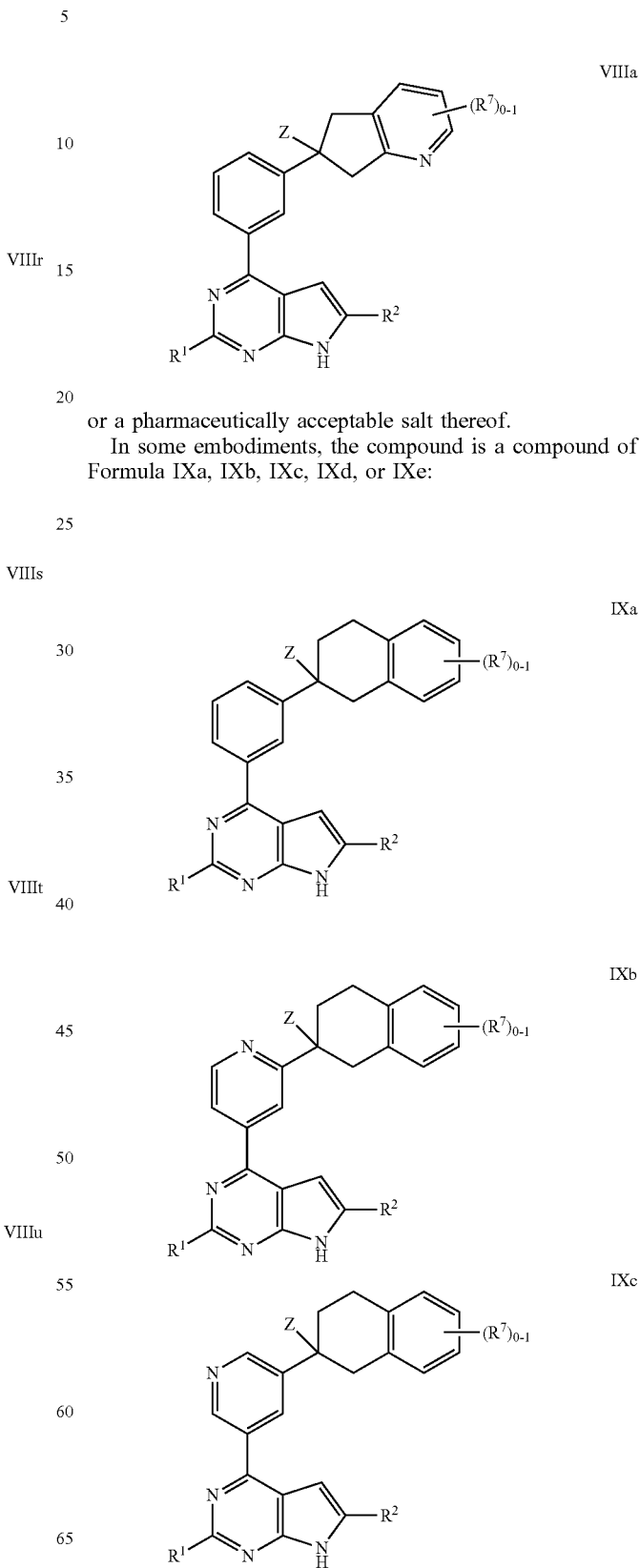
In some embodiments, the compound is a compound of Formula VIIIa:
or a pharmaceutically acceptable salt thereof.
In some embodiments, the compound is a compound of Formula IXa, IXb, IXc, IXd, or IXe:
or a pharmaceutically acceptable salt thereof.

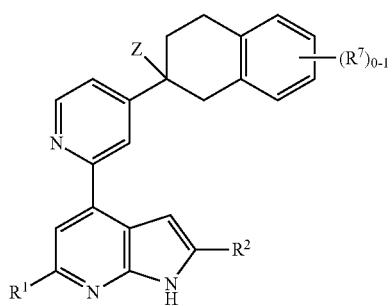
IXd
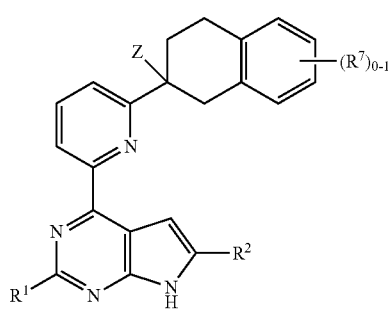
IXe
or a pharmaceutically acceptable salt thereof.
In some embodiments, the compound is a compound of Formula IXf, IXg, IXh, IXi, or
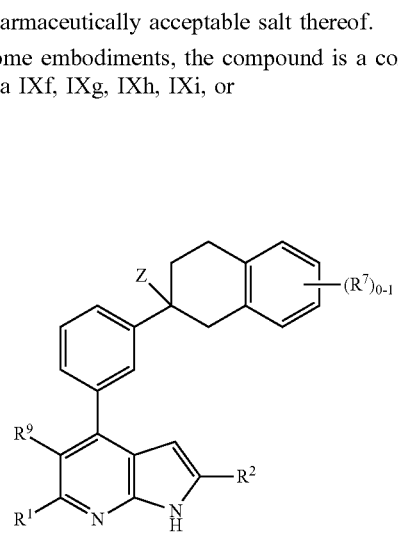
IXf
IXg
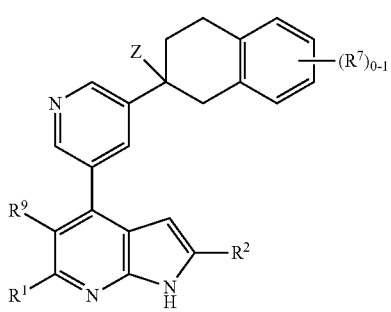
IXh
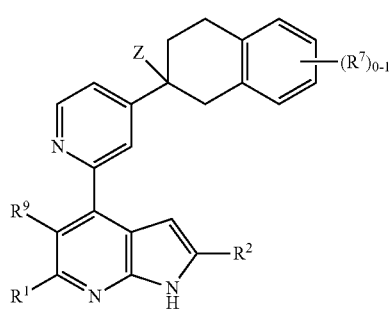
IXi
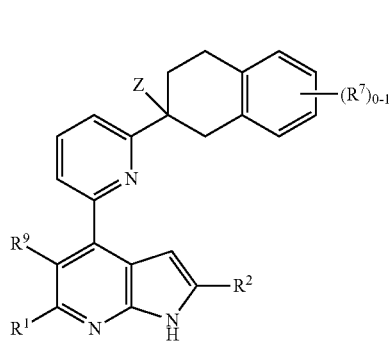
IXj
or a pharmaceutically acceptable salt thereof.
In some embodiments, the compound is a compound of Formula IXk, IXm, IXn, IXo, or IXp:
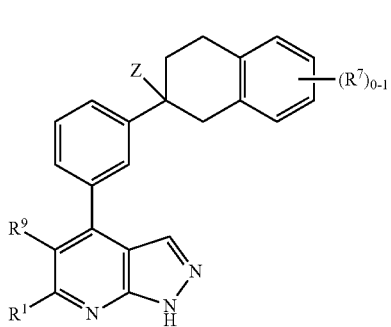
IXk

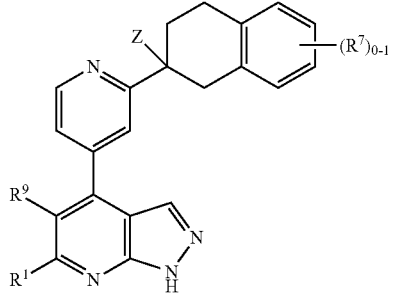
IXm
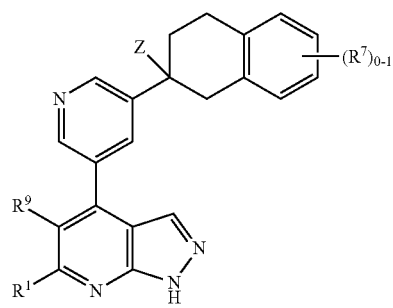
IXn
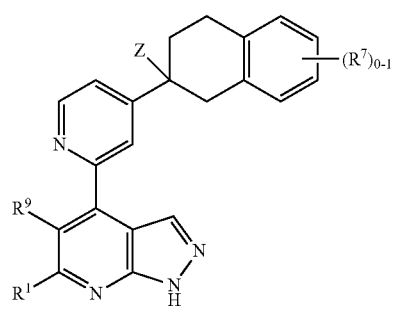
IXo
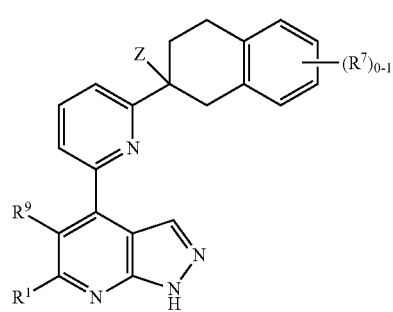
IXp
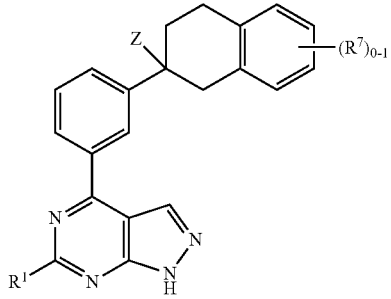
IXq
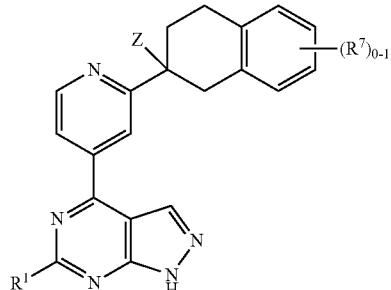
IXr
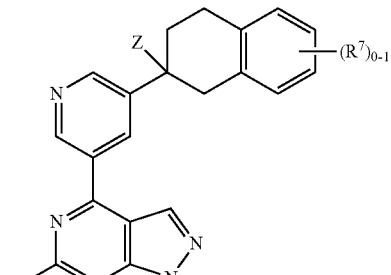
IXs
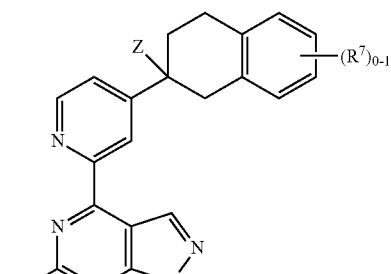
IXt
IXu
or a pharmaceutically acceptable salt thereof.
In some embodiments, the compound is a compound of Formula IXq, IXr, IXs, IXt, or IXu:
or a pharmaceutically acceptable salt thereof.
In some embodiments, the compound is a compound of Formula IXa:

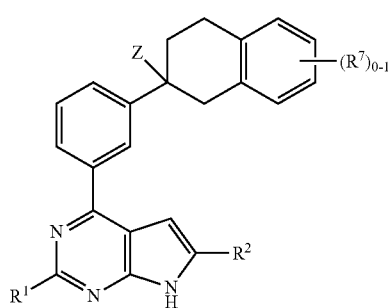

IXa

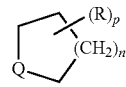

or a pharmaceutically acceptable salt thereof.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the term "fused" in the context of the fused A-B moiety means ortho-fused, wherein ring A and ring B have only two atoms and one bond (e.g., a double or single bond) in common (e.g., see the definition of ortho-fused in Pure & Appl. Chem., 70(1): 147 (1998) at FR-1.1.1). In the context of the A-B moiety, "fused" excludes spirocycles. At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

At certain places, the definitions or embodiments refer to specific rings (e.g., an azetidine ring, a pyridine ring, etc.). Unless otherwise indicated, these rings can be attached any ring member provided that the valency of the atom is not exceeded. For example, an azetidine ring may be attached at any position of the ring, whereas an azetidin-3-yl ring is attached at the 3-position.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R. In another example, when an optionally multiple substituent is designated in the form:

then it is to be understood that substituent R can occur p number of times on the ring, and R can be a different moiety at each occurrence. It is to be understood that each R group may replace any hydrogen atom attached to a ring atom, including one or both of the (CH$_2$)$_n$ hydrogen atoms. Further, in the above example, should the variable Q be defined to include hydrogens, such as when Q is said to be CH$_2$, NH, etc., any floating substituent such as R in the above example, can replace a hydrogen of the Q variable as well as a hydrogen in any other non-variable component of the ring.

As used herein, the phrase "optionally substituted" means unsubstituted or substituted. The substituents are independently selected, and substitution may be at any chemically accessible position. As used herein, the term "substituted" means that a hydrogen atom is removed and replaced by a substituent. A single divalent substituent, e.g., oxo, can replace two hydrogen atoms. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,1-diyl, ethan-1,2-diyl, propan-1,1,-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and isopropoxy), butoxy (e.g., n-butoxy and tert-butoxy), and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms. Examples of alkoxycarbonyl groups include, but are not limited to, methoxycarbonyl, ethoxycarbonyl, propoxycarbonyl (e.g., n-propoxycarbonyl and isopropoxycarbonyl), butoxycarbonyl (e.g., n-butoxycarbonyl and tert-butoxycarbonyl), and the like.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms. Examples of alkylcarbonyl groups include, but are not limited to, methylcarbonyl, ethylcarbonyl, propylcarbonyl (e.g., n-propylcarbonyl and isopropylcarbonyl), butylcarbonyl (e.g., n-butylcarbonyl and tert-butylcarbonyl), and the like.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH (alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylthio" refers to a group of formula —S-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "carboxy" refers to a —C(O)OH group.

As used herein, the term "cyano-$C_{n-m}$ alkyl" refers to a group of formula —($C_{n-m}$ alkylene)-CN, wherein the alkylene group has n to m carbon atoms.

As used herein, the terms "HO—$C_{n-m}$ alkyl" refers to a group of formula —($C_{n-m}$ alkylene)-OH, wherein the alkylene group has n to m carbon atoms.

As used herein, the terms "$C_{o-p}$ alkoxy-$C_{n-m}$ alkyl" refers to a group of formula —($C_{n-m}$ alkylene)-$C_{o-p}$ alkoxy, wherein the alkylene group has n to m carbon atoms and the alkoxy group has o to p carbon atoms.

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, "halo" refers to F, Cl, Br, or I. In some embodiments, halo is F, Cl, or Br. In some embodiments, halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Ring-forming carbon atoms of a cycloalkyl group can be optionally substituted by oxo or sulfido (e.g., C(O) or C(S)). Also included in the definition of cycloalkyl are moieties that have one or more aromatic rings fused (i.e., having a bond in common with) to the non-aromatic cyclic hydrocarbon, for example, benzo or thienyl derivatives of cyclopentane, cyclohexane, and the like. A cycloalkyl group containing a fused aromatic ring can be attached through any ring-forming atom including a ring-forming atom of the fused aromatic ring. Cycloalkyl groups can have 3, 4, 5, 6, 7, 8, 9, 10, 11, or 12 ring-forming atoms. In some embodiments, the cycloalkyl is a $C_{3-10}$ monocyclic or bicyclic cycloalkyl. In some embodiments, the cycloalkyl is a $C_{3-7}$ monocyclic cycloalkyl. In some embodiments, the cycloalkyl is a $C_{3-10}$ monocyclic or bicyclic non-aromatic carbocycle, which optionally has ring members which have oxo (=O) or sulfido (=S) substitution and which optionally has a phenyl or 5-6 membered aromatic heterocycle fused to the non-aromatic portion of the ring structure, wherein the heterocycle has 1-3 ring members independently selected from N, S, or O. In some embodiments, the cycloalkyl is a $C_{3-7}$ monocyclic non-aromatic carbocycle, which optionally has ring members which have oxo (=O) or sulfido (=S) substitution and which optionally has a phenyl or 5-6 membered aromatic heterocycle fused to the non-aromatic portion of the ring structure, wherein the heterocycle has 1-3 ring members independently selected from N, S, or O. In some embodiments, the cycloalkyl is a $C_{3-7}$ monocyclic cycloalkyl. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, or cyclohexyl.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In one embodiment the heteroaryl group is a 5 to 10 membered heteroaryl group. In another embodiment the heteroaryl group is a 5 to 6 membered heteroaryl group. In certain embodiments, the heteroaryl group is a monocyclic or bicyclic aromatic ring system having 5 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl. In another preferred embodiment, the heteroaryl group is a monocyclic aromatic ring system having 5 to 6 ring-forming atoms, wherein 1 to 4 ring-forming atoms are heteroatoms independently selected from N, O, and S, wherein the N and S as ring members are each optionally oxidized, the carbon ring members may be optionally replaced by carbonyl.

In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl, and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, 7-, 8-, 9- or 10-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl group is a morpholine ring, pyrrolidine ring, piperazine ring, piperidine ring, dihydropyran ring, tetrahydropyran ring, tetrahyropyridine, azetidine ring, or tetrahydrofuran ring. In certain embodiments, the heterocyloalkyl group is a monocyclic or bicyclic non-aromatic ring or ring system having 4 to 10 ring-forming atoms, wherein 1 to 4 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring, wherein the 5-6 membered heteroaryl ring may have 1-3 heteroatom ring members independently selected from N, S, and O. In another embodiment, the heterocyloalkyl group is a monocyclic non-aromatic ring or ring system having 4 to 6 ring-forming atoms, wherein 1 to 2 ring-forming atoms are heteroatoms independently selected from N, O, and S, wherein the N and S as ring members are each optionally oxidized, the carbon ring members may be optionally replaced by carbonyl, and the heterocycloalkyl group can be optionally fused to a 5-6 membered heteroaryl or phenyl ring, wherein the 5-6 membered heteroaryl ring may have 1-3 heteroatom ring members independently selected from N, S, and O.

As used herein, "$C_{n-m}$ cycloalkyl-$C_{o-p}$ alkylene" refers to a group of formula -alkylene-cycloalkyl, wherein the cycloalkyl group has n to m ring members and the alkylene group has o to p carbon atoms.

As used herein, "$C_{n-m}$ heterocycloalkyl-$C_{o-p}$ alkylene" refers to a group of formula —alkylene-heterocycloalkyl, wherein the heterocycloalkyl group has n to m ring members and the alkylene group has o to p carbon atoms.

As used herein, "phenyl-$C_{o-p}$ alkylene" refers to a group of formula -alkylene-phenyl, wherein the alkylene group has o to p carbon atoms.

As used herein, "$C_{n-m}$ aryl-$C_{o-p}$ alkylene" refers to a group of formula -alkylene-aryl, wherein the aryl group has n to m ring members and the alkylene group has o to p carbon atoms.

As used herein, "$C_{n-m}$ heteroaryl-$C_{o-p}$ alkylene" refers to a group of formula -alkylene-heteroaryl, wherein the heteroaryl group has n to m ring members and the alkylene group has o to p carbon atoms.

As used herein, the term "oxo" refers to an oxygen atom as a divalent substituent, forming a carbonyl group when attached to a carbon (e.g., C=O), or attached to a heteroatom forming a sulfoxide or sulfone group.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. In some embodiments, the compound has the (R)-configuration. In some embodiments, the compound has the (S)-configuration.

Resolution of racemic mixtures of compounds can be carried out by any of numerous methods known in the art. An example method includes fractional recrystallizaion using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein can also include all isotopes of atoms occurring in the intermediates or final compounds. Isotopes include those atoms having the same atomic number but different mass numbers. For example, isotopes of hydrogen include tritium and deuterium. One or more constituent atoms of the compounds provided herein can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7 or 8 deuterium atoms. Synthetic methods for including isotopes into organic compounds are known in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (ACN) are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

The following abbreviations may be used herein: AcOH (acetic acid); Ac$_2$O (acetic anhydride); aqueous (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DEAD (diethyl azodicarboxylate); DIAD (N,N'-diisopropyl azidodicarboxylate); DIPEA (N,N-diisopropylethylamine); DMF (N,N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); PMB (para-methoxybenzyl), POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" the TAM kinases with a compound of the invention includes the administration of a compound of the present invention to an individual or patient, such as a human, having TAM, as well as, for example, introducing a compound of the invention into a sample containing a cellular or purified preparation containing the TAM kinases.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) preventing the disease; for example, preventing a disease, condition or disorder in an individual who may be predisposed to the disease, condition or disorder but does not yet experience or display the pathology or symptomatology of the disease; 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

Synthesis

Compounds of the invention, including salts thereof, can be prepared using known organic synthesis techniques and according to various possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

The expressions, "ambient temperature", "room temperature", and "r.t.", as used herein, are understood in the art, and refer generally to a temperature, e.g. a reaction temperature, that is about the temperature of the room in which the reaction is carried out, for example, a temperature from about 20° C. to about 30° C.

Compounds as disclosed herein can be prepared by one skilled in the art according to preparatory routes known in the literature. Example synthetic methods for preparing compounds of the invention are provided in the Schemes 1-2 below, wherein constituent members of the depicted formulae are defined herein.

Compounds of formula 1-7 can be prepared according to Scheme 1. The commercially available intermediate of formula 1-1 (e.g., 2-(3-bromophenyl)acetonitrile) can be treated with dibromide or dichloride 1-9 (or di-mesylate prepared in situ from di-alcohol), in the presence of a base (sodium hydride, potassium tert-butoxide, etc) at room temperature or heated if necessary to form intermediate of formula 1-2. Suzuki reaction of the intermediate 1-2 with pinacol diboron provides the boronic ester 1-3. The subsequent Suzuki reaction of the intermediate 1-3 with intermediate 2-2, which may be prepared according to any procedure readily available to one of ordinary skill in the art from commercially available strating materials, gives the intermediate 1-4. The amination with an amine 1-8 under microwave conditions, or under Buchwald reaction conditions, converts the intermediate 1-4 into the intermediate 1-5. The cyano intermediate 1-5 can be reduced to the corresponding amine intermediate 1-6 using lithium aluminum hydride. Treatment of the intermediate 1-6 using either acid (TFA, HCl, etc), or base (e.g. sodium methoxide) removes the protecting group PG$_1$ (e.g. SEM or sulfonamide) and affords the final desired compound 1-7.

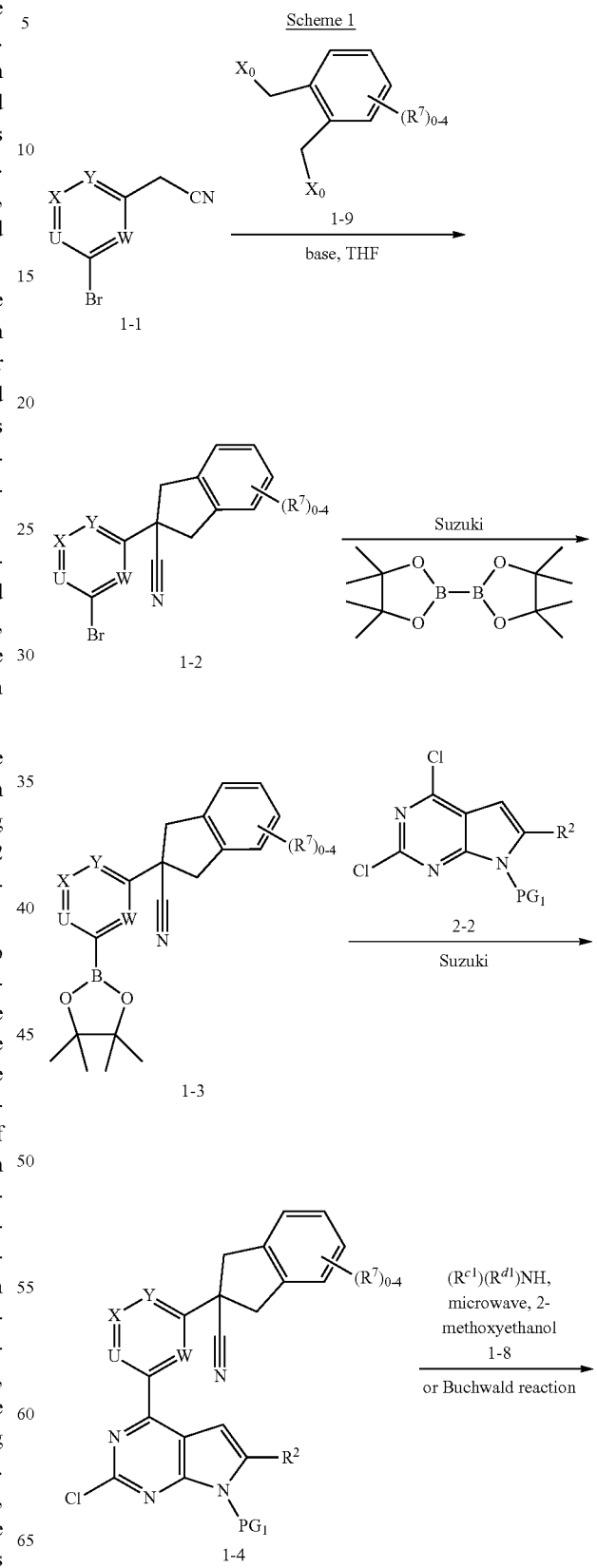

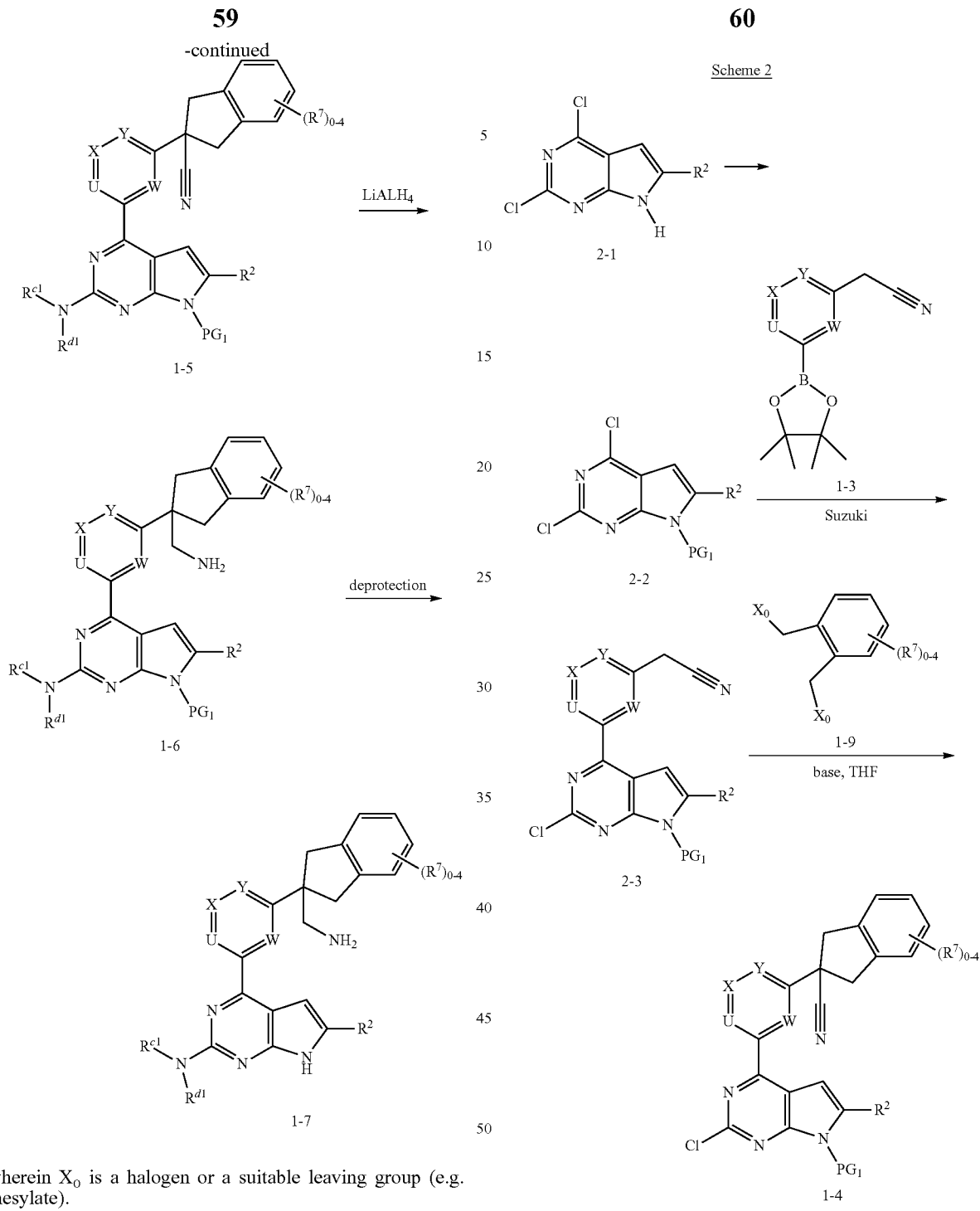

wherein $X_0$ is a halogen or a suitable leaving group (e.g. mesylate).

Alternatively, compounds of formula 1-4 can be prepared using a sequence depicted in Scheme 2. Commercially available intermediate 2-1 can be protected by a suitable protecting group, such as, for example, SEM or sulfonamide, to give the intermediate 2-2, followed by the Suzuki reaction with a variety of commercially available boronic esters 1-3 to provide the intermediate 2-3. The intermediate 2-3 can be treated with dibromide or dichloride 1-9, in the presence of a base (e.g. sodium hydride, potassium tert-butoxide, etc) at room temperature or heated if necessary to form the desired intermediate of formula 1-4. The compound of formula 1-7 may be obtained from intermediate 1-4 according to procedures and methods described in Scheme 1 above.

wherein $X_0$ is a halogen or a suitable leaving group (e.g. mesylate).

TAM Kinases

Receptor tyrosine kinases (RTKs) are cell surface proteins that transmit signals from the extracellular environment to the cell cytoplasm and nucleus to regulate cellular events such as survival, growth, proliferation, differentiation, adhesion and migration. All RTKs contain an extracellular ligand binding domain and a cytoplasmic protein tyrosine kinase domain. Ligand binding leads to the dimerization of RTKs, which triggers the activation of the cytoplasmic kinase and initiates downstream signal transduction pathways. RTKs can be classified into distinct subfamilies based on their sequence similarity. The TAM subfamily consists of three RTKs including TYRO3, AXL and MER (Graham et al., 2014, Nature reviews Cancer 14, 769-785; and Linger et al., 2008, Oncogene 32, 3420-3431). TAM kinases are characterized by an extracellular ligand binding domain consisting of two immunoglobulin-like domains and two fibronectin type III domains. Two ligands, growth arrest specific 6 (GAS6) and protein S (ProS), have been identified for TAM kinases. GAS6 can bind to and activate all three TAM kinases, while ProS is a ligand for MER and TYRO3 (Graham et al., 2014, Nature reviews Cancer 14, 769-785).

TAM kinases are over-expressed in many cancers and play important roles in tumor initiation and maintenance; therefore, TAM inhibition represents an attractive approach for targeting another class of oncogenic RTKs (Graham et al., 2014, Nature reviews Cancer 14, 769-785; and Linger et al., 2008, Oncogene 32, 3420-3431).

Axl was originally identified as a transforming gene from DNA of patients with chronic myelogenous leukemia (O'Bryan et al., 1991, Molecular and cellular biology 11, 5016-5031). GAS6 binds to Axl and induces subsequent auto-phosphorylation and activation of Axl tyrosine kinase. Axl activates several downstream signaling pathways including PI3K-Akt, Raf-MAPK, PLC-PKC (Feneyrolles et al., 2014, Molecular cancer therapeutics 13, 2141-2148; Linger et al., 2008, Oncogene 32, 3420-3431). AXL is over-expressed or amplified in a variety of malignancies including lung cancer, prostate cancer, colon cancer, breast cancer, melanoma, and renal cell carcinoma (Linger et al., 2008, Oncogene 32, 3420-3431). Over-expression of AXL is correlated with poor prognosis (Linger et al., 2008, Oncogene 32, 3420-3431). As a result, AXL activation promotes cancer cell survival, proliferation, angiogenesis, metastasis, and resistance to chemotherapy and targeted therapies. AXL knockdown or AXL antibody can inhibit the migration of breast cancer and NSCLC cancer in vitro, and blocked tumor growth in xenograft tumor models (Li et al., 2009, Oncogene 28, 3442-3455). In pancreatic cancer cells, inhibition of AXL decreased cell proliferation and survival (Koorstra et al., 2009, Cancer biology & therapy 8, 618-626). In prostate cancer, AXL inhibition decreased cell migration, invasion, and proliferation (Tai et al., 2008, Oncogene 27, 4044-4055). In addition, AXL over-expression or amplification is a major mechanism for resistance to EGFR inhibitors by lung cancer cells, and AXL inhibition can reverse the resistance (Zhang et al., 2012, Nature genetics 44, 852-860).

Mer was originally identified as a phospho-protein from a lymphoblastoid expression library (Graham et al., 1995, Oncogene 10, 2349-2359). Both GAS6 and ProS can bind to Mer and induce the phosphorylation and activation of Mer kinase (Lew et al., 2014. eLife, 3:e03385). Like Axl, Mer activation also conveys downstream signaling pathways including PI3K-Akt and Raf-MAPK (Linger et al., 2008, Oncogene 32, 3420-3431). MER is over-expressed in many cancers including multiple myeloma, gastric, prostate, breast, melanoma and rhabdomyosarcoma (Linger et al., 2008, Oncogene 32, 3420-3431). MER knockdown inhibits multiple myeloma cell growth in vitro and in xenograft models (Waizenegger et al., 2014, Leukemia, 1-9). In acute myeloid leukemia, MER knockdown induced apoptosis, decreased colony formation, and increased survival in a mouse model (Lee-Sherick et al., 2013, Oncogene 32, 5359-5368). MER inhibition increased apoptosis, decreased colony formation, increased chemo-sensitivity, and decreased tumor growth in NSCLC (Linger et al., 2013, Oncogene 32, 3420-3431). Similar effects are observed for MER knockdown in melanoma (Schlegel et al., 2013) and glioblastoma (Wang et al., 2013, Oncogene 32, 872-882).

Tyro3 was originally identified through a PCR-based cloning study (Lai and Lemke, 1991, Neuron 6, 691-704). Both ligands, GAS6 and ProS, can bind to and activate Tyro3. TYRO3 also plays a role in cancer growth and proliferation. TYRO3 is over-expressed in melanoma cells, and knockdown of TYRO3 induces apoptosis in these cells (Demarest et al., 2013, Biochemistry 52, 3102-3118).

In addition to their role as transforming oncogenes, TAM kinases have emerged as potential immune-oncology targets. The durable clinical responses to immune checkpoint blockade observed in cancer patients clearly indicate that the immune system plays a critical role in tumor initiation and maintenance. Genetic mutations from cancer cells can provide a diverse set of antigens that the immune cells can use to distinguish tumor cells from their normal counterpart. However, cancer cells have evolved multiple mechanisms to evade host immune surveillance. In fact, one hallmark of human cancer is its ability to avoid immune destruction. Cancer cells can induce an immune-suppressive microenvironment by promoting the formation of M2 tumor associated macrophages, myeloid derived suppressor cells (MDSC), and regulatory T cells. Cancer cells can also produce high levels of immune checkpoint proteins such as PD-L1 to induce T cell anergy or exhaustion. It is now clear that tumors co-opt certain immune-checkpoint pathways as a major mechanism of immune resistance (Pardoll, 2012, Cancer 12, 252-264). Antagonizing these negative regulators of T-cell function with antibodies has shown striking efficacy in clinical trials of a number of malignancies including advanced melanoma, non-small cell lung and bladder cancer. While these therapies have shown encouraging results, not all patients mount an anti-tumor response suggesting that other immune-suppressive pathways may also be important.

TAM kinases have been shown to function as checkpoints for immune activation in the tumor milieu. All TAM kinases are expressed in NK cells, and TAM kinases inhibit the anti-tumor activity of NK cells. LDC1267, a small molecule TAM inhibitor, activates NK cells, and blocks metastasis in tumor models with different histologies (Paolino et al., 2014, Nature 507, 508-512). In addition, MER kinase promotes the activity of tumor associated macrophages through the increased secretion of immune suppressive cytokines such as IL10 and IL4, and decreased production of immune activating cytokines such as IL12 (Cook et al., 2013, The Journal of clinical investigation 123, 3231-3242). MER inhibition has been shown to reverse this effect. As a result, MER knockout mice are resistant to PyVmT tumor formation (Cook et al., 2013, The Journal of clinical investigation 123, 3231-3242). The role of TAM kinases in the immune response is also supported by knockout mouse studies. TAM triple knockout mice (TKO) are viable. However, these mice displayed signs of autoimmune disease including enlarged spleen and lymph nodes, autoantibody production, swollen footpad and joints, skin lesions, and systemic lupus erythematosus (Lu and Lemke, 2001, Science 293, 306-311). This is consistent with the knockout phenotype for approved immune-oncology targets such as CTLA4 and PD-1. Both CTLA-4 and PD-1 knockout mice showed signs of autoimmune disease, and these mice die within a few weeks after birth (Chambers et al., 1997, Immunity 7, 885-895; and Nishimura et al., 2001, Science 291, 319-322).

TAM inhibition will have not only direct activity against neoplastic cells, but also activate the anti-cancer immune response. Thus TAM inhibitors represent an attractive approach for the treatment of cancer as single agents. In addition, TAM inhibitors may be combined with other targeted therapies, chemotherapies, radiation, or immunotherapeutic agents to achieve maximal efficacy in the clinic.

Methods of Use

Compounds of the present disclosure can modulate or inhibit the activity of TAM kinases. For example, the compounds of the disclosure can be used to inhibit activity of a TAM kinase in a cell or in an individual or patient in need of inhibition of the kinases by administering an inhibiting amount of a compound of the disclosure to the cell, individual, or patient.

In some embodiments, the compounds of the disclosure are selective for the TAM kinases over one or more of other kinases. In some embodiments, the compounds of the disclosure are selective for the TAM kinases over other kinases. In some embodiments, the selectivity is 2-fold or more, 3-fold or more, 5-fold or more, 10-fold or more, 25-fold or more, 50-fold or more, or 100-fold or more.

As TAM kinases inhibitors, the compounds of the disclosure are useful in the treatment of various diseases associated with abnormal expression or activity of the TAM kinases. Compounds which inhibit TAM kinases will be useful in providing a means of preventing the growth or inducing apoptosis in tumors, particularly by inhibiting angiogenesis. It is therefore anticipated that the compounds will prove useful in treating or preventing proliferative disorders such as cancers. In particular tumours with activating mutants of receptor tyrosine kinases or upregulation of receptor tyrosine kinases may be particularly sensitive to the inhibitors.

In certain embodiments, the disclosure provides a method for treating a disease or disorder mediated by TAM kinases in a patient in need thereof, comprising the step of administering to said patient a compound according to the invention, or a pharmaceutically acceptable composition thereof.

For example, the compounds of the disclosure are useful in the treatment of cancer. Example cancers include bladder cancer, breast cancer, cervical cancer, colorectal cancer, cancer of the small intestine, colon cancer, rectal cancer, cancer of the anus, endometrial cancer, gastric cancer, head and neck cancer (e.g., cancers of the larynx, hypopharynx, nasopharynx, oropharynx, lips, and mouth), kidney cancer, liver cancer (e.g., hepatocellular carcinoma, cholangiocellular carcinoma), lung cancer (e.g., adenocarcinoma, small cell lung cancer and non-small cell lung carcinomas, parvicellular and non-parvicellular carcinoma, bronchial carcinoma, bronchial adenoma, pleuropulmonary blastoma), ovarian cancer, prostate cancer, testicular cancer, uterine cancer, esophageal cancer, gall bladder cancer, pancreatic cancer (e.g. exocrine pancreatic carcinoma), stomach cancer, thyroid cancer, parathyroid cancer, skin cancer (e.g., squamous cell carcinoma, Kaposi sarcoma, Merkel cell skin cancer), and brain cancer (e.g., astrocytoma, medulloblastoma, ependymoma, neuro-ectodermal tumors, pineal tumors).

Further example cancers include hematopoietic malignancies such as leukemia or lymphoma, multiple myeloma, chronic lymphocytic lymphoma, adult T cell leukemia, B-cell lymphoma, cutaneous T-cell lymphoma, acute myelogenous leukemia, Hodgkin's or non-Hodgkin's lymphoma, myeloproliferative neoplasms (e.g., polycythemia vera, essential thrombocythemia, and primary myelofibrosis), Waldenstrom's Macroglubulinemia, hairy cell lymphoma, chronic myelogenic lymphoma, acute lymphoblastic lymphoma, AIDS-related lymphomas, and Burkitt's lymphoma.

Other cancers treatable with the compounds of the disclosure include tumors of the eye, glioblastoma, melanoma, rhabdosarcoma, lymphosarcoma, and osteosarcoma.

Compounds of the disclosure can also be useful in the inhibition of tumor metastasis.

In some embodiments, the present disclosure provides a method for treating hepatocellular carcinoma in a patient in need thereof, comprising the step of administering to said patient a compound of Formula (I) or a compound as disclosed herein, or a pharmaceutically acceptable salt thereof, or a composition comprising a compound of Formula (I) or a compound as disclosed herein.

In some embodiments, the present disclosure provides a method for treating Rhabdomyosarcoma, esophageal cancer, breast cancer, or cancer of a head or neck, in a patient in need thereof, comprising the step of administering to said patient a compound Formula (I) or a compound as disclosed herein, or a pharmaceutically acceptable salt thereof, or a composition comprising a compound of Formula (I) or a compound as disclosed herein.

In some embodiments, the present disclosure provides a method of treating cancer, wherein the cancer is selected from hepatocellular cancer, breast cancer, bladder cancer, colorectal cancer, melanoma, mesothelioma, lung cancer, prostate cancer, pancreatic cancer, testicular cancer, thyroid cancer, squamous cell carcinoma, glioblastoma, neuroblastoma, uterine cancer, and rhabdosarcoma.

In some embodiments, the present disclosure provides a method for inhibiting a TAM kinase, comprising: contacting the TAM kinase with the compound of any one of Formulae described herein, or a pharmaceutically acceptable salt thereof.

In some embodiments, the present disclosure provides a method for treating cancer in a patient, comprising: administering to the patient a therapeutically effective amount of the compound of any one of Formulae described herein, or a pharmaceutically acceptable salt thereof.

In some embodiments, the present disclosure provides a method for treating cancer, wherein the cancer is selected from hepatocellular cancer, bladder cancer, breast cancer, cervical cancer, colorectal cancer, endometrial cancer, gastric cancer, head and neck cancer, kidney cancer, liver cancer, lung cancer, ovarian cancer, prostate cancer, esophageal cancer, gall bladder cancer, pancreatic cancer, thyroid cancer, skin cancer, leukemia, multiple myeloma, chronic lymphocytic lymphoma, adult T cell leukemia, B-cell lymphoma, acute myelogenous leukemia, Hodgkin's or non-Hodgkin's lymphoma, Waldenstrom's Macroglubulinemia, hairy cell lymphoma, Burkett's lymphoma, glioblastoma, melanoma, and rhabdosarcoma.

In some embodiments, the present disclosure provides a method for treating cancer, wherein the cancer is lung cancer, prostate cancer, colon cancer, breast cancer, melanoma, renal cell carcinoma, multiple myeloma, gastric cancer, or rhabdomyosarcoma.

Combination Therapy

One or more additional pharmaceutical agents or treatment methods such as, for example, anti-viral agents, chemotherapeutics or other anti-cancer agents, immune enhancers, immunosuppressants, radiation, anti-tumor and anti-viral vaccines, cytokine therapy (e.g., IL2, GM-CSF, etc.), and/or tyrosine kinase inhibitors can be used in combination with the compounds of Formula (I) or a compound as described herein for treatment of TAM-associated diseases, disorders or conditions. The agents can be combined with the present compounds in a single dosage form, or the agents can be administered simultaneously or sequentially as separate dosage forms.

Suitable antiviral agents contemplated for use in combination with the compounds of the present disclosure can comprise nucleoside and nucleotide reverse transcriptase inhibitors (NRTIs), non-nucleoside reverse transcriptase inhibitors (NNRTIs), protease inhibitors and other antiviral drugs.

Example suitable NRTIs include zidovudine (AZT); didanosine (ddl); zalcitabine (ddC); stavudine (d4T); lamivudine (3TC); abacavir (1592U89); adefovir dipivoxil [bis(POM)-PMEA]; lobucavir (BMS-180194); BCH-10652; emitricitabine [(−)-FTC]; beta-L-FD4 (also called beta-L-D4C and named beta-L-2', 3'-dicleoxy-5-fluoro-cytidene); DAPD, ((−)-beta-D-2,6,-diamino-purine dioxolane); and lodenosine (FddA). Typical suitable NNRTIs include nevirapine (BI-RG-587); delaviradine (BHAP, U-90152); efavirenz (DMP-266); PNU-142721; AG-1549; MKC-442 (1-(ethoxy-methyl)-5-(1-methylethyl)-6-(phenylmethyl)-(2,4 (1H,3H)-pyrimidinedione); and (+)-calanolide A (NSC-675451) and B. Typical suitable protease inhibitors include saquinavir (Ro 31-8959); ritonavir (ABT-538); indinavir (MK-639); nelfnavir (AG-1343); amprenavir (141W94); lasinavir (BMS-234475); DMP-450; BMS-2322623; ABT-378; and AG-1 549. Other antiviral agents include hydroxyurea, ribavirin, IL-2, IL-12, pentafuside and Yissum Project No. 11607.

The TAM inhibitors of the application invention can be used in combination with one or more other kinase inhibitors for the treatment of diseases, such as cancer, that are impacted by multiple signaling pathways. For example, the compounds of the invention can be combined with one or more inhibitors of the following kinases for the treatment of cancer: PIM, Pim1, Pim2, Pim3, IDO, Akt1, Akt2, Akt3, TGF-βR, PKA, PKG, PKC, CaM-kinase, phosphorylase kinase, MEKK, ERK, MAPK, mTOR, EGFR, HER2, HER3, HER4, INS-R, IGF-1R, IR-R, PDGFαR, PDGFβR, CSFIR, KIT, FLK-II, KDR/FLK-1, FLK-4, fit-1, FGFR, FGFR1, FGFR2, FGFR3, FGFR4, c-Met, Ron, Sea, TRKA, TRKB, TRKC, FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf Additionally, the TAM inhibitors of the invention can be combined with inhibitors of kinases associated with the PI3K/Akt/mTOR signaling pathway, such as PI3K, including PI3Kγ, PI3Kδ, Akt (including Akt1, Akt2 and Akt3) and mTOR kinases.

The TAM inhibitors of the present application can be used in combination with one or more other BET bromodomain inhibitors such a BRD2, BRD3, BRD4 and BRDT that are useful for the treatment of diseases, such as cancer.

The TAM inhibitors of the present application can further be used in combination with other methods of treating cancers, for example by chemotherapy, irradiation or surgery. The compounds can be administered in combination with one or more anti-cancer drugs, such as a chemotherapeutics. Example chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat and zoledronate.

Suitable agents for use in combination with the compounds of the present invention for the treatment of cancer include chemotherapeutic agents, targeted cancer therapies, immunotherapies or radiation therapy. Compounds of this invention may be effective in combination with anti-hormonal agents for treatment of breast cancer and other tumors. Suitable examples are anti-estrogen agents including but not limited to tamoxifen and toremifene, aromatase inhibitors including but not limited to letrozole, anastrozole, and exemestane, adrenocorticosteroids (e.g. prednisone), progestins (e.g. megastrol acetate), and estrogen receptor antagonists (e.g. fulvestrant). Suitable anti-hormone agents used for treatment of prostate and other cancers may also be combined with compounds of the present invention. These include anti-androgens including but not limited to flutamide, bicalutamide, and nilutamide, luteinizing hormone-releasing hormone (LHRH) analogs including leuprolide, goserelin, triptorelin, and histrelin, LHRH antagonists (e.g. degarelix), androgen receptor blockers (e.g. enzalutamide) and agents that inhibit androgen production (e.g. abiraterone).

Compounds of the present invention may be combined with or in sequence with other agents against membrane receptor kinases especially for patients who have developed primary or acquired resistance to the targeted therapy. These therapeutic agents include inhibitors or antibodies against EGFR, Her2, VEGFR, c-Met, Ret, IGFR1, PDGFR, FGFR1, FGFR2, FGFR3, FGFR4, TrkA, TrkB, TrkC, ROS, c-Kit, or Flt-3 and against cancer-associated fusion protein kinases such as Bcr-Abl and EML4-Alk. Inhibitors against EGFR include gefitinib and erlotinib, and inhibitors against EGFR/Her2 include but are not limited to dacomitinib, afatinib, lapitinib and neratinib. Antibodies against the EGFR include but are not limited to cetuximab, panitumumab and necitumumab. Inhibitors of c-Met may be used in combination with TAM inhibitors. These include onartumzumab, tivantnib, and INC-280. Agents against FGFRs include but not limited to AZD4547, BAY1187982, ARQ087, BGJ398, BIBF1120, TKI258, lucitanib, dovitinib, TAS-120, JNJ-42756493, and Debiol347. Agents against Trks include but not limited to LOXO-101, and RXDX-101. Agents against Abl (or Bcr-Abl) include imatinib, dasatinib, nilotinib, and ponatinib and those against Alk (or EML4-ALK) include crizotinib.

Angiogenesis inhibitors may be efficacious in some tumors in combination with TAM inhibitors. These include antibodies against VEGF or VEGFR or kinase inhibitors of VEGFR. Antibodies or other therapeutic proteins against VEGF include bevacizumab and aflibercept. Inhibitors of VEGFR kinases and other anti-angiogenesis inhibitors include but are not limited to sunitinib, sorafenib, axitinib, cediranib, pazopanib, regorafenib, brivanib, and vandetanib Activation of intracellular signaling pathways is frequent in cancer, and agents targeting components of these pathways have been combined with receptor targeting agents to enhance efficacy and reduce resistance. Examples of agents that may be combined with compounds of the present invention include inhibitors of the PI3K-AKT-mTOR pathway, inhibitors of the Raf-MAPK pathway, inhibitors of JAK-STAT pathway, inhibitors of Pim kinases, and inhibitors of protein chaperones and cell cycle progression.

Agents against the PI3 kinase include but are not limited topilaralisib, idelalisib, buparlisib and IPI-549. In some embodiments, the PI3K inhibitor is selective for PI3K alpha, PI3K beta, PI3K gamma or PI3K delta. Inhibitors of mTOR such as rapamycin, sirolimus, temsirolimus, and everolimus may be combined with TAM kinases inhibitors. Other suitable examples include but are not limited to vemurafenib and dabrafenib (Raf inhibitors) and trametinib, selumetinib and GDC-0973 (MEK inhibitors). Inhibitors of one or more JAKs (e.g., ruxolitinib, baricitinib, and tofacitinib), selective JAK1 inhibitors (e.g., INCB039110), IDO inhibitors (e.g., INCB024360), PI3Kδ inhibitors (e.g., INCB040093, INCB050465), sp90 (e.g., tanespimycin), cyclin dependent kinases (e.g., palbociclib), PARP (e.g., olaparib), and proteasomes (e.g., bortezomib, carfilzomib) can also be combined with compounds of the present invention. In some embodiments, the JAK inhibitor is selective for JAK1 over JAK2 and JAK3. Agents against Pim kinases include but not limited to LGH447, INCB053914, SGI-1776.

Other suitable agents for use in combination with the compounds of the present invention include chemotherapy combinations such as platinum-based doublets used in lung cancer and other solid tumors (cisplatin or carboplatin plus gemcitabine; cisplatin or carboplatin plus docetaxel; cisplatin or carboplatin plus paclitaxel; cisplatin or carboplatin plus pemetrexed) or gemcitabine plus paclitaxel bound particles (Abraxane®).

Suitable chemotherapeutic or other anti-cancer agents include, for example, alkylating agents (including, without limitation, nitrogen mustards, ethylenimine derivatives, alkyl sulfonates, nitrosoureas and triazenes) such as uracil mustard, chlormethine, cyclophosphamide (Cytoxan™), ifosfamide, melphalan, chlorambucil, pipobroman, triethylene-melamine, triethylenethiophosphoramine, busulfan, carmustine, lomustine, streptozocin, dacarbazine, and temozolomide.

Other suitable agents for use in combination with the compounds of the present invention include: dacarbazine (DTIC), optionally, along with other chemotherapy drugs such as carmustine (BCNU) and cisplatin; the "Dartmouth regimen," which consists of DTIC, BCNU, cisplatin and tamoxifen; a combination of cisplatin, vinblastine, and DTIC; or temozolomide. Compounds according to the invention may also be combined with immunotherapy drugs, including cytokines such as interferon alpha, interleukin 2, and tumor necrosis factor (TNF) inhibitors.

Suitable chemotherapeutic or other anti-cancer agents include, for example, antimetabolites (including, without limitation, folic acid antagonists, pyrimidine analogs, purine analogs and adenosine deaminase inhibitors) such as methotrexate, 5-fluorouracil, floxuridine, cytarabine, 6-mercaptopurine, 6-thioguanine, fludarabine phosphate, pentostatine, and gemcitabine.

Suitable chemotherapeutic or other anti-cancer agents further include, for example, certain natural products and their derivatives (for example, vinca alkaloids, antitumor antibiotics, enzymes, lymphokines and epipodophyllotoxins) such as vinblastine, vincristine, vindesine, bleomycin, dactinomycin, daunorubicin, doxorubicin, epirubicin, idarubicin, ara-C, paclitaxel (TAXOL™), mithramycin, deoxycoformycin, mitomycin-C, L-asparaginase, interferons (especially IFN-a), etoposide, and teniposide.

Other cytotoxic agents include navelbene, CPT-11, anastrazole, letrazole, capecitabine, reloxafine, cyclophosphamide, ifosamide, and droloxafine.

Also suitable are cytotoxic agents such as epidophyllotoxin; an antineoplastic enzyme; a topoisomerase inhibitor; procarbazine; mitoxantrone; platinum coordination complexes such as cis-platin and carboplatin; biological response modifiers; growth inhibitors; antihormonal therapeutic agents; leucovorin; tegafur; and haematopoietic growth factors.

Other anti-cancer agent(s) include antibody therapeutics such as trastuzumab (Herceptin), antibodies to costimulatory molecules such as CTLA-4, 4-1BB, PD-1, and PD-L1 or antibodies to cytokines (IL-10, TGF-β, etc.).

Other anti-cancer agents include CSF1R inhibitors (PLX3397, LY3022855, etc.) and CSF1R antibodies (IMC-CS4, RG7155, etc).

Other anti-cancer agents include BET inhibitors (INCB054329, OTX015, CPI-0610, etc.), LSD1 inhibitors (GSK2979552, INCB059872, etc), HDAC inhibitors (panobinostat, vorinostat, etc), DNA methyl transferase inhibitors (azacitidine and decitabine), and other epigenetic modulators.

Other anti-cancer agents include Bcl2 inhibitor ABT-199, and other Bcl-2 family protein inhibitors.

Other anti-cancer agents include TGF beta receptor kinase inhibitor such as LY2157299.

Other anti-cancer agents include BTK inhibitor such as ibrutinib.

Other anti-cancer agents include beta catenin pathway inhibitors, notch pathway inhibitors and hedgehog pathway inhibitors.

Other anti-cancer agents include inhibitors of kinases associated cell proliferative disorder. These kinases include but not limited to Aurora-A, CDK1, CDK2, CDK3, CDK5, CDK7, CDK8, CDK9, ephrin receptor kinases, CHK1, CHK2, SRC, Yes, Fyn, Lck, Fer, Fes, Syk, Itk, Bmx, GSK3, JNK, PAK1, PAK2, PAK3, PAK4, PDK1, PKA, PKC, Rsk and SGK.

Other anti-cancer agents also include those that block immune cell migration such as antagonists to chemokine receptors, including CCR2 and CCR4.

Other anti-cancer agents also include those that augment the immune system such as adjuvants or adoptive T cell transfer.

Anti-cancer vaccines include dendritic cells, synthetic peptides, DNA vaccines and recombinant viruses.

One or more additional immune checkpoint inhibitors can be used in combination with a compound as described herein for treatment of TAM-associated diseases, disorders or conditions. Exemplary immune checkpoint inhibitors include inhibitors against immune checkpoint molecules such as CD27, CD28, CD40, CD122, CD96, CD73, CD47, OX40, GITR, CSF1R, JAK, PI3K delta, PI3K gamma, TAM, arginase, CD137 (also known as 4-1BB), ICOS, A2AR, B7-H3, B7-H4, BTLA, CTLA-4, LAG3, TIM3, VISTA, CD96, TIGIT, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, CD96, TIGIT and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), pidilizumab, SHR-1210, PDR001, or AMP-224. In some embodiments, the anti-PD-1 monoclonal antibody is nivolumab, pembrolizumab or PDR001. In some embodiments, the anti-PD1 antibody is pembrolizumab.

In some embodiments, the inhibitor of an immune checkpoint molecule is an inhibitor of PD-L1, e.g., an anti-PD-L1 monoclonal antibody. In some embodiments, the anti-PD-L1 monoclonal antibody is BMS-935559, MEDI4736, MPDL3280A (also known as RG7446), or MSB0010718C. In some embodiments, the anti-PD-L1 monoclonal antibody is MPDL3280A (atezolizumab) or MEDI4736 (durvalumab).

In some embodiments, the inhibitor of an immune checkpoint molecule is an inhibitor of CTLA-4, e.g., an anti-CTLA-4 antibody. In some embodiments, the anti-CTLA-4 antibody is ipilimumab or tremelimumab.

In some embodiments, the inhibitor of an immune checkpoint molecule is an inhibitor of LAG3, e.g., an anti-LAG3 antibody. In some embodiments, the anti-LAG3 antibody is BMS-986016 or LAG525.

In some embodiments, the inhibitor of an immune checkpoint molecule is an inhibitor of GITR, e.g., an anti-GITR antibody. In some embodiments, the anti-GITR antibody is TRX518, MK-4166, INCAGN01876 or MK-1248.

In some embodiments, the inhibitor of an immune checkpoint molecule is an inhibitor of OX40, e.g., an anti-OX40 antibody or OX40L fusion protein. In some embodiments, the anti-OX40 antibody is MEDI0562, INCAGN01949, GSK2831781, GSK-3174998, MOXR-0916, PF-04518600 or LAG525. In some embodiments, the OX40L fusion protein is MEDI6383.

Compounds of the present disclosure can be used in combination with one or more agents for the treatment of diseases such as cancer. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

The compounds of the present application can be used in combination with a selective JAK1 inhibitor. As used herein, a "selective JAK1 inhibitor" is an inhibitor of JAK1 which is selective for JAK1 over JAK2, JAK3 and TYK2. In some embodiments, the compounds or salts are about 10-fold more selective for JAK1 over JAK2. In some embodiments, the compounds or salts are about 10-fold, about 15-fold, or about 20-fold more selective for JAK1 over JAK2 as calculated by measuring $IC_{50}$ at 1 mM ATP (e.g., see Example A).

In some embodiments, the selective JAK1 inhibitor is a compound of Table A, or a pharmaceutically acceptable salt thereof. The compounds in Table A are selective JAK1 inhibitors (selective over JAK2, JAK3, and TYK2). The $IC_{50}$s obtained by the method of Assay A at 1 mM ATP as described in the US Patent Publications in Table A.

TABLE A

| # | Source | Name | Structure | JAK1 $IC_{50}$ (nM) | JAK2/JAK1 |
|---|---|---|---|---|---|
| 1 | US 2014/0121198 | ((2R,5S)-5-{2-[(1R)-1-hydroxyethyl]-1H-imidazo[4,5-d]thieno[3,2-b]pyridin-1-yl}tetrahydro-2H-pyran-2-yl)acetonitrile | 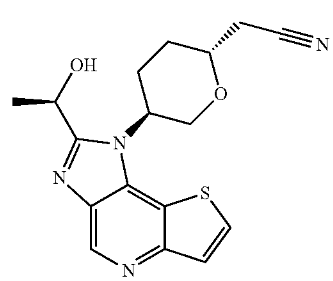 [SMILES: C[C@@H](O)c1nc2cnc3ccsc3c2n1[C@H]1CC[C@H](CC#N)OC1] | ++ | >10 |

TABLE A-continued

| # | Source | Name | Structure | JAK1 IC$_{50}$ (nM) | JAK2/JAK1 |
|---|---|---|---|---|---|
| 2 | US 2014/0121198 | 4-[3-(cyanomethyl)-3-(3',5'-dimethyl-1H,1'H-4,4'-bipyrazol-1-yl)azetidin-1-yl]-2,5-difluoro-N-[(1S)-2,2,2-trifluoro-1-methylethyl]benzamide | 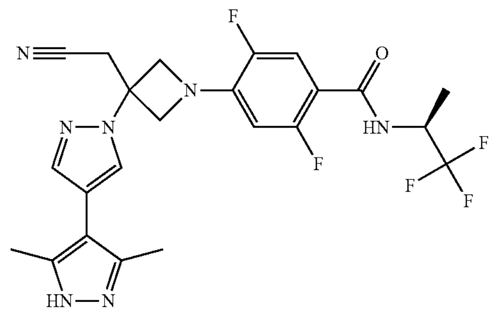 [SMILES: Cc1n[nH]c(C)c1-c1cnn(C2(CC#N)CN(c3cc(F)c(C(=O)N[C@@H](C)C(F)(F)F)cc3F)C2)c1] | +++ | >10 |
| 3 | US 2010/0298334 (Example 2)$^a$ | 3-[1-(6-chloropyridin-2-yl)pyrrolidin-3-yl]-3-[4-(7H-pyrrolo[2,3-d]pyrimidin-4-yl)-1H-pyrazol-1-yl]propanenitrile | 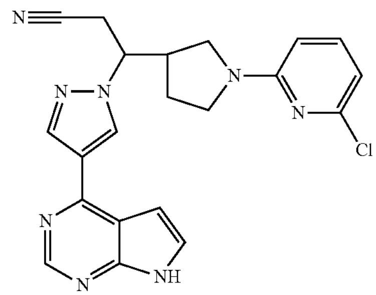 [SMILES: N#CCC(C1CCN(c2cccc(Cl)n2)C1)n1cc(-c2ncnc3[nH]ccc23)cn1] | + | >10 |
| 4 | US 2010/0298334 (Example 13c) | 3-(1-[1,3]oxazolo[5,4-b]pyridin-2-ylpyrrolidin-3-yl)-3-[4-(7H-pyrrolo[2,3-d]pyrimidin-4-yl)-1H-pyrazol-1-yl]propanenitrile | 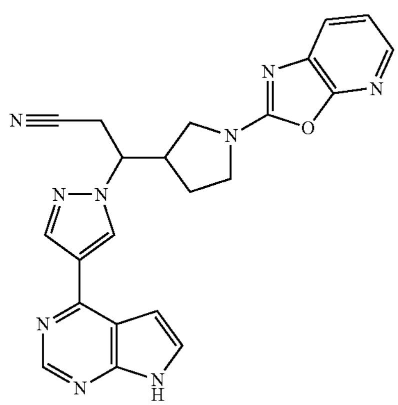 [SMILES: N#CCC(C1CCN(c2nc3cccnc3o2)C1)n1cc(-c2ncnc3[nH]ccc23)cn1] | + | >10 |
| 5 | US 2011/0059951 (Example 12) | 4-[(4-{3-cyano-2-[4-(7H-pyrrolo[2,3-d]pyrimidin-4-yl)-1H-pyrazol-1-yl]propyl}piperazin-1-yl)carbonyl]-3-fluorobenzonitrile | 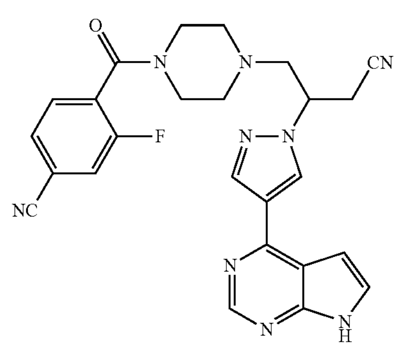 [SMILES: N#CCC(CN1CCN(C(=O)c2ccc(C#N)cc2F)CC1)n1cc(-c2ncnc3[nH]ccc23)cn1] | + | >10 |

TABLE A-continued

| # | Source | Name | Structure | JAK1 IC$_{50}$ (nM) | JAK2/JAK1 |
|---|---|---|---|---|---|
| 6 | US 2011/0059951 (Example 13) | 4-[(4-{3-cyano-2-[3-(7H-pyrrolo[2,3-d]pyrimidin-4-yl)-1H-pyrrol-1-yl]propyl}piperazin-1-yl)carbonyl]-3-fluorobenzonitrile | 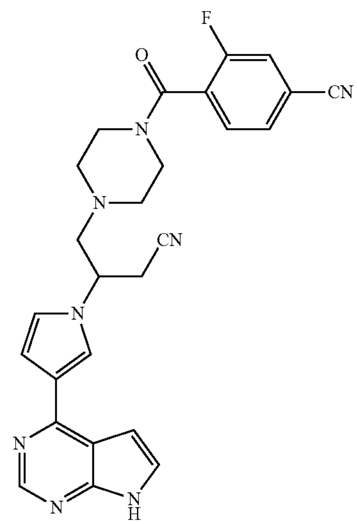 [SMILES: N#CCC(CN1CCN(C(=O)c2ccc(C#N)cc2F)CC1)n1ccc(-c2ncnc3[nH]ccc23)c1] | + | >10 |
| 7 | US 2011/0224190 (Example 1) | {1-{1-[3-Fluoro-2-(trifluoromethyl)isonicotinoyl]piperidin-4-yl}-3-[4-(7H-pyrrolo[2,3-d]pyrimidin-4-yl)-1H-pyrazol-1-yl]azetidin-3-yl}acetonitrile | 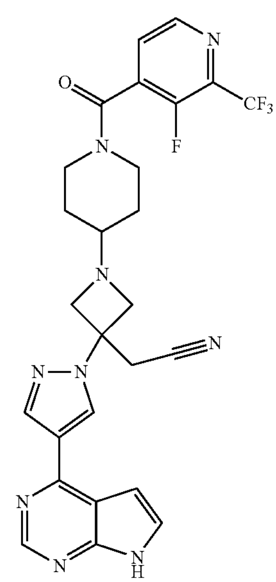 [SMILES: N#CCC1(n2cc(-c3ncnc4[nH]ccc34)cn2)CN(C2CCN(C(=O)c3ccnc(C(F)(F)F)c3F)CC2)C1] | + | >10 |

TABLE A-continued

| # | Source | Name | Structure | JAK1 IC$_{50}$ (nM) | JAK2/JAK1 |
|---|---|---|---|---|---|
| 8 | US 2011/0224190 (Example 154) | 4-{3-(Cyanomethyl)-3-[4-(7H-pyrrolo[2,3-d]pyrimidin-4-yl)-1H-pyrazol-1-yl]azetidin-1-yl}-N-[4-fluoro-2-(trifluoromethyl)phenyl]piperidine-1-carboxamide | 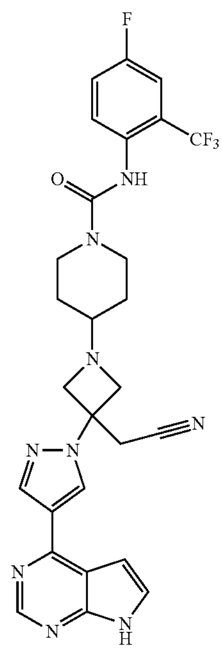 [SMILES: N#CCC1(n2cc(-c3ncnc4[nH]ccc34)cn2)CN(C2CCN(C(=O)Nc3ccc(F)cc3C(F)(F)F)CC2)C1] | + | >10 |
| 9 | US 2011/0224190 (Example 85) | [3-[4-(7H-pyrrolo[2,3-d]pyrimidin-4-yl)-1H-pyrazol-1-yl]-1-(1-{[2-(trifluoromethyl)pyrimidin-4-yl]carbonyl}piperidin-4-yl)azetidin-3-yl]acetonitrile | 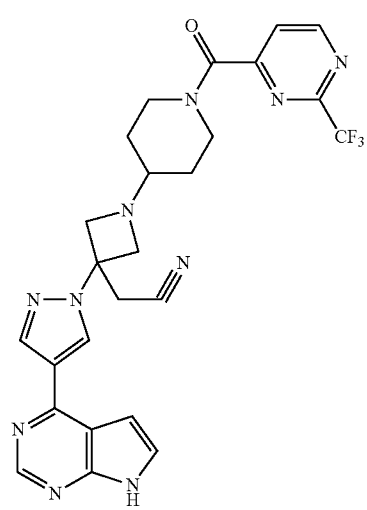 [SMILES: N#CCC1(n2cc(-c3ncnc4[nH]ccc34)cn2)CN(C2CCN(C(=O)c3ccnc(C(F)(F)F)n3)CC2)C1] | + | >10 |

TABLE A-continued

| # | Source | Name | Structure | JAK1 IC$_{50}$ (nM) | JAK2/JAK1 |
|---|---|---|---|---|---|
| 10 | US 2012/0149681 (Example 7b) | [trans-1-[4-(7H-pyrrolo[2,3-d]pyrimidin-4-yl)-1H-pyrazol-1-yl]-3-(4-{[2-(trifluoromethyl)pyrimidin-4-yl]carbonyl}piperazin-1-yl)cyclobutyl]acetonitrile | 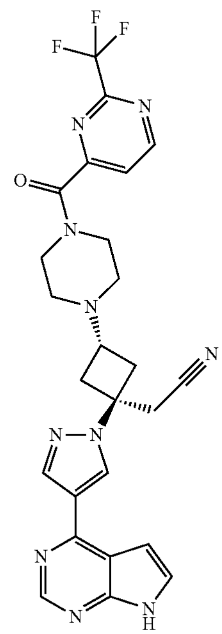 [SMILES: N#CC[C@]1(n2cc(-c3ncnc4[nH]ccc34)cn2)C[C@H](N2CCN(C(=O)c3ccnc(C(F)(F)F)n3)CC2)C1] | + | >10 |
| 11 | US 2012/0149681 (Example 157) | {trans-3-(4-{[4-[(3-hydroxyazetidin-1-yl)methyl]-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 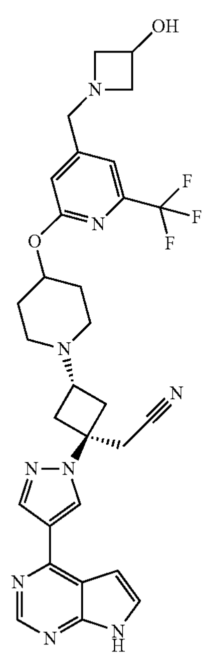 [SMILES: N#CC[C@]1(n2cc(-c3ncnc4[nH]ccc34)cn2)C[C@H](N2CCC(Oc3cc(CN4CC(O)C4)cc(C(F)(F)F)n3)CC2)C1] | + | >10 |

TABLE A-continued

| # | Source | Name | Structure | JAK1 IC$_{50}$ (nM) | JAK2/JAK1 |
|---|---|---|---|---|---|
| 12 | US 2012/0149681 (Example 161) | {trans-3-(4-{[4-{[(2S)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 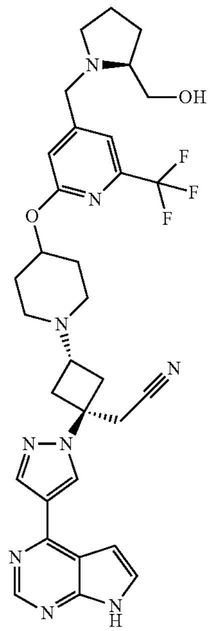 [SMILES: N#CC[C@]1(n2cc(-c3ncnc4[nH]ccc34)cn2)C[C@H](N2CCC(Oc3cc(CN4CCC[C@H]4CO)cc(C(F)(F)F)n3)CC2)C1] | + | >10 |
| 13 | US 2012/0149681 (Example 162) | {trans-3-(4-{[4-{[(2R)-2-(hydroxymethyl)pyrrolidin-1-yl]methyl}-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 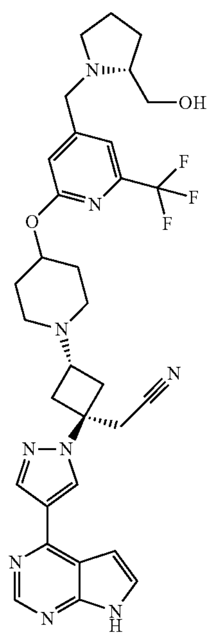 [SMILES: N#CC[C@]1(n2cc(-c3ncnc4[nH]ccc34)cn2)C[C@H](N2CCC(Oc3cc(CN4CCC[C@@H]4CO)cc(C(F)(F)F)n3)CC2)C1] | + | >10 |
| 14 | US 2012/0149682 (Example 20)[b] | 4-(4-{3-[(dimethylamino)methyl]-5-fluorophenoxy}piperidin-1-yl)-3-[4-(7H-pyrrolo[2,3-d]pyrimidin-4-yl)-1H-pyrazol-1-yl]butanenitrile | 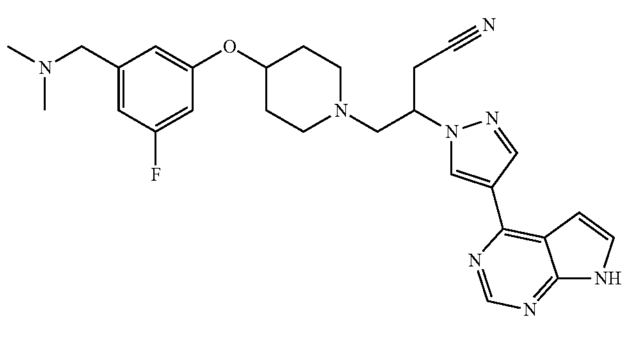 [SMILES: CN(C)Cc1cc(F)cc(OC2CCN(CC(CC#N)n3cc(-c4ncnc5[nH]ccc45)cn3)CC2)c1] | + | >10 |

TABLE A-continued

| # | Source | Name | Structure | JAK1 IC$_{50}$ (nM) | JAK2/JAK1 |
|---|---|---|---|---|---|
| 15 | US 2013/0018034 (Example 18) | 5-{3-(cyanomethyl)-3-[4-(7H-pyrrolo[2,3-d]pyrimidin-4-yl)-1H-pyrazol-1-yl]azetidin-1-yl}-N-isopropylpyrazine-2-carboxamide | 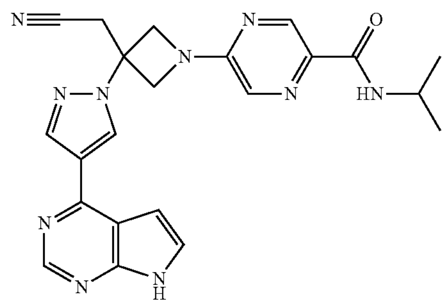 [SMILES: CC(C)NC(=O)c1cnc(N2CC(CC#N)(n3cc(-c4ncnc5[nH]ccc45)cn3)C2)cn1] | + | >10 |
| 16 | US 2013/0018034 (Example 28) | 4-{3-(cyanomethyl)-3-[4-(7H-pyrrolo[2,3-d]pyrimidin-4-yl)-1H-pyrazol-1-yl]azetidin-1-yl}-2,5-difluoro-N-[(1S)-2,2,2-trifluoro-1-methylethyl]benzamide | 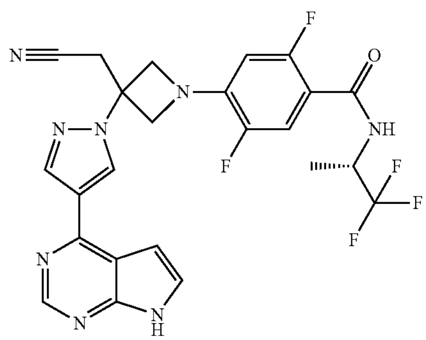 [SMILES: C[C@H](NC(=O)c1cc(F)c(N2CC(CC#N)(n3cc(-c4ncnc5[nH]ccc45)cn3)C2)cc1F)C(F)(F)F] | + | >10 |
| 17 | US 2013/0018034 (Example 34) | 5-{3-(cyanomethyl)-3-[4-(1H-pyrrolo[2,3-b]pyridin-4-yl)-1H-pyrazol-1-yl]azetidin-1-yl}-N-isopropylpyrazine-2-carboxamide | 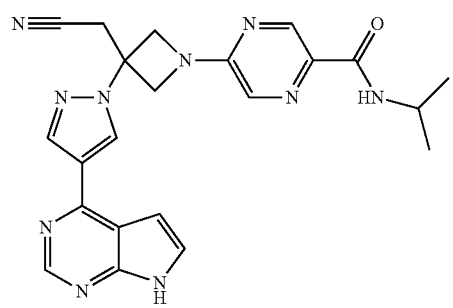 [SMILES: CC(C)NC(=O)c1cnc(N2CC(CC#N)(n3cc(-c4ncnc5[nH]ccc45)cn3)C2)cn1] | + | >10 |
| 18 | US 2013/0045963 (Example 45) | {1-(cis-4-{[6-(2-hydroxyethyl)-2-(trifluoromethyl)pyrimidin-4-yl]oxy}cyclohexyl)-3-[4-(7H-pyrrolo[2,3-d]pyrimidin-4-yl)-1H-pyrazol-1-yl]azetidin-3-yl}acetonitrile | 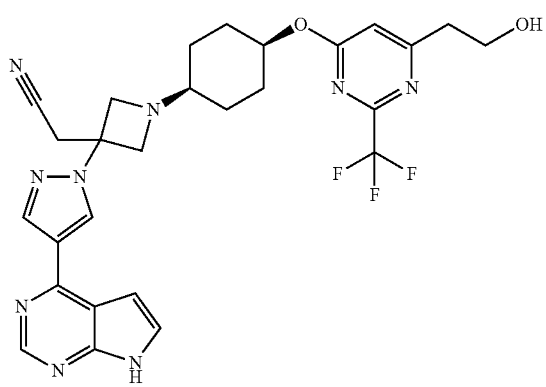 [SMILES: N#CCC1(n2cc(-c3ncnc4[nH]ccc34)cn2)CN([C@H]2CC[C@@H](Oc3cc(CCO)nc(C(F)(F)F)n3)CC2)C1] | + | >10 |

TABLE A-continued

| # | Source | Name | Structure | JAK1 IC$_{50}$ (nM) | JAK2/JAK1 |
|---|--------|------|-----------|---------------------|-----------|
| 19 | US 2013/0045963 (Example 65) | {1-(cis-4-{[4-[(ethylamino)methyl]-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 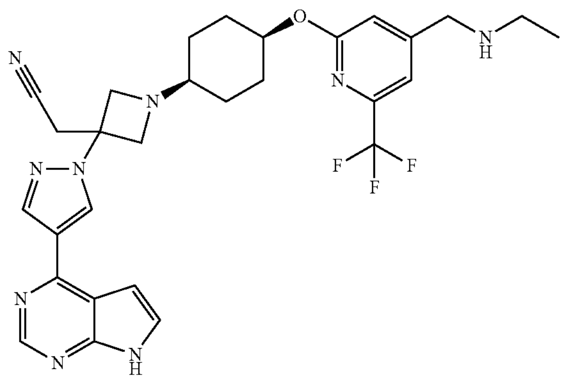 [SMILES: CCNCc1cc(O[C@H]2CC[C@@H](N3CC(CC#N)(n4cc(-c5ncnc6[nH]ccc56)cn4)C3)CC2)nc(C(F)(F)F)c1] | + | >10 |
| 20 | US 2013/0045963 (Example 69) | {1-cis-4-{[4-(1-hydroxy-1-methylethyl)-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}aceionitrile | 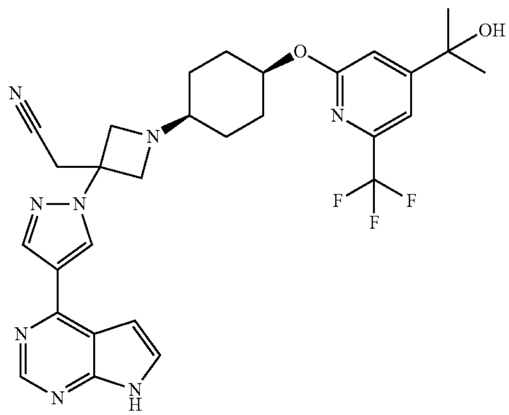 [SMILES: CC(C)(O)c1cc(O[C@H]2CC[C@@H](N3CC(CC#N)(n4cc(-c5ncnc6[nH]ccc56)cn4)C3)CC2)nc(C(F)(F)F)c1] | + | >10 |
| 21 | US 2013/0045963 (Example 95) | {1-(cis-4-{[4-{[(3R)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl}acetonitrile | 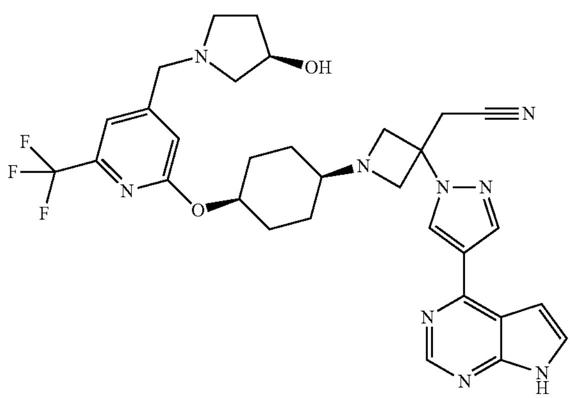 [SMILES: N#CCC1(n2cc(-c3ncnc4[nH]ccc34)cn2)CN([C@H]2CC[C@@H](Oc3cc(CN4CC[C@@H](O)C4)cc(C(F)(F)F)n3)CC2)C1] | + | >10 |
| 22 | US 2013/0045963 (Example 95) | {1-(cis-4-{[4-{[(3S)-3-hydroxypyrrolidin-1-yl]methyl}-6-(trifluoromethyl)pyridin-2-yl]oxy}cyclohexyl)-3-[4-(7H-pyrrolo[2,3-d]pyrimidin-4-yl)-1H-pyrazol-1-yl]azetidin-3-yl jacetonitrile | 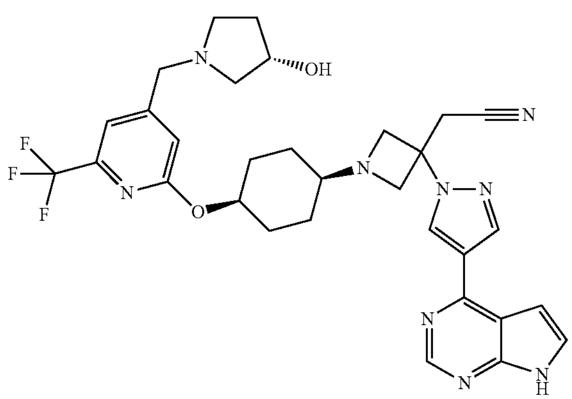 [SMILES: N#CCC1(n2cc(-c3ncnc4[nH]ccc34)cn2)CN([C@H]2CC[C@@H](Oc3cc(CN4CC[C@H](O)C4)cc(C(F)(F)F)n3)CC2)C1] | + | >10 |

TABLE A-continued

| # | Source | Name | Structure | JAK1 IC$_{50}$ (nM) | JAK2/JAK1 |
|---|---|---|---|---|---|
| 23 | US 2014/0005166 (Example 1) | {trans-3-(4-{[4-({[(1S)-2-hydroxy-1-methylethyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 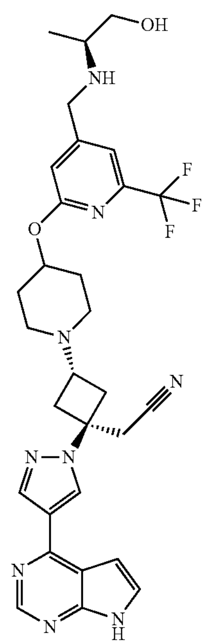 [SMILES: C[C@@H](CO)NCc1cc(OC2CCN([C@H]3C[C@](CC#N)(n4cc(-c5ncnc6[nH]ccc56)cn4)C3)CC2)nc(C(F)(F)F)c1] | + | >10 |
| 24 | US 2014/0005166 (Example 14) | {trans-3-(4-{[4-({[(2R)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl}acetonitrile | 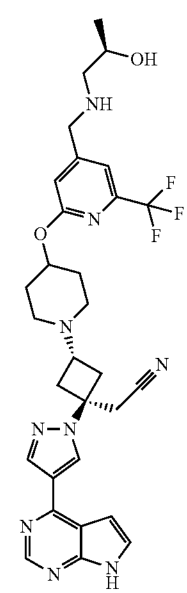 [SMILES: C[C@@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |

TABLE A-continued

| # | Source | Name | Structure | JAK1 IC$_{50}$ (nM) | JAK2/ JAK1 |
|---|---|---|---|---|---|
| 25 | US 2014/ 0005166 (Example 15) | {trans-5-3-(4-{[4-({[(2S)-2-hydroxypropyl]amino}methyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl} acetonitrile | 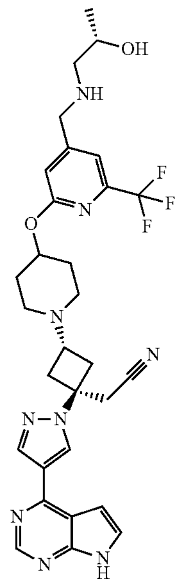 [SMILES: C[C@H](O)CNCc1cc(OC2CCN([C@H]3C[C@](CC#N)(n4cc(-c5ncnc6[nH]ccc56)cn4)C3)CC2)nc(C(F)(F)F)c1] | + | >10 |
| 26 | US 2014/ 0005166 (Example 20) | trans-3-(4-{[4-(2-hydroxyethyl)-6-(trifluoromethyl)pyridin-2-yl]oxy}piperidin-1-yl)-1-[4-(7H-pyrrolo[2,3-d]pyrimidin-4-yl)-1H-pyrazol-1-yl]cyclobutyl} acetonitrile | 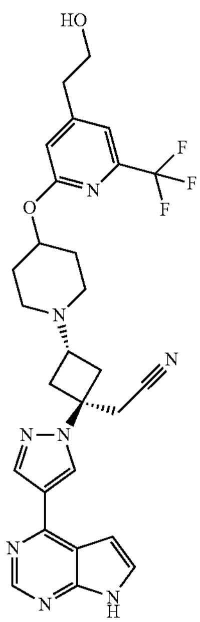 [SMILES: N#CC[C@]1(n2cc(-c3ncnc4[nH]ccc34)cn2)C[C@H](N2CCC(Oc3cc(CCO)cc(C(F)(F)F)n3)CC2)C1] | + | >10 |

+ means <10 nM (see Example A for assay conditions)
++ means ≤100 nM (see Example A for assay conditions)
+++ means ≤300 nM (see Example A for assay conditions)
$^a$Data for enantiomer 1
$^b$Data for enantiomer 2

The compounds of the present application can be used in combination with a PI3Kδ inhibitor. In some embodiments, the PI3Kδ inhibitor is selective. By "selective" is meant that the compound binds to or inhibits a kinase with greater affinity or potency, respectively, compared to at least one other kinase. In some embodiments, the PI3Kδ inhibitors are selective inhibitors of PI3Kδ (e.g., over PI3Kα, PI3Kβ and PI3Kγ). In some embodiments, selectivity can be at least about 2-fold, 5-fold, 10-fold, at least about 20-fold, at least about 50-fold, at least about 100-fold, at least about 200-fold, at least about 500-fold or at least about 1000-fold.

Selectivity can be measured by methods routine in the art. In some embodiments, selectivity can be tested at the K$_m$ ATP concentration of each enzyme. In some embodiments, the selectivity of compounds described herein can be determined by cellular assays associated with particular PI3K kinase activity.

In some embodiments, the inhibitor of PI3Kδ is a compound shown in Table B. The compounds of Table B have been tested in the enzyme assays in the patent publications in Table B and shown to be inhibitors of PI3Kδ with the IC$_{50}$s shown below.

TABLE B

| # | Prep. | Name | Structure | PI3Kδ IC$_{50}$ (nM) |
|---|---|---|---|---|
| 27 | US 2011/0015212 (Example 10) | 7-(1-(9H-purin-6-ylamino)ethyl)-6-(3-fluorophenyl)-3-methyl-5H-thiazolo[3,2-a]pyrimidin-5-one | 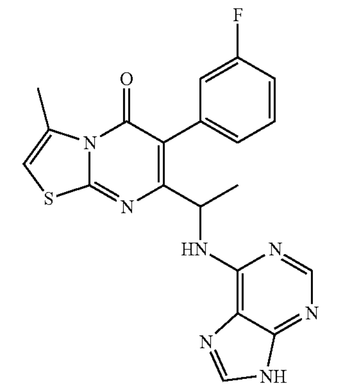 [SMILES: Cc1csc2nc(C(C)Nc3ncnc4[nH]cnc34)c(-c3cccc(F)c3)c(=O)n12] | + |
| 28 | US 2011/0015212 (Example 15) | (S)-7-(1-(9H-purin-6-ylamino)ethyl)-6-(3-fluorophenyl)-3-methyl-5H-thiazolo[3,2-a]pyrimidin-5-one | 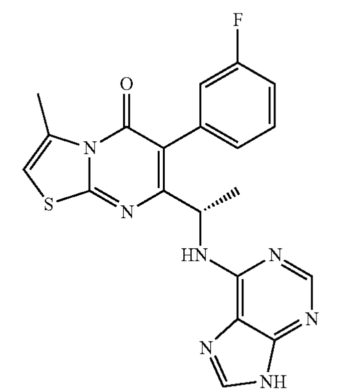 [SMILES: Cc1csc2nc([C@H](C)Nc3ncnc4[nH]cnc34)c(-c3cccc(F)c3)c(=O)n12] | + |
| 29 | US 2013/0059835 (Example 269) | 4-[1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile | 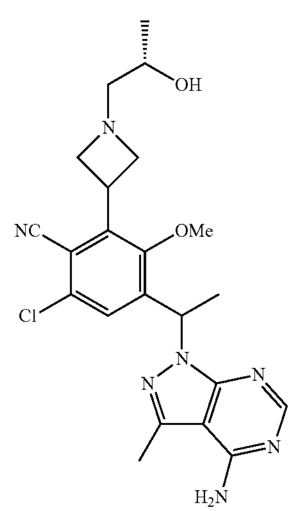 [SMILES: COc1c(C(C)n2nc(C)c3c(N)ncnc32)cc(Cl)c(C#N)c1C1CN(C[C@H](C)O)C1] | + |

TABLE B-continued

| # | Prep. | Name | Structure | PI3Kδ IC$_{50}$ (nM) |
|---|---|---|---|---|
| 30 | US 2013/ 0059835 (Example 268) | 4-[1-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile | 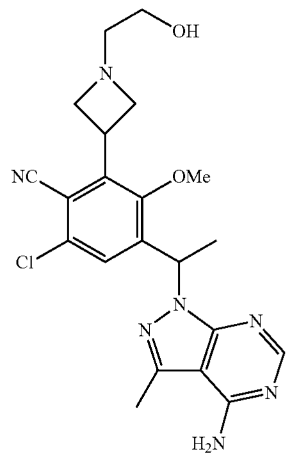 [SMILES: COc1c(C(C)n2nc(C)c3c(N)ncnc32)cc(Cl)c(C#N)c1C1CN(CCO)C1] | + |
| 31 | US 2013/ 0059835 (Example 314) | 5-{3-[1-(4-amino-3-methyl-1H-pyrazolo[3,4 d]pyrimidin-1-yl)ethyl]-6-cyano-2-ethoxy-5-methylphenyl}-N,N-dimethylpyridine-2-carboxamide | 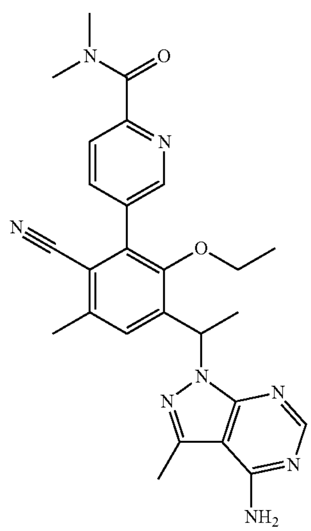 [SMILES: CCOc1c(C(C)n2nc(C)c3c(N)ncnc32)cc(C)c(C#N)c1-c1ccc(C(=O)N(C)C)nc1] | + |
| 32a, 32b, 32c, 32d | US 2013/ 0059835 (Example 345-348 (four diastereomers)) Compound 32a, 32b, 32c, and 32d are Examples 345, 346, 347, and 348 respectively | 4-{3-[1-(4-amino-3-methyl-1H-pyrazolo[3,4 d]pyrimidin-1-yl)ethyl]-5-chloro-2-ethoxy-6-fluorophenyl}pyrrolidin-2-one | 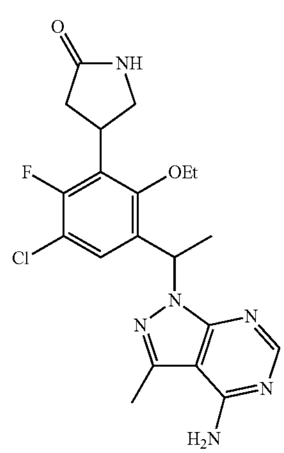 [SMILES: CCOc1c(C(C)n2nc(C)c3c(N)ncnc32)cc(Cl)c(F)c1C1CNC(=O)C1] | 32a (++), 32b (+) 32c (+) 32d (++) |

TABLE B-continued

| # | Prep. | Name | Structure | PI3Kδ IC$_{50}$ (nM) |
|---|---|---|---|---|
| 33 | US 2011/0183985 (Example 17- single enantiomer) | N-{1-[5-chloro-8-(3-fluorophenyl)cinnolin-7-yl]ethyl}-9H-purin-6-amine | 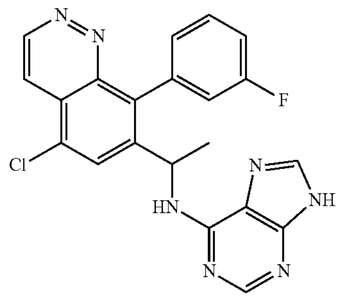 [SMILES: CC(Nc1ncnc2[nH]cnc12)c1cc(Cl)c2ccnnc2c1-c1cccc(F)c1] | + |
| 34 | US 2012/0157430 | 4-chloro-3'-fluoro-3-methyl-6-[1-(9H-purin-6-ylamino)ethyl]biphenyl-2-carbonitrile | 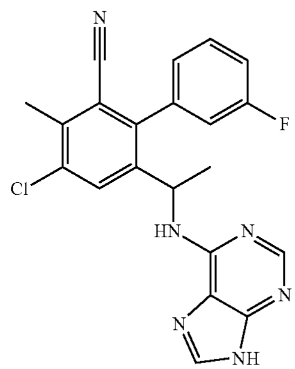 [SMILES: Cc1c(Cl)cc(C(C)Nc2ncnc3[nH]cnc23)c(-c2cccc(F)c2)c1C#N] | +++ |

+ means <50 nM
++ means 50 nM to 200 nM
+++ means 50 nM to 100 nM

In some embodiments, the inhibitor of PI3Kδ is selected from:
(S)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((S)-1-(4-amino-3-methyl-1H-pyrazolo[3,4-d]pyrimidin-1-yl)ethyl)-5-chloro-2-ethoxy-6-fluorophenyl)pyrrolidin-2-one;
(S)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;
(R)-4-(3-((R)-1-(4-amino-3-methyl-1H-pyrazolo[3,4-d]pyrimidin-1-yl)ethyl)-5-chloro-2-ethoxy-6-fluorophenyl)pyrrolidin-2-one;
N-{(1S)-1-[5-chloro-8-(3-fluorophenyl)cinnolin-7-yl]ethyl}-9H-purin-6-amine;
and pharmaceutically acceptable salts of any of the aforementioned.

In some embodiments, the inhibitor of PI3Kδ is (S)-7-(1-(9H-purin-6-ylamino)ethyl)-6-(3-fluorophenyl)-3-methyl-5H-thiazolo[3,2-a]pyrimidin-5-one, or a pharmaceutically acceptable salt thereof.

In some embodiments, the inhibitor of PI3Kδ is 4-[1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile, or a pharmaceutically acceptable salt thereof.

In some embodiments, the inhibitor of PI3Kδ is 4-[1-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile, or a pharmaceutically acceptable salt thereof.

In some embodiments, the inhibitor of PI3Kδ is 5-{3-[1-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide, or a pharmaceutically acceptable salt thereof.

In some embodiments, the inhibitor of PI3Kδ is selected from:
4-[(R)-1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile;
4-[1 (R)-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile;
5-{3-[1 (R)-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide;
4-[(S)-1-(4-amino-3-methyl-1H-pyrazolo[3,4-d]pyrimidin-1-yl)ethyl]-6-chloro-2-{1-[(2S)-2-hydroxypropyl]azetidin-3-yl}-3-methoxybenzonitrile;
4-[1 (S)-(4-amino-3-methyl-1H-pyrazolo[3,4-d]pyrimidin-1-yl)ethyl]-6-chloro-2-[1-(2-hydroxyethyl)azetidin-3-yl]-3-methoxybenzonitrile;
5-{3-[1(S)-(4-amino-3-methyl-1H-pyrazolo[3,4-d]pyrimidin-1-yl)ethyl]-6-cyano-2-ethoxy-5-methylphenyl}-N,N-dimethylpyridine-2-carboxamide;
and pharmaceutically acceptable salts of any of the aforementioned.

Pharmaceutical Formulations and Dosage Forms

When employed as pharmaceuticals, the compounds of the invention can be administered in the form of pharmaceutical compositions which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh.

The Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid pre-formulation composition containing a homogeneous mixture of a compound of the present invention. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.1 to about 500 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

The Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compounds of the invention can also be formulated in combination with one or more additional active ingredients which can include any pharmaceutical agent such as antiviral agents, vaccines, antibodies, immune enhancers, immune suppressants, anti-inflammatory agents and the like.

Labeled Compounds and Assay Methods

Another aspect of the present invention relates to fluorescent dye, spin label, heavy metal or radio-labeled compounds of the invention that would be useful not only in imaging but also in assays, both in vitro and in vivo, for localizing and quantitating the TAM kinases in tissue samples, including human, and for identifying TAM kinases ligands by inhibition binding of a labeled compound. Accordingly, the present invention includes TAM kinases assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^2$H (also written as D for deuterium), $^3$H (also written as T for tritium), $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro TAM kinases labeling and competition assays, compounds that incorporate $^3$H, $^{14}$C, $^{82}$Br, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled" or "labeled compound" is a compound that has incorporated at least one radionuclide. In some embodiments the radionuclide is selected from the group consisting of $^3$H, $^{14}$C, $^{125}$, $^{35}$S and $^{82}$Br.

Synthetic methods for incorporating radio-isotopes into organic compounds are applicable to compounds of the invention and are well known in the art.

A radio-labeled compound of the invention can be used in a screening assay to identify/evaluate compounds. In general terms, a newly synthesized or identified compound (i.e., test compound) can be evaluated for its ability to reduce binding of the radio-labeled compound of the invention to the TAM kinases. Accordingly, the ability of a test compound to compete with the radio-labeled compound for binding to the TAM kinases directly correlates to its binding affinity.

Kits

The present invention also includes pharmaceutical kits useful, for example, in the treatment or prevention of TAM-associated diseases or disorders, obesity, diabetes and other diseases referred to herein which include one or more containers containing a pharmaceutical composition comprising a therapeutically effective amount of a compound of the invention. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of TAM kinases as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.*, 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.*, 5, 670 (2003); and "Preparative LC-MS Purification: Improved Compound Specific Method Optimization", K. Blom, B. Glass, R. Sparks, A. Combs, *J. Combi. Chem.*, 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 m particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with the 30×100 mm column was 60 mL/minute.

pH=10 purifications: Waters XBridge $C_{18}$ 5 m particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, *J. Comb. Chem.*, 6, 874-883 (2004)]. Typically, the flow rate used with 30×100 mm column was 60 mL/minute.

Example 1

1-{2-[5-(7H-Pyrrolo[2,3-d]pyrimidin-4-yl)pyridin-3-yl]-2,3-dihydro-1H-inden-2-yl}methanamine

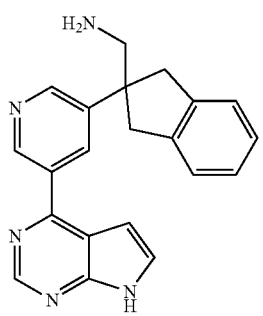 [SMILES: NCC1(c2cncc(-c3ncnc4[nH]ccc34)c2)Cc2ccccc2C1]

Step 1. 4-Chloro-7-{[2-(trimethylsilyl)ethoxy]methyl}-7H-pyrrolo[2,3-d]pyrimidine

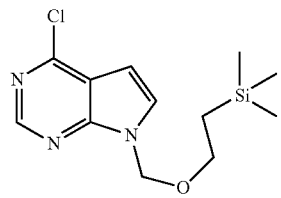 [SMILES: C[Si](C)(C)CCOCn1ccc2c(Cl)ncnc21]

At 0° C. to a suspension of sodium hydride (5.2 g, 130 mmol) in N,N-dimethylformamide (200 mL) was added 4-chloropyrrolo[2,3-d]pyrimidine (from Aldrich, 16.6 g, 108 mmol) portionwise with stirring. The reaction mixture was stirred at this temperature for 1 hour. Then to the reaction mixture was added dropwise neat [β-(trimethylsilyl)ethoxy]methyl chloride (23 mL, 130 mmol) at 0° C. with stirring. After completion of addition the reaction mixture was stirred and gradually warmed up to room temperature (1.5 hour). The reaction mixture was diluted with ethyl ether and quenched with saturated $NaHCO_3$ solution. After layers separation the organic layer was washed with water and brine once, then concentrated in vacuo. The residue was purified on silica column (0-10% EtOAc/hexanes) to give the product (29 g, 94%). LCMS cacld for $C_{12}H_{19}ClN_3OSi$ $[M+H]^+$: m/z=284.1. Found: 284.1.

Step 2.
2-(5-Bromopyridin-3-yl)indane-2-carbonitrile

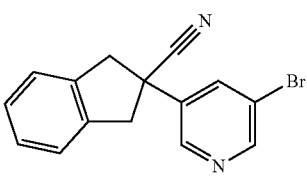 [SMILES: N#CC1(c2cncc(Br)c2)Cc2ccccc2C1]

A solution of (5-bromopyridin-3-yl)acetonitrile (from J&W Pharmlab, 455 mg, 2.31 mmol) in tetrahydrofuran (6 mL) was added dropwise to a suspension of sodium hydride (277 mg, 6.93 mmol) in tetrahydrofuran (6 mL) at 0° C. The reaction mixture was stirred at rt for 10 min, after which time a solution of 1,2-bis(bromomethyl)-benzene (from Aldrich, 609.5 mg, 2.309 mmol) in tetrahydrofuran (6 mL) was added at 0° C. The reaction mixture was heated to 100° C. for 3 h. The reaction mixture was diluted with EtOAc, quenched with saturated aqueous $NaHCO_3$ solution. The organic layer was separated, concentrated and purified on silica gel column (0-10% methanol/dichloromethane) to give the desired product (640 mg, 93%). LCMS cacld for $C_{15}H_{12}BrN_2$ $[M+H]^+$: m/z=299.0. Found: 299.0.

Step 3. 2-[5-(4,4,5,5-Tetramethyl-1,3,2-dioxaborolan-2-yl)pyridin-3-yl]indane-2-carbonitrile

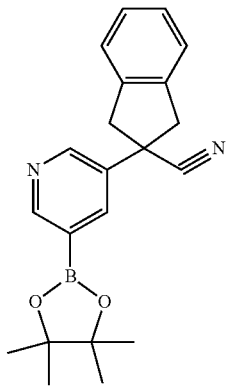 [SMILES: CC1(C)OB(c2cncc(C3(C#N)Cc4ccccc4C3)c2)OC1(C)C]

A mixture of 2-(5-bromopyridin-3-yl)indane-2-carbonitrile (0.10 g, 0.33 mmol), 4,4,5,5,4',4',5',5'-octamethyl-[2,2']bi[[1,3,2]dioxaborolanyl] (0.10 g, 0.40 mmol), potassium acetate (0.066 g, 0.67 mmol) and [1,1'-bis(diphenylphosphino)ferrocene]dichloropalladium (II) (0.024 g, 0.033 mmol) in 1,4-dioxane (1 mL) was vacuumed and refilled $N_2$ for 3 times, then sealed and heated at 95° C. for 2 h. The reaction mixture was cooled, filtered and used in the next step directly. LCMS cacld for $C_{21}H_{24}BN_2O_2[M+H]^+$: m/z=347.2. Found: 347.2.

Step 4. 2-[5-(7-{[2-(Trimethylsilyl)ethoxy]methyl}-1H-pyrrolo[2,3-d]pyrimidin-4-yl)pyridin-3-yl]indane-2-carbonitrile

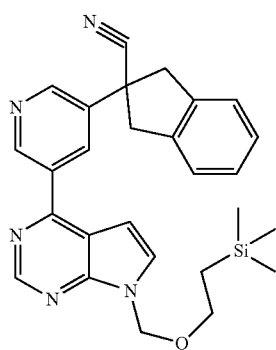

A mixture of 2-[5-(4,4,5,5-tetramethyl-1,3,2-dioxaborolan-2-yl)pyridin-3-yl]indane-2-carbonitrile (0.12 g, 0.35 mmol), 4-chloro-7-{[2-(trimethylsilyl)ethoxy]methyl}-7H-pyrrolo[2,3-d]pyrimidine (0.0984 g, 0.346 mmol), cesium carbonate (0.22 g, 0.69 mmol) and dicyclohexyl(2',4',6'-triisopropylbiphenyl-2-yl)phosphine-(2'-aminobiphenyl-2-yl)(chloro)palladium (1:1) (0.027 g, 0.035 mmol) in 1,4-dioxane (0.4 mL)/water (0.2 mL) was stirred for 1 h at 80° C. The reaction mixture was purified on silica gel column (0-100% EtOAc/hexanes) to give the desired product. LCMS cacld for $C_{27}H_{30}N_5OSi [M+H]^+$: m/z=468.2. Found: 468.3.

Step 5. 1-{2-[5-(7-{[2-(Trimethylsilyl)ethoxy]methyl}-7H-pyrrolo[2,3-d]pyrimidin-4-yl)pyridin-3-yl]-2,3-dihydro-1H-inden-2-yl}methanamine

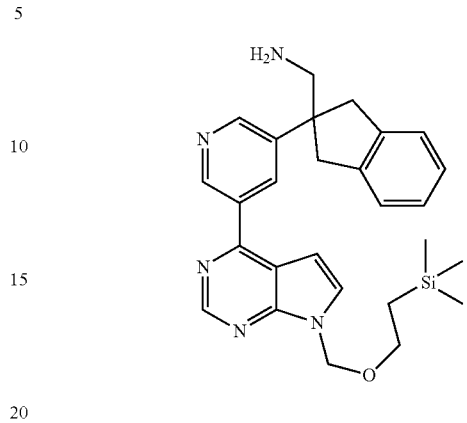

To a solution of 2-[5-(7-{[2-(trimethylsilyl)ethoxy]methyl}-7H-pyrrolo[2,3-d]pyrimidin-4-yl)pyridin-3-yl]indane-2-carbonitrile (36 mg, 0.077 mmol) in tetrahydrofuran (1 mL) at 0° C. was added 1.0 M lithium tetrahydroaluminate in tetrahydrofuran (0.0847 mL, 0.0847 mmol). The reaction mixture was stirred for 1 h. The reaction was quenched with aqueous saturated $NaHCO_3$ solution, extracted with EtOAc. The separated organic layers were combined, washed with water, dried over $MgSO_4$ and concentrated to give the product to be used in the next step directly. LCMS cacld for $C_{27}H_{34}N_5OSi [M+H]^+$: m/z=472.3. Found: 472.3.

Step 6. 1-{2-[5-(7H-Pyrrolo[2,3-d]pyrimidin-4-yl)pyridin-3-yl]-2,3-dihydro-1H-inden-2-yl}methanamine 1-{2-[5-(7-{[2-(Trimethylsilyl)ethoxy]methyl}-7H-pyrrolo[2,3-d]pyrimidin-4-yl)pyridin-3-yl]-2,3-dihydro-1H-inden-2-yl}methanamine (31 mg, 0.066 mmol) was treated with trifluoroacetic acid (0.15 mL, 1.9 mmol) in methylene chloride (0.5 mL) at r.t. for 1 h and then concentrated in vacuo. The crude was re-dissolved in methanol (0.2 mL) and treated with ethylenediamine (0.2 mL, 3 mmol) for 1 h. The mixture was concentrated and purified using RP-HPLC (XBridge™ C18 column, eluting with a gradient of MeCN/water containing 0.1% ammonium hydroxide, at a flow rate of 60 mL/min) to give the desired product (0.7 mg, 3%). LCMS cacld for $C_{21}H_{20}N_5 [M+H]^+$: m/z=342.2. Found: 342.1.

Example 2

1-{2-[6-(7H-Pyrrolo[2,3-d]pyrimidin-4-yl)pyridin-2-yl]-2,3-dihydro-1H-inden-2-yl}methanamine

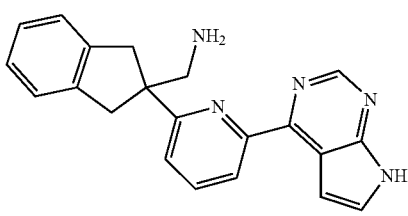 [SMILES: NCC1(c2cccc(-c3ncnc4[nH]ccc34)n2)Cc2ccccc2C1]

Step 1.
2-(6-Bromopyridin-2-yl)indane-2-carbonitrile

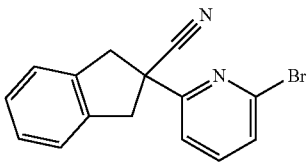 [SMILES: N#CC1(c2cccc(Br)n2)Cc2ccccc2C1]

A solution of (6-bromopyridin-2-yl)acetonitrile (from Anichem, 270 mg, 1.4 mmol) in tetrahydrofuran (4 mL) was added dropwise to a suspension of sodium hydride (164 mg, 4.11 mmol) in tetrahydrofuran (4 mL) at 0° C. The reaction mixture was stirred at r.t. for 10 min, after which time a solution of 1,2-bis(bromomethyl)-benzene (361.7 mg, 1.370 mmol) in tetrahydrofuran (4 mL) was added at 0° C. The reaction mixture was heated to 100° C. for 3 h. The reaction mixture was cooled, diluted with EtOAc, quenched with saturated aqueous NaHCO$_3$ solution. The organic layer was separated, concentrated and purified on silica gel column (0-10% methanol/dichloromethane) to give the desired product (230 mg, 56%). LCMS cacld for $C_{15}H_{12}BrN_2$ [M+H]$^+$: m/z=299.0. Found: 299.0.

Step 2. 2-[6-(4,4,5,5-Tetramethyl-1,3,2-dioxaborolan-2-yl)pyridin-2-yl]indane-2-carbonitrile

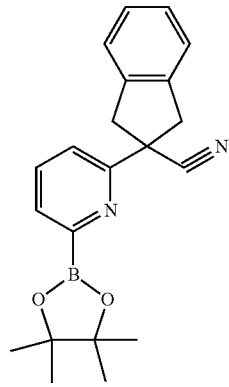 [SMILES: CC1(C)OB(c2cccc(C3(C#N)Cc4ccccc4C3)n2)OC1(C)C]

A mixture of 2-(6-bromopyridin-2-yl)indane-2-carbonitrile (0.19 g, 0.64 mmol), 4,4,5,5,4',4',5',5'-octamethyl-[2,2']bi[[1,3,2]dioxaborolanyl] (0.19 g, 0.76 mmol), potassium acetate (0.12 g, 1.3 mmol) and [1,1'-bis(diphenylphosphino)ferrocene]dichloropalladium (II) (0.046 g, 0.064 mmol) in 1,4-dioxane (2 mL) was vacuumed and refilled N$_2$ for 3 times, then sealed and heated at 95° C. for 2 h. The reaction mixture was filtered and filtrate was used in the next step directly. LCMS cacld for $C_{21}H_{24}BN_2O_2$ [M+H]$^+$: m/z=347.2. Found: 347.2.

Step 3. 2-[6-(7-{[2-(Trimethylsilyl)ethoxy]methyl}-1H-pyrrolo[2,3-d]pyrimidin-4-yl)pyridin-2-yl]indane-2-carbonitrile

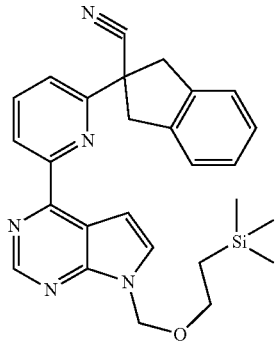

A mixture of 2-[6-(4,4,5,5-tetramethyl-1,3,2-dioxaborolan-2-yl)pyridin-2-yl]indane-2-carbonitrile (0.22 g, 0.64 mmol), 4-chloro-7-{[2-(trimethylsilyl)ethoxy]methyl}-7H-pyrrolo[2,3-d]pyrimidine (Prepared in Example 1, Step 1; 0.180 g, 0.635 mmol), cesium carbonate (0.41 g, 1.3 mmol) and dicyclohexyl(2',4',6'-triisopropylbiphenyl-2-yl)phosphine-(2'-aminobiphenyl-2-yl)(chloro)palladium (1:1) (0.050 g, 0.064 mmol) in 1,4-dioxane (0.8 mL)/water (0.4 mL) was stirred for 2 h at 60° C. The reaction mixture was purified on silica gel column (0-100% EtOAc/hexanes) to give the desired product (170 mg, 57%). LCMS cacld for $C_{27}H_{30}N_5OSi$ [M+H]$^+$: m/z=468.2. Found: 468.2.

Step 4. 1-{2-[6-(7-{[2-(Trimethylsilyl)ethoxy]methyl}-7H-pyrrolo[2,3-d]pyrimidin-4-yl)pyridin-2-yl]-2,3-dihydro-1H-inden-2-yl}methanamine

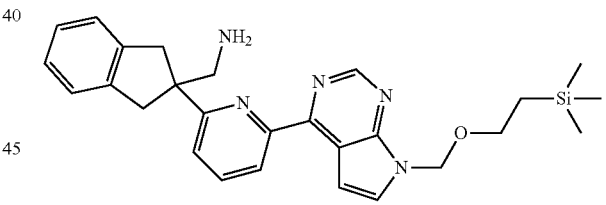

To a solution of 2-[6-(7-{[2-(trimethylsilyl)ethoxy]methyl}-7H-pyrrolo[2,3-d]pyrimidin-4-yl)pyridin-2-yl]indane-2-carbonitrile (1.70×10$^2$ mg, 0.364 mmol) in tetrahydrofuran (7 mL) at 0° C. was added 1.0 M lithium tetrahydroaluminate in tetrahydrofuran (0.40 mL, 0.40 mmol). The reaction mixture was stirred for 1 h. The reaction was quenched with aqueous saturated NaHCO$_3$ solution, extracted with EtOAc. The organic extracts were combined, washed with water, dried over MgSO$_4$ and concentrated to give the product to be used in the next step directly. LCMS cacld for $C_{27}H_{34}N_5OSi$ [M+H]$^+$: m/z=472.3. Found: 472.3.

Step 5. 1-{2-[6-(7H-Pyrrolo[2,3-d]pyrimidin-4-yl)pyridin-2-yl]-2,3-dihydro-1H-inden-2-yl}methanamine 1-{2-[6-(7-{[2-(Trimethylsilyl)ethoxy]methyl}-7H-pyrrolo[2,3-d]pyrimidin-4-yl)pyridin-2-yl]-2,3-dihydro-1H-inden-2-yl}methanamine (70 mg, 0.1 mmol) was treated with trifluoroacetic acid (0.3 mL, 4 mmol) in methylene chloride (0.5 mL) at r.t. for 1 h. The reaction mixture was concentrated in vacuo, then treated with ethylenediamine (0.2 mL, 4 mmol) in methanol (0.2 mL, 6 mmol) at r.t. for 1 h. The mixture was purified on prep-LCMS (XBridge™ C18 column, eluting with a gradient of MeCN/water containing 0.1% ammonium hydroxide, at a flow rate of 60 mL/min) to give the desired product (1.8 mg, 4%). LCMS cacld for $C_{21}H_{20}N_5$ [M+H]$^+$: m/z=342.2. Found: 342.2.

Example 3

1-{2-[4-(7H-Pyrrolo[2,3-d]pyrimidin-4-yl)pyridin-2-yl]-2,3-dihydro-1H-inden-2-yl}methanamine

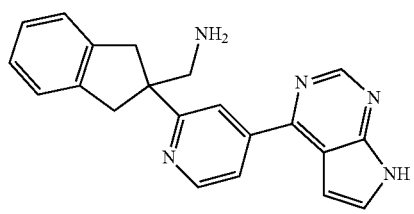

Step 1.
2-(4-Bromopyridin-2-yl)indane-2-carbonitrile

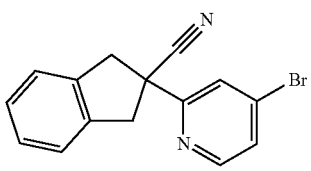 [SMILES: N#CC1(c2cc(Br)ccn2)Cc2ccccc2C1]

A solution of (4-bromopyridin-2-yl)acetonitrile (from Affinity Research Chemicals, 402 mg, 2.04 mmol) in tetrahydrofuran (5 mL) was added dropwise to a suspension of sodium hydride (245 mg, 6.12 mmol) in tetrahydrofuran (5 mL) at 0° C. The reaction mixture was stirred at r.t. for 10 min, after which time a solution of 1,2-bis(bromomethyl)-benzene (538.5 mg, 2.040 mmol) in tetrahydrofuran (5 mL) was added at 0° C. The reaction mixture was heated to 100° C. for 3 h. The reaction mixture was diluted with EtOAc, quenched with saturated aqueous NaHCO$_3$ solution. The organic layer was separated, concentrated and purified on silica gel column (0-10% methanol/dichloromethane) to give the desired product (470 mg, 77%). LCMS cacld for $C_{15}H_{12}BrN_2$ [M+H]$^+$: m/z=299.0. Found: 299.0.

Step 2. 2-[4-(4,4,5,5-Tetramethyl-1,3,2-dioxaborolan-2-yl)pyridin-2-yl]indane-2-carbonitrile

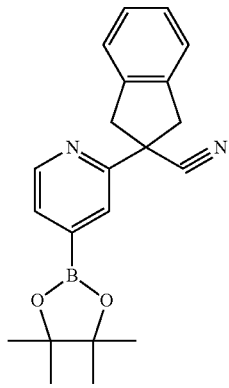 [SMILES: CC1(C)OB(c2ccnc(C3(C#N)Cc4ccccc4C3)c2)OC1(C)C]

A mixture of 2-(4-bromopyridin-2-yl)indane-2-carbonitrile (0.110 g, 0.368 mmol), 4,4,5,5,4',4',5',5'-octamethyl-[2,2']bi[[1,3,2]dioxaborolanyl] (0.11 g, 0.44 mmol), potassium acetate (0.072 g, 0.74 mmol) and [1,1'-bis(diphenylphosphino)ferrocene]dichloropalladium (II) (0.027 g, 0.037 mmol) in 1,4-dioxane (1 mL) was vacuumed and refilled with N$_2$ for 3 times, then sealed and heated at 95° C. for 2 h. The reaction mixture was cooled, filtered and the filtrate was used in the next step directly. LCMS cacld for $C_{21}H_{24}BN_2O_2$ [M+H]$^+$: m/z=347.2. Found: 347.2.

Step 3. 2-[4-(7-{[2-(Trimethylsilyl)ethoxy]methyl}-7H-pyrrolo[2,3-d]pyrimidin-4-yl)pyridin-2-yl]indane-2-carbonitrile

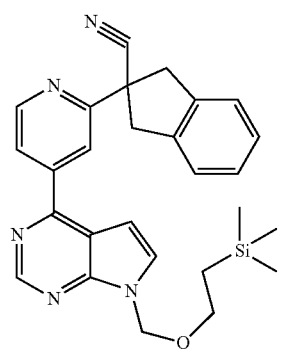 [SMILES: C[Si](C)(C)CCOCn1ccc2c(-c3ccnc(C4(C#N)Cc5ccccc5C4)c3)ncnc21]

A mixture of 2-[4-(4,4,5,5-tetramethyl-1,3,2-dioxaborolan-2-yl)pyridin-2-yl]indane-2-carbonitrile (0.12 g, 0.35 mmol), 4-chloro-7-{[2-(trimethylsilyl)ethoxy]methyl}-7H-pyrrolo[2,3-d]pyrimidine (Prepared in Example 1, Step 1; 0.0984 g, 0.346 mmol), cesium carbonate (0.22 g, 0.69 mmol) and dicyclohexyl(2',4',6'-triisopropylbiphenyl-2-yl)phosphine-(2'-aminobiphenyl-2-yl)(chloro)palladium (1:1) (0.027 g, 0.035 mmol) in 1,4-dioxane (0.4 mL)/water (0.2 mL) was stirred for 2 h at 60° C. The reaction mixture was purified on silica gel column (0-100% EtOAc/hexanes) to give the desired product (70 mg, 43%). LCMS cacld for $C_{27}H_{30}N_5OSi$ [M+H]$^+$: m/z=468.2. Found: 468.2.

Step 4. 1-{2-[4-(7-{[2-(Trimethylsilyl) ethoxy] methyl}-7H-pyrrolo[2,3-d]pyrimidin-4-yl)pyridin-2-yl]-2,3-dihydro-1H-inden-2-yl}methanamine

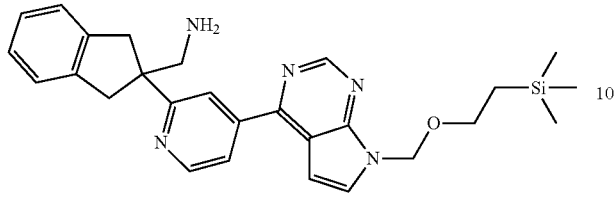

To a solution of 2-[4-(7-{[2-(trimethylsilyl)ethoxy]methyl}-7H-pyrrolo[2,3-d]pyrimidin-4-yl)pyridin-2-yl]indane-2-carbonitrile (70. mg, 0.15 mmol) in tetrahydrofuran (3 mL) at 0° C. was added 1.0 M lithium tetrahydroaluminate in tetrahydrofuran (0.165 mL, 0.165 mmol). The reaction mixture was stirred for 1 h. The reaction mixture was quenched with aqueous saturated NaHCO$_3$ solution, extracted with EtOAc. The organic layers were combined, washed with water, dried over MgSO$_4$ and concentrated to give the product to be used in the next step directly. LCMS cacld for C$_{27}$H$_{34}$N$_5$OSi [M+H]$^+$: m/z=472.3. Found: 472.2.

Step 5. 1-{2-[4-(7H-Pyrrolo[2,3-d]pyrimidin-4-yl)pyridin-2-yl]-2,3-dihydro-1H-inden-2-yl}methanamine 1-{2-[4-(7-{[2-(Trimethylsilyl)ethoxy]methyl}-7H-pyrrolo[2,3-d]pyrimidin-4-yl)pyridin-2-yl]-2,3-dihydro-1H-inden-2-yl}methanamine (70 mg, 0.1 mmol) was treated with trifluoroacetic acid (0.3 mL, 4 mmol) in methylene chloride (0.5 mL) at r.t. for 1 h. The reaction mixture was concentrated in vacuo, then treated with ethylenediamine (0.2 mL, 4 mmol) in methanol (0.2 mL) at r.t. for 1 h. The reaction mixture was purified on prep-LCMS (XBridge™ C18 column, eluting with a gradient of MeCN/water containing 0.1% ammonium hydroxide, at a flow rate of 60 mL/min) to give the desired product (1.3 mg, 2%). LCMS cacld for C$_{21}$H$_{20}$N$_5$ [M+H]$^+$: m/z=342.2. Found: 342.2. $^1$H NMR (DMSO-d$_6$, 500 MHz): δ 12.42 (1H, br s), 8.88 (1H, s), 8.80 (1H, d, J=5.0 Hz), 8.02 (1H, s), 8.01 (1H, s), 7.86 (2H, br s), 7.70 (1H, m), 7.30 (2H, m), 7.21 (2H, m), 6.54 (1H, m), 3.42 (6H, m), ppm.

Example 4

1-{2-[2-(7H-Pyrrolo[2,3-d]pyrimidin-4-yl)pyridin-4-yl]-2,3-dihydro-1H-inden-2-yl}methanamine

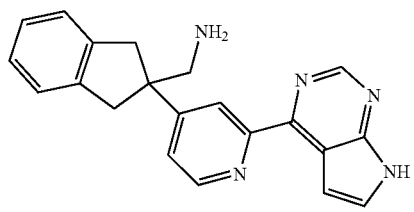 [SMILES: NCC1(c2ccnc(-c3ncnc4[nH]ccc34)c2)Cc2ccccc2C1]

Step 1. (2-Bromopyridin-4-yl)acetonitrile

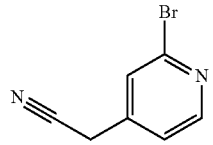

A mixture of 2-bromo-4-methylpyridine (from Aldrich, 5.12 g, 29.8 mmol) and tert-butoxybis(dimethylamino)methane (8.7 g, 50. mmol) was stirred at 110° C. overnight. The reaction solution was cooled and concentrated in vacuo. To the residue hydroxylamine-O-sulfonic acid (10 g, 90 mmol) and water (70 mL) were added and the resulting mixture was stirred at r.t. for 2 h. The reaction mixture was cooled in an ice bath, neutralized with 50% aqueous NaOH solution slowly to pH ~8, and then extracted with EtOAc. The extracts were combined, concentrated and purified on silica gel column (0-80% EtOAc/hexanes) to give the desired product (3 g, 51%). LCMS cacld for C$_7$H$_6$BrN$_2$ [M+H]$^+$: m/z=197.0. Found: 196.9.

Step 2. 2-(2-Bromopyridin-4-yl)indane-2-carbonitrile

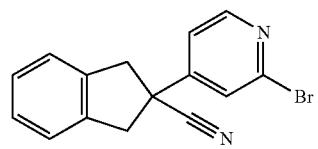 [SMILES: N#CC1(c2ccnc(Br)c2)Cc2ccccc2C1]

A solution of (2-bromopyridin-4-yl)acetonitrile (360 mg, 1.8 mmol) in tetrahydrofuran (5 mL) was added dropwise to a suspension of sodium hydride (440 mg, 11 mmol) in tetrahydrofuran (5 mL) at r.t. The reaction mixture was stirred at r.t. for 20 min, after which time a solution of 1,2-bis(bromomethyl)-benzene (506 mg, 1.92 mmol) in tetrahydrofuran (5 mL) was added dropwise. The reaction mixture was heated to 90° C. for 1 h. The reaction mixture was diluted with EtOAc, and the reaction was quenched with saturated aqueous NaHCO$_3$ solution. The organic layer was separated, concentrated and purified on silica gel column (0-100% EtOAc/hexanes) to give the desired product (300 mg, 50%). LCMS cacld for C$_{15}$H$_{12}$BrN$_2$ [M+H]$^+$: m/z=299.0. Found: 299.0.

Step 3. 4-Bromo-7-{[2-(trimethylsilyl)ethoxy]methyl}-7H-pyrrolo[2,3-d]pyrimidine

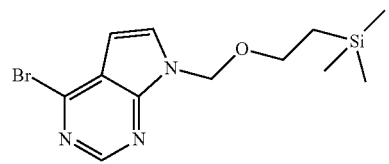 [SMILES: C[Si](C)(C)CCOCn1ccc2c(Br)ncnc21]

At 0° C. to a suspension of sodium hydride (1.3 g, 33 mmol) in N,N-dimethylformamide (40 mL) was added 4-bromo-7H-pyrrolo[2,3-d]pyrimidine (from Ark Pharm, 5.0 g, 25 mmol) portionwise with stirring. The reaction mixture was stirred at this temperature for 1 hour. Then to the reaction mixture was added dropwise neat [β-(trimethylsilyl)ethoxy]methyl chloride (5.4 mL, 30. mmol) at 0° C. with stirring. After completion of addition the reaction mixture was stirred and gradually warmed up to room temperature (1.5 hour). The reaction mixture was diluted with ethyl ether and quenched with saturated $NaHCO_3$ solution. After separation of layers, the organic layer was washed with water and brine once, concentrated and purified on silica gel column (0-10% EtOAc/hexanes) to give the desired product (6 g, 70%). LCMS cacld for $C_{12}H_{19}BrN_3OSi$ $[M+H]^+$: m/z=328.0. Found: 328.0.

Step 4. 4-(Tributylstannyl)-7-{[2-(trimethylsilyl)ethoxy]methyl}-7H-pyrrolo[2,3-d]pyrimidine

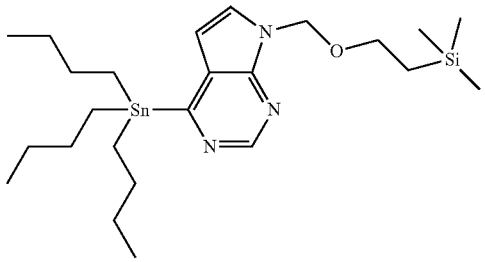 [SMILES: CCC[CH2][Sn]([CH2]CCC)([CH2]CCC)[c]1ncnc2c1ccn2COCC[Si](C)(C)C]

To a solution of 4-bromo-7-{[2-(trimethylsilyl)ethoxy]methyl}-7H-pyrrolo[2,3-d]pyrimidine (200 mg, 0.6 mmol) in tetrahydrofuran (4 mL) cooled to −78° C. was added dropwise 2.5 M n-butyllithium in hexanes (0.29 mL, 0.73 mmol). The reaction mixture was stirred for 5 min before the addition of tributyltin chloride (0.17 mL, 0.62 mmol) dropwise. The reaction mixture was stirred for 1 h, and then quenched with saturated aqueous $NaHCO_3$ solution, extracted with EtOAc. The combined organic layers were washed with brine, dried over $MgSO_4$ and concentrated to give the crude product to be used in the next step directly. LCMS cacld for $C_{24}H_{46}N_3OSiSn$ $[M+H]^+$: m/z=540.2. Found: 540.1.

Step 5. 2-[2-(7-{[2-(Trimethylsilyl)ethoxy]methyl}-1H-pyrrolo[2,3-d]pyrimidin-4-yl)pyridin-4-yl]indane-2-carbonitrile

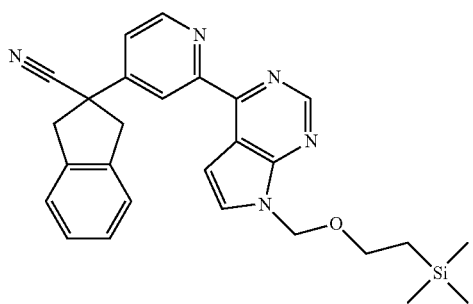 [SMILES: C[Si](C)(C)CCOCn1ccc2c(-c3cc(C4(C#N)Cc5ccccc5C4)ccn3)ncnc21]

A mixture of 2-(2-bromopyridin-4-yl)indane-2-carbonitrile (0.10 g, 0.33 mmol), 4-(tributylstannyl)-7-{[2-(trimethylsilyl)ethoxy]methyl})-7H-pyrrolo[2,3-d]pyrimidine (0.31 g, 0.58 mmol) and bis(triphenylphosphine)palladium(II) chloride (47 mg, 0.067 mmol) in N,N-dimethylformamide (1.20 mL) was bubbled with nitrogen gas and then heated to 110° C. overnight. The reaction mixture was diluted with EtOAc, washed with brine, concentrated and purified on silica gel (0-100% EtOAc/hexanes) to give the desired product. LCMS cacld for $C_{27}H_{30}N_5OSi$ $[M+H]^+$: m/z=468.2. Found: 468.2.

Step 6. 1-{2-[2-(7-{[2-(Trimethylsilyl)ethoxy]methyl}-7H-pyrrolo[2,3-d]pyrimidin-4-yl)pyridin-4-yl]-2,3-dihydro-1H-inden-2-yl}methanamine

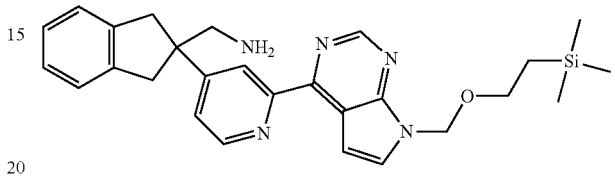

At 0° C. to a solution of 2-[2-(7-{[2-(trimethylsilyl)ethoxy]methyl}-7H-pyrrolo[2,3-d]pyrimidin-4-yl)pyridin-4-yl]indane-2-carbonitrile (0.072 g, 0.15 mmol) in methanol (1.0 mL) was added sequentially nickel chloride hexahydrate (5.5 mg, 0.023 mmol), followed by sodium tetrahydroborate (41 mg, 1.1 mmol) portion-wise over 15 min. The reaction mixture was stirred at r.t. for 5 h. The resulting solution was diluted with EtOAc, washed with aqueous saturated $NaHCO_3$ solution, dried over $MgSO_4$ and evaporated to give the product to be used in the next step directly. LCMS cacld for C27H33N5OSi $[M+H]^+$: m/z=472.3. Found: 472.2.

Step 7. 1-{2-[2-(7H-Pyrrolo[2,3-d]pyrimidin-4-yl)pyridin-4-yl]-2,3-dihydro-1H-inden-2-yl}methanamine 1-{2-[2-(7-{[2-(Trimethylsilyl)ethoxy]methyl}-7H-pyrrolo[2,3-d]pyrimidin-4-yl)pyridin-4-yl]-2,3-dihydro-1H-inden-2-yl}methanamine (60 mg, 0.1 mmol) was treated with trifluoroacetic acid (0.5 mL, 6 mmol) in methylene chloride (1 mL) at r.t. for 1 h. The reaction mixture was concentrated in vacuo and then treated with ethylenediamine (0.3 mL, 4 mmol) in methanol (1 mL) at r.t. for 1 h. The reaction mixture was purified on prep-LCMS (XBridge™ C18 column, eluting with a gradient of MeCN/water containing 0.1% ammonium hydroxide, at a flow rate of 60 mL/min) to give the product (1.6 mg, 4%). LCMS cacld for $C_{21}H_{20}N_5$ $[M+H]^+$: m/z=342.2. Found: 342.2.

Example 5

1-{6-[3-(7H-Pyrrolo[2,3-d]pyrimidin-4-yl)phenyl]-6,7-dihydro-5H-cyclopenta[c]pyridin-6-yl}methanamine

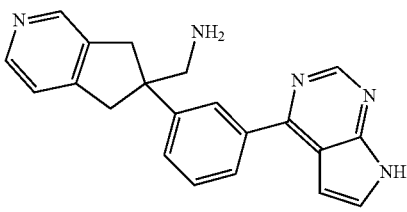 [SMILES: NCC1(c2cccc(-c3ncnc4[nH]ccc34)c2)Cc2ccncc2C1]

Step 1: [3-(7-{[2-(trimethylsilyl)ethoxy]methyl}-1H-pyrrolo[2,3-d]pyrimidin-4-yl)phenyl]acetonitrile

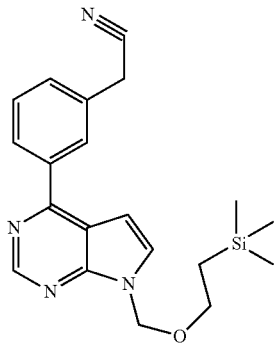 [SMILES: C[Si](C)(C)CCOCn1ccc2c(-c3cccc(CC#N)c3)ncnc21]

To a stirring solution of 4-chloro-7-{[2-(trimethylsilyl)ethoxy]methyl}-7H-pyrrolo[2,3-d]pyrimidine (Prepared in Example 1, Step 1; 1.17 g, 4.11 mmol) in 1,4-dioxane (6.4 mL) was slowly added [3-(4,4,5,5-tetramethyl-1,3,2-dioxaborolan-2-yl)phenyl]acetonitrile (from Combi-Blocks, 1.00 g, 4.11 mmol), 2.0 M sodium carbonate in water (4.1 mL, 8.2 mmol) and tetrakis(triphenylphosphine)palladium(0) (0.475 g, 0.41 mmol). The reaction mixture was sealed in a sealed flask and was heated at 80° C. for 16 h. The reaction mixture was diluted with EtOAc, filtered, washed with water. The aqueous layer was extracted with EtOAc and the combined organic layers were dried, filtered and concentrated under vacuum. The resulting crude was purified by Biotage silica gel column (0 to 50% EtOAc in hexanes) to afford the desired product as a brown thick oil (0.814 g, 54%). LCMS calcd for $C_{20}H_{25}N_4OSi$ $[M+H]^+$: m/z=365.2. Found: 365.1.

Step 2. 6-[3-(7-{[2-(Trimethylsilyl)ethoxy]methyl}-7H-pyrrolo[2,3-d]pyrimidin-4-yl)phenyl]-6,7-dihydro-5H-cyclopenta[c]pyridine-6-carbonitrile

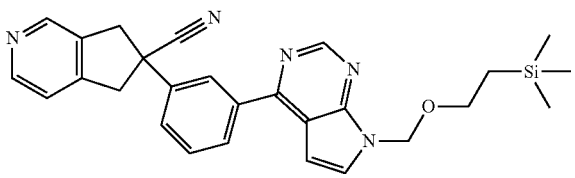 [SMILES: C[Si](C)(C)CCOCn1ccc2c(-c3cccc(C4(C#N)Cc5ccncc5C4)c3)ncnc21]

To a suspension of sodium hydride (0.20 g, 5.0 mmol) in tetrahydrofuran (2 mL) at r.t. was added a solution of [3-(7-{[2-(trimethylsilyl)ethoxy]methyl}-7H-pyrrolo[2,3-d]pyrimidin-4-yl)phenyl]acetonitrile (230 mg, 0.63 mmol) in tetrahydrofuran (4 mL) dropwise. The reaction mixture was stirred for 20 min and then a solution of 3,4-bis(bromomethyl)pyridine hydrobromide (from Enamine, 218.2 mg, 0.6310 mmol) and N,N-diisopropylethylamine (0.16 mL, 0.95 mmol) in tetrahydrofuran (2 mL) was added dropwise. The reaction was heated at 90° C. for 1 h. The reaction mixture was diluted with EtOAc, quenched with saturated aqueous $NaHCO_3$ solution. The organic layer was separated, concentrated and purified on silica gel (0-100% EtOAc/hexanes followed by 0-5% methanol/dichloromethane) to give the product (41 mg, 14%). LCMS calcd for $C_{27}H_{30}N_5OSi$ $[M+H]^+$: m/z=468.2. Found: 468.2.

Step 3. 1-{6-[3-(7-{[2-(Trimethylsilyl)ethoxy]methyl}-7H-pyrrolo[2,3-d]pyrimidin-4-yl)phenyl]-6,7-dihydro-5H-cyclopenta[c]pyridin-6-yl}methanamine

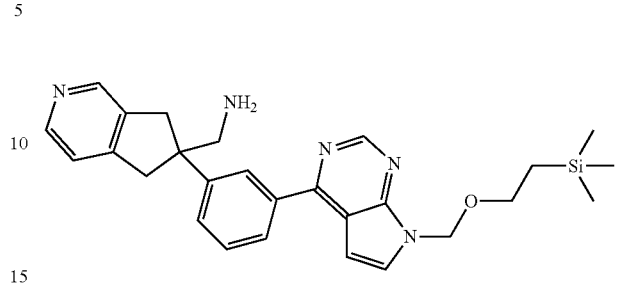

To a solution of 6-[3-(7-{[2-(trimethylsilyl)ethoxy]methyl}-7H-pyrrolo[2,3-d]pyrimidin-4-yl)phenyl]-6,7-dihydro-5H-cyclopenta[c]pyridine-6-carbonitrile (41 mg, 0.088 mmol) in tetrahydrofuran (2 mL) at 0° C. was added 1.0 M lithium tetrahydroaluminate in tetrahydrofuran (0.0964 mL, 0.0964 mmol). The reaction mixture was stirred for 1 h. The reaction was quenched with aqueous saturated $NaHCO_3$ solution, and the mixture was extracted with EtOAc. The combined organic layers were washed with water, dried over $MgSO_4$ and concentrated to give the product to be used in the next step directly. LCMS cacld for $C_{27}H_{34}N_5OSi$ $[M+H]^+$: m/z=472.3. Found: 472.2.

Step 4. 1-{6-[3-(7H-Pyrrolo[2,3-d]pyrimidin-4-yl)phenyl]-6,7-dihydro-5H-cyclopenta[c]pyridin-6-yl}methanamine 1-{6-[3-(7-{[2-(Trimethylsilyl)ethoxy]methyl}-7H-pyrrolo[2,3-d]pyrimidin-4-yl)phenyl]-6,7-dihydro-5H-cyclopenta[c]pyridin-6-yl}methanamine (34 mg, 0.072 mmol) was treated with trifluoroacetic acid (0.5 mL, 6 mmol) in methylene chloride (1 mL) at r.t. for 1 h. The reaction mixture was concentrated in vacuo and then treated with ethylenediamine (0.3 mL, 4 mmol) in methanol (1 mL) at r.t. for 1 h. The mixture was purified on prep-LCMS (XBridge™ C18 column, eluting with a gradient of MeCN/water containing 0.1% ammonium hydroxide, at a flow rate of 60 mL/min) to give the product (1.0 mg, 4.1%). LCMS cacld for $C_{21}H_{20}N_5$ $[M+H]^+$: m/z=342.2. Found: 342.2.

Example 6

1-{6-[3-(7H-Pyrrolo[2,3-d]pyrimidin-4-yl)phenyl]-6,7-dihydro-5H-cyclopenta[b]pyridin-6-yl}methanamine

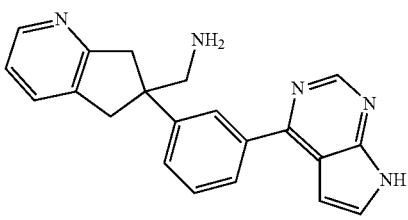 [SMILES: NCC1(c2cccc(-c3ncnc4[nH]ccc34)c2)Cc2cccnc2C1]

Step 1. 6-[3-(7-{[2-(Trimethylsilyl)ethoxy]methyl}-7H-pyrrolo[2,3-d]pyrimidin-4-yl)phenyl]-6,7-dihydro-5H-cyclopenta[b]pyridine-6-carbonitrile

To a suspension of sodium hydride (0.16 g, 4.0 mmol) in tetrahydrofuran (2 mL) was added a solution of [3-(7-{[2-(trimethylsilyl)ethoxy]methyl}-7H-pyrrolo[2,3-d]pyrimidin-4-yl)phenyl]acetonitrile (Prepared in Example 5, Step 1; 230 mg, 0.63 mmol) in tetrahydrofuran (4 mL) dropwise at r.t. The reaction mixture was stirred for 20 min and then a solution of 2,3-bis(chloromethyl)pyridine hydrochloride (from Small Molecules, 134 mg, 0.631 mmol) and N,N-diisopropylethylamine (0.16 mL, 0.92 mmol) in tetrahydrofuran (2 mL) was added dropwise. The reaction was heated at 90° C. for 1 h. The mixture was diluted with EtOAc, quenched with saturated aqueous NaHCO$_3$ solution. The organic layer was separated, concentrated and purified on silica gel (0-100% EtOAc/hexanes) to give the product (136 mg, 46%). LCMS cacld for $C_{27}H_{30}N_5OSi$ [M+H]$^+$: m/z=468.2. Found: 468.2.

Step 2. 1-{6-[3-(7-{[2-(Trimethylsilyl)ethoxy]methyl}-7H-pyrrolo[2,3-d]pyrimidin-4-yl)phenyl]-6,7-dihydro-5H-cyclopenta[b]pyridin-6-yl}methanamine

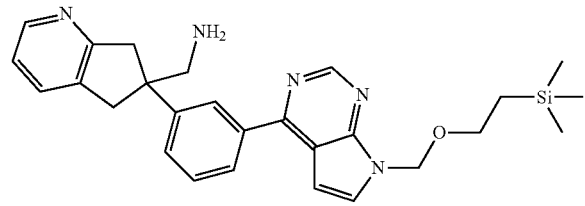 [SMILES: C[Si](C)(C)CCOCn1ccc2c(-c3cccc(C4(CN)Cc5cccnc5C4)c3)ncnc21]

To a solution of 6-[3-(7-{[2-(trimethylsilyl)ethoxy]methyl}-7H-pyrrolo[2,3-d]pyrimidin-4-yl)phenyl]-6,7-dihydro-5H-cyclopenta[b]pyridine-6-carbonitrile (136 mg, 0.291 mmol) in tetrahydrofuran (5 mL) at 0° C. was added 1.0 M lithium tetrahydroaluminate in tetrahydrofuran (0.32 mL, 0.32 mmol). The reaction mixture was stirred for 1 h. The reaction was quenched with aqueous saturated NaHCO$_3$ solution, extracted with EtOAc. The combined extracts were washed with water, dried over MgSO$_4$ and concentrated to give the crude product (80 mg, 58%) to be used in the next step directly. LCMS cacld for $C_{27}H_{34}N_5OSi$ [M+H]$^+$: m/z=472.3. Found: 472.2.

Step 3. 1-{6-[3-(7H-Pyrrolo[2,3-d]pyrimidin-4-yl)phenyl]-6,7-dihydro-5H-cyclopenta[b]pyridin-6-yl}methanamine 1-{6-[3-(7-{[2-(Trimethylsilyl)ethoxy]methyl}-7H-pyrrolo[2,3-d]pyrimidin-4-yl)phenyl]-6,7-dihydro-5H-cyclopenta[b]pyridin-6-yl}methanamine (80 mg, 0.2 mmol) was treated with trifluoroacetic acid (0.5 mL, 6 mmol) in methylene chloride (1 mL) at r.t. for 1 h. The reaction mixture was concentrated in vacuo and then treated with ethylenediamine (0.3 mL, 4 mmol) in methanol (1 mL) at r.t. for 1 h. The mixture was purified on prep-LCMS (XBridge™ C18 column, eluting with a gradient of MeCN/water containing 0.1% ammonium hydroxide, at a flow rate of 60 mL/min) to give the desired product (1.5 mg, 2%). LCMS cacld for $C_{21}H_{20}N_5$ [M+H]$^+$: m/z=342.2. Found: 342.2.

Example 7

1-{2-[6-Chloro-4-(7H-pyrrolo[2,3-d]pyrimidin-4-yl)pyridin-2-yl]-2,3-dihydro-1H-inden-2-yl}methanamine

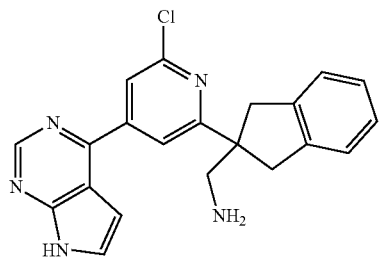 [SMILES: NCC1(c2cc(-c3ncnc4[nH]ccc34)cc(Cl)n2)Cc2ccccc2C1]

Step 1. Methyl (4-bromo-6-chloropyridin-2-yl)acetate

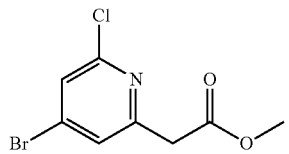

To a solution of (4-bromo-6-chloropyridin-2-yl)acetic acid (from Anichem, 3.5 g, 14 mmol) and potassium carbonate (4.8 g, 35 mmol) in N,N-dimethylformamide (9 mL) at 0° C. was added methyl iodide (1.3 mL, 21 mmol) dropwise. After stirring at room temperature for 2 h, the reaction was quenched with aqueous saturated NaHCO$_3$ solution, extracted with EtOAc, concentrated and purified on silica gel (0-100 EtOAc/hexanes) to give the product (3.0 g, 81%). LCMS cacld for $C_8H_8BrClNO_2$ [M+H]$^+$: m/z=263.9. Found: 263.9.

Step 2. Methyl 2-(4-bromo-6-chloropyridin-2-yl)indane-2-carboxylate

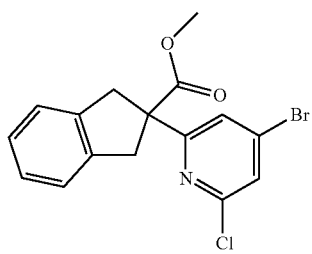 [SMILES: COC(=O)C1(c2cc(Br)cc(Cl)n2)Cc2ccccc2C1]

A solution of methyl (4-bromo-6-chloropyridin-2-yl)acetate (3.0 g, 11 mmol) in tetrahydrofuran (30 mL) was added dropwise to a suspension of sodium hydride (2.7 g, 68 mmol) in tetrahydrofuran (30 mL) at r.t. The reaction mixture was stirred at r.t. for 20 min, after which time a solution of 1,2-bis(bromomethyl)-benzene (3.14 g, 11.9 mmol) in tetrahydrofuran (30 mL) was added dropwise. The reaction mixture was stirred at r.t. for 1 h. The mixture was diluted with EtOAc, quenched with saturated aqueous NaHCO₃ solution. The organic layer was separated, concentrated and purified on silica gel (0-70% EtOAc/hexanes) to give the product (2.9 g, 70%). LCMS cacld for $C_{16}H_{14}BrClNO_2$ [M+H]⁺: m/z=366.0. Found: 366.1.

Step 3. 2-(4-Bromo-6-chloropyridin-2-yl)indane-2-carboxylic acid

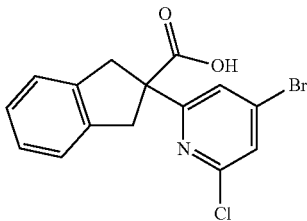 [SMILES: O=C(O)C1(c2cc(Br)cc(Cl)n2)Cc2ccccc2C1]

To a solution of methyl 2-(4-bromo-6-chloropyridin-2-yl)indane-2-carboxylate (2.9 g, 7.9 mmol) in methanol (5 mL)/tetrahydrofuran (5 mL) was added a solution of lithium hydroxide, monohydrate (1.0 g, 24 mmol) in water (5 mL). The reaction mixture was stirred at r.t. overnight. The reaction mixture was neutralized with aqueous 6N HCl solution to pH ~4. The solid was collected by filtration, washed with water and dried to give the product (2.8 g, 100%). LCMS cacld for $C_{15}H_{12}BrClNO_2$ [M+H]⁺: m/z=352.0. Found: 352.0.

Step 4. [2-(4-Bromo-6-chloropyridin-2-yl)-2,3-dihydro-1H-inden-2-yl]methanol

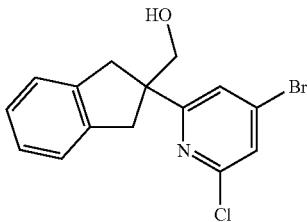 [SMILES: OCC1(c2cc(Br)cc(Cl)n2)Cc2ccccc2C1]

To a mixture of 2-(4-bromo-6-chloropyridin-2-yl)indane-2-carboxylic acid (2.8 g, 7.9 mmol) and triethylamine (1.16 mL, 8.34 mmol) in tetrahydrofuran (40 mL) cooled in an ice bath was added tert-butyl chloridocarbonate (1.09 mL, 8.34 mmol) dropwise. The reaction mixture was stirred for 1 h. The solid was filtered off. The filtrate was cooled again and a solution of sodium tetrahydroborate (0.60 g, 16 mmol) in water (2 mL) was added dropwise. The reaction mixture was stirred for 30 min, then quenched with aqueous saturated NaHCO₃ solution, extracted with EtOAc. The combined extracts were concentrated and purified on silica gel (0-100% EtOAc/hexanes) to give the product (2.8 g, 100%). LCMS cacld for $C_{15}H_{14}BrClNO$ [M+H]⁺: m/z=338.0. Found: 338.0.

Step 5. 2-(4-Bromo-6-chloropyridin-2-yl)indane-2-carbaldehyde

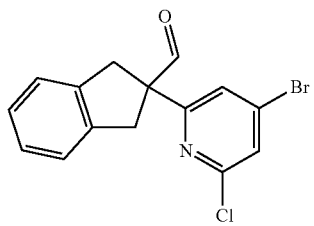 [SMILES: O=CC1(c2cc(Br)cc(Cl)n2)Cc2ccccc2C1]

To a stirred solution of [2-(4-bromo-6-chloropyridin-2-yl)-2,3-dihydro-1H-inden-2-yl]methanol (2.8 g, 8.3 mmol) in methylene chloride (60 mL) at 0° C. were added pyridine (0.80 mL) and Dess-Martin periodinane (3.68 g, 8.68 mmol). The reaction mixture was stirred overnight at r.t., then quenched with solutions of NaHCO₃ and Na₂S₂O₃. The resulting mixture was stirred for 30 min. Then the product was extracted with dichloromethane. The combined organic layers were concentrated and purified by silica gel (0-100% EtOAc/hexanes) to give the product (1 g, 36%). LCMS cacld for $C_{15}H_{12}BrClNO$ [M+H]⁺: m/z=336.0. Found: 335.9.

Step 6. tert-Butyl {[2-(4-bromo-6-chloropyridin-2-yl)-2,3-dihydro-1H-inden-2-yl]methyl}carbamate

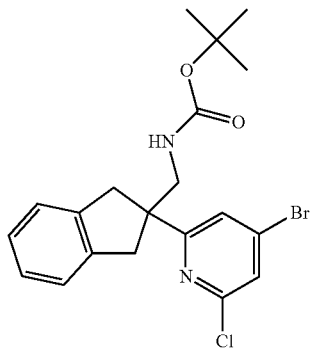 [SMILES: CC(C)(C)OC(=O)NCC1(c2cc(Br)cc(Cl)n2)Cc2ccccc2C1]

A solution of 2-(4-bromo-6-chloropyridin-2-yl)indane-2-carbaldehyde (1.0 g, 3.0 mmol), t-butyl carbamate (1.01 g, 8.66 mmol), triethylsilane (1.39 mL, 8.72 mmol) and trifluoroacetic acid (0.44 mL, 5.8 mmol) in acetonitrile (10 mL) was stirred at r.t. overnight. The mixture was diluted with EtOAc, washed with aqueous saturated NaHCO₃ solution, concentrated and purified on silica gel (0-100% EtOAc/hexanes) to give the product. LCMS cacld for $C_{15}H_{12}BrClNO$ [M-Boc+H]⁺: m/z=336.0. Found: 336.0.

Step 7. tert-Butyl ({2-[6-chloro-4-(4,4,5,5-tetramethyl-1,3,2-dioxaborolan-2-yl)pyridin-2-yl]-2,3-dihydro-1H-inden-2-yl}methyl)carbamate

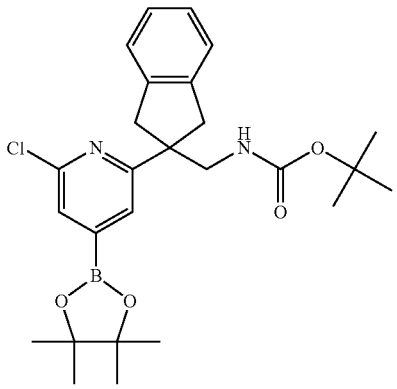 [SMILES: CC(C)(C)OC(=O)NCC1(c2cc(B3OC(C)(C)C(C)(C)O3)cc(Cl)n2)Cc2ccccc2C1]

A mixture of tert-butyl {[2-(4-bromo-6-chloropyridin-2-yl)-2,3-dihydro-1H-inden-2-yl]methyl}carbamate (1.17 g, 2.67 mmol), 4,4,5,5,4',4',5',5'-octamethyl-[2,2']bi[[1,3,2]dioxaborolanyl] (0.685 g, 2.70 mmol), potassium acetate (0.52 g, 5.3 mmol) and [1,1'-bis(diphenylphosphino)ferrocene]dichloropalladium (II) (0.20 g, 0.27 mmol) in 1,4-dioxane (10 mL) was vacuumed and backfilled with N$_2$ for 3 times, then sealed and heated at 95° C. for 1 h. The mixture was cooled to rt and filtered. The filtrate was used in the next step directly. LCMS cacld for C$_{26}$H$_{35}$BClN$_2$O$_4$ [M+H]$^+$: m/z=485.2. Found: 485.2.

Step 8. tert-Butyl ({2-[6-chloro-4-(7-{[2-(trimethylsilyl)ethoxy]methyl}-7H-pyrrolo[2,3-d]pyrimidin-4-yl)pyridin-2-yl]-2,3-dihydro-1H-inden-2-yl}methyl)carbamate

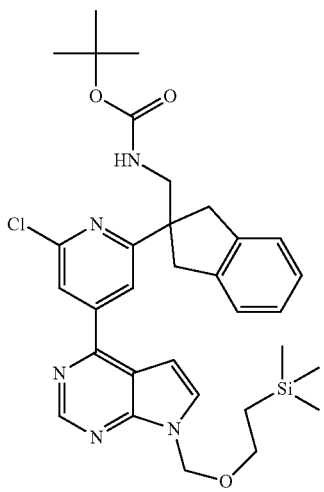 [SMILES: CC(C)(C)OC(=O)NCC1(c2cc(-c3ncnc4c3ccn4COCC[Si](C)(C)C)cc(Cl)n2)Cc2ccccc2C1]

A mixture of tert-butyl ({2-[6-chloro-4-(4,4,5,5-tetramethyl-1,3,2-dioxaborolan-2-yl)pyridin-2-yl]-2,3-dihydro-1H-inden-2-yl}methyl)carbamate (1.30 g, 2.68 mmol), 4-chloro-7-{[2-(trimethylsilyl)ethoxy]methyl}-7H-pyrrolo[2,3-d]pyrimidine (Prepared in Example 1, Step 1; 0.84 g, 2.9 mmol), cesium carbonate (1.7 g, 5.4 mmol) and dicyclohexyl(2',4',6'-triisopropylbiphenyl-2-yl)phosphine-(2'-aminobiphenyl-2-yl)(chloro)palladium (1:1) (0.21 g, 0.27 mmol) in 1,4-dioxane (3 mL)/water (2 mL) was stirred for 2 h at 50° C. The reaction mixture was purified on silica gel (0-100% EtOAc/hexanes) to give the product (380 mg, 72%). LCMS cacld for C$_{32}$H$_{41}$ClN$_5$O$_3$Si [M+H]$^+$: m/z=606.3. Found: 606.2.

Step 9. 1-{2-[6-Chloro-4-(7H-pyrrolo[2,3-d]pyrimidin-4-yl)pyridin-2-yl]-2,3-dihydro-1H-inden-2-yl}methanamine tert-Butyl ({2-[6-chloro-4-(7-{[2-(trimethylsilyl)ethoxy]methyl}-7H-pyrrolo[2,3-d]pyrimidin-4-yl)pyridin-2-yl]-2,3-dihydro-1H-inden-2-yl}methyl)carbamate (0.050 g, 0.082 mmol) was treated with trifluoroacetic acid (0.5 mL, 6 mmol) in methylene chloride (0.5 mL) at r.t. for 1 h. The reaction mixture was concentrated to dryness, and treated with ethylenediamine (0.5 mL, 7 mmol) in methanol (0.5 mL) at r.t. for 20 min. The mixture was purified on prep-LCMS (XBridge™ C18 column, eluting with a gradient of MeCN/water containing 0.1% ammonium hydroxide, at a flow rate of 60 mL/min) to give the product (1.1 mg, 3.5%). LCMS cacld for C$_{21}$H$_{19}$ClN$_5$ [M+H]$^+$: m/z=376.1. Found: 376.1.

Example 8

N-({2-[4-(7H-Pyrrolo[2,3-d]pyrimidin-4-yl)pyridin-2-yl]-2,3-dihydro-1H-inden-2-yl}methyl)acetamide

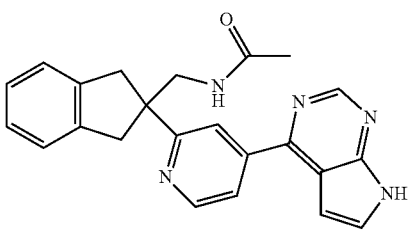 [SMILES: CC(=O)NCC1(c2cc(-c3ncnc4[nH]ccc34)ccn2)Cc2ccccc2C1]

To a solution of 1-{2-[4-(7H-pyrrolo[2,3-d]pyrimidin-4-yl)pyridin-2-yl]-2,3-dihydro-1H-inden-2-yl}methanamine (Prepared in Example 3; 2.0 mg, 0.0058 mmol) in tetrahydrofuran (0.0238 mL) and 1.0 M sodium bicarbonate in water (0.0117 mL, 0.0117 mmol) was added slowly acetic anhydride (0.829 µL, 0.00879 mmol). The reaction mixture was stirred at r.t. for 20 min, after which time the reaction mixture was concentrated under reduced pressure, and the crude residue was purified by prep-LCMS (XBridge™ C18 column, eluting with a gradient of MeCN/water containing 0.1% ammonium hydroxide, at a flow rate of 60 mL/min) to give the desired product (0.4 mg, 20%). LCMS cacld for C$_{23}$H$_{22}$N$_5$O [M+H]$^+$: m/z=384.2. Found: 384.2.

Example 10

N-({6-[3-(7H-Pyrrolo[2,3-d]pyrimidin-4-yl)phenyl]-6,7-dihydro-5H-cyclopenta[c]pyridin-6-yl}methyl)acetamide

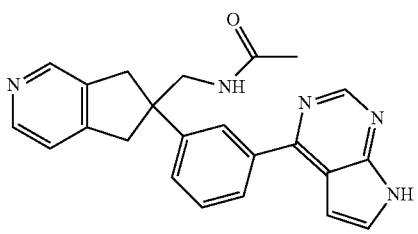 [SMILES: CC(=O)NCC1(c2cccc(-c3ncnc4[nH]ccc34)c2)Cc2ccncc2C1]

To a solution of 1-{6-[3-(7H-pyrrolo[2,3-d]pyrimidin-4-yl)phenyl]-6,7-dihydro-5H-cyclopenta[c]pyridin-6-yl}methanamine (Prepared in Example 5; 3.0 mg, 0.0088 mmol) in tetrahydrofuran (0.0356 mL) and 1.0 M sodium bicarbonate in water (0.0176 mL, 0.0176 mmol) was added slowly acetic anhydride (1.24 µL, 0.0132 mmol). The reaction mixture was stirred at r.t. for 20 min, After which time the reaction mixture was concentrated under reduced pressure, the crude residue was purified by prep-LCMS (XBridge™ C18 column, eluting with a gradient of MeCN/water containing 0.1% ammonium hydroxide, at a flow rate of 60 mL/min) to give the desired product (0.8 mg, 20%). LCMS cacld for $C_{23}H_{22}N_5O$ $[M+H]^+$: m/z=384.2. Found: 384.2.

Example 11

1-{2-[3-(7H-Pyrrolo[2,3-d]pyrimidin-4-yl)phenyl]-2,3-dihydro-1H-inden-2-yl}methanamine

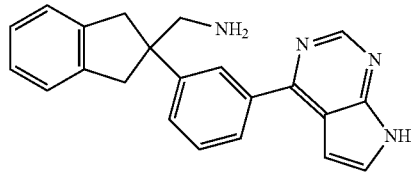 [SMILES: NCC1(c2cccc(-c3ncnc4[nH]ccc34)c2)Cc2ccccc2C1]

Step 1: 2-[3-(7-{[2-(trimethylsilyl)ethoxy]methyl}-1H-pyrrolo[2,3-d]pyrimidin-4-yl)phenyl]indane-2-carbonitrile

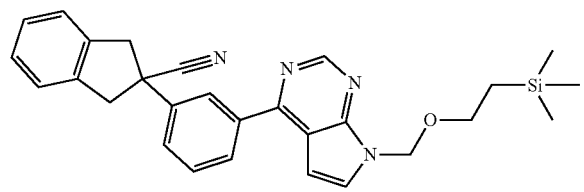 [SMILES: C[Si](C)(C)CCOCn1ccc2c(-c3cccc(C4(C#N)Cc5ccccc5C4)c3)ncnc21]

To a solution of [3-(7-{[2-(trimethylsilyl)ethoxy]methyl}-7H-pyrrolo[2,3-d]pyrimidin-4-yl)phenyl]acetonitrile (Prepared in Example 5, Step 1; 0.600 g, 1.65 mmol) in tetrahydrofuran (8.57 mL) was slowly added sodium hydride (198 mg, 4.94 mmol) at room temperature. The reaction mixture was stirred for 10 min, followed by the addition of a solution of 1,2-bis(bromomethyl)-benzene (435 mg, 1.65 mmol) in tetrahydrofuran (1.7 mL). The reaction mixture was heated at 50° C. for 18 h. The reaction mixture was diluted with EtOAc and water added. The aqueous layer was extracted with EtOAc. The organic layers were combined, dried, filtered and concentrated under vacuum. The crude residue was purified by Biotage column (0 to 30% EtOAc in hexanes) to give the desired product as pale yellow gum (300 mg, 39%). LCMS calcd for $C_{28}H_{31}N_4OSi$ $(M+H)^+$: m/z=467.2. Found: 467.3.

Step 2: 1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine

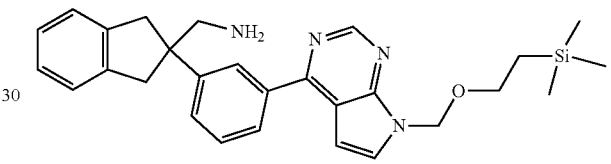

To a solution of 2-[3-(7-{[2-(trimethylsilyl)ethoxy]methyl}-7H-pyrrolo[2,3-d]pyrimidin-4-yl)phenyl]indane-2-carbonitrile (30.0 mg, 0.064 mmol) in tetrahydrofuran (0.52 mL) was added 1.0 M lithium tetrahydroaluminate in tetrahydrofuran (0.084 mL, 0.084 mmol) at 0° C. The reaction mixture was stirred at rt for 3 h. The reaction was quenched with NaOH (1 N), washed with water and extracted with EtOAc. The crude as light yellow gum (30 mg, 100%) was used directly in the next reaction. LCMS calcd for $C_{28}H_{35}N_4OSi$ $(M+H)^+$: m/z=471.3. Found: 471.2.

Step 3: 1-{2-[3-(7H-Pyrrolo[2,3-d]pyrimidin-4-yl)phenyl]-2,3-dihydro-1H-inden-2-yl}methanamine To a solution of 1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine (30 mg, 0.064 mmol) in methylene chloride (0.15 mL) was added trifluoroacetic acid (0.30 mL, 3.9 mmol). The reaction mixture was stirred for 1 h, and then concentrated under vacuum. To this residue was added methanol (0.10 mL) and ethylenediamine (0.033 mL, 0.50 mmol). The reaction mixture was stirred for 15 min and then concentrated under vacuum. The crude residue was purified by prep LC-MS (pH=10 method; XBridge™ PrepC18 5 µm OBD™ column, 30×10 mm, 60 mL/min, eluting with a gradient of MeCN and water with $NH_4OH$) to give the desired product as a white powder (7.3 mg, 34%). LCMS calcd for $C_{22}H_{21}N_4$ $(M+H)^+$: m/z=341.2. Found: 341.3.

Example 12

{2-[3-(7H-Pyrrolo[2,3-d]pyrimidin-4-yl)phenyl]-2,3-dihydro-1H-inden-2-yl}methanol

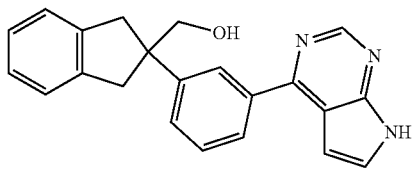 [SMILES: OCC1(c2cccc(-c3ncnc4[nH]ccc34)c2)Cc2ccccc2C1]

Step 1: 2-[3-(7-{[2-(trimethylsilyl)ethoxy]methyl}-7H-pyrrolo[2,3-d]pyrimidin-4-yl)phenyl]indane-2-carbaldehyde

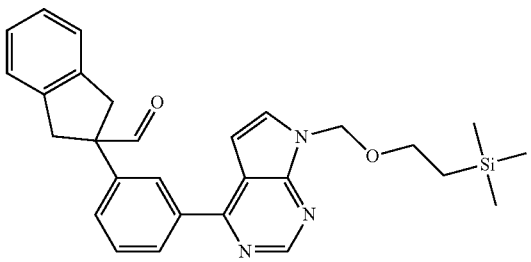 [SMILES: C[Si](C)(C)CCOCn1ccc2c(-c3cccc(C4(C=O)Cc5ccccc5C4)c3)ncnc21]

To a solution of 2-[3-(7-{[2-(trimethylsilyl)ethoxy]methyl}-7H-pyrrolo[2,3-d]pyrimidin-4-yl)phenyl]indane-2-carbonitrile (Prepared in Example 11, Step 1; 50 mg, 0.11 mmol) in methylene chloride (0.45 mL) at −78° C. was slowly added a solution of 1.0 M diisobutylaluminum hydride in dichloromethane (0.27 mL, 0.27 mmol). The reaction mixture was stirred at −78° C. for 20 min. The dry-ice bath was removed, and MeOH (50 uL) was added to quench the reaction. The reaction mixture was treated with water and the aluminum salts chelated with 1 mL of a 1M aqueous solution of sodium potassium tartrate. The reaction mixture was partitioned between water and methylene chloride. The organic phase was dried over $Na_2SO_4$, filtered, and concentrated. The crude product (48 mg, 95%) was used in the next reaction without further purification. LCMS calcd for $C_{28}H_{32}N_3O_2Si$ (M+H)$^+$: m/z=470.2. Found: 470.3.

Step 2: {2-[3-(7-{[2-(trimethylsilyl)ethoxy]methyl}-7H-pyrrolo[2,3-d]pyrimidin-4-yl)phenyl]-2,3-dihydro-1H-inden-2-yl}methanol

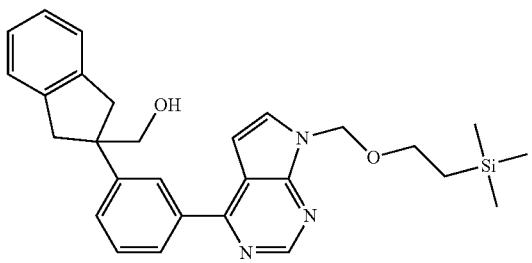 [SMILES: C[Si](C)(C)CCOCn1ccc2c(-c3cccc(C4(CO)Cc5ccccc5C4)c3)ncnc21]

2-[3-(7-{[2-(Trimethylsilyl)ethoxy]methyl}-7H-pyrrolo[2,3-d]pyrimidin-4-yl)phenyl]indane-2-carbaldehyde (25 mg, 0.053 mmol) was dissolved in tetrahydrofuran (0.80 mL), followed by the addition of sodium tetrahydroborate (16 mg, 0.42 mmol) at 0° C. The reaction mixture was stirred at rt for 18 h. The mixture was filtered and concentrated under vacuum to give the desired crude product, which was used directly in the next step. LCMS calcd for $C_{28}H_{34}N_3O_2Si$ (M+H)$^+$: m/z=472.2. Found: 472.3.

Step 3: {2-[3-(7H-Pyrrolo[2,3-d]pyrimidin-4-yl)phenyl]-2,3-dihydro-1H-inden-2-yl}methanol To a solution of {2-[3-(7-{[2-(trimethylsilyl)ethoxy]methyl}-7H-pyrrolo[2,3-d]pyrimidin-4-yl)phenyl]-2,3-dihydro-1H-inden-2-yl}methanol (11.5 mg, 0.024 mmol) in methylene chloride (0.06 mL) was added trifluoroacetic acid (0.115 mL, 1.5 mmol). The reaction mixture was stirred for 20 min, and then concentrated in vacuo. To this residue was added methanol (0.10 mL) and ethylenediamine (0.04 mL, 0.5 mmol). The reaction mixture was stirred for 20 min and then concentrated in vacuo. The crude was purified by prep LC-MS (pH=10 method; XBridge™ PrepC18 5 μm OBD™ column, 30×10 mm, 60 mL/min, eluting with a gradient of MeCN and water with $NH_4OH$) to give the desired product as a white powder (1.3 mg, 16%). LCMS calcd for $C_{22}H_{20}N_3O$ (M+H)$^+$: m/z=342.2. Found: 342.3.

Example 16

N-({2-[3-(7H-Pyrrolo[2,3-d]pyrimidin-4-yl)phenyl]-2,3-dihydro-1H-inden-2-yl}methyl)acetamide

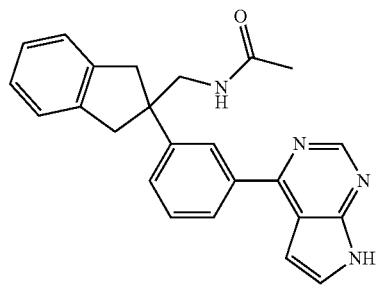 [SMILES: CC(=O)NCC1(c2cccc(-c3ncnc4[nH]ccc34)c2)Cc2ccccc2C1]

To a solution of 1-{2-[3-(7H-pyrrolo[2,3-d]pyrimidin-4-yl)phenyl]-2,3-dihydro-1H-inden-2-yl}methanamine (Prepared in Example 11; 5.0 mg, 0.015 mmol) in tetrahydrofuran (0.06 mL) and 1.0 M sodium bicarbonate in water (0.029 mL, 0.029 mmol) at 0° C., was added slowly acetic anhydride (4.0 mg, 0.04 mmol). The reaction mixture was stirred at rt for 20 min. After concentrated under reduced pressure, the crude was purified by prep LC-MS (pH=10 method; XBridge™ PrepC18 5 μm OBD™ column, 30×10 mm, 60 mL/min, eluting with a gradient of MeCN and water with $NH_4OH$) to give the desired product as a white powder (2.8 mg, 50%). LCMS calcd for $C_{24}H_{23}N_4O$ (M+H)$^+$: m/z=383.2. Found: 383.3.

Example 17

2-Methyl-N-({2-[3-(7H-pyrrolo[2,3-d]pyrimidin-4-yl)phenyl]-2,3-dihydro-1H-inden-2-yl}methyl)propanamide

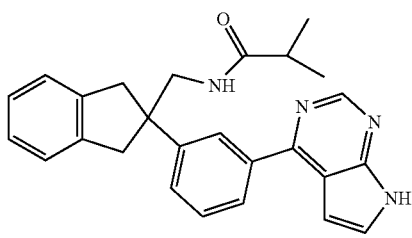 [SMILES: CC(C)C(=O)NCC1(c2cccc(-c3ncnc4[nH]ccc34)c2)Cc2ccccc2C1]

To a solution of 1-{2-[3-(7H-pyrrolo[2,3-d]pyrimidin-4-yl)phenyl]-2,3-dihydro-1H-inden-2-yl}methanamine (Prepared in Example 11; 3.0 mg, 0.01 mmol) in tetrahydrofuran (0.036 mL) and 1.0 M sodium bicarbonate in water (0.018 mL, 0.018 mmol) at 0° C., was added slowly 2-methylpropanoic acid anhydride (2.8 mg, 0.018 mmol). The reaction mixture was stirred at rt for 30 min. After concentrated under reduced pressure, the crude was purified by prep LC-MS (pH=10 method; XBridge™ PrepC18 5 m OBD™ column, 30×10 mm, 60 mL/min, eluting with a gradient of MeCN and water with NH$_4$OH) to give the desired product as a white powder (1.8 mg, 50%). LCMS calcd for C$_{26}$H$_{27}$N$_4$O (M+H)$^+$: m/z=411.2. Found: 411.3.

Example 18

N-({2-[3-(7H-Pyrrolo[2,3-d]pyrimidin-4-yl)phenyl]-2,3-dihydro-1H-inden-2-yl}methyl)cyclopropanecarboxamide

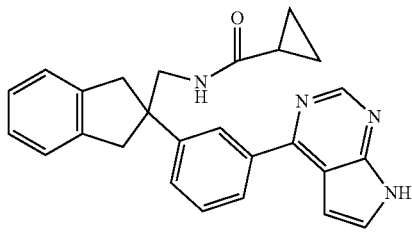 [SMILES: O=C(NCC1(c2cccc(-c3ncnc4[nH]ccc34)c2)Cc2ccccc2C1)C1CC1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.024 mL) and 1.0 M sodium bicarbonate in water (0.012 mL, 0.012 mmol) at 0° C., was added slowly cyclopropanecarbonyl chloride (2.5 mg, 0.023 mmol). The reaction mixture was stirred at rt for 15 min. After the reaction mixture was concentrated to dryness under reduced pressure, the crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.1 mg, 46%). LCMS calcd for C$_{26}$H$_{25}$N$_4$O (M+H)$^+$: m/z=409.3. Found: 409.3.

Example 19

4-{3-[2-(Fluoromethyl)-2,3-dihydro-1H-inden-2-yl]phenyl}-7H-pyrrolo[2,3-d]pyrimidine

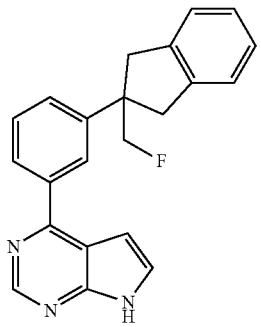 [SMILES: FCC1(c2cccc(-c3ncnc4[nH]ccc34)c2)Cc2ccccc2C1]

Step 1: 4-{3-[2-(Fluoromethyl)-2,3-dihydro-1H-inden-2-yl]phenyl}-7-{[2-(trimethylsilyl)ethoxy]methyl}-7H-pyrrolo[2,3-d]pyrimidine

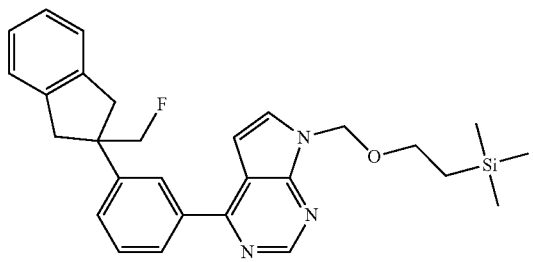 [SMILES: C[Si](C)(C)CCOCn1ccc2c(-c3cccc(C4(CF)Cc5ccccc5C4)c3)ncnc21]

{2-[3-(7-{[2-(Trimethylsilyl)ethoxy]methyl}-7H-pyrrolo[2,3-d]pyrimidin-4-yl)phenyl]-2,3-dihydro-1H-inden-2-yl}methanol (Prepared in Example 12, Step 2; 6.0 mg, 0.013 mmol) was dissolved in methylene chloride (0.08 mL), cooled to −78° C., and then treated with diethylaminosulfur trifluoride (6.2 mg, 0.04 mmol). The resulting reaction mixture was warmed to rt and stirred at rt for 30 min. The reaction mixture was diluted with water and MeOH, and then was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.7 mg, 28%). LCMS calcd for C$_{28}$H$_{33}$FN$_3$OSi (M+H)$^+$: m/z=474.2. Found: 474.3.

Step 2: 4-{3-[2-(Fluoromethyl)-2,3-dihydro-1H-inden-2-yl]phenyl}-7H-pyrrolo[2,3-d]pyrimidine To a solution of 4-{3-[2-(fluoromethyl)-2,3-dihydro-1H-inden-2-yl]phenyl}-7-{[2-(trimethylsilyl)ethoxy]methyl}-7H-pyrrolo[2,3-d]pyrimidine (3.0 mg, 0.006 mmol) in methylene chloride (0.015 mL) was added trifluoroacetic acid (0.03 mL, 0.4 mmol). The reaction mixture was stirred for 30 min, and then concentrated under vacuum. To this residue was added methanol (0.20 mL) and ethylenediamine (0.01 mL, 0.15 mmol). The reaction mixture was stirred for 10 min and then concentrated under vacuum. The crude was purified by prep LC-MS (pH=10 method; XBridge™ PrepC18 5 μm OBD™ column, 30×10 mm, 60 mL/min, eluting with a gradient of MeCN and water with NH₄OH) to give the desired product as a white powder (1.0 mg, 40%). LCMS calcd for $C_{22}H_{19}FN_3$ (M+H)⁺: m/z=344.2. Found: 344.2.

Example 20

4-{3-[2-(Difluoromethyl)-2,3-dihydro-1H-inden-2-yl]phenyl}-7H-pyrrolo[2,3-d]pyrimidine

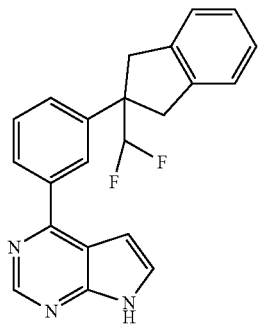 [SMILES: FC(F)C1(c2cccc(-c3ncnc4[nH]ccc34)c2)Cc2ccccc2C1]

Step 1: 4-{3-[2-(Difluoromethyl)-2,3-dihydro-1H-inden-2-yl]phenyl}-7-{[2-(trimethylsilyl)ethoxy]methyl}-7H-pyrrolo[2,3-d]pyrimidine

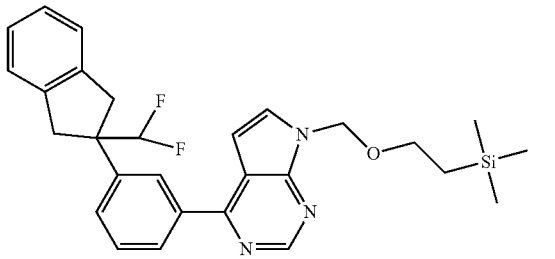

2-[3-(7-{[2-(Trimethylsilyl)ethoxy]methyl}-7H-pyrrolo[2,3-d]pyrimidin-4-yl)phenyl]indane-2-carbaldehyde (Prepared in Example 12, Step 1; 6.0 mg, 0.013 mmol) was dissolved in methylene chloride (0.08 mL), cooled to −78° C., and then treated with diethylaminosulfur trifluoride (8.2 mg, 0.05 mmol). The resulting reaction mixture was warmed up to rt and stirred at rt for 80 min. The reaction mixture was diluted with water and MeOH, and then was purified by prep LC-MS (pH=10 method; XBridge™ PrepC18 5 μm OBD™ column, 30×10 mm, 60 mL/min, eluting with a gradient of MeCN and water with NH₄OH) to give the desired product as a white powder (2.0 mg, 32%). LCMS calcd for $C_{28}H_{32}F_2N_3OSi$ (M+H)⁺: m/z=492.2. Found: 492.3.

Step 2: 4-{3-[2-(Difluoromethyl)-2,3-dihydro-1H-inden-2-yl]phenyl}-7H-pyrrolo[2,3-d]pyrimidine To a solution of 4-{3-[2-(difluoromethyl)-1H-inden-2-yl]phenyl}-7-{[2-(trimethylsilyl)ethoxy]methyl}-7H-pyrrolo[2,3-d]pyrimidine (2.5 mg, 0.005 mmol) in methylene chloride (0.03 mL) was added trifluoroacetic acid (0.06 mL, 0.78 mmol). The reaction mixture was stirred for 30 min, and then concentrated under vacuum. To this residue was added methanol (0.08 mL) and ethylenediamine (0.01 mL, 0.15 mmol). The reaction mixture was stirred for 10 min and then concentrated under vacuum. The crude was purified by prep LC-MS (pH=10 method; XBridge™ PrepC18 5 μm OBD™ column, 30×10 mm, 60 mL/min, eluting with a gradient of MeCN and water with NH₄OH) to give the desired product as a white powder (1.2 mg, 65%). LCMS calcd for $C_{22}H_{18}F_2N_3$ (M+H)⁺: m/z=362.2. Found: 362.3.

Example 21

N-({2-[3-(7H-Pyrrolo[2,3-d]pyrimidin-4-yl)phenyl]-2,3-dihydro-1H-inden-2-yl}methyl)methanesulfonamide

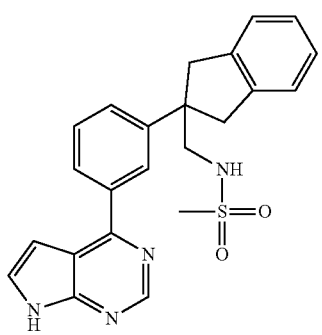 [SMILES: CS(=O)(=O)NCC1(c2cccc(-c3ncnc4[nH]ccc34)c2)Cc2ccccc2C1]

Step 1: N-({2-[3-(7-{[2-(Trimethylsilyl)ethoxy]methyl}-7H-pyrrolo[2,3-d]pyrimidin-4-yl)phenyl]-2,3-dihydro-1H-inden-2-yl}methyl)methanesulfonamide

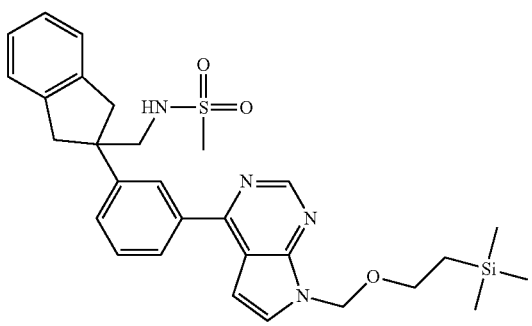 [SMILES: C[Si](C)(C)CCOCn1ccc2c(-c3cccc(C4(CNS(C)(=O)=O)Cc5ccccc5C4)c3)ncnc21]

To a mixture of 1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine (Prepared in Example 11, Step 2; 8.0 mg, 0.017 mmol) in methylene chloride (0.11 mL) was added triethylamine (3.6 μL, 0.03 mmol), followed by the addition of methanesulfonyl chloride (2.7 mg, 0.02 mmol) at 0° C. The reaction mixture was stirred at rt for 1 h, then concentrated to dryness under reduced pressure. The resulting crude residue was used directly in next step. LCMS calcd for $C_{29}H_{37}N_4O_3SSi$ (M+H)⁺: m/z=549.2. Found: 549.3.

Step 2: N-({2-[3-(7H-Pyrrolo[2,3-d]pyrimidin-4-yl)phenyl]-2,3-dihydro-1H-inden-2-yl}methyl)methanesulfonamide To a solution of N-({2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)methanesulfonamide (9.3 mg, 0.017 mmol) in methylene chloride (0.04 mL) was added trifluoroacetic acid (0.08 mL, 1.0 mmol). The reaction mixture was stirred at rt for 30 min, and then concentrated under vacuum.

To this residue was added methanol (0.20 mL) and ethylenediamine (0.013 mL, 0.2 mmol). The reaction mixture was stirred for 10 min and then concentrated under vacuum. The crude was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (3.6 mg, 51%). LCMS calcd for $C_{23}H_{23}N_4O_2S$ (M+H)$^+$: m/z=419.2. Found: 419.3.

Example 22

Methyl ({2-[3-(7H-pyrrolo[2,3-d]pyrimidin-4-yl)phenyl]-2,3-dihydro-1H-inden-2-yl}methyl)carbamate

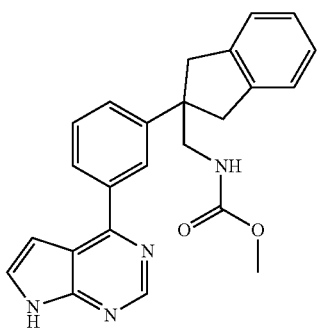 [SMILES: COC(=O)NCC1(c2cccc(-c3ncnc4[nH]ccc34)c2)Cc2ccccc2C1]

Step 1: Methyl ({2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate

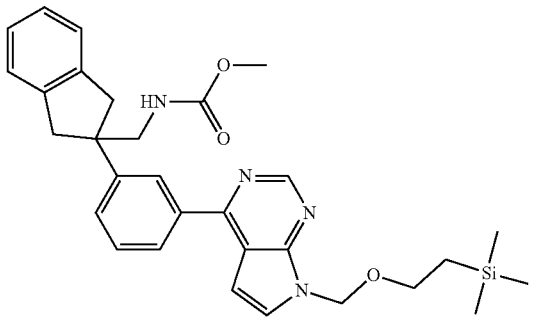 [SMILES: COC(=O)NCC1(c2cccc(-c3ncnc4c3ccn4COCC[Si](C)(C)C)c2)Cc2ccccc2C1]

To a mixture of 1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine (Prepared in Example 11, Step 2; 8.0 mg, 0.017 mmol) in methylene chloride (0.11 mL) was added triethylamine (3.6 μL, 0.03 mmol), followed by the addition of methyl chloroformate (2.1 mg, 0.02 mmol) at 0° C. The reaction mixture was stirred at rt for 1 h, then concentrated to dryness under reduced pressure. The resulting crude was used directly in next step. LCMS calcd for $C_{30}H_{37}N_4O_3Si$ (M+H)$^+$: m/z=529.3. Found: 529.3.

Step 2: Methyl ({2-[3-(7H-pyrrolo[2,3-d]pyrimidin-4-yl)phenyl]-2,3-dihydro-1H-inden-2-yl}methyl)carbamate To a solution of methyl ({2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (9.0 mg, 0.017 mmol) in methylene chloride (0.04 mL) was added trifluoroacetic acid (0.08 mL, 1.0 mmol). The reaction mixture was stirred for 30 min, and then concentrated under vacuum. To this residue was added methanol (0.20 mL) and ethylenediamine (0.01 mL, 0.16 mmol). The reaction mixture was stirred for 10 min and then concentrated under vacuum. The crude was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (3.2 mg, 47%). LCMS calcd for $C_{24}H_{23}N_4O_2$ (M+H)$^+$: m/z=399.2. Found: 399.3.

Example 23

N,N-Dimethyl-1-{2-[3-(7H-pyrrolo[2,3-d]pyrimidin-4-yl)phenyl]-2,3-dihydro-1H-inden-2-yl}methanamine

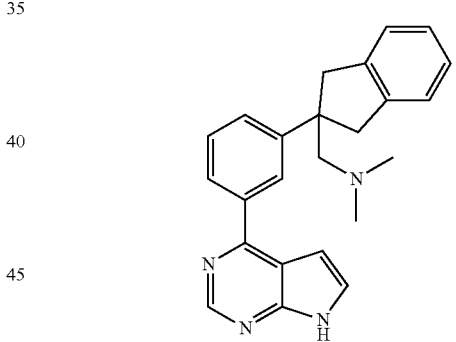

Step 1: N,N-Dimethyl-1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine

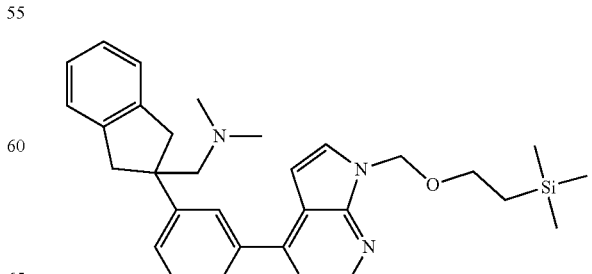

A solution of 2-[3-(7-{[2-(trimethylsilyl)ethoxy]methyl}-7H-pyrrolo[2,3-d]pyrimidin-4-yl)phenyl]indane-2-carbaldehyde (Prepared in Example 12, Step 1; 5.0 mg, 0.011 mmol) in dry methylene chloride (0.04 mL) was treated with 2.0 M dimethylamine in THF (0.027 mL, 0.05 mmol), followed by the addition of sodium triacetoxyborohydride (9.0 mg, 0.04 mmol) and stirred at rt for 20 min. The reaction mixture was diluted with H$_2$O and EtOAc. The aqueous layer was extracted with EtOAc (×3). The combined organic layers were dried, filtered and concentrated under vacuum to give the desired product, which was used as crude in the next step. LCMS calcd for C$_{30}$H$_{39}$N$_4$OSi (M+H)$^+$: m/z=499.3. Found: 499.3.

Step 2: N,N-Dimethyl-1-{2-[3-(7H-pyrrolo[2,3-d]pyrimidin-4-yl)phenyl]-2,3-dihydro-1H-inden-2-yl}methanamine To a solution of N,N-dimethyl-1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine (Prepared in Example 11, Step 2; 5.3 mg, 0.011 mmol) in methylene chloride (0.025 mL) was added trifluoroacetic acid (0.05 mL, 0.65 mmol). The reaction mixture was stirred for 30 min, and then concentrated under vacuum. To this residue was added methanol (0.20 mL) and ethylenediamine (0.01 mL, 0.17 mmol). The reaction mixture was stirred for 10 min and then concentrated under vacuum. The crude was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (2.5 mg, 64%). LCMS calcd for C$_{24}$H$_{25}$N$_4$(M+H)$^+$: m/z=369.2. Found: 369.3.

Example 24

N-Methyl-1-{2-[3-(7H-pyrrolo[2,3-d]pyrimidin-4-yl)phenyl]-2,3-dihydro-1H-inden-2-yl}methanamine

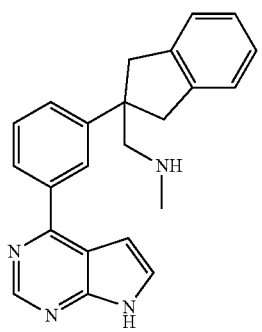

Step 1: N-Methyl-1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine

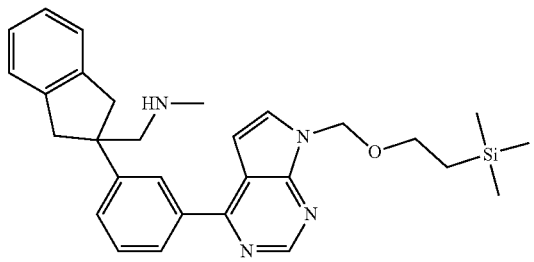 [SMILES: CNCC1(c2cccc(-c3ncnc4c3ccn4COCC[Si](C)(C)C)c2)Cc2ccccc2C1]

A solution of 2-[3-(7-{[2-(trimethylsilyl)ethoxy]methyl}-7H-pyrrolo[2,3-d]pyrimidin-4-yl)phenyl]indane-2-carbaldehyde (Prepared in Example 12, Step 1; 4.0 mg, 0.01 mmol) in dry methylene chloride (0.033 mL) was treated with 2.0 M methylamine in THF (0.021 mL, 0.042 mmol) at rt, followed by the addition of sodium triacetoxyborohydride (7.2 mg, 0.034 mmol) and two drops of AcOH. The reaction mixture was stirred at rt for 30 min. The reaction mixture was diluted with H$_2$O and EtOAc. The aqueous layer was extracted with EtOAc (×3). The combined organic layers were dried, filtered and concentrated under vacuum to give the desired product, which was used as crude in the next step. LCMS calcd for C$_{29}$H$_{37}$N$_4$OSi (M+H)$^+$: m/z=485.3. Found: 485.3.

Step 2: N-Methyl-1-{2-[3-(7H-pyrrolo[2,3-d]pyrimidin-4-yl)phenyl]-2,3-dihydro-1H-inden-2-yl}methanamine To a solution of N-methyl-1-{2-[3-(7-{[2-(trimethylsilyl)ethoxy]methyl}-7H-pyrrolo[2,3-d]pyrimidin-4-yl)phenyl]-2,3-dihydro-1H-inden-2-yl}methanamine (Prepared in Example 11, Step 2; 4.1 mg, 0.008 mmol) in methylene chloride (0.02 mL) was added trifluoroacetic acid (0.04 mL, 0.5 mmol). The reaction mixture was stirred for 30 min, and then concentrated under vacuum. To this residue was added methanol (0.20 mL) and ethylenediamine (0.03 mL, 0.05 mmol). The reaction mixture was stirred for 10 min and then concentrated under vacuum. The crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (2.1 mg, 70%). LCMS calcd for C$_{23}$H$_{23}$N$_4$(M+H)$^+$: m/z=355.2. Found: 355.3.

Example 25

4-{3-[2-(Methoxymethyl)-2,3-dihydro-1H-inden-2-yl]phenyl}-7H-pyrrolo[2,3-d]pyrimidine

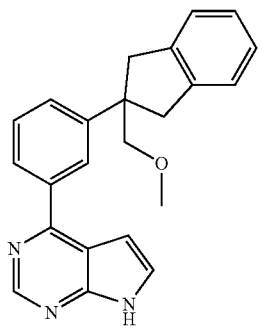 [SMILES: COCC1(c2cccc(-c3ncnc4[nH]ccc34)c2)Cc2ccccc2C1]

Step 1: 4-{3-[2-(Methoxymethyl)-2,3-dihydro-1H-inden-2-yl]phenyl}-7-{[2-(trimethylsilyl)ethoxy]methyl}-7H-pyrrolo[2,3-d]pyrimidine

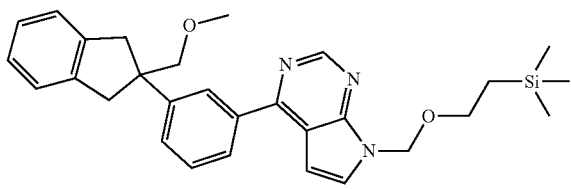 [SMILES: COCC1(c2cccc(-c3ncnc4c3ccn4COCC[Si](C)(C)C)c2)Cc2ccccc2C1]

To a solution of {2-[3-(7-{[2-(trimethylsilyl)ethoxy]methyl}-7H-pyrrolo[2,3-d]pyrimidin-4-yl)phenyl]-2,3-dihydro-1H-inden-2-yl}methanol (Prepared in Example 12, Step 2; 8.5 mg, 0.02 mmol) in tetrahydrofuran (0.15 mL) was slowly added sodium hydride (5.8 mg, 0.14 mmol) at room temperature and the reaction mixture was stirred for 10 min, followed by the addition of methyl iodide (20. mg, 0.14 mmol). The reaction mixture was stirred at rt for 16 h, then diluted with EtOAc and water. The aqueous layer was extracted with ethyl acetate. The organic layers were combined, dried, filtered and concentrated under vacuum. The crude was purified by prep LC-MS (pH=10 method; XBridge™ PrepC18 5 μm OBD™ column, 30×10 mm, 60 mL/min, eluting with a gradient of MeCN and water with NH₄OH) to give the desired product as a white powder (2.5 mg, 28%). LCMS calcd for $C_{29}H_{36}N_3O_2Si$ (M+H)⁺: m/z=486.3. Found: 486.3.

Step 2: 4-{3-[2-(Methoxymethyl)-2,3-dihydro-1H-inden-2-yl]phenyl}-7H-pyrrolo[2,3-d]pyrimidine To a solution of 4-{3-[2-(methoxymethyl)-2,3-dihydro-1H-inden-2-yl]phenyl}-7-{[2-(trimethylsilyl)ethoxy]methyl}-7H-pyrrolo[2,3-d]pyrimidine (2.5 mg, 0.005 mmol) in methylene chloride (0.012 mL) was added trifluoroacetic acid (0.024 mL, 0.3 mmol). The reaction mixture was stirred for 30 min, and then concentrated under vacuum. To this residue was added methanol (0.20 mL) and ethylenediamine (0.008 mL, 0.12 mmol). The reaction mixture was stirred for 10 min and then concentrated under vacuum. The crude was purified by prep LC-MS (pH=10 method; XBridge™ PrepC18 5 m OBD™ column, 30×10 mm, 60 mL/min, eluting with a gradient of MeCN and water with NH₄OH) to give the desired product as a white powder (1.3 mg, 71%). LCMS calcd for $C_{23}H_{22}N_3O$ (M+H)⁺: m/z=356.2. Found: 356.3.

Example 26

N-({2-[3-(7H-Pyrrolo[2,3-d]pyrimidin-4-yl)phenyl]-2,3-dihydro-1H-inden-2-yl}methyl)cyclobutanecarboxamide

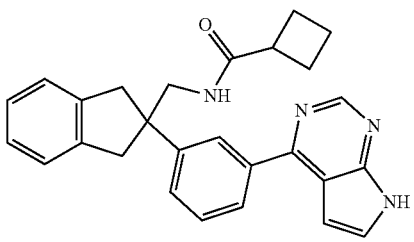 [SMILES: O=C(NCC1(c2cccc(-c3ncnc4[nH]ccc34)c2)Cc2ccccc2C1)C1CCC1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.05 mL) and 1.0 M sodium bicarbonate in water (0.012 mL, 0.012 mmol) at 0° C., was added slowly cyclobutanecarboxylic acid chloride (3.5 mg, 0.03 mmol). The reaction mixture was stirred at rt for 30 min. After the reaction mixture was concentrated under reduced pressure, the crude residue was purified by prep LC-MS (pH=10 method; XBridge™ PrepC18 5 μm OBD™ column, 30×10 mm, 60 mL/min, eluting with a gradient of MeCN and water with NH₄OH) to give the desired product as a white powder (1.2 mg, 45%). LCMS calcd for $C_{27}H_{27}N_4O$ (M+H)⁺: m/z=423.2. Found: 423.3.

Example 27

N-({2-[3-(7H-Pyrrolo[2,3-d]pyrimidin-4-yl)phenyl]-2,3-dihydro-1H-inden-2-yl}methyl)cyclopentanecarboxamide

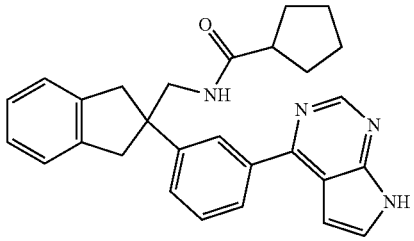 [SMILES: O=C(NCC1(c2cccc(-c3ncnc4[nH]ccc34)c2)Cc2ccccc2C1)C1CCCC1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at 0° C., was added slowly cyclopentanecarbonyl chloride (3.1 mg, 0.023 mmol). The reaction mixture was stirred at rt for 10 min. After the reaction mixture was concentrated to dryness under reduced pressure, the crude was purified by prep LC-MS (pH=10 method; XBridge™ PrepC18 5 µm OBD™ column, 30×10 mm, 60 mL/min, eluting with a gradient of MeCN and water with NH₄OH) to give the desired product as a white powder (1.0 mg, 39%). LCMS calcd for $C_{28}H_{29}N_{4}O$ (M+H)⁺: m/z=437.2. Found: 437.3.

Example 28

N-((((2-3-(7H-Pyrrolo[2-3-d]pyrimidin-4-yl)phenyl)-2,3-dihydro-1H-inden-2-yl)methyl)thiophene-2-carboxamide

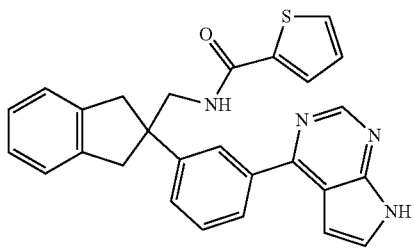 [SMILES: O=C(NCC1(c2cccc(-c3ncnc4[nH]ccc34)c2)Cc2ccccc2C1)c1cccs1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly 2-thiophenecarboxylic acid chloride (8.6 mg, 0.06 mmol). The reaction mixture was stirred at rt for 10 min. After concentrated under reduced pressure, the crude was purified by prep LC-MS (pH=10 method; XBridge™ PrepC18 5 µm OBD™ column, 30×10 mm, 60 mL/min, eluting with a gradient of MeCN and water with NH₄OH) to give the desired product as a white powder (1.2 mg, 45%). LCMS calcd for $C_{27}H_{23}N_{4}OS$ (M+H)⁺: m/z=451.2. Found: 451.3.

Example 29

1-Methyl-N-({2-[3-(7H-pyrrolo[2,3-d]pyrimidin-4-yl)phenyl]-2,3-dihydro-1H-inden-2-yl}methyl)-1H-pyrazole-3-carboxamide

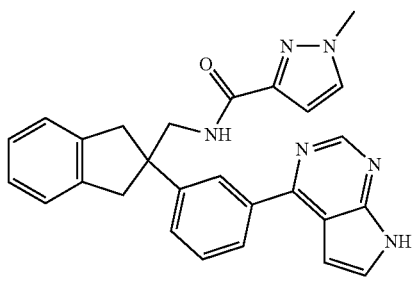 [SMILES: Cn1ccc(C(=O)NCC2(c3cccc(-c4ncnc5[nH]ccc45)c3)Cc3ccccc3C2)n1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly 1-methyl-1H-pyrazole-3-carbonyl chloride (from Aldrich; 4.2 mg, 0.03 mmol). The reaction mixture was stirred at rt for 10 min. After the reaction mixture was concentrated under reduced pressure, the crude residue was purified by prep LC-MS (pH=10 method; XBridge™ PrepC18 5 µm OBD™ column, 30×10 mm, 60 mL/min, eluting with a gradient of MeCN and water with NH₄OH) to give the desired product as a white powder (2.0 mg, 76%). LCMS calcd for $C_{27}H_{25}N_{6}O$ (M+H)⁺: m/z=449.2. Found: 449.3.

Example 30

4-Methyl-N-({2-[3-(7H-pyrrolo[2,3-d]pyrimidin-4-yl)phenyl]-2,3-dihydro-1H-inden-2-yl}methyl)-1,3-oxazole-5-carboxamide

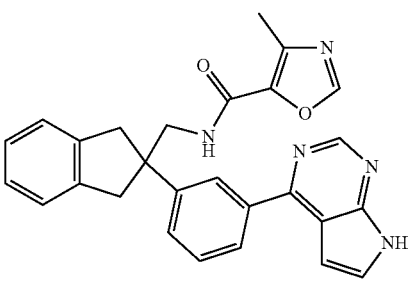 [SMILES: Cc1ncoc1C(=O)NCC1(c2cccc(-c3ncnc4[nH]ccc34)c2)Cc2ccccc2C1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly 4-methyl-1,3-oxazole-5-carbonyl chloride (from Asta Tech; 4.3 mg, 0.03 mmol). The reaction mixture was stirred at rt for 60 min. After the reaction mixture was concentrated under reduced pressure, the crude was purified by prep LC-MS (pH=10 method; XBridge™ PrepC18 5 µm OBD™ column, 30×10 mm, 60 mL/min, eluting with a gradient of MeCN and water with NH₄OH) to give the desired product as a white powder (1.3 mg, 45%). LCMS calcd for $C_{27}H_{24}N_{5}O_{2}$ (M+H)⁺: m/z=450.2. Found: 450.3.

Example 31

N-({2-[3-(7H-Pyrrolo[2,3-d]pyrimidin-4-yl)phenyl]-2,3-dihydro-1H-inden-2-yl}methyl)isoxazole-5-carboxamide

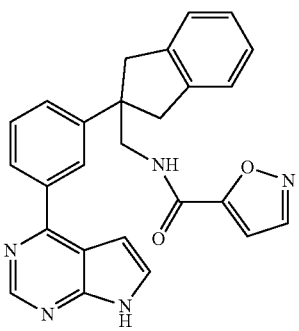 [SMILES: O=C(NCC1(c2cccc(-c3ncnc4[nH]ccc34)c2)Cc2ccccc2C1)c1ccno1]

1-{2-[3-(7H-Pyrrolo[2,3-d]pyrimidin-4-yl)phenyl]-2,3-dihydro-1H-inden-2-yl}methanamine (Prepared in Example 11; 2.0 mg, 0.006 mmol), isoxazole-5-carboxylic acid (from Combi-Block; 1.0 mg, 0.009 mmol), N,N,N',N'-tetramethyl- O-(7-azabenzotriazol-1-yl)uronium hexafluorophosphate (5.6 mg, 0.015 mmol) in N,N-dimethylformamide (0.08 mL) and N,N-diisopropylethylamine (2.3 mg, 0.02 mmol) were mixed together and stirred at rt for 1 h. The reaction mixture was filtered, concentrated and purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.6 mg, 62%). LCMS calcd for C$_{26}$H$_{22}$N$_5$O$_2$ (M+H)$^+$: m/z=436.2. Found: 436.3.

Example 32

1-Methyl-N-({2-[3-(7H-pyrrolo[2,3-d]pyrimidin-4-yl)phenyl]-2,3-dihydro-1H-inden-2-yl}methyl)-1H-pyrazole-5-carboxamide

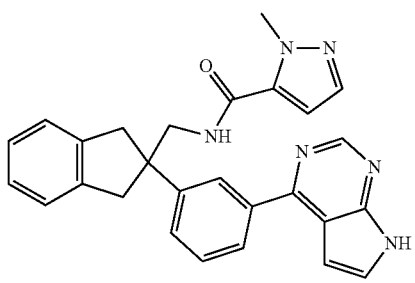 [SMILES: Cn1nccc1C(=O)NCC1(c2cccc(-c3ncnc4[nH]ccc34)c2)Cc2ccccc2C1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly 1-methyl-1H-pyrazole-5-carbonyl chloride (from Combi-Block; 4.2 mg, 0.03 mmol). The reaction mixture was stirred at rt for 10 min. After the reaction mixture was concentrated, the crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (2.2 mg, 83%). LCMS calcd for C$_{27}$H$_{25}$N$_6$O (M+H)$^+$: m/z=449.2. Found: 449.3.

Example 33

1-Methyl-N-({2-[3-(7H-pyrrolo[2,3-d]pyrimidin-4-yl)phenyl]-2,3-dihydro-1H-inden-2-yl}methyl)-1H-pyrazole-4-carboxamide

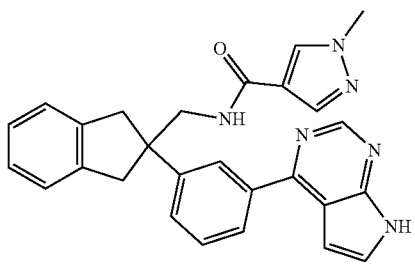 [SMILES: Cn1cc(C(=O)NCC2(c3cccc(-c4ncnc5[nH]ccc45)c3)Cc3ccccc3C2)cn1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly 1-methyl-1H-pyrazole-4-carbonyl chloride (from Combi-Block; 4.2 mg, 0.03 mmol). The reaction mixture was stirred at rt for 10 min. After the reaction mixture was concentrated under reduced pressure, the crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.8 mg, 68%). LCMS calcd for C$_{27}$H$_{25}$N$_6$O (M+H)$^+$: m/z=449.2. Found: 449.3.

Example 34

N-({2-[3-(7H-Pyrrolo[2,3-d]pyrimidin-4-yl)phenyl]-2,3-dihydro-1H-inden-2-yl}methyl)-2-furamide

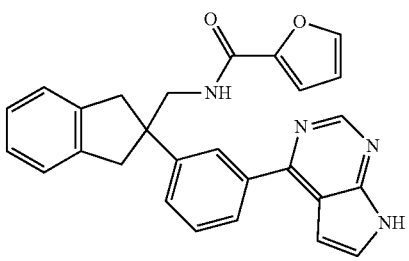 [SMILES: O=C(NCC1(c2cccc(-c3ncnc4[nH]ccc34)c2)Cc2ccccc2C1)c1ccco1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly 2-furancarbonyl chloride (from Anichem; 7.7 mg, 0.06 mmol). The reaction mixture was stirred at rt for 40 min. After the reaction mixture was concentrated under reduced pressure, the crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (0.9 mg, 40%). LCMS calcd for C$_{27}$H$_{23}$N$_4$O$_2$ (M+H)$^+$: m/z=435.2. Found: 435.3.

Example 35

N-({2-[3-(7H-Pyrrolo[2,3-d]pyrimidin-4-yl)phenyl]-2,3-dihydro-1H-inden-2-yl}methyl)morpholine-4-carboxamide

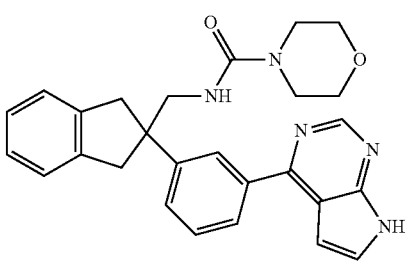 [SMILES: O=C(NCC1(c2cccc(-c3ncnc4[nH]ccc34)c2)Cc2ccccc2C1)N1CCOCC1]

To a solution of 1-{2-[3-(7H-pyrrolo[2,3-d]pyrimidin-4-yl)phenyl]-2,3-dihydro-1H-inden-2-yl}methanamine (Prepared in Example 11; 2.0 mg, 0.006 mmol) in tetrahydrofuran (0.048 mL) and 1.0 M sodium bicarbonate in water (0.012 mL, 0.012 mmol) at rt, was added slowly morpholine-4-carbonyl chloride (from Aldrich; 8.8 mg, 0.06 mmol). The reaction mixture was stirred at rt for 20 min. After the reaction mixture was concentrated, the crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.5 mg, 56%). LCMS calcd for $C_{27}H_{28}N_5O_2$ (M+H)$^+$: m/z=454.2. Found: 454.3.

Example 36

{2-[3-(7H-Pyrrolo[2,3-d]pyrimidin-4-yl)phenyl]-2,3-dihydro-1H-inden-2-yl}acetonitrile

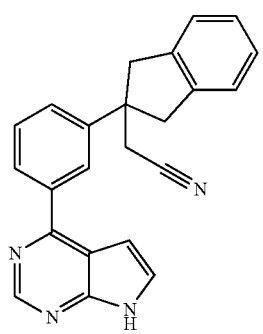 [SMILES: N#CCC1(c2cccc(-c3ncnc4[nH]ccc34)c2)Cc2ccccc2C1]

Step 1: {2-[3-(7-{[2-(trimethylsilyl)ethoxy]methyl}-7H-pyrrolo[2,3-d]pyrimidin-4-yl)phenyl]-2,3-dihydro-1H-inden-2-yl}acetonitrile

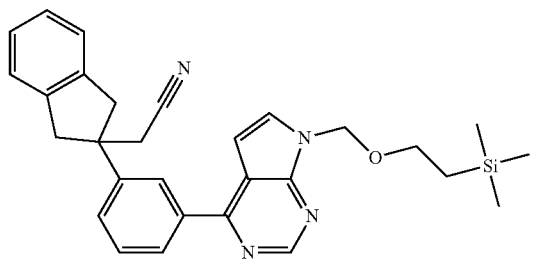 [SMILES: C[Si](C)(C)CCOCn1ccc2c(-c3cccc(C4(CC#N)Cc5ccccc5C4)c3)ncnc21]

To a mixture of {2-[3-(7-{[2-(trimethylsilyl)ethoxy]methyl}-7H-pyrrolo[2,3-d]pyrimidin-4-yl)phenyl]-2,3-dihydro-1H-inden-2-yl}methanol (Prepared in Example 12, Step 2; 10.0 mg, 0.02 mmol) in methylene chloride (0.14 mL) was added triethylamine (8.9 μL, 0.06 mmol), followed by the addition of methanesulfonyl chloride (12.1 mg, 0.11 mmol) at 0° C.

After the reaction mixture was stirred at rt for 1 h, the resultant reaction mixture was concentrated to dryness under reduced pressure. The resulting crude mesylate was dissolved in N,N-dimethylformamide (0.12 mL) and treated with sodium cyanide (103.9 mg, 2.1 mmol) at 120° C. for 16 h. After filtration, the crude filtrate was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (6.6 mg, 65%). LCMS calcd for $C_{29}H_{33}N_4OSi$ (M+H)$^+$: m/z=481.2. Found: 481.3.

Step 2: {2-[3-(7H-Pyrrolo[2,3-d]pyrimidin-4-yl)phenyl]-2,3-dihydro-1H-inden-2-yl}acetonitrile To a solution of {2-[3-(7-{[2-(trimethylsilyl)ethoxy]methyl}-7H-pyrrolo[2,3-d]pyrimidin-4-yl)phenyl]-2,3-dihydro-1H-inden-2-yl}acetonitrile (3.0 mg, 0.006 mmol) in methylene chloride (0.015 mL) was added trifluoroacetic acid (0.029 mL, 0.38 mmol). The reaction mixture was stirred for 30 min, and then concentrated under vacuum. To this residue was added methanol (0.20 mL) and ethylenediamine (0.007 mL, 0.10 mmol). The reaction mixture was stirred for 10 min and then concentrated under vacuum. The crude was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.5 mg, 68%). LCMS calcd for $C_{23}H_{19}N_4$(M+H)$^+$: m/z=351.2. Found: 351.3.

Example 37

2-{2-[3-(7H-Pyrrolo[2,3-d]pyrimidin-4-yl)phenyl]-2,3-dihydro-1H-inden-2-yl}ethanamine

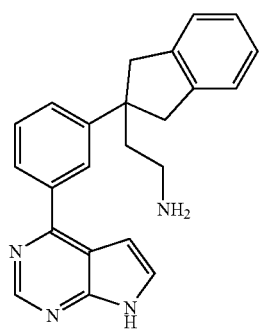 [SMILES: NCCC1(c2cccc(-c3ncnc4[nH]ccc34)c2)Cc2ccccc2C1]

Step 1: 2-{2-[3-(7-{[2-(trimethylsilyl)ethoxy]methyl}-7H-pyrrolo[2,3-d]pyrimidin-4-yl)phenyl]-2,3-dihydro-1H-inden-2-yl}ethanamine

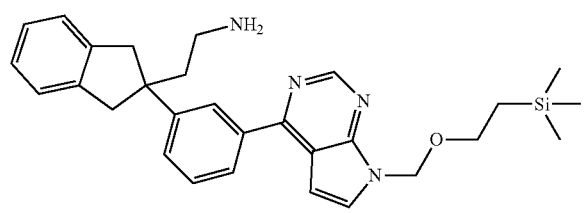 [SMILES: C[Si](C)(C)CCOCn1ccc2c(-c3cccc(C4(CCN)Cc5ccccc5C4)c3)ncnc21]

To a solution of {2-[3-(7-{[2-(trimethylsilyl)ethoxy]methyl}-7H-pyrrolo[2,3-d]pyrimidin-4-yl)phenyl]-2,3-dihydro-1H-inden-2-yl}acetonitrile (Prepared in Example 36, Step 1; 4.6 mg, 0.01 mmol) in tetrahydrofuran (0.08 mL) was added 1.0 M lithium tetrahydroaluminate in tetrahydrofuran (0.012 mL, 0.012 mmol) at 0° C. The reaction mixture was stirred at rt for 40 min. The reaction was quenched with NaOH (1N), washed with water and extracted with EtOAc. After the reaction mixture was concentrated, the crude product (4.6 mg, 100%) was used directly in the next reaction. LCMS calcd for $C_{29}H_{37}N_4OSi$ (M+H)$^+$: m/z=485.3. Found: 485.3.

Step 2: 2-{2-[3-(7H-Pyrrolo[2,3-d]pyrimidin-4-yl)phenyl]-2,3-dihydro-1H-inden-2-yl}ethanamine To a solution of 2-{2-[3-(7-{[2-(trimethylsilyl)ethoxy]methyl}-7H-pyrrolo[2,3-d]pyrimidin-4-yl)phenyl]-2,3-dihydro-1H-inden-2-yl}ethanamine (4.6 mg, 0.01 mmol) in methylene chloride (0.02 mL) was added trifluoroacetic acid (0.045 mL, 0.6 mmol). The reaction mixture was stirred for 30 min, and then concentrated under vacuum. To this residue was added methanol (0.20 mL) and ethylenediamine (0.008 mL, 0.11 mmol). The reaction mixture was stirred for 10 min and then concentrated under vacuum. The crude was purified by prep LC-MS (pH=10 method; XBridge™ PrepC18 5 m OBD™ column, 30×10 mm, 60 mL/min, eluting with a gradient of MeCN and water with NH$_4$OH) to give the desired product as a white powder (1.2 mg, 36%). LCMS calcd for $C_{23}H_{23}N_4$(M+H)$^+$: m/z=355.2. Found: 355.3.

Example 38

2-Methyl-N-(2-{2-[3-(7H-pyrrolo[2,3-d]pyrimidin-4-yl)phenyl]-2,3-dihydro-1H-inden-2-yl}ethyl)propanamide

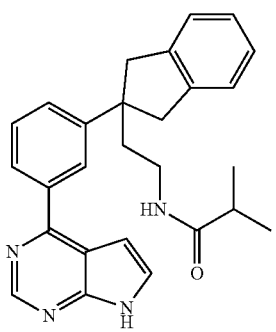 [SMILES: CC(C)C(=O)NCCC1(c2cccc(-c3ncnc4[nH]ccc34)c2)Cc2ccccc2C1]

To a solution of 2-{2-[3-(7H-pyrrolo[2,3-d]pyrimidin-4-yl)phenyl]-2,3-dihydro-1H-inden-2-yl}ethanamine (Prepared in Example 37; 2.0 mg, 0.006 mmol) in tetrahydrofuran (0.02 mL) and 1.0 M sodium bicarbonate in water (0.01 mL, 0.01 mmol) at 0° C., was added slowly isobutyryl chloride (2.4 mg, 0.02 mmol). The reaction mixture was stirred at rt for 10 min. After the reaction mixture was concentrated in vacuo, the crude residue was purified by prep LC-MS (pH=10 method; XBridge™ PrepC18 5 m OBD™ column, 30×10 mm, 60 mL/min, eluting with a gradient of MeCN and water with NH$_4$OH) to give the desired product as a white powder (1.5 mg, 63%). LCMS calcd for $C_{27}H_{29}N_4O$ (M+H)$^+$: m/z=425.2. Found: 425.2.

Example 39

N-(2-{2-[3-(7H-Pyrrolo[2,3-d]pyrimidin-4-yl)phenyl]-2,3-dihydro-1H-inden-2-yl}ethyl)cyclopropanecarboxamide

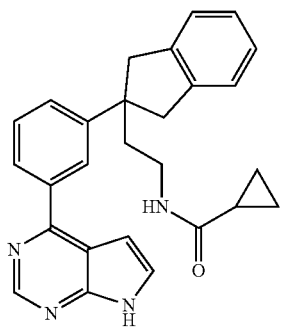 [SMILES: O=C(NCCC1(c2cccc(-c3ncnc4[nH]ccc34)c2)Cc2ccccc2C1)C1CC1]

To a solution of 2-{2-[3-(7H-pyrrolo[2,3-d]pyrimidin-4-yl)phenyl]-2,3-dihydro-1H-inden-2-yl}ethanamine (Prepared in Example 37; 2.0 mg, 0.006 mmol) in tetrahydrofuran (0.02 mL) and 1.0 M sodium bicarbonate in water (0.01 mL, 0.01 mmol) at 0° C., was added slowly cyclopropanecarbonyl chloride (2.4 mg, 0.02 mmol). The reaction mixture was stirred at rt for 20 min. After the reaction mixture was concentrated in vacuo, the crude residue was purified by prep LC-MS (pH=10 method; XBridge™ PrepC18 5 μm OBD™ column, 30×10 mm, 60 mL/min, eluting with a gradient of MeCN and water with NH$_4$OH) to give the desired product as a white powder (1.9 mg, 80%). LCMS calcd for $C_{27}H_{27}N_4O$ (M+H)$^+$: m/z=423.2. Found: 423.3.

Example 40

N-((2-(3-(7H-Pyrrolo[2,3-d]pyrimidin-4-yl)phenyl)-2-(aminomethyl)-2,3-dihydro-1H-inden-5-yl)methyl)cyclopropanamine

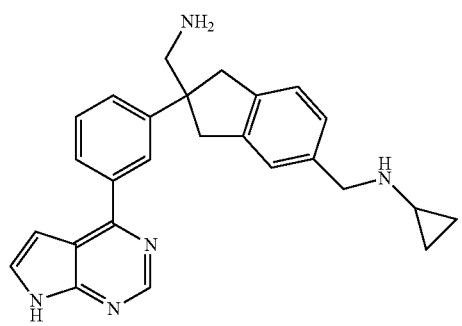 [SMILES: NCC1(c2cccc(-c3ncnc4[nH]ccc34)c2)Cc2ccc(CNC3CC3)cc2C1]

Step 1: 5-Bromo-2-[3-(7-{[2-(trimethylsilyl)ethoxy]methyl}-7H-pyrrolo[2,3-d]pyrimidin-4-yl) phenyl]indane-2-carbonitrile

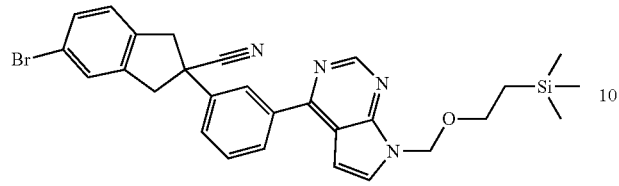

To a mixture of sodium hydride (0.176 g, 4.40 mmol) in anhydrous tetrahydrofuran (5 mL) was added [3-(7-{[2-(trimethylsilyl)ethoxy]methyl}-7H-pyrrolo[2,3-d]pyrimidin-4-yl)phenyl]acetonitrile (Prepared in Example 5, Step 1; 0.400 g, 1.10 mmol) and the resulting solution was stirred for 30 min. 4-Bromo-1,2-bis(bromomethyl)benzene (from Ark Pharm; 0.376 g, 1.10 mmol) was added and the resulting mixture was stirred at ambient temperature overnight. The crude reaction mixture was quenched by the addition of methanol, filtered through a pad of Celite and washed with ethyl acetate. The filtrate was concentrated in-vacuo and the residue was purified by column chromatography on silica gel using a CombiFlash® apparatus eluting with ethyl acetate/hexanes (0-30%) to afford 0.356 g of the desired product (59% yield). LCMS calcd. for $C_{28}H_{30}N_4O_3SiBr$ $(M+H)^+$: m/z=545.1. found: 545.1.

Step 2: tert-butyl ({5-bromo-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate

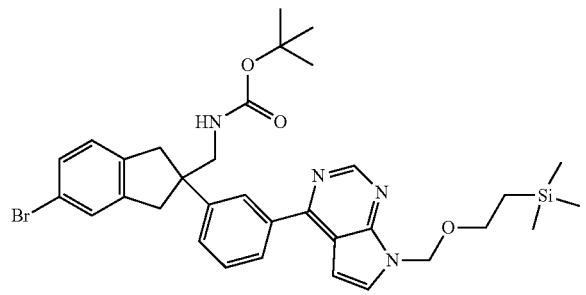 [SMILES: CC(C)(C)OC(=O)NCC1(c2cccc(-c3ncnc4c3ccn4COCC[Si](C)(C)C)c2)Cc2ccc(Br)cc2C1]

To a 0° C. solution of 5-bromo-2-[3-(7-{[2-(trimethylsilyl)ethoxy]methyl}-7H-pyrrolo[2,3-d]pyrimidin-4-yl)phenyl]indane-2-carbonitrile (1.785 g, 3.3 mmol) in methanol (25 mL) was added sequentially nickel chloride hexahydrate (117 mg, 0.49 mmol), di-tert-butyldicarbonate (1.5 mL, 6.5 mmol), and sodium tetrahydroborate (0.866 g, 22.9 mmol) portion-wise over 1 h. After stirring overnight, a second aliquot of nickel chloride hexahydrate (117 mg, 0.49 mmol), di-tert-butyldicarbonate (0.75 mL, 3.3 mmol), and sodium tetrahydroborate (1.0 g, 26.5 mmol) was added and stirring was continued at ambient temperature for 1 h. The crude reaction mixture was filtered through a pad of Celite and washed with ethyl acetate. The filtrate was concentrated in-vacuo and the residue was purified by column chromatography on silica gel using a CombiFlash® apparatus eluting with ethyl acetate/hexanes (0-30%) to afford 1.486 g of the desired product (70% yield). LCMS calcd. for $C_{33}H_{41}N_4O_3SiBr$ $(M+H)^+$: m/z=649.2. found: 649.2.

Step 3: tert-Butyl ({2-[3-(7-{[2-(trimethylsilyl)ethoxy]methyl}-7H-pyrrolo[2,3-d]pyrimidin-4-yl)phenyl]-5-vinyl-2,3-dihydro-1H-inden-2-yl}methyl)carbamate

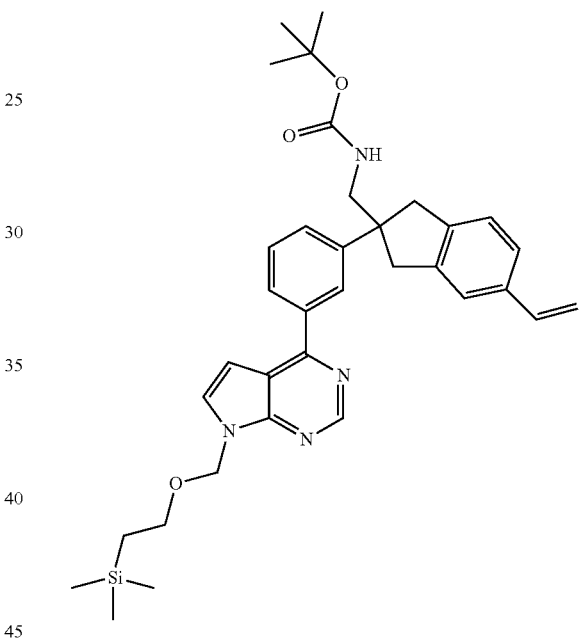

A mixture of tert-butyl ({5-bromo-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (300 mg, 0.462 mmol), 4,4, 5,5-tetramethyl-2-vinyl-1,3,2-dioxaborolane (160 µL, 0.92 mmol), cesium carbonate (450 mg, 1.4 mmol), and tetrakis(triphenylphosphine)palladium (0) (37 mg, 0.032 mmol) in 1,4-dioxane (3.0 mL), ethanol (0.30 mL), and water (0.10 mL) was de-gassed and purged with $N_2$ (g) several times prior to heating in a sealed vial and stirred overnight. The crude reaction mixture was filtered through a pad of Celite and washed with ethyl acetate. The filtrate was concentrated in-vacuo and the residue was purified by column chromatography on silica gel using a CombiFlash apparatus eluting with ethyl acetate/hexanes (0-20%) to afford 276 mg of the desired product (100% yield). LCMS calcd. for $C_{35}H_{45}N_4O_3Si$ $(M+H)^+$: m/z 597.3. found: 597.3.

Step 4: tert-Butyl ({5-formyl-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate

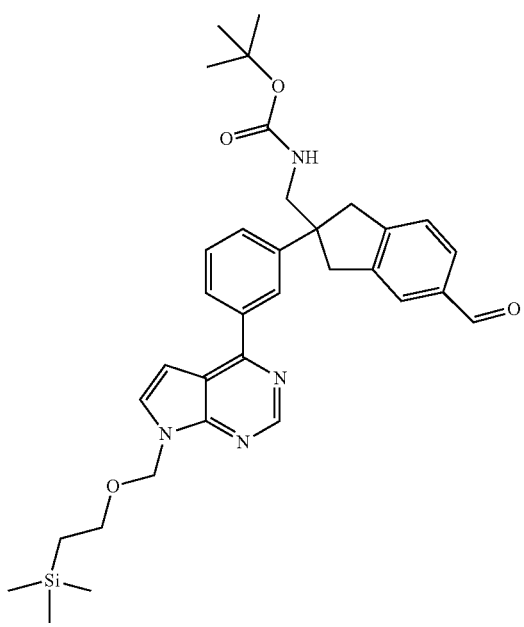 [SMILES: CC(C)(C)OC(=O)NCC1(c2cccc(-c3ncnc4c3ccn4COCC[Si](C)(C)C)c2)Cc2ccc(C=O)cc2C1]

A mixture of tert-butyl ({2-[3-(7-{[2-(trimethylsilyl)ethoxy]methyl}-7H-pyrrolo[2,3-d]pyrimidin-4-yl)phenyl]-5-vinyl-2,3-dihydro-1H-inden-2-yl}methyl)carbamate (210 mg, 0.35 mmol), sodium periodate (150 mg, 0.70 mmol) and a 2.5% solution of osmium tetraoxide in tert-butyl alcohol (78 μL, 0.0077 mmol) in 1,4-dioxane (3 mL) and water (200 μL) was stirred at ambient temperature for 2 h. The crude reaction mixture was filtered through a pad of celite and washed with ethyl acetate. The filtrate was concentrated in-vacuo and the residue was purified by column chromatography on silica gel using a CombiFlash® apparatus eluting with ethyl acetate/hexanes (0-40%) to afford 182 mg of the desired product (87% yield). LCMS calcd. for $C_{34}H_{43}N_4O_4Si$ $(M+H)^+$: m/z 599.3. found: 599.3.

Step 5: N-((2-(3-(7H-Pyrrolo[2,3-d]pyrimidin-4-yl)phenyl)-2-(aminomethyl)-2,3-dihydro-1H-inden-5-yl)methyl) cyclopropanamine To a solution of tert-butyl ({5-formyl-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (18 mg, 0.030 mmol) and cyclopropylamine (6.2 μL, 0.090 mmol) was added sodium triacetoxyborohydride (13 mg, 0.060 mmol) and the resulting solution was stirred at ambient temperature overnight to afford the desired protected intermediate. Trifluoroacetic acid (0.5 mL, 6 mmol) was added to the reaction mixture containing the intermediate, and stirring was continued for 1 h. The volatiles were removed in-vacuo and the residue was azeotropically washed with acetonitrile two times. The residue was dissolved in acetonitrile (1 mL) and treated with 20% ethylene diamine in methanol (0.2 mL, 0.6 mmol) and stirred for 30 min. The reaction mixture was diluted with methanol and purified on prep-LCMS (XBridge™ C18 column, eluting with a gradient of MeCN/water containing 0.05% TFA, at a flow rate of 60 mL/min) to afford the title compound as a white powder. LCMS calcd. for $C_{26}H_{28}N_5(M+H)^+$: m/z=410.2. found: 410.2.

Example 41

N-((2-(3-(7H-Pyrrolo[2,3-d]pyrimidin-4-yl)phenyl)-2-(aminomethyl)-2,3-dihydro-1H-inden-5-yl)methyl) cyclobutanamine

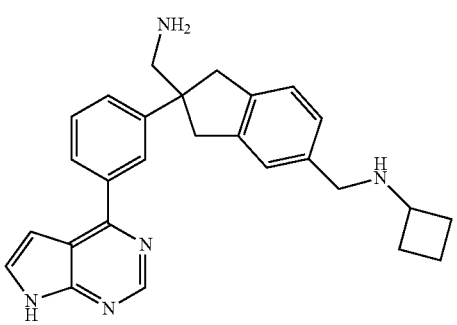 [SMILES: NCC1(c2cccc(-c3ncnc4[nH]ccc34)c2)Cc2ccc(CNC3CCC3)cc2C1]

The title compound was prepared using procedures analogous to those as described for the synthesis of Example 40 using cyclobutanamine (7.7 μL, 0.090 mmol) to replace cyclopropylamine in Step 5. LCMS calcd. for $C_{27}H_{30}N_5$ $(M+H)^+$: m/z=424.2. found: 424.2.

Example 42

N-((2-(3-(7H-Pyrrolo[2,3-d]pyrimidin-4-yl)phenyl)-2-(aminomethyl)-2,3-dihydro-1H-inden-5-yl)methyl)-3,3-difluorocyclobutanamine

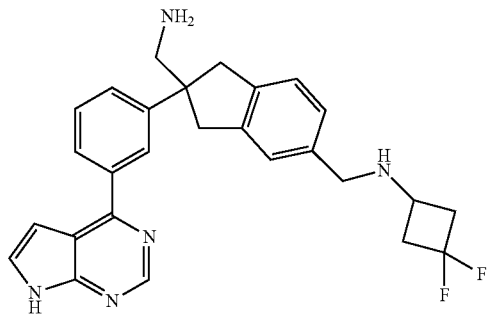 [SMILES: NCC1(c2cccc(-c3ncnc4[nH]ccc34)c2)Cc2ccc(CNC3CC(F)(F)C3)cc2C1]

The title compound was prepared using procedures analogous to those as described for the synthesis of Example 40 using 3,3-difluorocyclobutanamine hydrochloride (13 mg, 0.090 mmol) to replace cyclopropylamine in Step 5 and diisopropylethylamine (16 μL, 0.090 mmol) to neutralize the amine. LCMS calcd. for $C_{27}H_{28}N_5F_2$ $(M+H)^+$: m/z=460.2. found: 460.2.

Example 43

(2R)-1-((2-(3-(7H-Pyrrolo[2,3-d]pyrimidin-4-yl)phenyl)-2-(aminomethyl)-2,3-dihydro-1H-inden-5-yl)methyl)pyrrolidine-2-carboxamide

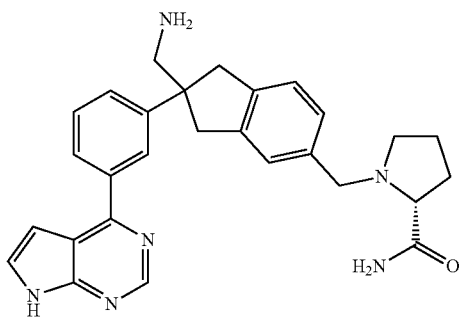 [SMILES: NCC1(c2cccc(-c3ncnc4[nH]ccc34)c2)Cc2ccc(CN3CCC[C@@H]3C(N)=O)cc2C1]

The title compound was prepared using procedures analogous to those as described for the synthesis of Example 40 using (2R)-pyrrolidine-2-carbonitrile hydrochloride (12 mg, 0.090 mmol) to replace cyclopropylamine in Step 5 and diisopropylethylamine (16 μL, 0.090 mmol) to neutralize the amine. LCMS calcd. for $C_{28}H_{31}N_6O$ (M+H)$^+$: m/z 467.3. found: 467.2.

Example 44

(3S)-1-((2-(3-(7H-Pyrrolo[2,3-d]pyrimidin-4-yl)phenyl)-2-(aminomethyl)-2,3-dihydro-1H-inden-5-yl)methyl)pyrrolidine-3-carboxamide

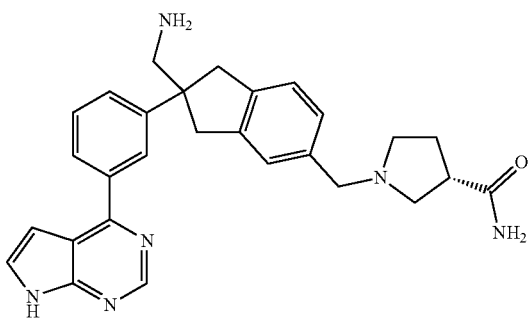 [SMILES: NCC1(c2cccc(-c3ncnc4[nH]ccc34)c2)Cc2ccc(CN3CC[C@H](C(N)=O)C3)cc2C1]

The title compound was prepared using procedures analogous to those as described for the synthesis of Example 40 using (3S)-pyrrolidine-3-carbonitrile hydrochloride (12 mg, 0.090 mmol) to replace cyclopropylamine in Step 5 and diisopropylethylamine (16 μL, 0.090 mmol) to neutralize the amine. LCMS calcd. for $C_{28}H_{31}N_6O$ (M+H)$^+$: m/z 467.3. found: 467.2.

Example 45

(3S)-1-((2-(3-(7H-Pyrrolo[2,3-d]pyrimidin-4-yl)phenyl)-2-(aminomethyl)-2,3-dihydro-1H-inden-5-yl)methyl)pyrrolidine-3-carbonitrile

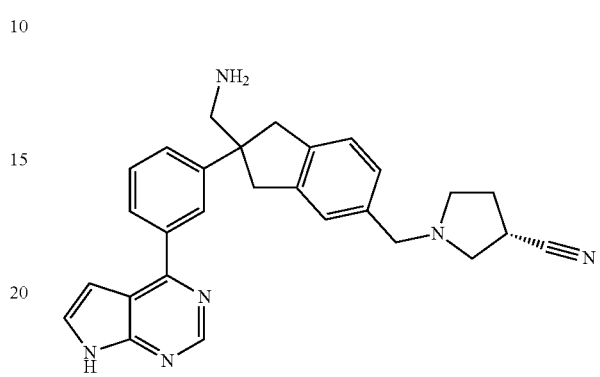

The title compound was prepared using procedures analogous to those as described for the synthesis of Example 40 using (3S)-pyrrolidine-3-carbonitrile hydrochloride (12 mg, 0.090 mmol) to replace cyclopropylamine in Step 5 and diisopropylethylamine (16 μL, 0.090 mmol) to neutralize the amine. LCMS calcd. for $C_{28}H_{29}N_6$(M+H)$^+$: m/z 449.2. found: 449.3.

Example 46

(2-(3-(7H-Pyrrolo[2,3-d]pyrimidin-4-yl)phenyl)-5-(azetidin-1-ylmethyl)-2,3-dihydro-1H-inden-2-yl)methanamine

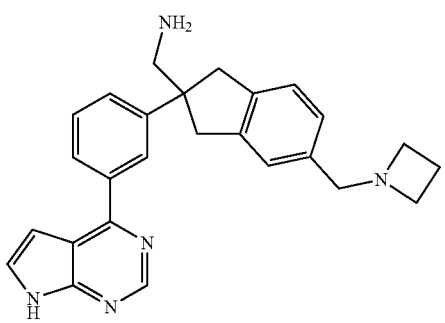 [SMILES: NCC1(c2cccc(-c3ncnc4[nH]ccc34)c2)Cc2ccc(CN3CCC3)cc2C1]

The title compound was prepared using procedures analogous to those as described for the synthesis of Example 40 using azetidine hydrochloride (8.0 mg, 0.085 mmol) to replace cyclopropylamine in Step 5 and diisopropylethylamine (15 μL, 0.085 mmol) to neutralize the amine. LCMS calcd. for $C_{26}H_{28}N_5$(M+H)$^+$: m/z 410.2. found: 410.3.

Example 47

(2-(3-(7H-Pyrrolo[2,3-d]pyrimidin-4-yl)phenyl)-5-((3-fluoroazetidin-1-yl)methyl)-2,3-dihydro-1H-inden-2-yl)methanamine

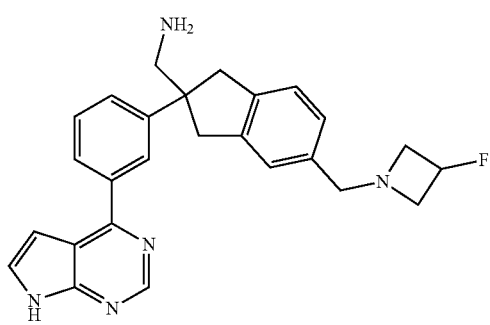 [SMILES: NCC1(c2cccc(-c3ncnc4[nH]ccc34)c2)Cc2ccc(CN3CC(F)C3)cc2C1]

The title compound was prepared using procedures analogous to those as described for the synthesis of Example 40 using azetidine hydrochloride (9.5 mg, 0.085 mmol) to replace cyclopropylamine in Step 5 and diisopropylethylamine (15 µL, 0.085 mmol) to neutralize the amine. LCMS calcd. for $C_{26}H_{27}N_5F$ (M+H)$^+$: m/z=428.2. found: 428.3.

Example 48

1-((2-(3-(7H-Pyrrolo[2,3-d]pyrimidin-4-yl)phenyl)-2-(aminomethyl)-2,3-dihydro-1H-inden-5-yl)methyl)azetidin-3-ol

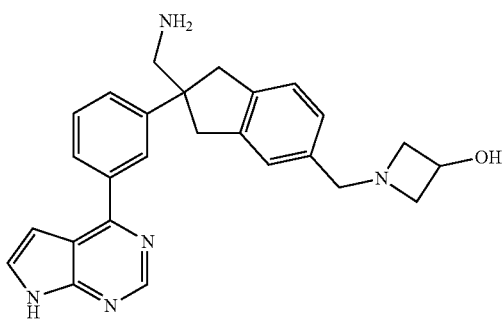 [SMILES: NCC1(c2cccc(-c3ncnc4[nH]ccc34)c2)Cc2ccc(CN3CC(O)C3)cc2C1]

The title compound was prepared using procedures analogous to those as described for the synthesis of Example 40 using azetidine hydrochloride (9.5 mg, 0.085 mmol) to replace cyclopropylamine in Step 5 and diisopropylethylamine (15 µL, 0.085 mmol) to neutralize the amine. LCMS calcd. for $C_{26}H_{28}N_5O$ (M+H)$^+$: m/z=426.2. found: 426.2.

Example 49

2-(Aminomethyl)-2-[3-(7H-pyrrolo[2,3-d]pyrimidin-4-yl)phenyl]indane-5-carbonitrile

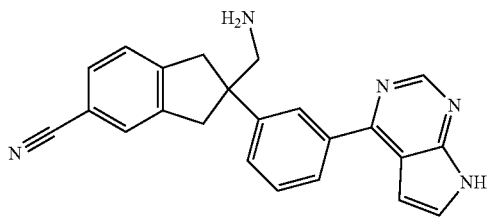 [SMILES: N#Cc1ccc2c(c1)CC(CN)(c1cccc(-c3ncnc4[nH]ccc34)c1)C2]

A mixture of tert-butyl ({5-bromo-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (Prepared in Example 40, Step 2; 40 mg, 0.062 mmol), zinc cyanide (15 mg, 0.13 mmol), N,N,N',N'-tetramethylethylenediamine (5 µL, 0.03 mmol), (9,9-dimethyl-9H-xanthene-4,5-diyl)bis(diphenylphosphoranol) (4.0 mg, 0.0065 mmol), and tris(dibenzylideneacetone)dipalladium(0) (3.0 mg, 0.0033 mmol) in N,N-dimethylformamide (0.4 mL) was de-gassed and purged with N₂ (g) several times prior to heating by microwave irradiation at 130° C. for 10 min. The crude reaction mixture was filtered through a pad of celite and washed with ethyl acetate. The filtrate was concentrated in-vacuo and the residue was purified by column chromatography on silica gel using a CombiFlash® apparatus eluting with ethyl acetate/hexanes (0-40%) to afford 25 mg of the desired protected intermediate (68% yield). The protected intermediate was dissolved in trifluoroacetic acid (0.5 mL, 6 mmol) and stirred at ambient temperature for 1 h. The volatiles were removed in-vacuo and the residue was azeotropically washed with acetonitrile two times. The residue was dissolved in acetonitrile (1 mL) and treated with 20% ethylene diamine in methanol (0.2 mL, 0.6 mmol) and stirred for 30 min. The reaction mixture was diluted with methanol and purified on prep-LCMS (XBridge™ C18 column, eluting with a gradient of MeCN/water containing 0.05% TFA, at a flow rate of 60 mL/min) to afford the title compound as a TFA salt. LCMS calcd. for $C_{23}H_{20}N_5$(M+H)$^+$: m/z=366.2. found: 366.1.

Example 50

N-({5-Cyano-2-[3-(7H-pyrrolo[2,3-d]pyrimidin-4-yl)phenyl]-2,3-dihydro-1H-inden-2-yl}methyl)cyclopropanecarboxamide

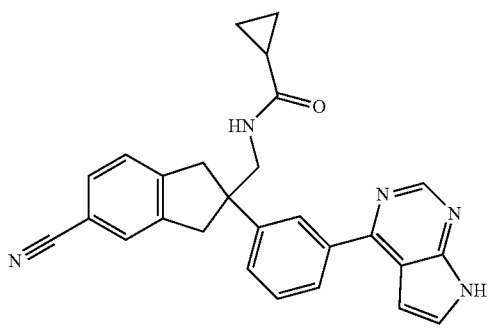 [SMILES: N#Cc1ccc2c(c1)CC(CNC(=O)C1CC1)(c1cccc(-c3ncnc4[nH]ccc34)c1)C2]

A solution of 2-(aminomethyl)-2-[3-(7H-pyrrolo[2,3-d]pyrimidin-4-yl)phenyl]indane-5-carbonitrile trifluoroacetic acid (Prepared in Example 49; 6.0 mg, 0.010 mmol), cyclopropanecarboxylic acid (2.0 μL, 0.025 mmol), N,N,N',N'-tetramethyl-O-(7-azabenzotriazol-1-yl)uronium hexafluorophosphate (12 mg, 0.030 mmol), and N,N-diisopropylethylamine (10 μL, 0.057 mmol) in 1,2-dichloroethane (0.4 mL) was stirred at ambient temperature overnight. The reaction mixture was diluted with methanol and purified on prep-LCMS (XBridge™ C18 column, eluting with a gradient of MeCN/water containing 0.05% TFA, at a flow rate of 60 mL/min) to afford the title compound. LCMS calcd. for $C_{23}H_{24}N_5O$ (M+H)$^+$: m/z=434.2. found: 434.2.

Example 51

(3S)-1-{2-(Aminomethyl)-2-[3-(7H-pyrrolo[2,3-d]pyrimidin-4-yl)phenyl]-2,3-dihydro-1H-inden-5-yl}pyrrolidine-3-carbonitrile

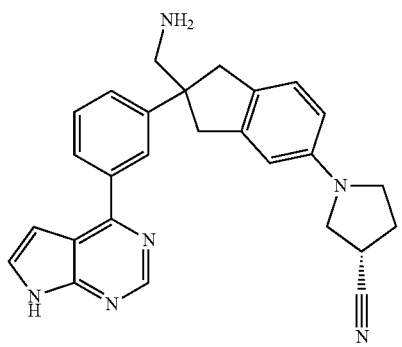 [SMILES: N#C[C@H]1CCN(c2ccc3c(c2)CC(CN)(c2cccc(-c4ncnc5[nH]ccc45)c2)C3)C1]

A mixture of tert-butyl ({5-bromo-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (Prepared in Example 40, Step 2; 25 mg, 0.038 mmol), cesium carbonate (38 mg, 0.12 mmol), dicyclohexyl(2',6'-diisopropoxybiphenyl-2-yl)phosphine-(2'-aminobiphenyl-2-yl)(chloro)palladium (1:1) (3.0 mg, 0.0038 mmol) (RuPhos Pd G2), (3S)-pyrrolidine-3-carbonitrile hydrogen chloride (from Anichem; 15 mg, 0.12 mmol) that was neutralized with diisopropylethylamine (20 μL, 0.12 mmol) in anhydrous tert-butyl alcohol (0.6 mL) was de-gassed and purged with N$_2$(g) several times prior to heating in a sealed vial at 90° C. overnight. The crude reaction mixture was filtered through a pad of celite and washed with ethyl acetate. The residue was dissolved in trifluoroacetic acid (0.5 mL) and stirred at ambient temperature for 1 h. The volatiles were removed in-vacuo and the residue was azeotropically washed with acetonitrile two times. The residue was dissolved in acetonitrile (1 mL) and treated with 20% ethylene diamine in methanol (0.2 mL) and stirred for 30 min. The reaction mixture was diluted with methanol and purified on prep-LCMS (XBridge™ C18 column, eluting with a gradient of MeCN/water containing 0.05% TFA, at a flow rate of 60 mL/min) to afford the title compound as a white powder. LCMS calcd. for $C_{27}H_{27}N_6$(M+H)$^+$: m/z 435.2. found: 435.3.

Example 52

1-{2-(Aminomethyl)-2-[3-(7H-pyrrolo[2,3-d]pyrimidin-4-yl)phenyl]-2,3-dihydro-1H-inden-5-yl}-N,N-dimethylpyrrolidin-3-amine

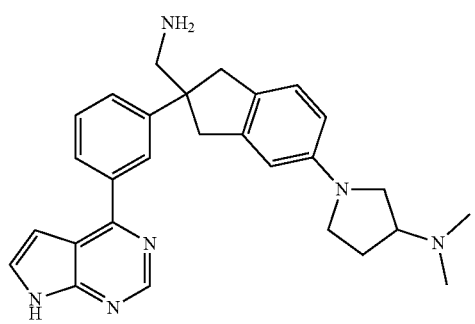 [SMILES: CN(C)C1CCN(c2ccc3c(c2)CC(CN)(c2cccc(-c4ncnc5[nH]ccc45)c2)C3)C1]

The title compound was prepared using procedures analogous to those as described for the synthesis of Example 51 using N,N-dimethylpyrrolidine-3-amine (from Oakwood; 29 μL, 0.23 mmol) to replace (3S)-pyrrolidine-3-carbonitrile. LCMS calcd. for $C_{28}H_{33}N_6$(M+H)$^+$: m/z=453.3. found: 453.3.

Example 53

1-{2-(Aminomethyl)-2-[3-(7H-pyrrolo[2,3-d]pyrimidin-4-yl)phenyl]-2,3-dihydro-1H-inden-5-yl}-N-methylpyrrolidin-3-amine

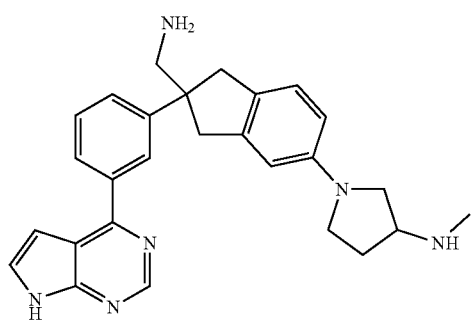 [SMILES: CNC1CCN(c2ccc3c(c2)CC(CN)(c2cccc(-c4ncnc5[nH]ccc45)c2)C3)C1]

The title compound was prepared using procedures analogous to those as described for the synthesis of Example 51 using N-methylpyrrolidine-3-amine (from TCI; 12 mg, 0.12 mmol) to replace (3S)-pyrrolidine-3-carbonitrile. LCMS calcd. for $C_{27}H_{31}N_6$(M+H)$^+$: m/z=439.3. found: 439.2.

Example 54

1-{2-(Aminomethyl)-2-[3-(7H-pyrrolo[2,3-d]pyrimidin-4-yl)phenyl]-2,3-dihydro-1H-inden-5-yl}pyrrolidin-3-ol

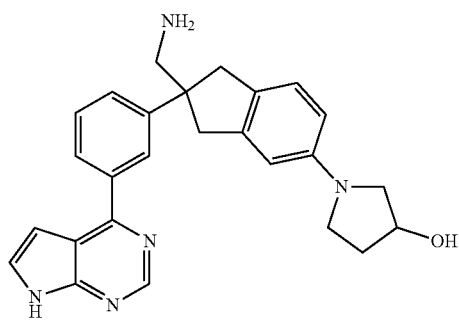 [SMILES: NCC1(c2cccc(-c3ncnc4[nH]ccc34)c2)Cc2ccc(N3CCC(O)C3)cc2C1]

The title compound was prepared using procedures analogous to those as described for the synthesis of Example 51 using 3-pyrrolidinol (from Aldrich; 9.3 µL, 0.12 mmol) to replace (3S)-pyrrolidine-3-carbonitrile. LCMS calcd. for $C_{26}H_{28}N_5O$ (M+H)$^+$: m/z=426.2. found: 426.2.

Example 55

1-(1-{2-(Aminomethyl)-2-[3-(7H-pyrrolo[2,3-d]pyrimidin-4-yl)phenyl]-2,3-dihydro-1H-inden-5-yl}pyrrolidin-3-yl)ethanol

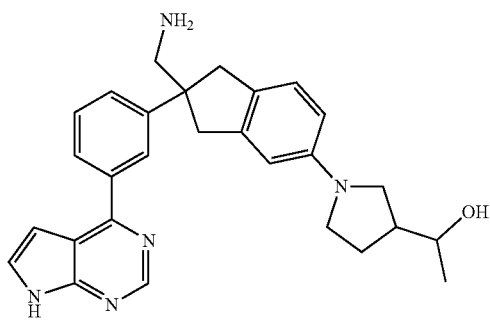 [SMILES: CC(O)C1CCN(c2ccc3c(c2)CC(CN)(c2cccc(-c4ncnc5[nH]ccc45)c2)C3)C1]

The title compound was prepared using procedures analogous to those as described for the synthesis of Example 51 using 1-pyrrolidin-3-ylethanol (from Enamine Ltd; 13 mg, 0.12 mmol) to replace (3S)-pyrrolidine-3-carbonitrile. LCMS calcd. for $C_{28}H_{32}N_5O$ (M+H)$^+$: m/z 454.3. found: 454.2.

Example 56

1-{5-(3-Fluoroazetidin-1-yl)-2-[3-(7H-pyrrolo[2,3-d]pyrimidin-4-yl)phenyl]-2,3-dihydro-1H-inden-2-yl}methanamine

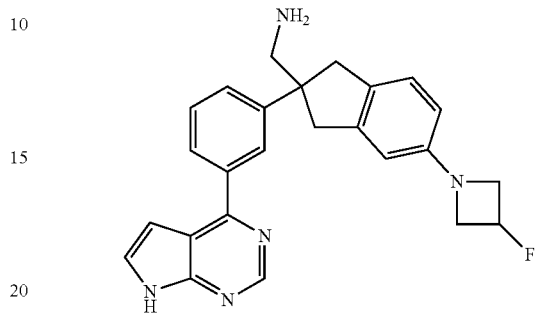

The title compound was prepared using procedures analogous to those as described for the synthesis of Example 51 using 3-fluoroazetidine hydrochloride (from PharmaBlock; 13 mg, 0.12 mmol) to replace (3S)-pyrrolidine-3-carbonitrile and diisopropylethylamine (20 µL, 0.12 mmol) to neutralize the amine. LCMS calcd. for $C_{25}H_{25}N_5F$ (M+H)$^+$: m/z 414.2. found: 414.2.

Example 57

1-{2-(Aminomethyl)-2-[3-(7H-pyrrolo[2,3-d]pyrimidin-4-yl)phenyl]-2,3-dihydro-1H-inden-5-yl}azetidin-3-ol

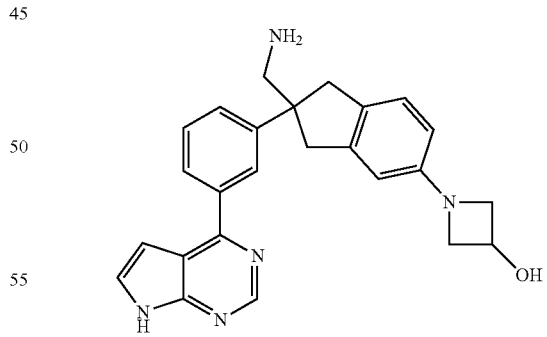

The title compound was prepared using procedures analogous to those as described for the synthesis of Example 51 using azetidine-3-ol hydrochloride (from Matrix Scientific; 13 mg, 0.12 mmol) to replace (3S)-pyrrolidine-3-carbonitrile and diisopropylethylamine (20 µL, 0.12 mmol) to neutralize the amine. LCMS calcd. for $C_{25}H_{26}N_5O$ (M+H)$^+$: m/z 412.2. found: 412.3.

Example 58

1-{2-(Aminomethyl)-2-[3-(7H-pyrrolo[2,3-d]pyrimidin-4-yl)phenyl]-2,3-dihydro-1H-inden-5-yl}piperidin-3-ol

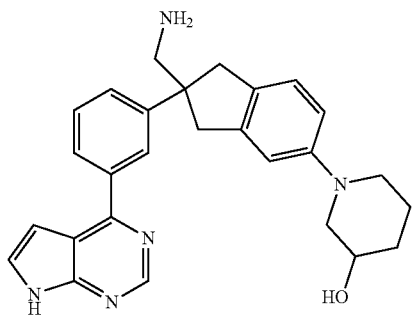 [SMILES: NCC1(c2cccc(-c3ncnc4[nH]ccc34)c2)Cc2ccc(N3CCCC(O)C3)cc2C1]

The title compound was prepared using procedures analogous to those as described for the synthesis of Example 51 using piperidin-3-ol (from Aldrich; 12 µL, 0.12 mmol) to replace (3S)-pyrrolidine-3-carbonitrile. LCMS calcd. for $C_{27}H_{30}N_5O$ (M+H)$^+$: m/z 440.2. found: 440.2.

Example 59

1-{2-(Aminomethyl)-2-[3-(7H-pyrrolo[2,3-d]pyrimidin-4-yl)phenyl]-2,3-dihydro-1H-inden-5-yl}piperidine-4-carbonitrile

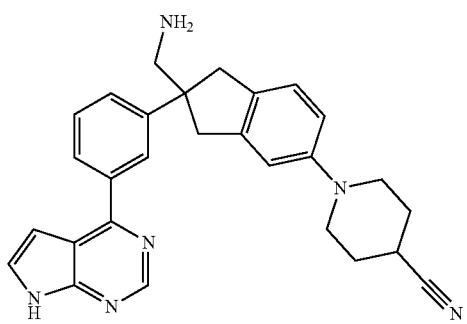 [SMILES: N#CC1CCN(c2ccc3c(c2)CC(CN)(c2cccc(-c4ncnc5[nH]ccc45)c2)C3)CC1]

The title compound was prepared using procedures analogous to those as described for the synthesis of Example 51 using piperidine-4-carbonitrile (from Alfa Aesar; 13 µL, 0.12 mmol) to replace (3S)-pyrrolidine-3-carbonitrile. LCMS calcd. for $C_{28}H_{29}N_6$(M+H)$^+$: m/z=449.2. found: 449.3.

Example 60

N-{2-(Aminomethyl)-2-[3-(7H-pyrrolo[2,3-d]pyrimidin-4-yl)phenyl]-2,3-dihydro-1H-inden-5-yl}tetrahydro-2H-pyran-4-amine

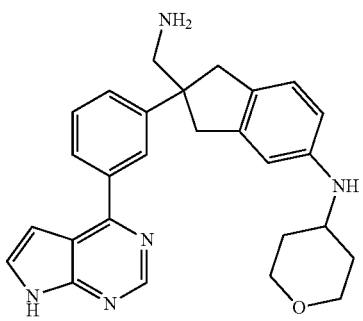 [SMILES: NCC1(c2cccc(-c3ncnc4[nH]ccc34)c2)Cc2ccc(NC3CCOCC3)cc2C1]

The title compound was prepared using procedures analogous to those as described for the synthesis of Example 51 using tetrahydro-2H-pyran-4-amine (from Combi-Blocks; 12 µL, 0.12 mmol) to replace (3S)-pyrrolidine-3-carbonitrile. LCMS calcd for $C_{27}H_{30}N_5O$ (M+H)$^+$: m/z=440.2. found: 440.3.

Example 61

1-{5-Pyrrolidin-1-yl-2-[3-(7H-pyrrolo[2,3-d]pyrimidin-4-yl)phenyl]-2,3-dihydro-1H-inden-2-yl}methanamine

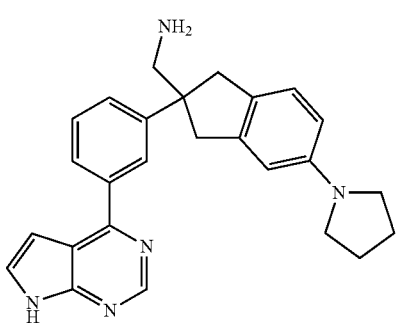 [SMILES: NCC1(c2cccc(-c3ncnc4[nH]ccc34)c2)Cc2ccc(N3CCCC3)cc2C1]

The title compound was prepared using procedures analogous to those as described for the synthesis of Example 51 using pyrrolidine (26 µL, 0.32 mmol) to replace (3S)-pyrrolidine-3-carbonitrile. LCMS calcd. for $C_{26}H_{28}N_5$(M+H)$^+$: m/z=410.2. found: 410.3.

Example 62

1-{5-Piperidin-1-yl-2-[3-(7H-pyrrolo[2,3-d]pyrimidin-4-yl)phenyl]-2,3-dihydro-1H-inden-2-yl}methanamine

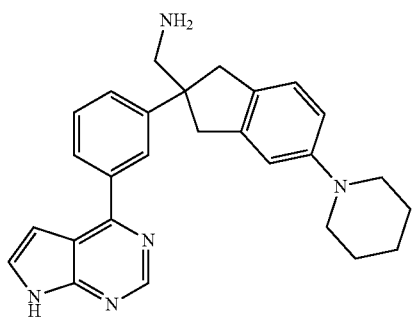 [SMILES: NCC1(c2cccc(-c3ncnc4[nH]ccc34)c2)Cc2ccc(N3CCCCC3)cc2C1]

The title compound was prepared using procedures analogous to those as described for the synthesis of Example 51 using piperdine (32 μL, 0.32 mmol) to replace (3S)-pyrrolidine-3-carbonitrile. LCMS calcd. for $C_{27}H_{30}N_5(M+H)^+$: m/z 424.2. found: 424.2.

Example 63

1-{5-Morpholin-4-yl-2-[3-(7H-pyrrolo[2,3-d]pyrimidin-4-yl)phenyl]-2,3-dihydro-1H-inden-2-yl}methanamine

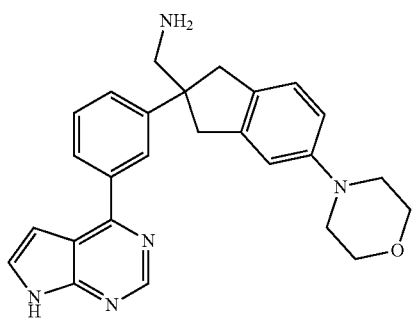 [SMILES: NCC1(c2cccc(-c3ncnc4[nH]ccc34)c2)Cc2ccc(N3CCOCC3)cc2C1]

The title compound was prepared using procedures analogous to those as described for the synthesis of Example 51 using morpholine (28 μL, 0.32 mmol) to replace (3S)-pyrrolidine-3-carbonitrile. LCMS calcd. for $C_{26}H_{28}N_5O$ (M+H)$^+$: m/z 426.2. found: 426.2.

Example 64

1-{2-(Aminomethyl)-2-[3-(7H-pyrrolo[2,3-d]pyrimidin-4-yl)phenyl]-2,3-dihydro-1H-inden-5-yl}piperidin-4-ol

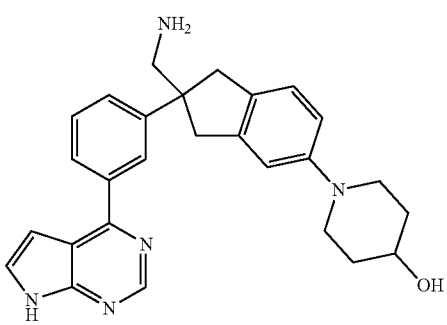 [SMILES: NCC1(c2cccc(-c3ncnc4[nH]ccc34)c2)Cc2ccc(N3CCC(O)CC3)cc2C1]

The title compound was prepared using procedures analogous to those as described for the synthesis of Example 51 using 4-hydroxypiperdine (from Aldrich; 32 μL, 0.32 mmol) to replace (3S)-pyrrolidine-3-carbonitrile. LCMS calcd. for $C_{27}H_{30}N_5O$ (M+H)$^+$: m/z=440.2. found: 440.3.

Example 65

2-(Aminomethyl)-N-(2-methoxyethyl)-2-[3-(7H-pyrrolo[2,3-d]pyrimidin-4-yl)phenyl]indan-5-amine

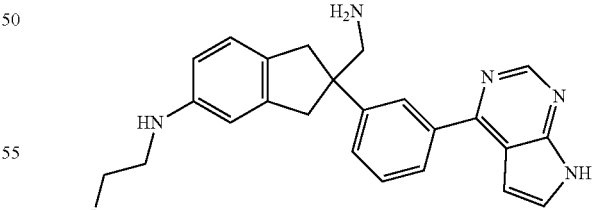

The title compound was prepared using procedures analogous to those as described for the synthesis of Example 51 using 2-methoxyethylamine (30 μL, 0.36 mmol) to replace (3S)-pyrrolidine-3-carbonitrile. LCMS calcd for $C_{25}H_{28}N_5O$ (M+H)$^+$: m/z=414.2. found: 414.3.

Example 66

2-(Aminomethyl)-N-(3-methoxypropyl)-2-[3-(7H-pyrrolo[2,3-d]pyrimidin-4-yl)phenyl]indan-5-amine

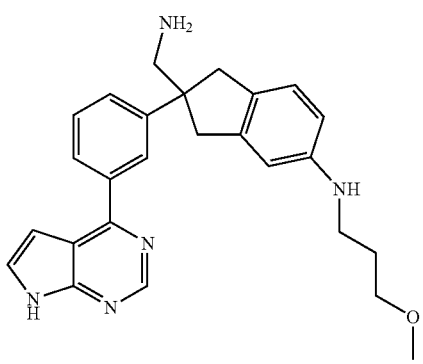 [SMILES: COCCCNc1ccc2c(c1)CC(CN)(c1cccc(-c3ncnc4[nH]ccc34)c1)C2]

The title compound was prepared using procedures analogous to those as described for the synthesis of Example 51 using 3-methoxy-1-propanamine (36 μL, 0.36 mmol) to replace (3S)-pyrrolidine-3-carbonitrile. LCMS calcd. for $C_{26}H_{30}N_5O$ (M+H)$^+$: m/z=428.2. found: 428.3.

Example 67

2-(Aminomethyl)-N-[1-(methoxymethyl)cyclopropyl]-2-[3-(7H-pyrrolo[2,3-d]pyrimidin-4-yl)phenyl]indan-5-amine

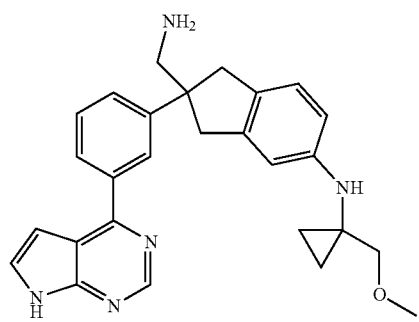 [SMILES: COCC1(Nc2ccc3c(c2)CC(CN)(c2cccc(-c4ncnc5[nH]ccc45)c2)C3)CC1]

The title compound was prepared using procedures analogous to those as described for the synthesis of Example 51 using 1-(methoxymethyl)cyclopropanamine (from J&W Pharm; 36 mg, 0.36 mmol) to replace (3S)-pyrrolidine-3-carbonitrile. LCMS calcd. for $C_{27}H_{30}N_5O$ (M+H)$^+$: m/z 440.2. found: 440.2.

Example 68

1-{5-Phenyl-2-[3-(7H-pyrrolo[2,3-d]pyrimidin-4-yl)phenyl]-2,3-dihydro-1H-inden-2-yl}methanamine

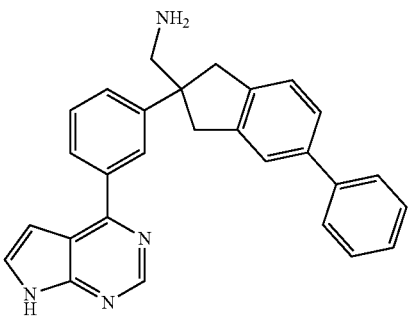 [SMILES: NCC1(c2cccc(-c3ncnc4[nH]ccc34)c2)Cc2ccc(-c3ccccc3)cc2C1]

A mixture of tert-butyl ({5-bromo-2-[3-(7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (Prepared in Example 40, Step 2; 31 mg, 0.048 mmol), phenylboronic acid (24 mg, 0.19 mmol), cesium carbonate (47 mg, 0.14 mmol), and tetrakis(triphenylphosphine)palladium (0) (5.5 mg, 0.0048 mmol) in 1,4-dioxane (0.40 mL), ethanol (0.10 mL), and water (0.040 mL) was de-gassed and purged with $N_2$ (g) several times prior to heating in a sealed vial overnight. The crude reaction mixture was filtered through a pad of celite and washed with ethyl acetate. The filtrate was concentrated in-vacuo and the residue was purified by column chromatography on silica gel using a CombiFlash apparatus eluting with ethyl acetate/hexanes (0-30%) to afford the desired protected intermediate. The protected intermediate was dissolved in trifluoroacetic acid (0.5 mL) and stirred at ambient temperature for 1 h. The volatiles were removed in-vacuo and the residue was azeotropically washed with acetonitrile two times. The residue was re-dissolved in acetonitrile (1 mL) and treated with 20% ethylene diamine in methanol (0.2 mL) and stirred for 30 min. The reaction mixture was diluted with methanol and purified on prep-LCMS (XBridge™ C18 column, eluting with a gradient of MeCN/water containing 0.05% TFA, at a flow rate of 60 mL/min) to afford the title compound. LCMS calcd. for $C_{28}H_{25}N_4$(M+H)$^+$: m/z=417.2. found: 417.2.

Example 69

1-{5-(2-Fluorophenyl)-2-[3-(7H-pyrrolo[2,3-d]pyrimidin-4-yl)phenyl]-2,3-dihydro-1H-inden-2-yl}methanamine

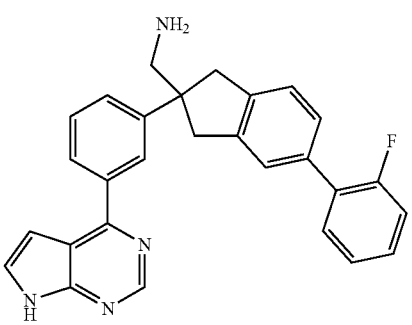 [SMILES: NCC1(c2cccc(-c3ncnc4[nH]ccc34)c2)Cc2ccc(-c3ccccc3F)cc2C1]

The title compound was prepared using procedures analogous to those as described for the synthesis of Example 68 using (2-fluorophenyl)boronic acid (from Aldrich; 26 mg, 0.19 mmol) to replace phenylboronic acid. LCMS calcd. for $C_{28}H_{24}N_4F$ (M+H)$^+$: m/z=435.2. found: 435.2.

Example 70

1-{5-(3-Fluorophenyl)-2-[3-(7H-pyrrolo[2,3-d]pyrimidin-4-yl)phenyl]-2,3-dihydro-1H-inden-2-yl}methanamine

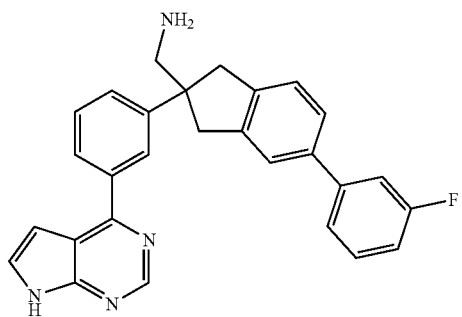 [SMILES: NCC1(c2cccc(-c3ncnc4[nH]ccc34)c2)Cc2ccc(-c3cccc(F)c3)cc2C1]

The title compound was prepared using procedures analogous to those as described for the synthesis of Example 68 using (3-fluorophenyl)boronic acid (from Aldrich; 26 mg, 0.19 mmol) to replace phenylboronic acid. LCMS calcd. for $C_{28}H_{24}N_4F$ (M+H)$^+$: m/z=435.2. found: 435.2.

Example 71

1-{5-(4-Fluorophenyl)-2-[3-(7H-pyrrolo[2,3-d]pyrimidin-4-yl)phenyl]-2,3-dihydro-1H-inden-2-yl}methanamine

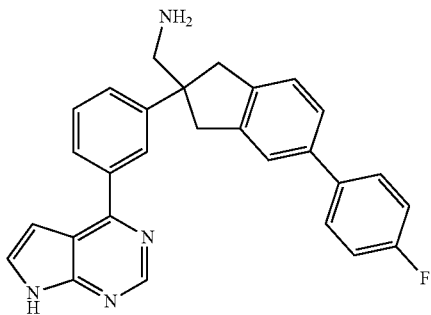 [SMILES: NCC1(c2cccc(-c3ncnc4[nH]ccc34)c2)Cc2ccc(-c3ccc(F)cc3)cc2C1]

The title compound was prepared using procedures analogous to those as described for the synthesis of Example 68 using (4-fluorophenyl)boronic acid (from Aldrich; 26 mg, 0.19 mmol) to replace phenylboronic acid. LCMS calcd. for $C_{28}H_{24}N_4F$ (M+H)$^+$: m/z=435.2. found: 435.2.

Example 72

4-{2-(Aminomethyl)-2-[3-(7H-pyrrolo[2,3-d]pyrimidin-4-yl)phenyl]-2,3-dihydro-1H-inden-5-yl}-N,N-dimethylaniline

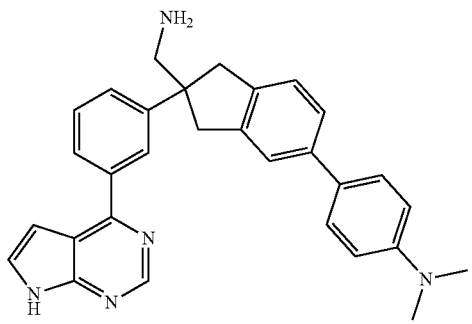 [SMILES: CN(C)c1ccc(-c2ccc3c(c2)CC(CN)(c2cccc(-c4ncnc5[nH]ccc45)c2)C3)cc1]

The title compound was prepared using procedures analogous to those as described for the synthesis of Example 68 using [4-(dimethylamino)phenyl)]boronic acid (from Aldrich; 32 mg, 0.19 mmol) to replace phenylboronic acid. LCMS calcd. for $C_{30}H_{30}N_5$(M+H)$^+$: m/z 460.2. found: 460.3.

Example 73

1-{5-Imidazo[1,2-a]pyridin-6-yl-2-[3-(7H-pyrrolo[2,3-d]pyrimidin-4-yl)phenyl]-2,3-dihydro-1H-inden-2-yl}methanamine

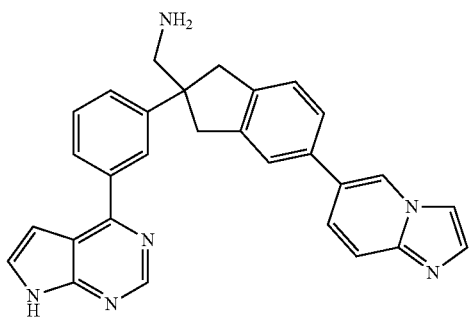 [SMILES: NCC1(c2cccc(-c3ncnc4[nH]ccc34)c2)Cc2ccc(-c3ccc4nccn4c3)cc2C1]

The title compound was prepared using procedures analogous to those as described for the synthesis of Example 68 using imidazo[1,2-a]pyridine-6-ylboronic acid (from Combi-Blocks; 15 mg, 0.095 mmol) to replace phenylboronic acid. LCMS calcd. for $C_{29}H_{25}N_6$(M+H)$^+$: m/z 457.2. found: 457.2.

Example 74

1-{5-(3-Methyl-3H-imidazo[4,5-b]pyridin-6-yl)-2-[3-(7H-pyrrolo[2,3-d]pyrimidin-4-yl)phenyl]-2,3-dihydro-1H-inden-2-yl}methanamine

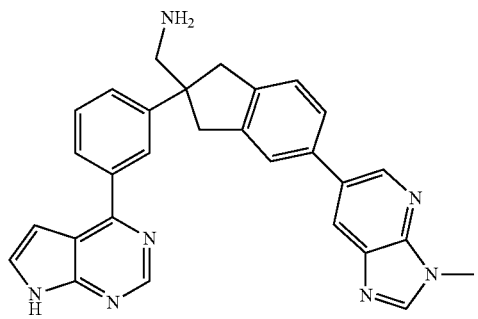 [SMILES: Cn1cnc2cc(-c3ccc4c(c3)CC(CN)(c3cccc(-c5ncnc6[nH]ccc56)c3)C4)cnc21]

The title compound was prepared using procedures analogous to those as described for the synthesis of Example 68 using 3-methyl-6-(4,4,5,5-tetramethyl-1,3,2-dioxaborolan-2-yl)-3H-imidazo[4,5-b]pyridine (from Adesis; 25 mg, 0.095 mmol) to replace phenylboronic acid. LCMS calcd. for $C_{29}H_{26}N_7(M+H)^+$: m/z 472.2. found: 472.2.

Example 75

1-{5-(6-Pyrrolidin-1-ylpyridin-3-yl)-2-[3-(7H-pyrrolo[2,3-d]pyrimidin-4-yl)phenyl]-2,3-dihydro-1H-inden-2-yl}methanamine

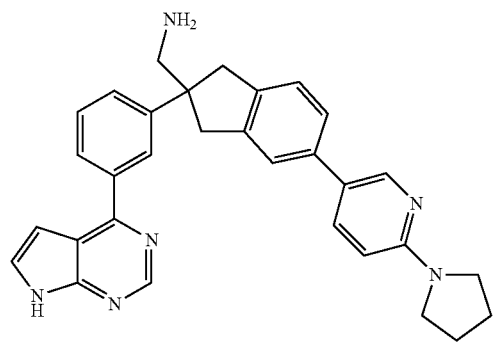 [SMILES: NCC1(c2cccc(-c3ncnc4[nH]ccc34)c2)Cc2ccc(-c3ccc(N4CCCC4)nc3)cc2C1]

The title compound was prepared using procedures analogous to those as described for the synthesis of Example 68 using ((6-pyrrolidin-1-yl)pyridin-3-yl)boronic acid (from Aldrich; 18 mg, 0.095 mmol) to replace phenylboronic acid. LCMS calcd. for $C_{31}H_{31}N_6(M+H)^+$: m/z=487.3. found: 487.2.

Example 76

1-{5-(1-Ethyl-1H-imidazol-4-yl)-2-[3-(7H-pyrrolo[2,3-d]pyrimidin-4-yl)phenyl]-2,3-dihydro-1H-inden-2-yl}methanamine

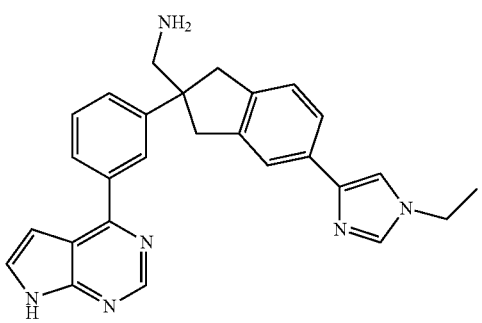 [SMILES: CCn1cnc(-c2ccc3c(c2)CC(CN)(c2cccc(-c4ncnc5[nH]ccc45)c2)C3)c1]

The title compound was prepared using procedures analogous to those as described for the synthesis of Example 68 using 1-ethyl-4-(4,4,5,5-tetramethyl-1,3,2-dioxaborolan-2-yl)-1H-imidazole (from Combi-Blocks; 21 mg, 0.095 mmol) to replace phenylboronic acid. LCMS calcd. for $C_{27}H_{27}N_6(M+H)^+$: m/z=435.2. found: 435.2.

Example 77

(2-(3-(7H-Pyrrolo[2,3-d]pyrimidin-4-yl)phenyl)-5-(pyridin-3-yl)-2,3-dihydro-1H-inden-2-yl)methanamine

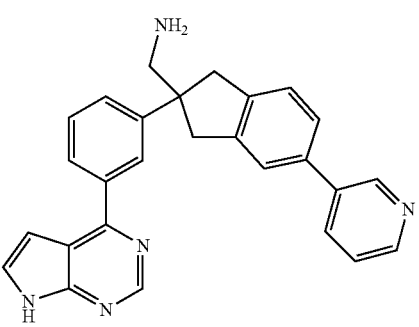 [SMILES: NCC1(c2cccc(-c3ncnc4[nH]ccc34)c2)Cc2ccc(-c3cccnc3)cc2C1]

The title compound was prepared using procedures analogous to those as described for the synthesis of Example 68 using 3-pyridineboronic acid (from Aldrich; 12 mg, 0.095 mmol) to replace phenylboronic acid. LCMS calcd. for $C_{27}H_{24}N_5(M+H)^+$: m/z=418.2. found: 418.2.

Example 78

(2-{3-(7H-Pyrrolo[2,3-d]pyrimidin-4-yl)phenyl}-5-(pyridin-4-yl)-2,3-dihydro-1H-inden-2-yl)methanamine

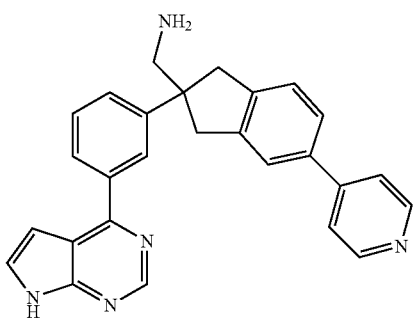 [SMILES: NCC1(c2cccc(-c3ncnc4[nH]ccc34)c2)Cc2ccc(-c3ccncc3)cc2C1]

The title compound was prepared using procedures analogous to those as described for the synthesis of Example 68 using 4-pyridineboronic acid (from Aldrich; 12 mg, 0.095 mmol) to replace phenylboronic acid. LCMS calcd. for $C_{27}H_{24}N_5(M+H)^+$: m/z 418.2. found: 418.2.

Example 80

4-{3-[2-(Aminomethyl)-2,3-dihydro-1H-inden-2-yl]phenyl}-N-butyl-7H-pyrrolo[2,3-d]pyrimidin-2-amine

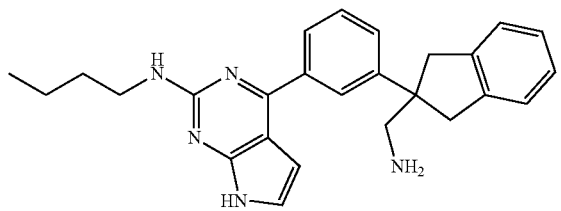 [SMILES: CCCCNc1nc(-c2cccc(C3(CN)Cc4ccccc4C3)c2)c2cc[nH]c2n1]

Step 1. 2-(3-Bromophenyl)indane-2-carbonitrile

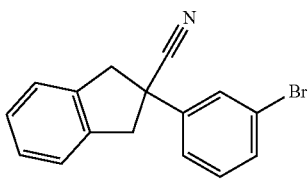 [SMILES: N#CC1(c2cccc(Br)c2)Cc2ccccc2C1]

To a solution of (3-bromophenyl)acetonitrile (from Aldrich; 1.00 g, 5.10 mmol) in tetrahydrofuran (50 mL) was added sodium hydride (1.02 g, 25.5 mmol) at rt. The color of the reaction mixture turned orange. The reaction mixture was stirred for 20 min and then 1,2-bis(bromomethyl)benzene (1.35 g, 5.10 mmol) was added. The reaction mixture was stirred overnight and then the reaction was quenched with NH₄Cl solution. The solvent was evaporated and the mixture diluted with EtOAc. The organic layer was washed with water and brine, dried (Na₂SO₄), filtered and concentrated. The residue was purified on Biotage Isolera (40 g Agela cartridge, eluted with 0-30% EtOAc/hexanes over 15 min) to give 0.84 g of the desired product.

Step 2. 2-[3-(4,4,5,5-Tetramethyl-1,3,2-dioxaborolan-2-yl)phenyl]indane-2-carbonitrile

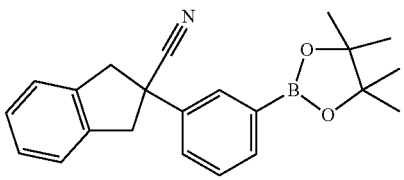 [SMILES: CC1(C)OB(c2cccc(C3(C#N)Cc4ccccc4C3)c2)OC1(C)C]

A mixture of 2-(3-bromophenyl)indane-2-carbonitrile (0.75 g, 2.5 mmol), 4,4,5,5,4',4',5',5'-octamethyl-[2,2']bi[[1,3,2]dioxaborolanyl] (0.89 g, 3.5 mmol), [1,1'-bis(diphenylphosphino)ferrocene]dichloropalladium (II) (55.2 mg, 0.0754 mmol), and potassium acetate (494 mg, 5.03 mmol) in 1,4-dioxane (13.0 mL) and dimethyl sulfoxide (0.40 mL) was degassed for 5 min then heated to 90° C. and stirred for 3 h. The reaction mixture was partitioned between ethyl acetate and water and filtered through a plug of Celite. The layers were separated and the organic layer was washed with saturated aqueous sodium chloride, dried over anhydrous sodium sulfate, filtered, and concentrated to give 0.75 g of a dark residue. LCMS calcd. for $C_{22}H_{25}BNO_2 (M+H)^+$: m/z 346.2. found: 346.2. The crude residue was stored at 4° C. and used as is for subsequent reactions.

Step 3. 2,4-Dichloro-7-{[2-(trimethylsilyl)ethoxy]methyl}-7H-pyrrolo[2,3-d]pyrimidine

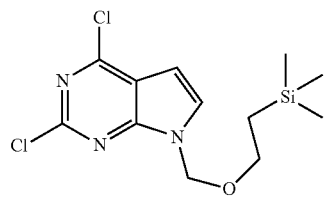 [SMILES: C[Si](C)(C)CCOCn1ccc2c(Cl)nc(Cl)nc21]

At 0° C. to a suspension of sodium hydride (1.69 g, 42.3 mmol) in N,N-dimethylformamide (50 mL) was added 2,4-dichloropyrrolo[2,3-d]pyrimidine (from Ark Pharm, 5.00 g, 26.6 mmol) portionwise. The reaction mixture was stirred for 30 min before adding [3-(trimethylsilyl)ethoxy]methyl chloride (6.91 mL, 39.1 mmol) at 0° C. with stirring. The reaction mixture was stirred and gradually warmed up to room temperature (1.5 hour). The reaction was quenched with water and diluted with ether. The layers were separated and the organic washed with water, dried (sodium sulfate), filtered and concentrated. The residue was purified on Biotage Isolera (120 g Agela cartridge, eluted with 0-20% EtOAc/hexanes over 15 min) to give 5.4 g of the product as a clear oil. LCMS calcd. for $C_{12}H_{18}Cl_2N_3OSi (M+H)^+$: m/z 318.1. found: 318.0.

Step 4. 2-[3-(2-Chloro-7-{[2-(trimethylsilyl)ethoxy]methyl}-7H-pyrrolo[2,3-d]pyrimidin-4-yl)phenyl]indane-2-carbonitrile

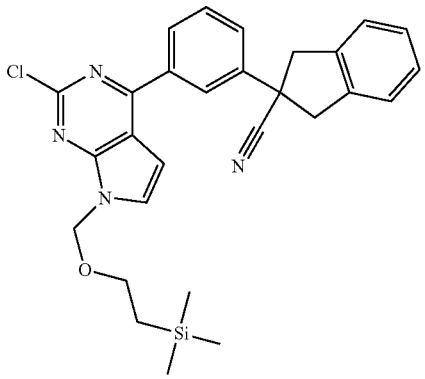 [SMILES: C[Si](C)(C)CCOCn1ccc2c(-c3cccc(C4(C#N)Cc5ccccc5C4)c3)nc(Cl)nc21]

Into a microwave vial was added 2,4-dichloro-7-{[2-(trimethylsilyl)ethoxy]methyl}-7H-pyrrolo[2,3-d]pyrimidine (150 mg, 0.47 mmol), 2-[3-(4,4,5,5-tetramethyl-1,3,2-dioxaborolan-2-yl)phenyl]indane-2-carbonitrile (183 mg, 0.530 mmol), and tetrakis(triphenylphosphine)palladium(0) (27.2 mg, 0.0236 mmol). 1,4-Dioxane (2.7 mL, 35 mmol) and 2.0 M sodium carbonate in water (0.707 mL, 1.41 mmol) were added to the reaction mixture. The reaction mixture was degassed, vial capped, and heated in the microwave at 150° C. for 20 min. The reaction mixture was partitioned between dichlormethane and water. The layers were separated and the organic washed with brine, dried (MgSO$_4$), filtered and concentrated. The residue was purified on Biotage Isolera (12 g Agela cartridge, eluted with 0-20% EtOAc/hexanes over 15 min) to yield 0.16 g of the desired product. LCMS calcd. for C$_{28}$H$_{30}$ClN$_4$OSi (M+H)$^+$: m/z 501.2. found: 501.2.

Step 5. 2-[3-(2-(Butylamino)-7-{[2-(trimethylsilyl)ethoxy]methyl}-7H-pyrrolo[2,3-d]pyrimidin-4-yl)phenyl]indane-2-carbonitrile

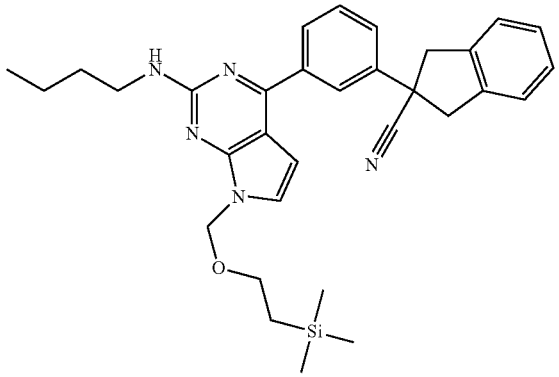 [SMILES: CCCCNc1nc(-c2cccc(C3(C#N)Cc4ccccc4C3)c2)c2ccn(COCC[Si](C)(C)C)c2n1]

A mixture of 2-[3-(2-chloro-7-{[2-(trimethylsilyl)ethoxy]methyl}-7H-pyrrolo[2,3-d]pyrimidin-4-yl)phenyl]indane-2-carbonitrile (21 mg, 0.042 mmol), 2-methoxyethanol (0.50 mL), 1-butanamine (6.21 µL, 0.0629 mmol) and 4.0 M hydrogen chloride in 1,4-dioxane (10.5 µL, 0.0419 mmol) were heated in the microwave at 180° C. for 1 h. The solvents were evaporated. The crude product was used for the next reaction. LCMS calcd. for C$_{32}$H$_{40}$N$_5$OSi (M+H)$^+$: m/z=538.3. found: 538.3.

Step 6. 4-{3-[2-(Aminomethyl)-2,3-dihydro-1H-inden-2-yl]phenyl}-N-butyl-7H-pyrrolo[2,3-d]pyrimidin-2-amine To a solution of 2-[3-(2-(butylamino)-7-{[2-(trimethylsilyl)ethoxy]methyl}-7H-pyrrolo[2,3-d]pyrimidin-4-yl)phenyl]indane-2-carbonitrile (21 mg, 0.039 mmol) in tetrahydrofuran (0.50 mL) was added 1.0 M lithium tetrahydroaluminate in THF (41 µL, 0.041 mmol). The resulting reaction mixture was stirred at rt for 6 h. The reaction was quenched with MeOH. After stirring for a few minutes, the mixture was filtered and concentrated. The crude residue containing the desired protected intermediate was dissolved in dichloromethane (0.2 mL) and TFA (0.2 mL) was added. The reaction mixture was stirred for 2 h then concentrated. To the concentrate was added MeOH (0.5 mL) and ethylenediamine (0.1 mL). The reaction mixture was stirred overnight, then purified using prep LC-MS (XBridge™ PrepC18 5 µm OBD™ column, 30×10 mm, 60 mL/min, eluting with a gradient of MeCN and water with 0.1% ammonium hydroxide) to give the desired product. LCMS calcd. for C$_{26}$H$_{30}$N$_5$(M+H)$^+$: m/z=412.2. found: 412.3.

Example 86

4-{3-[2-(Aminomethyl)-2,3-dihydro-1H-inden-2-yl]phenyl}-N-methyl-7H-pyrrolo[2,3-d]pyrimidin-2-amine

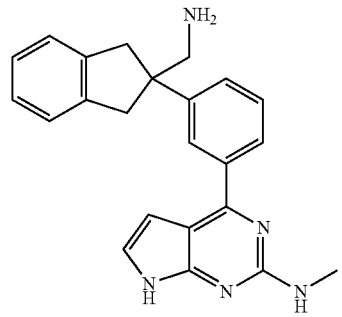 [SMILES: CNc1nc(-c2cccc(C3(CN)Cc4ccccc4C3)c2)c2cc[nH]c2n1]

Step 1. tert-Butyl {[2-(3-bromophenyl)-2,3-dihydro-1H-inden-2-yl]methyl}carbamate

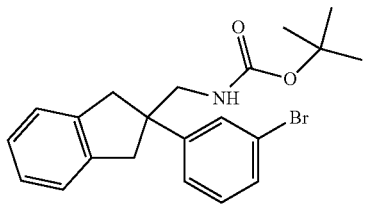 [SMILES: CC(C)(C)OC(=O)NCC1(c2cccc(Br)c2)Cc2ccccc2C1]

To a solution of 2-(3-bromophenyl)indane-2-carbonitrile (Prepared in Example 80, Step 1; 1.50 g, 5.03 mmol), di-tert-butyldicarbonate (2.20 g, 10.1 mmol) and nickel chloride hexahydrate (0.18 g, 0.75 mmol) in methanol (25.0 mL) stirring at about 0° C. was very slowly added sodium tetrahydroborate (1.33 g, 35.2 mmol). The reaction mixture was warmed to rt and stirred overnight. The precipitous mixture was filtered through a pad of celite and washed with EtOAc. The filtrate was concentrated to give a solid. The solid was suspended in dichloromethane and filtered. The filtrate was concentrated then purified on Biotage Isolera (40 g Agela cartridge, eluted with 0-40% EtOAc/hexanes over 15 min) to give 1.0 g of the desired product as a white solid. LCMS calcd. for $C_{17}H_{17}BrNO_2$ (M+H-Bu$^t$)$^+$: m/z 346.0. found: 346.1.

Step 2. tert-Butyl ({2-[3-(4,4,5,5-tetramethyl-1,3,2-dioxaborolan-2-yl)phenyl]-2,3-dihydro-1H-inden-2-yl}methyl)carbamate

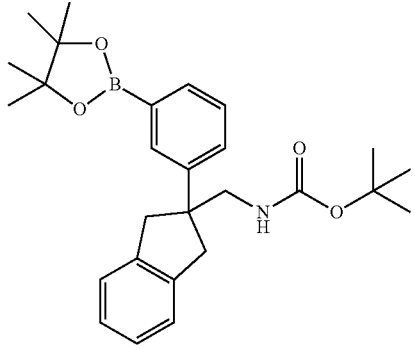 [SMILES: CC(C)(C)OC(=O)NCC1(c2cccc(B3OC(C)(C)C(C)(C)O3)c2)Cc2ccccc2C1]

A mixture of tert-butyl {[2-(3-bromophenyl)-2,3-dihydro-1H-inden-2-yl]methyl}carbamate (0.56 g, 1.4 mmol), 4,4,5,5,4',4',5',5'-octamethyl-[2,2']bi[[1,3,2]dioxaborolanyl] (0.495 g, 1.95 mmol), [1,1'-bis(diphenylphosphino)ferrocene]dichloropalladium (II) (30.6 mg, 0.0418 mmol), and potassium acetate (273 mg, 2.78 mmol) in 1,4-dioxane (7.2 mL) and dimethyl sulfoxide (0.22 mL) was degassed for 5 min then heated to 90° C. and stirred for 17 h. The reaction mixture was partitioned between ethyl acetate and water and filtered through a plug of Celite. The layers were separated and the organic layer was washed with water and brine, dried over anhydrous sodium sulfate, filtered, and concentrated. The residue was purified on Biotage Isolera (40 g Agela cartridge, eluted with 0-40% EtOAc/hexanes over 15 min) to give 0.43 g of the desired product as a white solid. LCMS calcd. for $C_{22}H_{29}BNO_2$(M+2H-Boc)$^+$: m/z=350.2. found: 350.2.

Step 3. tert-Butyl ({2-[3-(2-chloro-7-{[2-(trimethylsilyl)ethoxy]methyl}-7H-pyrrolo[2,3-d]pyrimidin-4-yl)phenyl]-2,3-dihydro-1H-inden-2-yl}methyl)carbamate

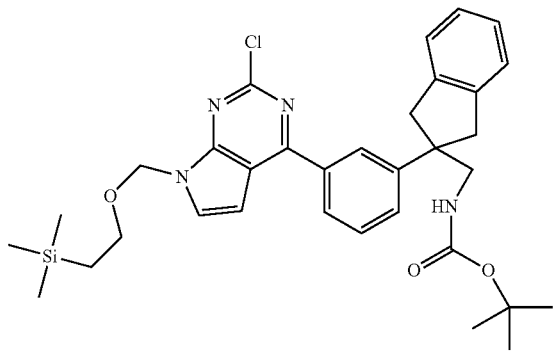 [SMILES: CC(C)(C)OC(=O)NCC1(c2cccc(-c3nc(Cl)nc4c3ccn4COCC[Si](C)(C)C)c2)Cc2ccccc2C1]

A mixture of 2,4-dichloro-7-{[2-(trimethylsilyl)ethoxy]methyl}-7H-pyrrolo[2,3-d]pyrimidine (Prepared in Example 80, Step 3; 78 mg, 0.24 mmol), tert-butyl ({2-[3-(4,4,5,5-tetramethyl-1,3,2-dioxaborolan-2-yl)phenyl]-2,3-dihydro-1H-inden-2-yl}methyl)carbamate (121 mg, 0.270 mmol), tetrakis(triphenylphosphine)palladium(0) (14.2 mg, 0.0122 mmol), 2.0 M sodium carbonate in water (0.368 mL, 0.735 mmol) and 1,4-dioxane (1.7 mL) was heated in the microwave at 150° C. for 20 min. The reaction mixture was partitioned between dichloromethane and water and the layers separated. The organic layer was washed with brine, dried (MgSO$_4$), filtered and concentrated. The residue was purified on Biotage Isolera (12 g Agela cartridge, eluted with 0-10% EtOAc/hexanes over 15 min).

Step 4. 4-{3-[2-(Aminomethyl)-2,3-dihydro-1H-inden-2-yl]phenyl}-N-methyl-7H-pyrrolo[2,3-d]pyrimidin-2-amine A mixture of tert-butyl ({2-[3-(2-chloro-7-{[2-(trimethylsilyl)ethoxy]methyl}-7H-pyrrolo[2,3-d]pyrimidin-4-yl)phenyl]-2,3-dihydro-1H-inden-2-yl}methyl)carbamate (19 mg, 0.031 mmol), methylammonium chloride (10.6 mg, 0.157 mmol) and 4.0 M hydrogen chloride in 1,4-dioxane (7.85 µL, 0.0314 mmol) in 2-methoxyethanol (0.50 mL) was heated in the microwave at 180° C. for 1 h. The reaction mixture was partitioned between dichloromethane and water. The layers separated and the organic concentrated to give the crude protected intermediate. The crude residue was dissolved in dichloromethane (0.2 mL) and TFA (0.2 mL) was added. The reaction mixture was stirred for 2 h then concentrated. To the concentrate was added MeOH (0.5 mL) and ethylenediamine (0.1 mL). After 30 min, the mixture was diluted and purified by prep LC-MS (XBridge™ PrepC18 5 µm OBD™ column, 30×10 mm, 60 mL/min, eluting with a gradient of MeCN and water with 0.1% ammonium hydroxide) to give the desired product. LCMS calcd. for $C_{23}H_{24}N_5$(M+H)$^+$: m/z=370.2. found: 370.1.

Example 87

4-{3-[2-(Aminomethyl)-2,3-dihydro-1H-inden-2-yl]phenyl}-N-ethyl-7H-pyrrolo[2,3-d]pyrimidin-2-amine

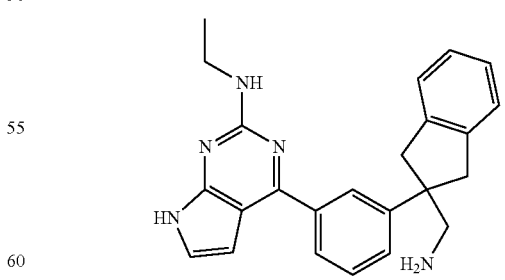

The title compound was prepared using procedures analogous to those as described for the synthesis of Example 86 using ethylamine hydrochloride (12.8 mg, 0.157 mmol) to replace methylammonium chloride. LCMS calcd for $C_{24}H_{26}N_5$(M+H)$^+$: m/z=384.2. found: 384.2.

Example 88

4-{3-[2-(Aminomethyl)-2,3-dihydro-1H-inden-2-yl]phenyl}-N-isopropyl-7H-pyrrolo[2,3-d]pyrimidin-2-amine

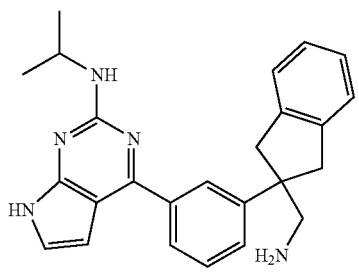 [SMILES: CC(C)Nc1nc(-c2cccc(C3(CN)Cc4ccccc4C3)c2)c2cc[nH]c2n1]

The title compound was prepared using procedures analogous to those as described for the synthesis of Example 86 using 2-propanamine (50 μL). LCMS calcd for $C_{25}H_{28}N_5$ (M+H)$^+$: m/z=398.2. found: 398.2.

Example 89

4-{3-[2-(Aminomethyl)-2,3-dihydro-1H-inden-2-yl]phenyl}-N-cyclobutyl-7H-pyrrolo[2,3-d]pyrimidin-2-amine

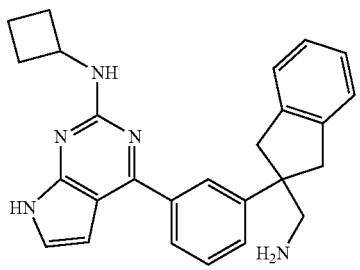 [SMILES: NCC1(c2cccc(-c3nc(NC4CCC4)nc4[nH]ccc34)c2)Cc2ccccc2C1]

The title compound was prepared using procedures analogous to those as described for the synthesis of Example 86 using cyclobutanamine (50 μL). LCMS calcd for $C_{26}H_{28}N_5$ (M+H): m/z 410.2. found: 410.2.

Example 90

4-{3-[2-(Aminomethyl)-2,3-dihydro-1H-inden-2-yl]phenyl}-N-cyclopentyl-7H-pyrrolo[2,3-d]pyrimidin-2-amine

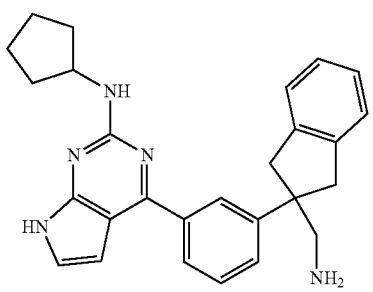 [SMILES: NCC1(c2cccc(-c3nc(NC4CCCC4)nc4[nH]ccc34)c2)Cc2ccccc2C1]

The title compound was prepared using procedures analogous to those as described for the synthesis of Example 86 using cyclopentanamine (13 μL). LCMS calcd for $C_{27}H_{30}N_5$ (M+H)$^+$: m/z 424.2. found: 424.2.

Example 91

4-{3-[2-(Aminomethyl)-2,3-dihydro-1H-inden-2-yl]phenyl}-N-cyclohexyl-7H-pyrrolo[2,3-d]pyrimidin-2-amine

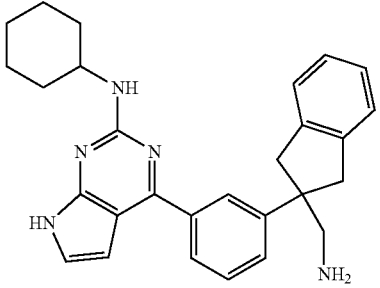 [SMILES: NCC1(c2cccc(-c3nc(NC4CCCCC4)nc4[nH]ccc34)c2)Cc2ccccc2C1]

The title compound was prepared using procedures analogous to those as described for the synthesis of Example 86 using cyclohexanamine (From Aldrich; 15 μL). LCMS calcd for $C_{28}H_{32}N_5$(M+H)$^+$: m/z 438.3. found: 438.3.

Example 93

1-{2-[3-(6-Methyl-7H-pyrrolo[2,3-d]pyrimidin-4-yl)phenyl]-2,3-dihydro-1H-inden-2-yl}methanamine

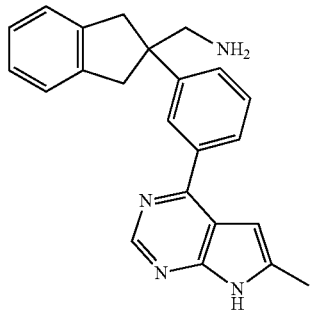 [SMILES: Cc1cc2c(-c3cccc(C4(CN)Cc5ccccc5C4)c3)ncnc2[nH]1]

Step 1. tert-Butyl 4-chloro-6-methyl-7H-pyrrolo[2,3-d]pyrimidine-7-carboxylate

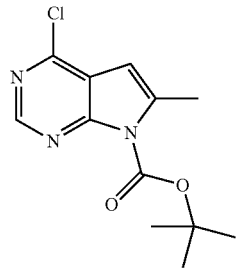 [SMILES: Cc1cc2c(Cl)ncnc2n1C(=O)OC(C)(C)C]

To a solution of 4-chloro-6-methyl-7H-pyrrolo[2,3-d]pyrimidine (from Ark Pharm, 103 mg, 0.614 mmol) in pyridine (3.1 mL) was added di-tert-butyldicarbonate (0.536 g, 2.46 mmol) followed by 4-dimethylaminopyridine (0.113 g, 0.922 mmol). The resulting reaction mixture was stirred at rt overnight. Water and dichloromethane were added and the layers separated. The organic was washed with water then separated using a phase separator funnel. The solvents were evaporated then the remaining pyridine was azeotroped with toluene. Drying in vacuo gave an orange solid (160 mg). LCMS calcd. for $C8H_6ClN_3O_2$ $(M+H-^{t}Bu)^+$: m/z=212.1. found: 212.1.

Step 2. 1-{2-[3-(6-Methyl-7H-pyrrolo[2,3-d]pyrimidin-4-yl)phenyl]-2,3-dihydro-1H-inden-2-yl}methanamine A mixture of tert-butyl 4-chloro-6-methyl-7H-pyrrolo[2,3-d]pyrimidine-7-carboxylate (12.0 mg, 0.0448 mmol), tert-butyl ({2-[3-(4,4,5,5-tetramethyl-1,3,2-dioxaborolan-2-yl)phenyl]-2,3-dihydro-1H-inden-2-yl}methyl)carbamate (Prepared in Example 86, Step 2; 21.1 mg, 0.0470 mmol), tetrakis(triphenylphosphine)palladium(0) (2.5 mg, 0.0021 mmol), 2.0 M sodium carbonate in water (64.0 µL, 0.128 mmol) and 1,4-dioxane (0.50 mL, 6.4 mmol) was heated in the microwave at 150° C. for 20 min. The reaction mixture was partitioned between dichloromethane and water. The organic was isolated using a phase separator funnel then concentrated to give the crude protected intermediate. To the crude intermediate was added 1:1 TFA/dichloromethane (0.6 mL) and the reaction mixture was stirred for 1 h. The solvents were evaporated and the residue purified using prep LC-MS (XBridge™ PrepC18 5 µm OBD™ column, 30×10 mm, 60 mL/min, eluting with a gradient of MeCN and water with 0.1% ammonium hydroxide) to give the desired product. LCMS calcd. for $C_{23}H_{23}N_4$ $(M+H)^+$: m/z=355.2. found: 355.2.

Example 94

4-{2-[2-(Aminomethyl)-2,3-dihydro-1H-inden-2-yl]pyridin-4-yl}-N-(1-methyl-1H-pyrazol-4-yl)-7H-pyrrolo[2,3-d]pyrimidin-2-amine

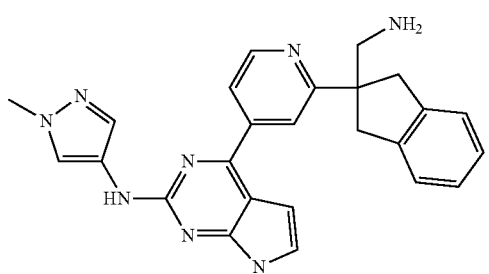 [SMILES: Cn1cc(Nc2nc(-c3ccnc(C4(CN)Cc5ccccc5C4)c3)c3cc[nH]c3n2)cn1]

Step 1. tert-Butyl {[2-(4-bromopyridin-2-yl)-2,3-dihydro-1H-inden-2-yl]methyl}carbamate

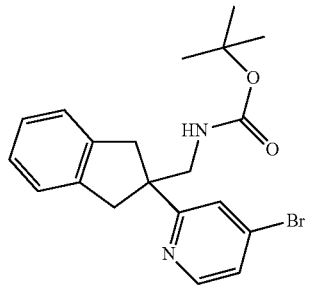 [SMILES: CC(C)(C)OC(=O)NCC1(c2cc(Br)ccn2)Cc2ccccc2C1]

To a solution of 2-(4-bromopyridin-2-yl)indane-2-carbonitrile (from Example 3 step 1, 4.10 g, 13.7 mmol), di-tert-butyldicarbonate (5.98 g, 27.4 mmol) and nickel chloride hexahydrate (0.49 g, 2.0 mmol) in methanol (90 mL) stirring at about 0° C. was very slowly added sodium tetrahydroborate (3.63 g, 95.9 mmol). The mixture was warmed to rt and stirred overnight. The precipitous mixture was filtered through a pad of Celite, washing with EtOAc. The filtration was very slow, the filter kept getting clogged. The filtrate was concentrated to give a solid, which was purified on Biotage Isolera (120 g Agela cartridge, eluted with 5-50% EtOAc/hexanes over 15 min) to give 1.75 g of the desired product as a white solid. LCMS calcd for $C_{20}H_{24}BrN_2O_2$ $(M+H)^+$: m/z 403.1. Found: 403.0. 0.67 g of the starting material recovered.

Step 2. tert-Butyl ({2-[4-(4,4,5,5-tetramethyl-1,3,2-dioxaborolan-2-yl)pyridin-2-yl]-2,3-dihydro-1H-inden-2-yl}methyl) carbamate

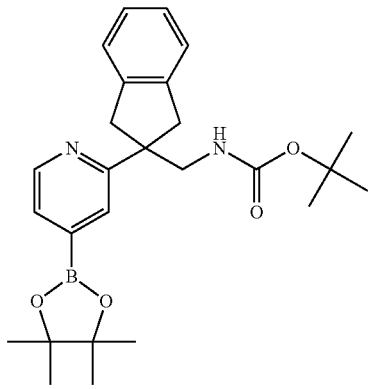 [SMILES: CC(C)(C)OC(=O)NCC1(c2cc(B3OC(C)(C)C(C)(C)O3)ccn2)Cc2ccccc2C1]

A mixture of tert-butyl {[2-(4-bromopyridin-2-yl)-2,3-dihydro-1H-inden-2-yl]methyl}carbamate (1.75 g, 4.34 mmol), 4,4,5,5,4',4',5',5'-octamethyl-[2,2']bi[[1,3,2]dioxaborolanyl] (1.65 g, 6.51 mmol), [1,1'-bis(diphenylphosphino)ferrocene]dichloropalladium (II) (95.2 mg, 0.130 mmol), and potassium acetate (852 mg, 8.68 mmol) in 1,4-dioxane (27 mL) and dimethyl sulfoxide (0.81 mL) was degassed for 5 min then heated to 90° C. and stirred for 17 h. The reaction mixture was partitioned between ethyl acetate and water and filtered through a plug of Celite. The layers were separated and the organic layer was washed with water and brine, dried over anhydrous sodium sulfate, filtered, and concentrated to give 3 g of a dark gum after drying in vacuo. LCMS calcd for $C_{26}H_{36}BN_2O_4(M+H)^+$: m/z 451.3. Found: 451.2. The crude produce was used directly in the next step without further purifications.

Step 3. tert-Butyl ({2-[4-(2-chloro-7-{[2-(trimethylsilyl)ethoxy]methyl}-7H-pyrrolo[2,3-d]pyrimidin-4-yl)pyridin-2-yl]-2,3-dihydro-1H-inden-2-yl}methyl)carbamate

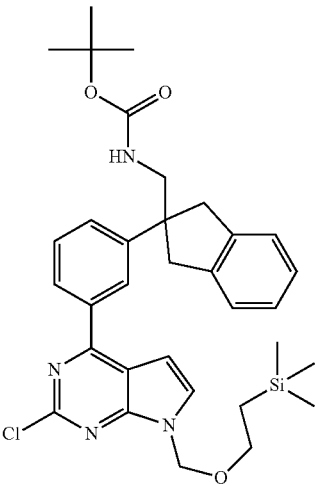 [SMILES: CC(C)(C)OC(=O)NCC1(c2cccc(-c3nc(Cl)nc4c3ccn4COCC[Si](C)(C)C)c2)Cc2ccccc2C1]

A mixture of 2,4-dichloro-7-{[2-(trimethylsilyl)ethoxy]methyl}-7H-pyrrolo[2,3-d]pyrimidine (from Example 80 step 3, 326.2 mg, 1.025 mmol), tert-butyl ({2-[4-(4,4,5,5-tetramethyl-1,3,2-dioxaborolan-2-yl)pyridin-2-yl]-2,3-dihydro-1H-inden-2-yl}methyl)carbamate (600 mg, 1.33 mmol), tetrakis(triphenylphosphine)palladium(0) (59.2 mg, 0.0512 mmol) and 2.0 M sodium carbonate in water (1.54 mL, 3.07 mmol) in 1,4-dioxane (7.1 mL) was heated in the microwave at 150° C. for 20 min. The mixture was partitioned between EtOAc and water. The organic layer was separated then washed with brine, dried, filtered and concentrated. The resulting residues was purified on Biotage Isolera (40 g Agela cartridge, eluted with 5-55% EtOAc/hexanes over 15 min) to give the desired product (0.33 g, 53% in 2 steps). LCMS calcd for $C_{32}H_{41}ClN_5O_3Si$ $(M+H)^+$: m/z 606.3. Found: 606.2.

Step 4. 4-{2-[2-(Aminomethyl)-2,3-dihydro-1H-inden-2-yl]pyridin-4-yl}-N-(1-methyl-1H-pyrazol-4-yl)-7H-pyrrolo[2,3-d]pyrimidin-2-amine In a microwave vial, a mixture of tert-butyl ({2-[4-(2-chloro-7-{[2-(trimethylsilyl)ethoxy]methyl}-7H-pyrrolo[2,3-d]pyrimidin-4-yl)pyridin-2-yl]-2,3-dihydro-1H-inden-2-yl}methyl)carbamate (17.0 mg, 0.0280 mmol), 1-methyl-1H-pyrazol-4-amine (from AstaTech, 8.4 mg, 0.086 mmol), Brettphos Pd G3 (from Aldrich, 3.1 mg, 0.0034 mmol) and cesium carbonate (33 mg, 0.10 mmol) in tert-butyl alcohol (0.7 mL, 7 mmol) was purged with $N_2$ then sealed and stirred at 100° C. for 3 h. The mixture was diluted with dichloromethane, filtered through Celite, and concentrated. The crude residue was dissolved in dichloromethane (0.3 mL) and TFA (0.2 mL) was added. The mixture was stirred for 2 h then concentrated. To the concentrate was added MeOH (0.5 mL) and ethylenediamine (0.1 mL). After stirred for 1 h, the mixture was diluted and prep-LCMS (XBridge™ C18 column, eluting with a gradient of MeCN/water containing 0.1% ammonium hydroxide, at a flow rate of 60 mL/min) to give the desired as a yellow solid (6.2 mg, 51%). LCMS calcd for $C_{25}H_{25}N_8(M+H)^+$: m/z 437.2. Found: 437.2.

Example 95

4-{2-[2-(Aminomethyl)-2,3-dihydro-1H-inden-2-yl]pyridin-4-yl}-N-[3-(morpholin-4-ylmethyl)phenyl]-7H-pyrrolo[2,3-d]pyrimidin-2-amine

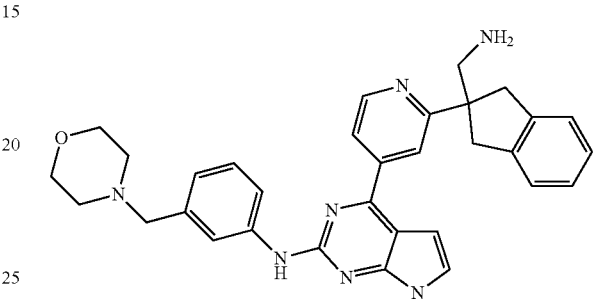

A mixture of tert-butyl ({2-[4-(2-chloro-7-{[2-(trimethylsilyl)ethoxy]methyl}-7H-pyrrolo[2,3-d]pyrimidin-4-yl)pyridin-2-yl]-2,3-dihydro-1H-inden-2-yl}methyl)carbamate (15.1 mg, 0.0249 mmol), 3-(morpholin-4-ylmethyl)aniline (from Ark Pharm, 15 mg, 0.076 mmol), Brettphos Pd G3 (from Aldrich, 2.7 mg, 0.0030 mmol) and cesium carbonate (29 mg, 0.090 mmol) in tert-butyl alcohol (0.6 mL) was purged with $N_2$ then sealed and stirred at 100° C. for 3 h. The mixture was diluted with dichloromethane, filtered through Celite, and concentrated. The crude residue was dissolved in dichloromethane (0.3 mL) and TFA (0.2 mL) was added. The mixture was stirred for 2 h then concentrated. To the concentrate was added MeOH (0.5 mL) and ethylenediamine (0.1 mL). After stirred for 1 h, the mixture was diluted and prep-LCMS (XBridge™ C18 column, eluting with a gradient of MeCN/water containing 0.1% ammonium hydroxide, at a flow rate of 60 mL/min) to give the desired product. LCMS calcd for $C_{32}H_{34}N_7O$ $(M+H)^+$: m/z 532.3. Found: 532.2.

Example 96

1-{2-[4-(5-Methoxy-1H-pyrrolo[2,3-b]pyridin-4-yl)pyridin-2-yl]-2,3-dihydro-1H-inden-2-yl}methanamine

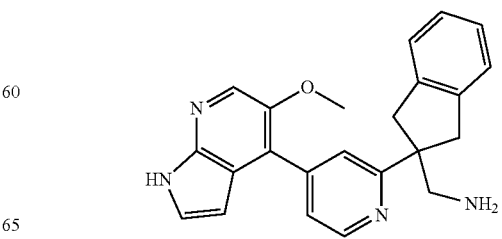

175

Step 1. 4-Chloro-5-methoxy-1-{[2-(trimethylsilyl)ethoxy]methyl}-1H-pyrrolo[2,3-b]pyridine

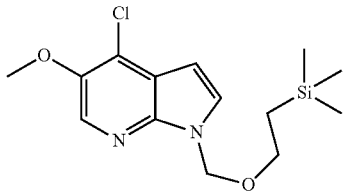

To a suspension of sodium hydride (0.085 g, 2.1 mmol) in N,N-dimethylformamide (4 mL) was added 4-chloro-5-methoxy-1H-pyrrolo[2,3-b]pyridine (from Adesis, 0.30 g, 1.6 mmol) portionwise at 0° C. The mixture was stirred for 1 h before the addition of [3-(trimethylsilyl)ethoxy]methyl chloride (0.38 mL, 2.1 mmol) dropwise. The reaction was stirred for 1 h, then diluted with Et$_2$O, washed with water, concentrated and purified on silica gel (0-20% EtOAc/hexanes) to give the desired product (0.48 g, 93%). LCMS calcd for C$_{14}$H$_{22}$ClN$_2$O$_2$Si (M+H)$^+$: m/z=313.1. Found: 313.1.

Step 2. tert-Butyl ({2-[4-(5-methoxy-1-{[2-(trimethylsilyl)ethoxy]methyl}-1H-pyrrolo[2,3-b]pyridin-4-yl)pyridin-2-yl]-2,3-dihydro-1H-inden-2-yl}methyl)carbamate

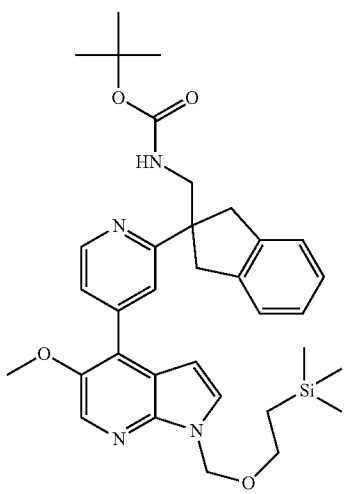

A mixture of tert-butyl ({2-[4-(4,4,5,5-tetramethyl-1,3,2-dioxaborolan-2-yl)pyridin-2-yl]-2,3-dihydro-1H-inden-2-yl}methyl)carbamate (from Example 94 step 2, 0.068 g, 0.15 mmol), 4-chloro-5-methoxy-1-{[2-(trimethylsilyl)ethoxy]methyl}-1H-pyrrolo[2,3-b]pyridine (0.047 g, 0.15 mmol), cesium carbonate (0.098 g, 0.30 mmol) and dicyclohexyl(2',4',6'-triisopropylbiphenyl-2-yl)phosphine-(2'-aminobiphenyl-2-yl)(chloro)palladium (1:1) (0.012 g, 0.015 mmol) in 1,4-dioxane (0.2 mL)/water (0.09 mL) was stirred for 1 h at 55° C. The reaction was purified on silica gel (0-100% EtOAc/hexanes) to give the desired product (78 mg, 86%). LCMS calcd for C$_{34}$H$_{45}$N$_4$O$_4$Si (M+H)$^+$: m/z=601.3. Found: 601.4.

176

Step 4. 1-{2-[4-(5-Methoxy-1H-pyrrolo[2,3-b]pyridin-4-yl)pyridin-2-yl]-2,3-dihydro-1H-inden-2-yl}methanamine tert-Butyl ({2-[4-(5-methoxy-1-{[2-(trimethylsilyl)ethoxy]methyl}-1H-pyrrolo[2,3-b]pyridin-4-yl)pyridin-2-yl]-2,3-dihydro-1H-inden-2-yl}methyl)carbamate (0.022 g, 0.037 mmol) was treated with trifluoroacetic acid (0.2 mL) in methylene chloride (0.2 mL) at rt for 1 h and then stripped to dryness. The residue was treated with ethylenediamine (0.2 mL, 3 mmol) in methanol (0.2 mL) overnight. The mixture was purified on prep-LCMS (XBridge™ C18 column, eluting with a gradient of MeCN/water containing 0.05% TFA, at a flow rate of 60 mL/min) to give the desired product as TFA salt (4.2 mg, 31%). LCMS calcd for C$_{23}$H$_{23}$N$_4$O (M+H)$^+$: m/z=371.2. Found: 371.2.

Example 97

1-{2-[4-(1H-Pyrazolo[3,4-b]pyridin-4-yl)pyridin-2-yl]-2,3-dihydro-1H-inden-2-yl}methanamine

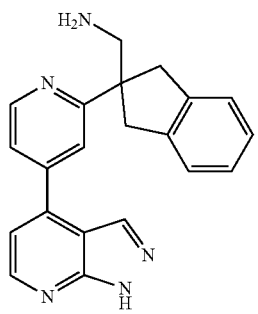 [SMILES: N=Cc1c(-c2ccnc(C3(CN)Cc4ccccc4C3)c2)ccnc1N]

Step 1. 4-Chloro-1-(phenylsulfonyl)-1H-pyrazolo[3,4-b]pyridine

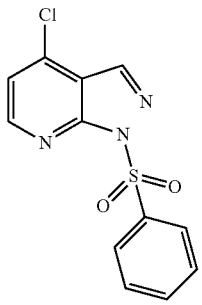 [SMILES: N=Cc1c(Cl)ccnc1NS(=O)(=O)c1ccccc1]

To a stirred suspension of a mixture of NaH in mineral oil (60%, 390 mg, 9.8 mmol) in tetrahydrofuran (20 mL) was added a solution of 4-chloro-1H-pyrazolo[3,4-b]pyridine (from Ark Pharm, 1.0 g, 6.5 mmol) in THF at 0° C. After 0.5 h, benzenesulfonyl chloride (1.0 mL, 7.8 mmol) was added. After stirred for another 1 h, the reaction mixture was quenched with sat. NH$_4$Cl solution, extracted with dichloromethane. The extracts were combined and concentrated. The resulting residue was purified on silica gel (0-80% EtOAc/hexanes) to give the desired product (1.7 g, 89%). LCMS calcd for C$_{12}$H$_9$ClN$_3$O$_2$S (M+H)$^+$: m/z=294.0. Found: 293.9.

Step 2. 2-{4-[1-(Phenylsulfonyl)-1H-pyrazolo[3,4-b]pyridin-4-yl]pyridin-2-yl}indane-2-carbonitrile

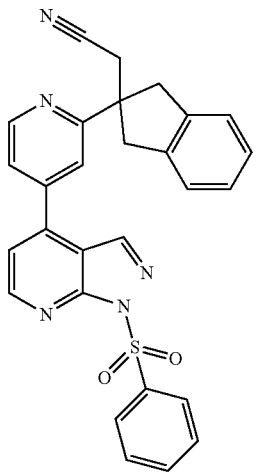 [SMILES: N#CCC1(c2cc(-c3ccnc(NS(=O)(=O)c4ccccc4)c3C=N)ccn2)Cc2ccccc2C1]

A mixture of 2-[4-(4,4,5,5-tetramethyl-1,3,2-dioxaborolan-2-yl)pyridin-2-yl]indane-2-carbonitrile (from Example 3 step 2, 0.055 g, 0.16 mmol), 4-chloro-1-(phenylsulfonyl)-1H-pyrazolo[3,4-b]pyridine (0.21 g, 0.71 mmol), cesium carbonate (0.10 g, 0.32 mmol) and dicyclohexyl(2',4',6'-triisopropylbiphenyl-2-yl)phosphine-(2'-aminobiphenyl-2-yl)(chloro)palladium (1:1) (0.012 g, 0.016 mmol) in 1,4-dioxane (0.9 mL/water (0.4 mL) was stirred for 1 h at 55° C. The reaction was cooled, diluted with EtOAc, washed with water, and then dried and concentrated under reduced pressure. The resulting residue was purified on silica gel (0-100% EtOAc/hexanes) to give the desired product (0.050 g, 66%). LCMS calcd for $C_{27}H_{20}N_5O_2S$ (M+H)$^+$: m/z 478.1. Found: 478.0.

Step 3. 1-(2-{4-[1-(Phenylsulfonyl)-1H-pyrazolo[3,4-b]pyridin-4-yl]pyridin-2-yl}-2,3-dihydro-1H-inden-2-yl)methanamine

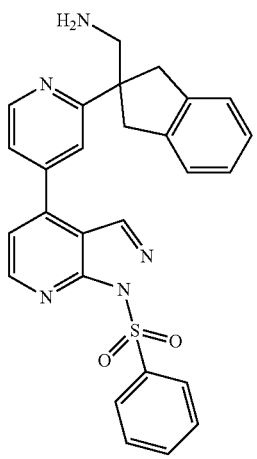 [SMILES: N=Cc1c(-c2ccnc(C3(CN)Cc4ccccc4C3)c2)ccnc1NS(=O)(=O)c1ccccc1]

2-{4-[1-(Phenylsulfonyl)-1H-pyrazolo[3,4-b]pyridin-4-yl]pyridin-2-yl}indane-2-carbonitrile (50 mg, 0.1 mmol) was dissolved in methylene chloride (0.45 mL) and cooled to −78° C. 1.0 M Diisobutylaluminum hydride in dichloromethane (0.32 mL, 0.32 mmol) was added dropwise, then the reaction was stirred at −78° C. for 1 h. The dry-ice bath was removed, and MeOH (25 uL) was added to quench the reaction. The reaction was treated with water and the aluminum salts chelated with 1 mL of 1M aqueous solution of sodium potassium tartrate. The reaction was partitioned between water and dichloromethane (small amount of THF added to improve solubility). The organic phase was dried over $MgSO_4$, filtered, and concentrated to give the product (21 mg, 48%). LCMS calcd for $C_{27}H_{24}N_5O_{52}S$ (M+H)$^+$: m/z 482.2. Found: 482.3.

Step 4. 1-{2-[4-(1H-Pyrazolo[3,4-b]pyridin-4-yl)pyridin-2-yl]-2,3-dihydro-1H-inden-2-yl}methanamine Sodium methoxide, 25 wt. % solution in methanol (0.048 mL, 0.53 mmol) was added to a solution of 1-(2-{4-[1-(phenylsulfonyl)-1H-pyrazolo[3,4-b]pyridin-4-yl]pyridin-2-yl}-2,3-dihydro-1H-inden-2-yl)methanamine (51 mg, 0.10 mmol) in tetrahydrofuran (2 mL). The reaction mixture was stirred at rt for 2 h. The reaction mixture was purified on prep-LCMS (XBridge™ C18 column, eluting with a gradient of MeCN/water containing 0.05% TFA, at a flow rate of 60 mL/min) to give the desired product as TFA salt (5.6 mg, 16%). LCMS calcd for $C_{21}H_{20}N_5$(M+H)$^+$: m/z 342.2. Found: 342.1.

Example 98

3-(Aminomethyl)-3-[3-(7H-pyrrolo[2,3-d]pyrimidin-4-yl)phenyl]indan-1-ol

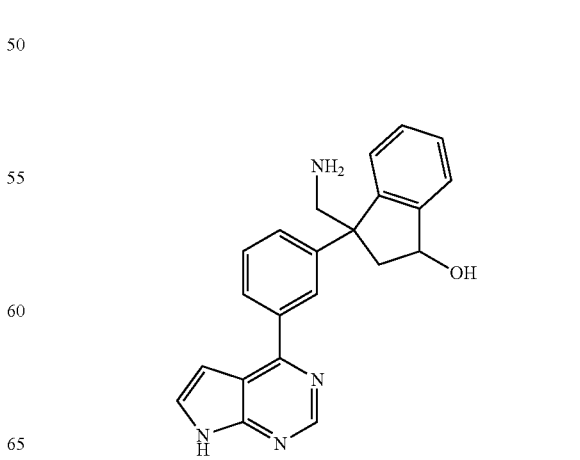

Step 1: 2-{Cyano[3-(7-{[2-(trimethylsilyl)ethoxy]methyl}-1H-pyrrolo[2,3-d]pyrimidin-4-yl)phenyl]methyl}benzonitrile

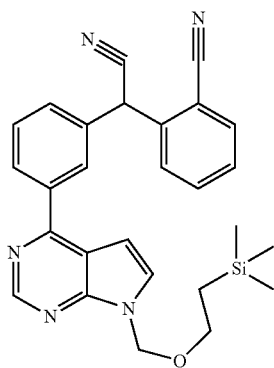 [SMILES: C[Si](C)(C)CCOCn1ccc2c(-c3cccc(C(C#N)c4ccccc4C#N)c3)ncnc21]

To a solution of [3-(7-{[2-(trimethylsilyl)ethoxy]methyl}-7H-pyrrolo[2,3-d]pyrimidin-4-yl)phenyl]acetonitrile (from Example 5 step 1, 200 mg, 0.549 mmol) in anhydrous tetrahydrofuran (2.0 mL) was added a 60% mixture of sodium hydride in mineral oil (88 mg, 2.2 mmol) and the resulting solution was stirred for 45 minutes prior to the addition of 2-fluorobenzonitrile (58 μL, 0.54 mmol). The resulting mixture was stirred at ambient temperature overnight. The crude reaction mixture was purified by column chromatography on silica gel using a CombiFlash® apparatus eluting with ethyl acetate/hexanes (0-30%) to afford 0.216 g of the desired product (85% yield). LCMS calcd. for $C_{27}H_{28}N_5OSi$ (M+H)$^+$: m/z=466.2. found: 466.1.

Step 2: tert-Butyl 3-amino-1-cyano-1-[3-(7-{[2-(trimethylsilyl)ethoxy]methyl}-7H-pyrrolo[2,3-d]pyrimidin-4-yl)phenyl]-1H-indene-2-carboxylate

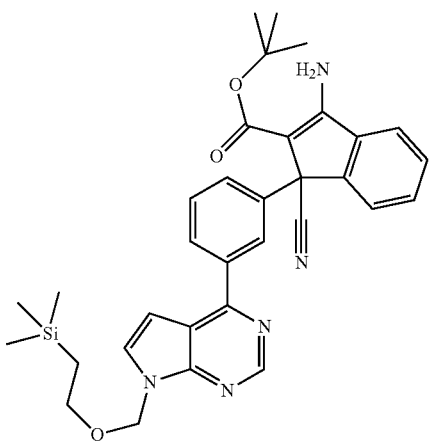 [SMILES: CC(C)(C)OC(=O)C1=C(N)c2ccccc2C1(C#N)c1cccc(-c2ncnc3c2ccn3COCC[Si](C)(C)C)c1]

To a solution of 2-{cyano[3-(7-{[2-(trimethylsilyl)ethoxy]methyl}-7H-pyrrolo[2,3-d]pyrimidin-4-yl)phenyl]methyl}benzonitrile (216 mg, 0.464 mmol) in anhydrous tetrahydrofuran (2.0 mL) was added potassium tert-butoxide (0.29 mL, 2.3 mmol) and the resulting solution was stirred for 20 minutes prior to the addition of tert-butyl 2-bromoacetate (140 μL, 0.93 mmol). The resulting solution was stirred at ambient temperature. After 4 h, a second aliquot of potassium tert-butoxide (0.29 mL, 2.3 mmol) was added and stirring was continued for an additional 2 h. The crude reaction mixture was purified by column chromatography on silica gel using a CombiFlash® apparatus eluting with ethyl acetate/hexanes (0-50%) to afford 0.220 g of the desired product (82% yield). LCMS calcd. for $C_{33}H_{38}N_5O_3Si$ (M+H): m/z=580.3. found: 580.3.

Step 3: 3-Oxo-1-[3-(7H-pyrrolo[2,3-d]pyrimidin-4-yl)phenyl]indane-1-carbonitrile

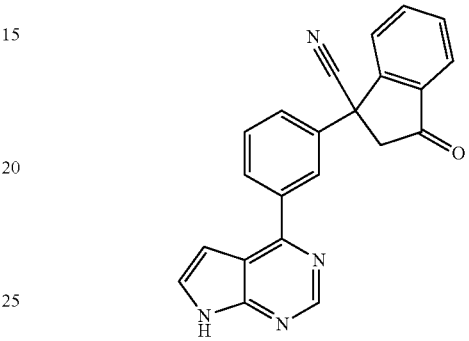

A solution of tert-butyl 3-amino-1-cyano-1-[3-(7-{[2-(trimethylsilyl)ethoxy]methyl}-7H-pyrrolo[2,3-d]pyrimidin-4-yl)phenyl]-1H-indene-2-carboxylate (63 mg, 0.12 mmol) and water (100 μL) in 4.0 M hydrogen chloride in 1,4-dioxane (3.0 mL) was heated at 90° C. in a sealed vial overnight. The volatiles were removed in-vacuo and the crude residue was used in the next step without further purification. LCMS calcd. for $C_{22}H_{15}N_4O$ (M+H)$^+$: m/z 351.1. found: 351.1.

Step 4: tert-Butyl ({3-hydroxy-1-[3-(7H-pyrrolo[2,3-d]pyrimidin-4-yl)phenyl]-2,3-dihydro-1H-inden-1-yl}methyl)carbamate

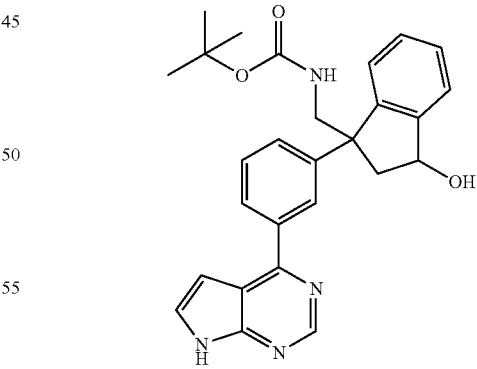

To a 0° C. mixture of 3-oxo-1-[3-(7H-pyrrolo[2,3-d]pyrimidin-4-yl)phenyl]indane-1-carbonitrile (45 mg, 0.13 mmol), nickel chloride hexahydrate (7.0 mg, 0.03 mmol), di-tert-butyldicarbonate (89 μL, 0.39 mmol) in methanol (2.0 mL) was added sodium tetrahydroborate (44 mg, 1.2 mmol) portion-wise over 15 minutes and the resulting mixture was allowed to gradually warm to ambient temperature while stirring overnight. The crude reaction mixture was purified by column chromatography on silica gel using a CombiFlash apparatus eluting with methanol/dichloromethane (0-20%) to afford 0.052 g of the desired product (89% yield). LCMS calcd. for $C_{27}H_{28}N_4O_3$ (M+H)$^+$: m/z 457.2. found: 457.2.

Step 5: 3-(3-(7H-Pyrrolo[2,3-d]pyrimidin-4-yl)phenyl)-3-(aminomethyl)-2,3-dihydro-1H-inden-1-ol A solution of tert-butyl ({3-hydroxy-1-[3-(7H-pyrrolo[2,3-d]pyrimidin-4-yl)phenyl]-2,3-dihydro-1H-inden-1-yl}methyl)carbamate (52 mg, 0.11 mmol) in dichloromethane (1.0 mL) and trifluoroacetic acid (1.0 mL) was stirred at ambient temperature for 1 h. The volatiles were removed in-vacuo and the resulting residue was diluted with methanol and purified by prep-LCMS (XBridge™ C18 column, eluting with a gradient of MeCN/water containing 0.05% TFA, at a flow rate of 60 mL/min) to afford two peaks, presumably two pairs of racemic diastereoisomers, that were the title compound. The two isolated diastereoisomers were isolated as a white solid. LCMS calcd. for $C_{22}H_{21}N_{4O}$ (M+H)$^+$: m/z=357.2. found: 357.1.

Example 99

1-{2-[3-(7H-Pyrrolo[2,3-d]pyrimidin-4-yl)phenyl]-1,2,3,4-tetrahydronaphthalen-2-yl}methanamine

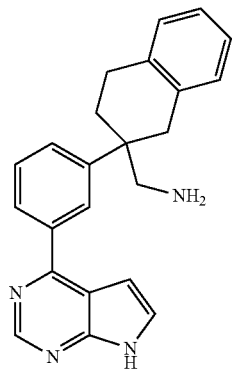 [SMILES: NCC1(c2cccc(-c3ncnc4[nH]ccc34)c2)CCc2ccccc2C1]

Step 1. 2-[2-(Hydroxymethyl)phenyl]ethanol

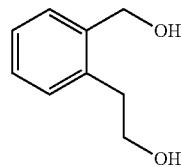 [SMILES: OCCc1ccccc1CO]

A solution of homophthalic acid (from Aldrich, 5.0 g, 28 mmol) in tetrahydrofuran (100 mL) was added dropwise to 1.0 M lithium tetrahydroaluminate in THF (91.6 mL, 91.6 mmol). After the addition was complete, the mixture was heated at reflux for 24 h. At the end of this time the mixture was cooled to 0° C. and was treated with 3.1 mL of water followed by 3.1 mL of 50% sodium hydroxide aqueous solution. The thick slurry was slowly treated with water until a fine grey precipitate had formed. The suspension was filtered and the filtrate was dried over sodium sulfate and concentrated under reduced pressure to give 3.23 g (95%) of 2-[2-(hydroxymethyl)phenyl]ethanol. LCMS cad for $C_9H_{13}O_2$(M+H)$^+$: m/z=153.1. found: 153.1.

Step 2. 1-(2-Chloroethyl)-2-(chloromethyl)benzene

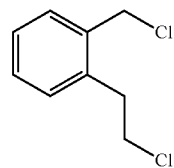

A mixture of 2-[2-(hydroxymethyl)phenyl]ethanol (3.0 g, 20. mmol) and triphenylphosphine (13.5 g, 51.5 mmol) in carbon tetrachloride (60 mL) was stirred at room temperature for 72 h. The white slurry that formed was treated with 80 mL of pentane and cooled to 0° C. so as to precipitate most of the triphenylphosphine oxide. The filtrate was concentrated under reduced pressure and the resulting oil was subjected to silica gel chromatography using hexane as the eluent. The major fraction contained 2.41 g (65%) of 1-(2-chloroethyl)-2-(chloromethyl)benzene.

Step 3. 2-(3-Bromophenyl)-1,2,3,4-tetrahydronaphthalene-2-carbonitrile

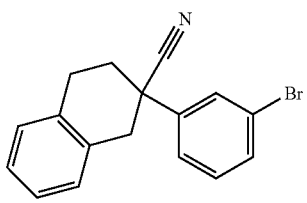 [SMILES: N#CC1(c2cccc(Br)c2)CCc2ccccc2C1]

To a solution of (3-bromophenyl)acetonitrile (308 mg, 1.56 mmol) in tetrahydrofuran (15 mL) stirring at about 0° C. was added sodium hydride (60%, 187 mg, 4.69 mmol). The mixture went from a clear solution to an orange one. The reaction was stirred for 20 min and then a solution of 1-(2-chloroethyl)-2-(chloromethyl)benzene (300 mg, 1.59 mmol) in tetrahydrofuran (10 mL) was added. The reaction was removed from the ice bath and heated to 70° C. for 2 h and then quenched with NH$_4$Cl aqueous solution. The mixture was diluted with EtOAc. The organic was washed with water and brine, dried (Na$_2$SO$_4$), filtered and concentrated. Purification on silica gel column gave 450 mg (92% yield) of the desired product when eluted with 0-30% EtOAc/hexanes over 15 min. LCMS cacd for $C_{17}H_{15}BrN$ (M+H): m/z=312.0. found: 312.1.

Step 4. tert-Butyl {[2-(3-bromophenyl)-1,2,3,4-tetrahydronaphthalen-2-yl]methyl}carbamate

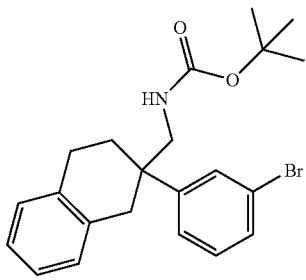 [SMILES: CC(C)(C)OC(=O)NCC1(c2cccc(Br)c2)CCc2ccccc2C1]

To a solution of 2-(3-bromophenyl)-1,2,3,4-tetrahydronaphthalene-2-carbonitrile (500 mg, 1.6 mmol) in methanol (20 mL) was added sequentially nickel chloride hexahydrate (76.5 mg, 0.319 mmol) and di-tert-butyldicarbonate (1.045 g, 4.8 mmol), followed by sodium tetrahydroborate (604 mg, 16 mmol) portion-wise over 15 min at 0° C. The mixture was stirred at room temperature overnight. The resulting solution was diluted with EtOAc, washed with aqueous sat. NaHCO$_3$ solution, evaporated and purified on FCC (0-100% EtOAc/hexanes) to give 570 mg (85% yield) of the desired product. LCMS calculated for $C_{22}H_{27}BrNO_2$ (M+H): 416.1. found: 416.3.

Step 5. tert-Butyl ({2-[3-(4,4,5,5-tetramethyl-1,3,2-dioxaborolan-2-yl)phenyl]-1,2,3,4-tetrahydronaphthalen-2-yl}methyl)carbamate

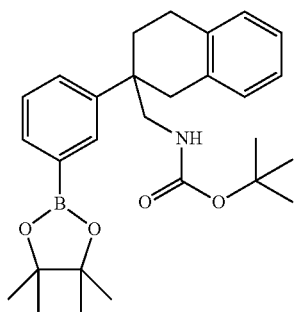 [SMILES: CC(C)(C)OC(=O)NCC1(c2cccc(B3OC(C)(C)C(C)(C)O3)c2)CCc2ccccc2C1]

A mixture of tert-butyl {[2-(3-bromophenyl)-1,2,3,4-tetrahydronaphthalen-2-yl]methyl}carbamate (100.0 mg, 0.24 mmol), 4,4,5,5,4',4',5',5'-octamethyl-[2,2']bi[[1,3,2]dioxaborolanyl] (91.49 mg, 0.36 mmol), DPPF (20. mg, 0.024 mmol) and potassium acetate (47.1 mg, 0.48 mmol) in 1,4-dioxane (20 mL) was stirred at 80° C. for 2 h. The reaction mixture was directly used in the next reaction without further purifications.

Step 6. tert-Butyl ({2-[3-(7-{[2-(trimethylsilyl)ethoxy]methyl}-7H-pyrrolo[2,3-d]pyrimidin-4-yl)phenyl]-1,2,3,4-tetrahydronaphthalen-2-yl}methyl)carbamate

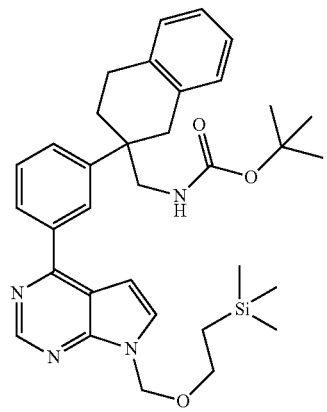 [SMILES: CC(C)(C)OC(=O)NCC1(c2cccc(-c3ncnc4c3ccn4COCC[Si](C)(C)C)c2)CCc2ccccc2C1]

A mixture of tert-butyl ({2-[3-(4,4,5,5-tetramethyl-1,3,2-dioxaborolan-2-yl)phenyl]-1,2,3,4-tetrahydronaphthalen-2-yl}methyl)carbamate (50 mg, 0.11 mmol), 4-chloro-7-{[2-(trimethylsilyl)ethoxy]methyl}-7H-pyrrolo[2,3-d]pyrimidine (31 mg, 0.11 mmol), tetrakis(triphenylphosphine)palladium(0) (13 mg, 0.011 mmol) and potassium carbonate (30 mg, 0.22 mmol) in water (1.0 mL) and 1,4-dioxane (10 mL) was stirred at 140° C. in a microwave oven for 40 min. The mixture was cooled and purified on prep-LCMS (XBridge™ C18 column, eluting with a gradient of MeCN/water containing 0.05% TFA, at a flow rate of 60 mL/min) to afford 15 mg (24% yield) of the desired product. LC-MS calculated for $C_{34}H_{45}N_4O_3Si$ (M+H): 585.3. found: 585.1.

Step 7. 1-{2-[3-(H-pyrrolo[2,3-d]pyrimidin-4-yl)phenyl]-1,2,3,4-tetrahydronaphthalen-2-yl}methanamine A mixture of tert-butyl ({2-[3-(7-{[2-(trimethylsilyl)ethoxy]methyl}-7H-pyrrolo[2,3-d]pyrimidin-4-yl)phenyl]-1,2,3,4-tetrahydronaphthalen-2-yl}methyl)carbamate (15 mg, 0.026 mmol) in trifluoroacetic acid (1.0 mL) was stirred at room temperature for 30 min. The solvent was evaporated and the residue was re-dissolved in methanol (1.0 mL). To the resulting solution was added ethylenediamine (0.1 mL). The reaction was stirred at room temperature overnight. The mixture was cooled and purified on prep-LCMS (XBridge™ C18 column, eluting with a gradient of MeCN/water containing 0.05% TFA, at a flow rate of 60 mL/min) to afford 5 mg (50% yield) of the desired product as TFA salt. LCMS calculated for $C_{23}H_{23}N_4$ (M+H): 355.2. found: 355.3.

Example 100

1-[2-(Aminomethyl)-2,3-dihydro-1H-inden-2-yl]-5-(7H-pyrrolo[2,3-d]pyrimidin-4-yl)pyridin-2(1H)-one

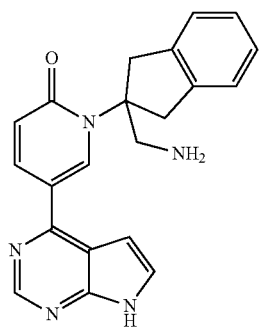 [SMILES: NCC1(n2cc(-c3ncnc4[nH]ccc34)ccc2=O)Cc2ccccc2C1]

Step 1.
(5-Bromo-2-oxopyridin-1(2H)-yl)acetonitrile

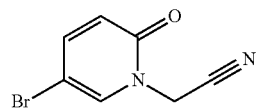 [SMILES: N#CCn1cc(Br)ccc1=O]

A mixture of 5-bromopyridin-2-ol (from Aldrich, 3.00 g, 17.2 mmol) and chloroacetonitrile (1.20 mL, 19.0 mmol) and potassium carbonate (4.76 g, 34.5 mmol) in N,N-dimethylformamide (30 mL) was stirred at room temperature overnight. 100 mL of EtOAc and 100 mL of water were added. The organic phase was washed three times with water, dried over $Na_2SO_4$, filtered and evaporated under reduced pressure. Purification on silica gel column afforded 2.2 g (60% yield) of the desired product. LCMS cacd for $C_7H_6BrN_2O$ $(M+H)^+$: m/z=213.0. found: 213.1.

Step 2. 2-(5-Bromo-2-oxopyridin-1(2H)-yl)indane-2-carbonitrile

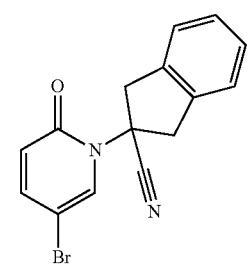 [SMILES: N#CC1(n2cc(Br)ccc2=O)Cc2ccccc2C1]

To a solution of (5-bromo-2-oxopyridin-1(2H)-yl)acetonitrile (500 mg, 2.35 mmol) in tetrahydrofuran (150 mL) stirring at about 0° C. was added sodium hydride (60%, 282 mg, 7.1 mmol). The mixture went from a clear solution to an orange one. The reaction was stirred for 20 min and then a solution of benzene, 1,2-bis(bromomethyl)-(619.5 mg, 2.3 mmol) in tetrahydrofuran (20 mL) was added. The reaction was removed from the ice bath and heated to 100° C. overnight and then quenched with sat. $NH_4Cl$ aqueous solution. The solvent was evaporated and the resulting mixture was diluted with EtOAc. The organic was washed with water and brine, dried ($Na_2SO_4$), filtered and concentrated. Purification on silica gel column afforded 71 mg (10% yield) of the desired product when eluted with 0-30% EtOAc/hexanes over 15 min. LCMS cacd for $C_{15}H_{12}BrN_2O$ $(M+H)^+$: 315.0. found: 315.1.

Step 3. 2-[2-Oxo-5-(4,4,5,5-tetramethyl-1,3,2-dioxaborolan-2-yl)pyridin-1(2H)-yl]indane-2-carbonitrile

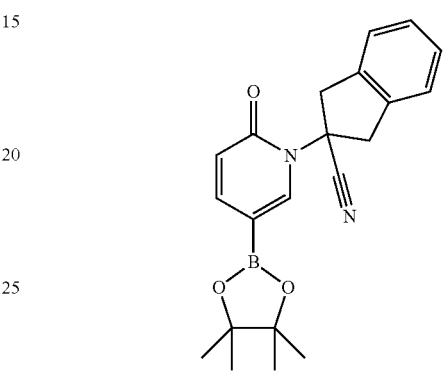

A mixture of 2-(5-bromo-2-oxopyridin-1(2H)-yl)indane-2-carbonitrile (230 mg, 0.73 mmol), 4,4,5,5,4',4',5',5'-octamethyl-[2,2']bi[[1,3,2]dioxaborolanyl] (278 mg, 1.1 mmol), DPPF (119 mg, 0.15 mmol) and potassium acetate (143 mg, 1.46 mmol) in 1,4-dioxane (20 mL) was stirred at 80° C. for 2 h. The reaction mixture was directly used in the next reaction without further purifications.

Step 4. 2-[2-Oxo-5-(7-{[2-(trimethylsilyl)ethoxy]methyl}-1H-pyrrolo[2,3-d]pyrimidin-4-yl)pyridin-1(2H)-yl]indane-2-carbonitrile

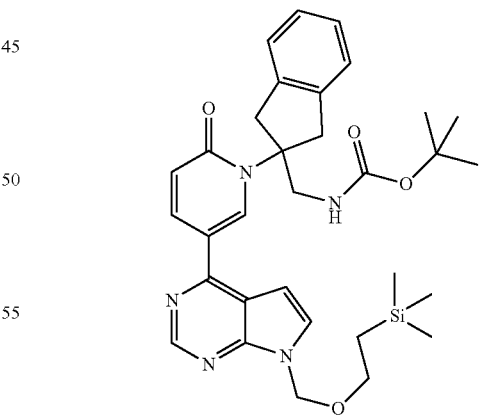

A mixture of 2-[2-oxo-5-(4,4,5,5-tetramethyl-1,3,2-dioxaborolan-2-yl)pyridin-1(2H)-yl]indane-2-carbonitrile (26 mg, 0.073 mmol), 4-chloro-7-{[2-(trimethylsilyl)ethoxy]methyl}-7H-pyrrolo[2,3-d]pyrimidine (21 mg, 0.073 mmol), tetrakis(triphenylphosphine)palladium(0) (17 mg, 0.015 mmol) and potassium carbonate (20 mg, 0.15 mmol) in water (1.0 mL) and 1,4-dioxane (10 mL) was stirred at 140° C. for 40 min in a microwave oven. The mixture was cooled and purified on prep-LCMS (XBridge™ C18 column, eluting with a gradient of MeCN/water containing 0.05% TFA, at a flow rate of 60 mL/min) to afford 20 mg (57% yield) of the desired product. LCMS cacd for $C_{27}H_{30}N_5O_2Si$ (M+H)$^+$: 484.2. found: 484.1.

Step 5. tert-Butyl ({2-[2-oxo-5-(7-{[2-(trimethylsilyl)ethoxy]methyl}-1H-pyrrolo[2,3-d]pyrimidin-4-yl)pyridin-1 (2H)-yl]-2,3-dihydro-1H-inden-2-yl}methyl) carbamate

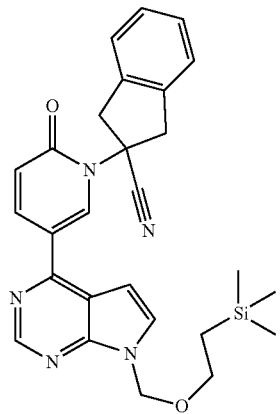 [SMILES: C[Si](C)(C)CCOCn1ccc2c(-c3ccc(=O)n(C4(C#N)Cc5ccccc5C4)c3)ncnc21]

At 0° C. to a solution of 2-[2-oxo-5-(7-{[2-(trimethylsilyl)ethoxy]methyl}-7H-pyrrolo[2,3-d]pyrimidin-4-yl)pyridin-1 (2H)-yl]indane-2-carbonitrile (20 mg, 0.041 mmol) in methanol (10 mL) was added sequentially nickel chloride hexahydrate (2.0 mg, 0.0083 mmol) and di-tert-butyldicarbonate (27 mg, 0.12 mmol), followed by sodium tetrahydroborate (16 mg, 0.41 mmol) portion-wise over 15 min. The mixture was stirred at rt overnight. The mixture was purified on prep-LCMS (XBridge™ C18 column, eluting with a gradient of MeCN/water containing 0.05% TFA, at a flow rate of 60 mL/min) to afford 5 mg (20% yield) of the desired product. LCMS cacd for $C_{32}H_{42}N_5O_4Si$ (M+H)$^+$: 588.3. found: 588.1.

Step 6. 1-[2-(Aminomethyl)-2,3-dihydro-1H-inden-2-yl]-5-(7H-pyrrolo[2,3-d]pyrimidin-4-yl)pyridin-2 (1H)-one A mixture of tert-butyl ({2-[2-oxo-5-(7-{[2-(trimethylsilyl)ethoxy]methyl}-7H-pyrrolo[2,3-d]pyrimidin-4-yl)pyridin-1 (2H)-yl]-2,3-dihydro-1H-inden-2-yl}methyl)carbamate (5.0 mg, 0.0085 mmol) in trifluoroacetic acid (1.0 mL) was stirred at room temperature for 30 min. The solvent was evaporated and the resulting residue was dissolved in methanol (1.0 mL). To the resulting solution was added ethylenediamine (0.1 mL). The reaction mixture was stirred at room temperature overnight. The mixture was purified on prep-LCMS (XBridge™ C18 column, eluting with a gradient of MeCN/water containing 0.05% TFA, at a flow rate of 60 mL/min) to afford the desired product. LCMS cacd for $C_{21}H_{20}N_5O$ (M+H)$^+$: 358.2. found: 358.1.

Example A

Evaluation of Biological Activity of Exemplified Compounds

Axl Autophosphorylation Assay

Autophosphorylation of Axl was carried out by incubating the recombinant Axl protein (Life Technologies, PV4275) in buffer containing 50 mM Tris, pH7.5, 0.2 mg/ml Axl, 5 mM ATP, 20 mM MgCl2 and 2 mM DTT at room temperature for 1 hour.

Axl Autophosphorylation Assay

Autophosphorylation of Axl was carried out by incubating the recombinant Axl protein (Life Technologies, PV4275) in buffer containing 50 mM Tris, pH7.5, 0.2 mg/ml Axl, 5 mM ATP, 20 mM MgCl2 and 2 mM DTT at room temperature for 1 hour.

TAM Kinase Assay

The kinase assay buffer contained 50 mM HEPES, pH7.5, 10 mM MgCl2, 1 mM EGTA, 0.01% NP-40 and 2 mM DTT. 0.1 ul test compounds dissolved in DMSO were transferred from compound plates to white 384-well assay plates (Greiner LUMITRAC plates). The final concentration of DMSO was 1.25%. Enzyme solutions of 5.1 nM phosphor-Axl (see Axl autophosphorylation assay above), or 0.0625 nM c-Mer (Carna Biosciences, 08-108), or 0.366 nM Tyro3 (Life Technologies, PR7480A) were prepared in assay buffer. A 1 mM stock solution of peptide substrate Biotin-EQEDEPEGDYFEWLE-amide SEQ ID NO: 1 (Quality Controlled Biochemicals, MA) dissolved in DMSO was diluted to 1 uM in assay buffer containing 2000 uM ATP. 4 ul enzyme solution (or assay buffer for the enzyme blank) was added to the appropriate wells in each plate, and then 4 ul/well substrate solution was added to initiate the reaction. The plate was protected from light and incubated at room temperature for 60 min. The reaction was stopped by adding 4 ul detection solution containing 50 mM Tris-HCl, pH7.8, 150 mM NaCl, 0.05% BSA, 45 mM EDTA, 180 nM SA-APC (Perkin Elmer, CR130-100) and 3 nM Eu—W1024 anti-phosphotyrosine PY20 (Perkin Elmer, AD0067). The plate was incubated for 1 h at room temperature, and HTRF (homogenous time resolved fluorescence) signal was measured on a PHERAstar FS plate reader (BMG labtech). Percentage of inhibition was calculated for each concentration and IC50 value was generated from curve fitting with GraphPad Prism software.

The compounds of the invention were found to be inhibitors of TAM according to the TAM Enzymatic Assay. Compounds of Formula (I) and all the compounds as described herein have been tested and exhibit an $IC_{50}$ of less than 1 μM.

The compounds of the invention were found to be inhibitors of one or more of AXL, MER, and TYRO3 according to the assay of Example A. $IC_{50}$ data is provided below in Table 1. The symbol "+" indicates an $IC_{50} \leq 500$ nM, "++" indicates an $IC_{50}$ more than 500 nM but ≤1 μM; "+++" indicates an $IC_{50}$ more than 1 μM, but ≤3 μM; "++++" indicates an $IC_{50}$ of more than 3 μM.

TABLE 1

| Example | c-Mer IC50 (nM) | Phospho-Axl IC50 (nM) | Tyro3 IC50 (nM) |
|---|---|---|---|
| 1 | + | + | ++++ |
| 2 | +++ | +++ | ++++ |
| 3 | + | + | +++ |

TABLE 1-continued

| Example | c-Mer IC50 (nM) | Phospho-Axl IC50 (nM) | Tyro3 IC50 (nM) |
|---|---|---|---|
| 4 | ++ | ++ | ++++ |
| 5 | + | + | +++ |
| 6 | + | + | ++++ |
| 7 | + | + | ++++ |
| 8 | n/t | +++ | ++++ |
| 10 | n/t | +++ | ++++ |
| 11 | + | + | +++ |
| 12 | + | + | ++++ |
| 16 | + | + | ++++ |
| 17 | + | + | ++++ |
| 18 | + | + | ++++ |
| 19 | ++++ | ++++ | ++++ |
| 20 | ++++ | ++++ | ++++ |
| 21 | +++ | ++ | ++++ |
| 22 | + | + | ++++ |
| 23 | + | + | ++++ |
| 24 | + | + | ++++ |
| 25 | ++++ | +++ | ++++ |
| 26 | ++ | + | ++++ |
| 27 | ++ | + | ++++ |
| 28 | ++++ | +++ | ++++ |
| 29 | +++ | +++ | ++++ |
| 30 | ++ | ++ | ++++ |
| 31 | ++++ | ++++ | ++++ |
| 32 | ++++ | ++++ | ++++ |
| 33 | ++++ | ++++ | ++++ |
| 34 | +++ | +++ | ++++ |
| 35 | ++++ | +++ | ++++ |
| 36 | +++ | ++ | ++++ |
| 37 | ++ | + | ++++ |
| 38 | +++ | ++ | ++++ |
| 39 | +++ | + | ++++ |
| 40 | ++++ | +++ | ++++ |
| 41 | ++++ | +++ | ++++ |
| 42 | ++ | +++ | +++ |
| 43 | +++ | ++++ | ++++ |
| 44 | ++++ | +++ | +++ |
| 45 | +++ | +++ | +++ |
| 46 | ++++ | n/t | n/t |
| 47 | ++++ | +++ | +++ |
| 48 | ++++ | ++++ | +++ |
| 49 | + | + | +++ |
| 50 | +++ | ++ | ++++ |
| 51 | +++ | ++ | +++ |
| 52 | +++ | ++++ | ++++ |
| 53 | +++ | ++++ | ++++ |
| 54 | ++ | +++ | ++++ |
| 55 | +++ | ++++ | ++++ |
| 56 | + | + | +++ |
| 57 | +++ | n/t | n/t |
| 58 | ++++ | +++ | + |
| 59 | ++++ | n/t | n/t |
| 60 | ++++ | n/t | n/t |
| 61 | ++ | +++ | ++++ |
| 62 | +++ | n/t | n/t |
| 63 | +++ | n/t | n/t |
| 64 | +++ | n/t | n/t |
| 65 | +++ | +++ | +++ |
| 66 | +++ | +++ | ++++ |
| 67 | +++ | +++ | ++++ |
| 68 | +++ | ++ | ++ |
| 69 | +++ | +++ | ++ |
| 70 | ++++ | +++ | ++ |
| 71 | ++++ | ++ | +++ |
| 72 | +++ | + | + |
| 73 | +++ | +++ | ++++ |
| 74 | +++ | +++ | ++ |
| 75 | +++ | + | ++++ |
| 76 | + | + | ++ |
| 77 | ++++ | +++ | + |
| 78 | ++++ | +++ | +++ |
| 80 | + | + | + |
| 86 | + | + | +++ |
| 87 | + | + | +++ |
| 88 | + | + | ++++ |
| 89 | + | + | + |
| 90 | + | + | ++ |
| 91 | + | + | +++ |
| 93 | +++ | +++ | ++++ |
| 94 | + | + | + |
| 95 | + | + | + |
| 96 | + | + | + |
| 97 | + | + | +++ |
| 98 (peak 1) | +++ | ++ | ++ |
| 98 (peak 2) | + | + | ++ |
| 99 | + | + | nt |
| 100 | + | + | nt |

Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A compound having Formula IVa, IVb, IVc, IVd, or IVe:

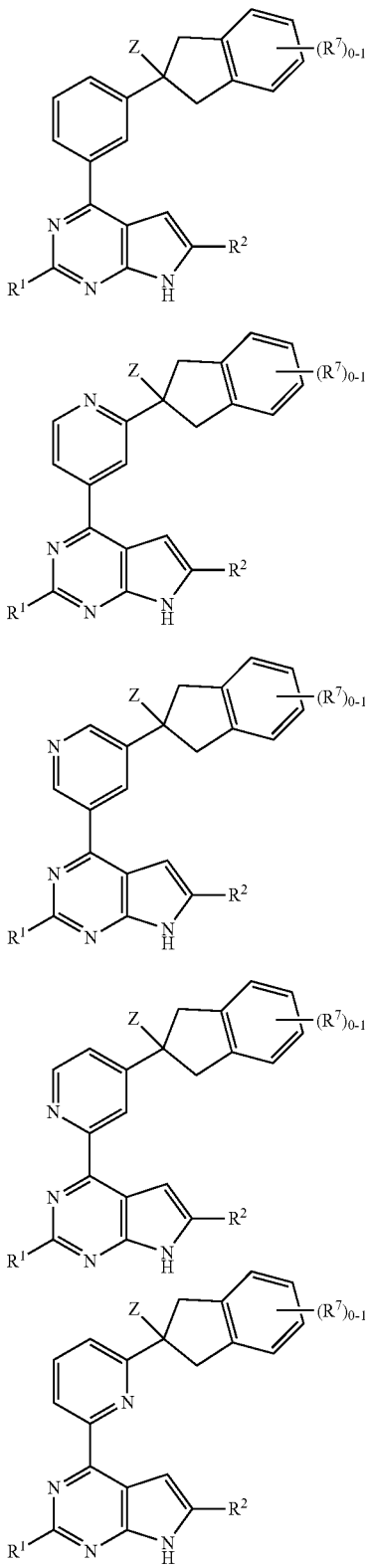

or a pharmaceutically acceptable salt thereof, wherein $R^1$ is H, halo, CN, $C_{1-6}$ alkyl, $C_{2-6}$ alkenyl, $C_{2-6}$ alkynyl, $C_{1-4}$ haloalkyl, $OR^{a1}$, $SR^{a1}C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}OR^{d1}$, $NR^{c1}C(O)R^{b1}$, $NR^{c1}C(O)OR^{b1}$, $NR^{c1}C(O)NR^{c1}R^{d1}NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, $S(O)_2NR^{c1}R^{d1}$, $C_{3-7}$ cycloalkyl, phenyl, 5-6 membered heteroaryl, 4-6 membered hererocycloalkyl, $C_{3-7}$ cycloalkyl-$C_{1-3}$ alkylene, 5-6 membered heteroaryl-$C_{1-3}$ alkylene, or 4-6 membered heterocycloalkyl-$C_{1-3}$ alkylene; wherein said $C_{1-6}$ alkyl, $C_{2-6}$ alkenyl, $C_{2-6}$ alkynyl, $C_{1-4}$ haloalkyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{l-3}$ alkylene, 5-6 membered heteroaryl-$C_{1-3}$ alkylene, and 4-6 membered heterocycloalkyl-$C_{1-3}$ alkylene are each optionally substituted with 1, 2, 3, or 4 independently selected $R^{11}$ groups;

$R^2$ is H, halo, OH, CN, $C_{1-4}$ alkyl, $C_{1-4}$ haloalkyl, $C_{1-6}$ alkoxy, $C_{1-4}$ haloalkoxy, amino, $C_{1-6}$ alkylamine, or di($C_{1-6}$ alkyl)amino;

each $R^7$ is independently selected from halo, $C_{1-6}$ alkyl, $C_{2-6}$ alkenyl, $C_{2-6}$ alkynyl, $C_{1-4}$ haloalkyl, CN, $NO_2$, Cy, —$C_{1-4}$ alkylene-Cy, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $C(=NR^e)R^b$, $C(=NR^e)NR^cR^d$, $NR^cC(=NR^e)NR^cR^d$, $NR^cS(O)_2R^b$, $NR^cS(O)_2R^b$, $NR^cS(O)_2NR^cR^d$, $S(O)R^b$, $S(O)NR^cR^d$ $S(O)_2R^b$ and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^8$ groups;

each $R^8$ is independently selected from halo, CN, $NO_2$, $C_{1-6}$ alkyl, $C_{2-6}$ alkenyl, $C_{2-6}$ alkynyl, $C_{1-4}$ haloalkyl, $Cy^2$, —$C_{1-4}$alkylene-$Cy^2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{a2}$, $NR^{c2}C(O)NR^{c2}R^{d2}$, $C(=NR^e)R^{b2}$, $C(=NR^e)NR^{c2}R^{d2}$, $NR^{c2}C(=NR^e)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2S(O)_2NR^{c2}R^{d2}$; wherein said $C_{1-6}$ alkyl, $C_{2-6}$ alkenyl, $C_{2-6}$ alkynyl, and $C_{1-4}$ haloalkyl are each optionally substituted with 1 ,2, 3 , or 4 independently selected $R^g$ groups;

Z is $C_{1-6}$ alkyl, $C_{1-6}$ haloalkyl, or —$C_{1-6}$ alkylene-$Z^1$;

$Z^1$ is CN, $Cy^3$, $OR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, or $S(O)_2NR^{c3}R^{d3}$;

each $R^{11}$ is independently selected from OH, $NO_2$, CN, halo, $C_{1-6}$ alkyl, $C_{2-6}$ alkenyl, $C_{2-6}$ alkynyl, $C_{1-4}$ haloalkyl,$C_{1-6}$ alkoxy, $C_{1-6}$ haloalkoxy, cyano-$C_{1-3}$ alkykl, HO—$C_{1-3}$ alkyl, amino, $C_{1-6}$alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkoxycarbonyl, $C_{1-6}$ alkylcarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, di($C_{1-6}$ alkyl)aminocarbonylamino, $C_{3-7}$ cycloalky, phenyl, 5-6 membred heteroaryl, 4-6 membered heterocycloalkyl, $C_{3-7}$cycloalkyl-$C_{1-3}$alkylene, phenyl-$C_{1-3}$ alkylene, 5-6 membered heteroaryl-$C_{1-3}$ alkylene, and 4-6 membered heterocycloalkyl-$C_{1-3}$ alkylene; wherein said $C_{1-6}$ alkyl, $C_{3-7}$ cycloalkyl, phenyl, 5-6 membered heteroaryl, 4-6membered heterocycloalkyl, $C_{3-7}$cycloalkyl-$C_{1-3}$alkylene, phenyl-$C_{1-3}$alkylene, 5-6 membered heteroaryl-$C_{1-3}$ alkylene, and 4-6 membered heterocycloalkykl-$C_{1-3}$ alkylene are each optionally substituted with 1, 2, 3 , or 4 groups independently selected from OH, CN, halo, $C_{1-4}$ alkyl, $C_{1-3}$ haloalkyl, $C_{1-4}$alkoxy, $C_{1-3}$haloalkoxy, cyano-$C_{1-3}$alkyl, HO—$C_{1-3}$alkyl, amino, $C_{1-4}$ alkylamino, di($C_{1-4}$ alkyl)amino, $C_{1-4}$ alkysulfinyl, $C_{1-4}$ alkoxycarbonyl, $C_{1-4}$ alkycarbonylamino, $C_{1-4}$ alkyl)carbamyl, carboxy, $C_{1-4}$ alkylcarbonyl, $C_{1-4}$ alkoxycarbonyl, $C_{1-4}$ alkylcarbonylamino, $C_{1-4}$ alkylsulfonylamino, aminosulfonyl, $C_{1-4}$alkylaminosulfonyl, and di($C_{1-4}$alkyl)aminosulfonyl;

each Cy is independently selected from 3-12 membered cycloalkyl, 6-10 membered aryl, 5-10 membered heteroaryl, and 4-12 membered heterocycloalkyl, each of which is optionally substituted by 1, 2, 3 , or 4 independently selected $R^8$ groups;

each $Cy^1$ is independently selected from 3-7 membered cycloalkyl, phenyl, 5-6 membered heteroaryl, and 4-6 membered heterocycloalkyl, each of which is optionally substituted by 1, 2, 3, or 4 independently selected $R^{11}$ groups;

each $Cy^2$ is independently selected from 3-7 membered cycloalkyl, phenyl, 5-6 membered heteroaryl, and 4-6 membered heterocycloalkyl, each of which is optionally substituted by 1, 2, 3, or 4 independently selected $R^g$ groups;

each $Cy^3$ is independently selected from 3-7 membered cycloalkyl, phenyl, 5-6 membered heteroaryl, and 4 -6 membered heterocycloalkyl, each of which is optionally substituted by 1, 2, 3 , or 4 independently selected from halo, OH, CN, $C_{1-3}$ alkyl, $C_{1-3}$ haloalkyl, $C_{1-3}$ alkkoxy, $C_{1-3}$ haloalkoxy, amino, $C_{1-3}$ alkylamine, and di($C_{1-3}$alkyl)amino;

each $R^a$, $R^c$, and $R^d$ is independently selected from H, $C_{1-6}$ alkyl, $C_{2-6}$ alkenyl, $C_{2-6}$ alkynyl, $C_{1-4}$ haloalkyl, Cy, and —$C_{1-4}$ alkylene-Cy; wherein said $C_{1-6}$ alkyl, $C_{2-6}$ alkenyl, $C_{2-6}$ alkynyl, and $C_{1-4}$ haloalkyl are each optionally substituted with 1, 2, 3 , or 4 independently selected $R^8$ groups;

each $R^b$ is independently selected from $C_{1-6}$ alkyl, $C_{2-6}$ alkenyl, $C_{2-6}$ alkynyl, $C_{1-4}$ haloalkyl, Cy, and —$C_{1-4}$ alkylene-Cy; wherein said $C_{1-6}$ alkyl, $C_{2-6}$ aldenyl, $C_{2-6}$ alkynyl, and $C_{1-4}$ haloalkyl are each optionally substituted with 1, 2, 3 , or 4 independently selected $R^8$ groups; alternatively, any $R^c$and $R^d$ attache to the same N atom, together with the N atom to which they are attached, from a 4-6 membered heterocycloalkyl group or a 5-6 membered heteroaryl group, each optionally substituted with 1, 2, 3 independently selected $R^8$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl) carbamyl,aminosulfonyl, $C_{1-6}$ alkylaminosulfonyl, and di($C_{1-6}$ alkyl)aminsosulfonyl;

$R^{a1}$,$R^{c1}$,and $R^{d1}$ are each independently selected from H, $C_{1-6}$ alkyl, $C_{2-6}$ alkenyl, $C_{2-6}$ alkynyl, and $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4independently selected $R^{11}$ groups;

$R^{b1}$ is independently selected from $C_{1-6}$ alkyl, $C_{2-6}$ alkenyl, $C_{2-6}$ alkynyl, $C_{1-4}$ haloalkyl, $Cy^1$, and —$C_{1-4}$ alkylene-$Cy^1$; wherein said $C_{1-6}$ alkyl, $C_{2-6}$ alkenyl, $C_{2-6}$alkynyl, and $C_{1-4}$haloalkyl are each optionally substituted with 1, 2, 3, or 4 independently selected $R^{11}$ groups; or alternatively, any $R^{c1}$ and $R^{d1}$ attached to the same N atom, together with the N atom to which they are attached, from a 4-, 5-, 6-, 7-membered heterocycloalkyl group optionally substitusted with 1, 2 or 3 independently selected $R^{11}$ groups;

each $R^{a2}$, $R^{c2}$, and $R^{d2}$ are independently selected from H, $C_{1-6}$ alkyl, $C_{2-6}$ alkenyl, $C_{2-6}$ alkynyl, $C_{1-4}$ haloalkyl, $Cy^2$, and —$C_{1-4}$ alkylene-$Cy^2$; wherein said $C_{1-6}$ alkyl, $C_{2-6}$ alkynyl, $C_{2-6}$ alkynyl, and $C_{1-4}$ haloalkyl are each optionally substituted with 1, 2, 3, or 4independently selected $R^g$ groups;

each $R^{b2}$ is independently selected from $C_{1-6}$ alkyl, $C_{2-6}$ alkenyl, $C_{2-6}$ alkynyl, $C_{1-4}$ haloalkyl, $Cy^2$,and —$C_{1-4}$ alkylene-$Cy^2$; wherein said $C_{1-6}$ alkyl, $C_{2-6}$ alkenyl, $C_{2-6}$ alkynyl, and $C_{1-4}$ haloalkyl are each optionally substituted with 1, 2, 3, or 4independently selected $R^g$groups; or alternatively, and $R^{c2}$ and $R^{d2}$ attached to the same N atom, together with the N atom to which they are attached, from a 4-, 5-, 6- or 7-membered heterocycloalkyl group optionally substituted with 1, 2or 3independently selected $R^g$ groups;

$R^{a3}$, $R^{c3}$, and $R^{d3}$ are each independently selected from H, $C_{1-6}$alkyl, $C_{2-6}$ alkenyl, $C_{2-6}$ alkynyl, $C_{1-4}$ haloalkyl, $Cy^3$, and —$C_{1-4}$ alkylene-$Cy^3$;

$R^{b3}$ is selected from $C_{1-6}$ alkyl, $C_{2-6}$ alkenyl, $C_{2-6}$ alkynyl, $C_{1-4}$ haloalyly, $Cy^3$, and —$C_{1-4}$ alkylene-$Cy^3$; and each $R^g$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cycano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkysulfinyl, $C_{1-6}$ alkysulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein $R^1$ is H or $NR^{c1}R^{d1}$.

3. The compound of claim 1, or a pharmaceutically acceptable salt thereof, wherein $R^{a1}$, $R^{c1}$, and $R^{d1}$ are each independently selected from H, $C_{1-6}$ alkyl, and $Cy^1$; and $R^{b1}$ is $C_{1-6}$ alkyl or $Cy^1$.

4. The compound of claim 1, or a pharmaceutically acceptable salt thereof, wherein each $Cy^1$ is independently selected from 3-7 membered cycloalkyl, phenyl, 5-6 membered heteroaryl, and 4-6 membered heterocycloalkyl, each of which is optionally substituted by 1 or 2 independently selected $R^{11}$ groups.

5. The compound of claim 1, or a pharmaceutically acceptable salt thereof, wherein each $R^{11}$ is independently selected from OH, CN, halo, $C_{1-6}$ alkyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, $C_{1-6}$ alkylsulfonyl, carbamyl, $C_{1-6}$ alkylcarbamyl, di($C_{1-6}$ alkyl)carbamyl, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, $C_{3-7}$ cycloalkyl, phenyl, 5-6 membered heteroaryl, 4-6 membered heterocycloalkyl, $C_{3-7}$ cycloalkyl-$C_{1-3}$ alkylene, phenyl-$C_{1-3}$ alkylene, 5-6 membered heteroaryl-$C_{1-3}$ alkylene, and 4-6 membered heterocycloalkyl-$C_{1-3}$ alkylene.

6. The compound of claim 1, or a pharmaceutically acceptable salt thereof, wherein $R^1$ is H, methylamino, ethylamino, isopropylamino, n-butylamino, cyclobutylamino, cyclopentylamino, cyclohexylamino, 1-ethyl-1H-imidazol-4-yl-amino, 1-methyl -1H-pyrazol-4-yl-amino, and 4-(morpholinylmethyl)phenylamino.

7. The compound of claim 1, or a pharmaceutically acceptable salt thereof, wherein $R^2$ is H or $C_{1-4}$ alkyl.

8. The compound of claim 1, or a pharmaceutically acceptable salt thereof, wherein each $R^7$ is independently selected from $C_{1-6}$ alkyl, CN, OH, $NR^cR^d$, —$CH_2$—$R^8$, Cy, and —$CH_2$—Cy.

9. The compound of claim 1, or a pharmaceutically acceptable salt thereof, wherein each $R^a$, $R^c$ and $R^d$ is independently selected from H, $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups; and each $R^b$ is independently selected from $C_{1-6}$ alkyl, $C_{1-4}$ haloalkyl, and Cy; wherein said $C_{1-6}$ alkyl and $C_{1-4}$ haloalkyl are each optionally substituted by 1, 2, 3, or 4 independently selected $R^8$ groups.

10. The compound of claim 1, or a pharmaceutically acceptable salt thereof, wherein each Cy is independently selected from azetidinyl, pyrrolidinyl, piperidinyl, morpholinyl, phenyl, imidazolyl, pyridinyl, imidazo[1,2-a]pyridinyl, and imidazo[4,5-b]pyridinyl; each of which is optionally substituted by 1, 2, 3, or 4 independently selected $R^8$ groups.

11. The compound of claim 1, or a pharmaceutically acceptable salt thereof, wherein each $R^8$ is independently selected from halo, CN, $C_{1-6}$ alkyl, $Cy^2$, $OR^{a2}$, $C(O)NR^{c2}R^{d2}$, and $NR^{c2}R^{d2}$; wherein said $C_{1-6}$ alkyl is optionally substituted with 1, 2, 3, or 4 independently selected $R^g$ groups.

12. The compound of claim 1, or a pharmaceutically acceptable salt thereof, wherein each $R^{a2}$, $R^{c2}$ and $R^{d2}$ is independently selected from H, $C_{1-6}$ alkyl, and $C_{1-4}$ haloalkyl; wherein said $C_{1-6}$ alkyl and $C_{1-4}$ haloalkyl are each optionally substituted with 1 or 2 independently selected $R^g$ groups; and each $R^{b2}$ is independently selected from $C_{1-6}$ alkyl and $C_{1-4}$ haloalkyl; wherein said $C_{1-6}$ alkyl and $C_{1-4}$ haloalkyl are each optionally substituted with 1 or 2 independently selected $R^g$ groups.

13. The compound of claim 1, or a pharmaceutically acceptable salt thereof, wherein each $R^g$ is independently selected from OH, CN, halo, $C_{1-6}$ alkoxy, $C_{1-6}$ haloalkoxy, amino, $C_{1-6}$ alkylamino, and di($C_{1-6}$ alkyl)amino.

14. The compound of claim 1, or a pharmaceutically acceptable salt thereof, wherein Z is —$CH_2$—$NH_2$.

15. The compound of claim 1, or a pharmaceutically acceptable salt thereof, wherein $R^{a3}$, $R^{c3}$ and $R^{d3}$ are each independently selected from H, methyl, ethyl, isopropyl, and $Cy^3$; $R^{b3}$ is selected from methyl, ethyl, isopropyl, and $Cy^3$; and each $Cy^3$ is independently selected from cyclopropyl, cyclobutyl, cyclopentyl, morpholinyl, phenyl, pyrazolyl, furanyl, thienyl, isooxazolyl, and oxazolyl, each of which is optionally substituted by 1 or 2 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino.

16. The compound of claim 1, or a pharmaceutically acceptable salt thereof, wherein $R^1$ is H, halo, CN, $C_{1-6}$ alkyl, $C_{1-4}$ haloalkyl, $OR^{a1}$, $C(O)R^{b1}$, $C(O)NR^{c1}R^{d1}$, $OC(O)R^{b1}$, $OC(O)NR^{c1}R^{d1}$, $NR^{c1}R^{d1}$, $NR^{c1}C(O)R^{b1}$, $NR^{c1}S(O)_2R^{b1}$, $S(O)_2R^{b1}$, or $S(O)_2NR^{c1}R^{d1}$; wherein said $C_{1-6}$ alkyl and $C_{1-4}$ haloalkyl are each optionally substituted with 1, 2, 3, or 4 independently selected $R^{11}$ groups.

17. The compound of claim 1, selected from:
1-{2-[5-(7H-Pyrrolo[2,3-d]pyrimidin-4-yl)pyridin-3-yl]-2,3-dihydro-1H-inden-2-yl}methanamine;
1-{2-[6-(7H-Pyrrolo[2,3-d]pyrimidin-4-yl)pyridin-2-yl]-2,3-dihydro-1H-inden-2-yl}methanamine;
1-{2-[4-(7H-Pyrrolo[2,3-d]pyrimidin-4-yl)pyridin-2-yl]-2,3-dihydro-1H-inden-2-yl}methanamine;
1-{2-[2-(7H-Pyrrolo[2,3-d]pyrimidin-4-yl)pyridin-4-yl]-2,3-dihydro-1H-inden-2-yl}methanamine;
N-({2-[4-(7H-Pyrrolo[2,3-d]pyrimidin-4-yl)pyridin-2-yl]-2,3-dihydro-1H-inden-2-yl}methyl)acetamide;
N-({6-[3-(7H-Pyrrolo[2,3-d]pyrimidin-4-yl)phenyl]-6,7-dihydro-5H-cyclopenta[c]pyridin-6-yl}methyl)acetamide;
1-{2-[3-(7H-Pyrrolo[2,3-d]pyrimidin-4-yl)phenyl]-2,3-dihydro-1H-inden-2-yl}methanamine;
{2-[3-(7H-Pyrrolo[2,3-d]pyrimidin-4-yl)phenyl]-2,3-dihydro-1H-inden-2-yl}methanol;
N-({2-[3-(7H-Pyrrolo[2,3-d]pyrimidin-4-yl)phenyl]-2,3-dihydro-1H-inden-2-yl}methyl)acetamide;
2-Methyl-N-({2-[3-(7H-pyrrolo[2,3-d]pyrimidin-4-yl)phenyl]-2,3-dihydro-1H-inden-2-yl}methyl)propanamide;
N-({2-[3-(7H-Pyrrolo[2,3-d]pyrimidin-4-yl)phenyl]-2,3-dihydro-1H-inden-2-yl}methyl)cyclopropanecarboxamide;
4-{3-[2-(Fluoromethyl)-2,3-dihydro-1H-inden-2-yl]phenyl}-7H-pyrrolo[2,3-d]pyrimidine;
4-{3-[2-(Difluoromethyl)-2,3-dihydro-1H-inden-2-yl]phenyl}-7H-pyrrolo[2,3-d]pyrimidine;
N-({2-[3-(7H-Pyrrolo[2,3-d]pyrimidin-4-yl)phenyl]-2,3-dihydro-1H-inden-2-yl)}methyl)methanesulfonamide;
Methyl ({2-[3-(7H-pyrrolo[2,3-d]pyrimidin-4-yl)phenyl]-2,3-dihydro-1H-inden-2-yl}methyl)carbamate;
N,N-Dimethyl-1-{2-[3-(7H-pyrrolo[2,3-d]pyrimidin-4-yl)phenyl]-2,3-dihydro-1H-inden-2-yl}methanamine;
N-Methyl-1-{2-[3-(7H-pyrrolo[2,3-d]pyrimidin-4-yl)phenyl]-2,3-dihydro-1H-inden-2-yl}methanamine;
4-{3-[2-(Methoxymethyl)-2,3-dihydro-1H-inden-2-yl]phenyl}-7H-pyrrolo[2,3-d]pyrimidine;
N-({2-[3-(7H-Pyrrolo[2,3-d]pyrimidin-4-yl)phenyl]-2,3-dihydro-1H-inden-2-yl}methyl)cyclobutanecarboxamide;
N-({2-[3-(7H-Pyrrolo[2,3-d]pyrimidin-4-yl)phenyl]-2,3-dihydro-1H-inden-2-yl}methyl)cyclopentanecarboxamide;
N-((((2-3-(7H-Pyrrolo[2-3-d]pyrimidin-4-yl)phenyl)-2,3-dihydro-1H-inden-2-yl)methyl)thiophene-2-carboxamide;
1-Methyl-N-({2-[3-(7H-pyrrolo[2,3-d]pyrimidin-4-yl)phenyl]-2,3-dihydro-1H-inden-2-yl}methyl)-1H-pyrazole-3-carboxamide;
4-Methyl-N-({2-[3-(7H-pyrrolo[2,3-d]pyrimidin-4-yl)phenyl]-2,3-dihydro-1H-inden-2-yl}methyl)-1,3-oxazole-5-carboxamide;
N-({2-[3-(7H-Pyrrolo[2,3-d]pyrimidin-4-yl)phenyl]-2,3-dihydro-1H-inden-2-yl}methyl)isoxazole-5-carboxamide;
1-Methyl-N-({2-[3-(7H-pyrrolo[2,3-d]pyrimidin-4-yl)phenyl]-2,3-dihydro-1H-inden-2-yl}methyl)-1H-pyrazole-5-carboxamide;
1-Methyl-N-({2-[3-(7H-pyrrolo[2,3-d]pyrimidin-4-yl)phenyl]-2,3-dihydro-1H-inden-2-yl}methyl)-1H-pyrazole-4-carboxamide;

N-({2-[3-(7H-Pyrrolo[2,3-d]pyrimidin-4-yl)phenyl]-2,3-dihydro-1H-inden-2-yl}methyl)-2-furamide;
N-({2-[3-(7H-Pyrrolo[2,3-d]pyrimidin-4-yl)phenyl]-2,3-dihydro-1H-inden-2-yl}methyl)morpholine-4-carboxamide;
{2-[3-(7H-Pyrrolo[2,3-d]pyrimidin-4-yl)phenyl]-2,3-dihydro-1H-inden-2-yl}acetonitrile;
2-{2-[3-(7H-Pyrrolo[2,3-d]pyrimidin-4-yl)phenyl]-2,3-dihydro-1H-inden-2-yl}ethanamine;
2-Methyl-N-(2-{2-[3-(7H-pyrrolo[2,3-d]pyrimidin-4-yl)phenyl]-2,3-dihydro-1H-inden-2-yl}ethyl)propanamide;
N-(2-{2-[3-(7H-Pyrrolo[2,3-d]pyrimidin-4-yl)phenyl]-2,3-dihydro-1H-inden-2-yl}ethyl)cyclopropanecarboxamide;
N-((2-(3-(7H-Pyrrolo[2,3-d]pyrimidin-4-yl)phenyl)-2-(aminomethyl)-2,3-dihydro-1H-inden-5-yl)methyl)cyclopropanamine;
N-((2-(3-(7H-Pyrrolo[2,3-d]pyrimidin-4-yl)phenyl)-2-(aminomethyl)-2,3-dihydro-1H-inden-5-yl)methyl)cyclobutanamine;
N-((2-(3-(7H-Pyrrolo[2,3-d]pyrimidin-4-yl)phenyl)-2-(aminomethyl)-2,3-dihydro-1H-inden-5-yl)methyl)-3,3-difluorocyclobutanamine;
(2R)-1-((2-(3-(7H-Pyrrolo[2,3-d]pyrimidin-4-yl)phenyl)-2-(aminomethyl)-2,3-dihydro-1H-inden-5-yl)methyl)pyrrolidine-2-carboxamide;
(3S)-1-((2-(3-(7H-Pyrrolo[2,3-d]pyrimidin-4-yl)phenyl)-2-(aminomethyl)-2,3-dihydro-1H-inden-5-yl)methyl)pyrrolidine-3-carboxamide;
(3S)-1-((2-(3-(7H-Pyrrolo[2,3-d]pyrimidin-4-yl)phenyl)-2-(aminomethyl)-2,3-dihydro-1H-inden-5-yl)methyl)pyrrolidine-3-carbonitrile;
(2-(3-(7H-Pyrrolo[2,3-d]pyrimidin-4-yl)phenyl)-5-(azetidin-1-ylmethyl)-2,3-dihydro-1H-inden-2-yl)methanamine;
(2-(3-(7H-Pyrrolo[2,3-d]pyrimidin-4-yl)phenyl)-5-((3-fluoroazetidin-1-yl)methyl)-2,3-dihydro-1H-inden-2-yl)methanamine;
1-((2-(3-(7H-Pyrrolo[2,3-d]pyrimidin-4-yl)phenyl)-2-(aminomethyl)-2,3-dihydro-1H-inden-5-yl)methyl)azetidin-3-ol;
2-(Aminomethyl)-2-[3-(7H-pyrrolo[2,3-d]pyrimidin-4-yl)phenyl]indane-5-carbonitrile;
N-({5-Cyano-2-[3-(7H-pyrrolo[2,3-d]pyrimidin-4-yl)phenyl]-2,3-dihydro-1H-inden-2-yl}methyl)cyclopropanecarboxamide;
(3S)-1-{2-(Aminomethyl)-2-[3-(7H-pyrrolo[2,3-d]pyrimidin-4-yl)phenyl]-2,3-dihydro-1H-inden-5-yl}pyrrolidine-3-carbonitrile;
1-{2-(Aminomethyl)-2-[3-(7H-pyrrolo[2,3-d]pyrimidin-4-yl)phenyl]-2,3-dihydro-1H-inden-5-yl}-N,N-dimethylpyrrolidin-3-amine;
1-{2-(Aminomethyl)-2-[3-(7H-pyrrolo[2,3-d]pyrimidin-4-yl)phenyl]-2,3-dihydro-1H-inden-5-yl}-N-methylpyrrolidin-3-amine;
1-{2-(Aminomethyl)-2-[3-(7H-pyrrolo[2,3-d]pyrimidin-4-yl)phenyl]-2,3-dihydro-1H-inden-5-yl}pyrrolidin-3-ol;
1-(1-{2-(Aminomethyl)-2-[3-(7H-pyrrolo[2,3-d]pyrimidin-4-yl)phenyl]-2,3-dihydro-1H-inden-5-yl}pyrrolidin-3-yl)ethanol;
1-{5-(3-Fluoroazetidin-1-yl)-2-[3-(7H-pyrrolo[2,3-d]pyrimidin-4-yl)phenyl]-2,3-dihydro-1H-inden-2-yl}methanamine;
1-{2-(Aminomethyl)-2-[3-(7H-pyrrolo[2,3-d]pyrimidin-4-yl)phenyl]-2,3-dihydro-1H-inden-5-yl}azetidin-3-ol;
1-{2-(Aminomethyl)-2-[3-(7H-pyrrolo[2,3-d]pyrimidin-4-yl)phenyl]-2,3-dihydro-1H-inden-5-yl}piperidin-3-ol;
1-{2-(Aminomethyl)-2-[3-(7H-pyrrolo[2,3-d]pyrimidin-4-yl)phenyl]-2,3-dihydro-1H-inden-5-yl}piperidine-4-carbonitrile;
N-{2-(Aminomethyl)-2-[3-(7H-pyrrolo[2,3-d]pyrimidin-4-yl)phenyl]-2,3-dihydro-1H-inden-5-yl}tetrahydro-2H-pyran-4-amine;
1-{5-Pyrrolidin-1-yl-2-[3-(7H-pyrrolo[2,3-d]pyrimidin-4-yl)phenyl]-2,3-dihydro-1H-inden-2-yl}methanamine;
1-{5-Piperidin-1-yl-2-[3-(7H-pyrrolo[2,3-d]pyrimidin-4-yl)phenyl]-2,3-dihydro-1H-inden-2-yl}methanamine;
1-{5-Morpholin-4-yl-2-[3-(7H-pyrrolo[2,3-d]pyrimidin-4-yl)phenyl]-2,3-dihydro-1H-inden-2-yl}methanamine;
1-{2-(Aminomethyl)-2-[3-(7H-pyrrolo[2,3-d]pyrimidin-4-yl)phenyl]-2,3-dihydro-1H-inden-5-yl}piperidin-4-ol;
2-(Aminomethyl)-N-(2-methoxyethyl)-2-[3-(7H-pyrrolo[2,3-d]pyrimidin-4-yl)phenyl]indan-5-amine;
2-(Aminomethyl)-N-(3-methoxypropyl)-2-[3-(7H-pyrrolo[2,3-d]pyrimidin-4-yl)phenyl]indan-5-amine;
2-(Aminomethyl)-N-[1-(methoxymethyl)cyclopropyl]-2-[3-(7H-pyrrolo[2,3-d]pyrimidin-4-yl)phenyl]indan-5-amine;
1-{5-Phenyl-2-[3-(7H-pyrrolo[2,3-d]pyrimidin-4-yl)phenyl]-2,3-dihydro-1H-inden-2-yl}methanamine;
1-{5-(2-Fluorophenyl)-2-[3-(7H-pyrrolo[2,3-d]pyrimidin-4-yl)phenyl]-2,3-dihydro-1H-inden-2-yl}methanamine;
1-{5-(3-Fluorophenyl)-2-[3-(7H-pyrrolo[2,3-d]pyrimidin-4-yl)phenyl]-2,3-dihydro-1H-inden-2-yl}methanamine;
1-{5-(4-Fluorophenyl)-2-[3-(7H-pyrrolo[2,3-d]pyrimidin-4-yl)phenyl]-2,3-dihydro-1H-inden-2-yl}methanamine;
4-{2-(Aminomethyl)-2-[3-(7H-pyrrolo[2,3-d]pyrimidin-4-yl)phenyl]-2,3-dihydro-1H-inden-5-yl}-N,N-dimethylaniline;
1-{5-Imidazo[1,2-a]pyridin-6-yl-2-[3-(7H-pyrrolo[2,3-d]pyrimidin-4-yl)phenyl]-2,3-dihydro-1H-inden-2-yl}methanamine;
1-{5-(3-Methyl-3H-imidazo[4,5-b]pyridin-6-yl)-2-[3-(7H-pyrrolo[2,3-d]pyrimidin-4-yl)phenyl]-2,3-dihydro-1H-inden-2-yl}methanamine;
1-{5-(6-Pyrrolidin-1-ylpyridin-3-yl)-2-[3-(7H-pyrrolo[2,3-d]pyrimidin-4-yl)phenyl]-2,3-dihydro-1H-inden-2-yl}methanamine;
1-{5-(1-Ethyl-1H-imidazol-4-yl)-2-[3-(7H-pyrrolo[2,3-d]pyrimidin-4-yl)phenyl]-2,3-dihydro-1H-inden-2-yl}methanamine;
(2-(3-(7H-Pyrrolo[2,3-d]pyrimidin-4-yl)phenyl)-5-(pyridin-3-yl)-2,3-dihydro-1H-inden-2-yl)methanamine;
(2-(3-(7H-Pyrrolo[2,3-d]pyrimidin-4-yl)phenyl)-5-(pyridin-4-yl)-2,3-dihydro-1H-inden-2-yl)methanamine;
4-{3-[2-(Aminomethyl)-2,3-dihydro-1H-inden-2-yl]phenyl}-N-butyl-7H-pyrrolo[2,3-d]pyrimidin-2-amine;
4-{3-[2-(Aminomethyl)-2,3-dihydro-1H-inden-2-yl]phenyl}-N-methyl-7H-pyrrolo[2,3-d]pyrimidin-2-amine;
4-{3-[2-(Aminomethyl)-2,3-dihydro-1H-inden-2-yl]phenyl}-N-ethyl-7H-pyrrolo[2,3-d]pyrimidin-2-amine;
4-{3-[2-(Aminomethyl)-2,3-dihydro-1H-inden-2-yl]phenyl}-N-isopropyl-7H-pyrrolo[2,3-d]pyrimidin-2-amine;

4-{3-[2-(Aminomethyl)-2,3-dihydro-1H-inden-2-yl]phenyl}-N-cyclobutyl-7H-pyrrolo[2,3-d]pyrimidin-2-amine;

4-{3-[2-(Aminomethyl)-2,3-dihydro-1H-inden-2-yl]phenyl}-N-cyclopentyl-7H-pyrrolo[2,3-d]pyrimidin-2-amine;

4-{3-[2-(Aminomethyl)-2,3-dihydro-1H-inden-2-yl]phenyl}-N-cyclohexyl-7H-pyrrolo[2,3-d]pyrimidin-2-amine;

1-{2-[3-(6-Methyl-7H-pyrrolo[2,3-d]pyrimidin-4-yl)phenyl]-2,3-dihydro-1H-inden-2-yl}methanamine;

4-{2-[2-(Aminomethyl)-2,3-dihydro-1H-inden-2-yl]pyridin-4-yl}-N-(1-methyl-1H-pyrazol-4-yl)-7H-pyrrolo[2,3-d]pyrimidin-2-amine; and 4-{2-[2-(Aminomethyl)-2,3-dihydro-1H-inden-2-yl]pyridin-4-yl}-N-[3-(morpholin-4-ylmethyl)phenyl]-7H-pyrrolo[2,3-d]pyrimidin-2-amine;

or a pharmaceutically acceptable salt thereof.

18. A pharmaceutical composition comprising a compound of claim 1, or a pharmaceutically acceptable salt thereof, and a pharmaceutically acceptable carrier.

19. The compound of claim 1, having Formula IVa:

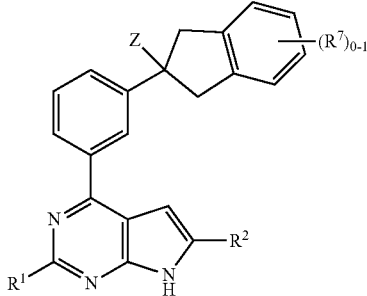

IVa or a pharmaceutically acceptable salt thereof.

20. The compound of claim 1, having Formula IVb:

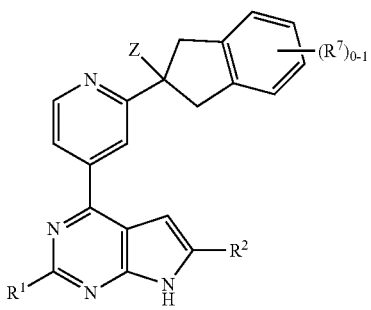

IVb or a pharmaceutically acceptable salt thereof.

21. The compound of claim 11, having Formula IVc:

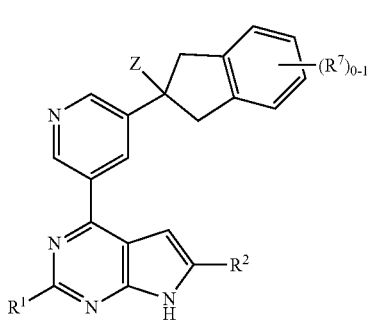

IVc or a pharmaceutically acceptable salt thereof.

22. The compound of claim 1, having Formula IVd:

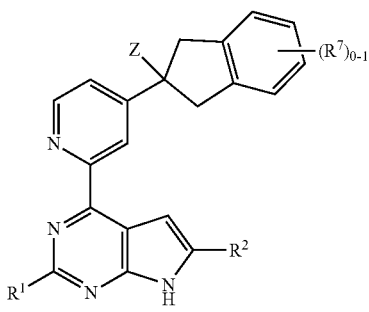

IVd or a pharmaceutically acceptable salt thereof.

23. The compound of claim 1, having Formula IVe:

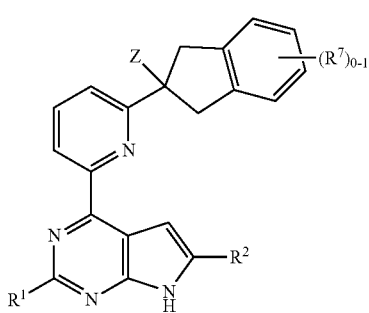

IVe or a pharmaceutically acceptable salt thereof.

24. The compound of claim 1, or a pharmaceutically acceptable salt thereof, wherein $R^2$ is H, halo, CN, $C_{1-4}$ alkyl, or $C_{1-4}$ haloalkyl.

25. The compound of claim 1, or a pharmaceutically acceptable salt thereof, wherein $R^2$ is H or methyl.

26. The compound of claim 1, or a pharmaceutically acceptable salt thereof, wherein $R^2$ is H.

27. The compound of claim 1, or a pharmaceutically acceptable salt thereof, wherein each $R^7$ is independently selected from halo, $C_{1-6}$ alkyl, $C_{1-4}$ haloalkyl, CN, Cy, —$C_{1-4}$ alkylene-Cy, $OR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^b$, $NR^cC(O)NR^cR^d$, $NR^cS(O)_2R^b$, $NR^cS(O)_2NR^cR^d$, $S(O)_2R^b$, and $S(O)_2NR^cR^d$; wherein said $C_{1-6}$ alkyl and $C_{1-4}$ haloalkyl are optionally substituted with 1, 2, 3, or 4 independently selected $R^8$ groups.

28. The compound of claim 1, or a pharmaceutically acceptable salt thereof, wherein each $R^7$ is independently selected from halo, $C_{1-6}$ alkyl, $C_{1-4}$ haloalkyl, CN, Cy, —$C_{1-4}$ alkylene-Cy, $OR^a$, $C(O)R^b$, $C(O)NR^cR^d$, $NR^cR^d$, $NR^cC(O)R^b$, $NR^cS(O)_2R^b$, $S(O)_2R^b$, and $S(O)_2NR^cR^d$; wherein said $C_{1-6}$ alkyl and $C_{1-4}$ haloalkyl are optionally substituted with 1, 2, 3, or 4 independently selected $R^8$ groups.

29. The compound of claim 1, or a pharmaceutically acceptable salt thereof, wherein each $R^7$ is independently selected from $C_{1-6}$ alkyl, CN, OH, $NR^cR^d$, Cy, and —$C_{1-4}$ alkylene-Cy; wherein said $C_{1-6}$ alkyl is optionally substituted with 1, 2, 3, or 4 independently selected $R^8$ groups.

30. The compound of claim 1, or a pharmaceutically acceptable salt thereof, wherein each $R^8$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}OR^{d2}$, $NR^{c2}C(O)R^{b2}$, $NR^{c2}C(O)OR^{b2}$, $NR^{c2}C(O)NR^{c2}R^{d2}$, $NR^{c2}S(O)_2R^{b2}$, $NR^{c2}S(O)_2NR^{c2}R^{d2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups.

31. The compound of claim 1, or a pharmaceutically acceptable salt thereof, wherein each $R^8$ is independently selected from halo, CN, $C_{1-6}$ alkyl, $C_{1-4}$ haloalkyl, $Cy^2$, —$C_{1-4}$ alkylene-$Cy^2$, $OR^{a2}$, $C(O)R^{b2}$, $C(O)NR^{c2}R^{d2}$, $NR^{c2}R^{d2}$, $NR^{c2}C(O)R^{b2}$, $NR^{c2}S(O)_2R^{b2}$, $S(O)_2R^{b2}$, and $S(O)_2NR^{c2}R^{d2}$; wherein said $C_{1-6}$ alkyl and $C_{1-4}$ haloalkyl are each optionally substituted with 1, 2, 3, or 4 independently selected $R^g$ groups.

32. The compound of claim 1, or a pharmaceutically acceptable salt thereof, wherein Z is $C_{1-4}$ alkyl, —$CH_2F$, —$CHF_2$, —$CH_2$—$Z^1$, —$CH_2$—$CH_2$—$Z^1$, or —$CH_2$—$CH_2$—$CH_2$—$Z^1$.

33. The compound of claim 1, or a pharmaceutically acceptable salt thereof, wherein Z is —$CH_2F$, —$CHF_2$, —$CH_2$—$Z^1$, or —$CH_2$—$CH_2$—$Z^1$.

34. The compound of claim 1, or a pharmaceutically acceptable salt thereof, wherein $Z^1$ is CN, $OR^{a3}$, $NR^{c3}R^{d3}$, $NR^{c3}C(O)R^{b3}$, $NR^{c3}C(O)OR^{b3}$, or $NR^{c3}S(O)_2R^{b3}$.

35. The compound of claim 1, or a pharmaceutically acceptable salt thereof, wherein $Z^1$ is $NR^{c3}R^{d3}$.

36. The compound of claim 1, or a pharmaceutically acceptable salt thereof, wherein $R^{a3}$, $R^{c3}$ and $R^{d3}$ are each independently selected from H, $C_{1-6}$ alkyl, and $Cy^3$; and each $Cy^3$ is independently 3-7 membered cycloalkyl, phenyl, 5-6 membered heteroaryl, or 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_{1-3}$ haloalkoxy, amino, $C_{1-3}$ alkylamine, and di($C_{1-3}$ alkyl)amino; $R^{b3}$ is selected from $C_{1-6}$ alkyl, and $Cy^3$; and each $Cy^3$ is independently selected from 3-7 membered cycloalkyl, phenyl, 5-6 membered heteroaryl, and 4-6 membered heterocycloalkyl, each of which is optionally substituted by 1, 2, 3, or 4 groups independently selected from halo, OH, CN, $C_{1-3}$ alkyl, $C_{1-3}$ haloalkyl, $C_{1-3}$ alkoxy, $C_1$-$_3$ haloalkoxy, amino, $C_{i-3}$ alkylamine, and di($C_{1-3}$ alkyl)amino.

37. A compound which is selected from:

1-{2-[4-(5-Methoxy-1H-pyrrolo[2,3-b]pyridin-4-yl)pyridin-2-yl]-2,3-dihydro-1H-inden-2-yl}methanamine;

1-{2-[4-(1H-Pyrazolo[3,4-b]pyridin-4-yl)pyridin-2-yl]-2,3-dihydro-1H-inden-2-yl}methanamine;

3-(Aminomethyl)-3-[3-(7H-pyrrolo[2,3-d]pyrimidin-4-yl)phenyl]indan-1-ol;

1-{2-[3-(7H-Pyrrolo[2,3-d]pyrimidin-4-yl)phenyl]-1,2,3,4-tetrahydronaphthalen-2-yl}methanamine;

1-[2-(Aminomethyl)-2,3-dihydro-1H-inden-2-yl]-5-(7H-pyrrolo[2,3-d]pyrimidin-4-yl)pyridin-2(1H)-one;

1-{6-[3-(7H-Pyrrolo[2,3-d]pyrimidin-4-yl)phenyl]-6,7-dihydro-5H-cyclopenta[c]pyridin-6-yl}methanamine;

1-{6-[3-(7H-Pyrrolo[2,3-d]pyrimidin-4-yl)phenyl]-6,7-dihydro-5H-cyclopenta[b]pyridin-6-yl}methanamine; and 1-{2-[6-Chloro-4-(7H-pyrrolo[2,3-d]pyrimidin-4-yl)pyridin-2-yl]-2,3-dihydro-1H-inden-2-yl}methanamine;

or a pharmaceutically acceptable salt thereof.

* * * * *

SEQUENCE LISTING

<160> NUMBER OF SEQ ID NOS: 1

<210> SEQ ID NO 1
<211> LENGTH: 15
<212> TYPE: PRT
<213> ORGANISM: Artificial Sequence
<220> FEATURE:
<223> OTHER INFORMATION: synthetic peptide

<400> SEQUENCE: 1

Glu Gln Glu Asp Glu Pro Glu Gly Asp Tyr Phe Glu Trp Leu Glu
1               5                   10                  15